US011338033B2

(12) United States Patent
Boyington et al.

(10) Patent No.: US 11,338,033 B2
(45) Date of Patent: May 24, 2022

(54) STABILIZED GROUP 2 INFLUENZA HEMAGGLUTININ STEM REGION TRIMERS AND USES THEREOF

(71) Applicant: THE USA, AS REPRESENTED BY THE SECRETARY, DEPT. OF HEALTH AND HUMAN SERVICES, Bethesda, MD (US)

(72) Inventors: Jeffrey C. Boyington, Clarksburg, MD (US); Barney S. Graham, Rockville, MD (US); John R. Mascola, Rockville, MD (US); Hadi M. Yassine, Doha (QA); Kizzmekia S. Corbett, Wheaton, MD (US); Syed M. Moin, Laurel, MD (US); Lingshu Wang, North Potomac, MD (US); Masaru Kanekiyo, Chevy Chase, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/329,592

(22) PCT Filed: Sep. 1, 2017

(86) PCT No.: PCT/US2017/049894

§ 371 (c)(1),
(2) Date: Feb. 28, 2019

(87) PCT Pub. No.: WO2018/045308

PCT Pub. Date: Mar. 8, 2018

(65) Prior Publication Data

US 2019/0192651 A1 Jun. 27, 2019

Related U.S. Application Data

(60) Provisional application No. 62/383,267, filed on Sep. 2, 2016.

(51) Int. Cl.

| | |
|---|---|
| *A61K 39/145* | (2006.01) |
| *C07K 14/195* | (2006.01) |
| *A61K 39/12* | (2006.01) |
| *C07K 14/005* | (2006.01) |
| *A61P 31/16* | (2006.01) |
| *A61K 39/00* | (2006.01) |

(52) U.S. Cl.

CPC ............ *A61K 39/145* (2013.01); *A61K 39/12* (2013.01); *A61P 31/16* (2018.01); *C07K 14/005* (2013.01); *C07K 14/195* (2013.01); *A61K 2039/55555* (2013.01); *C07K 2319/00* (2013.01); *C12N 2760/16122* (2013.01); *C12N 2760/16134* (2013.01)

(58) Field of Classification Search

CPC .. C07K 2319/00; A61K 39/42; A61K 39/145; A61K 39/12; A61K 2039/5258; A61K 2039/53; A61K 2039/575; A61K 2039/58; G01N 2333/11; G01N 2800/26; C12N 2760/16123; C12N 2760/18143; C12N 2760/16162; C12N 2760/16111; C12N 2760/16034; C12N 2760/16223; C12N 2760/18021; C12N 2710/10343; C12N 2710/20034; C12N 2740/11034; C12N 2740/16034; C12N 2710/20023; C12N 2710/20071; C12N 2730/10122; C12N 2730/10123; C12N 2730/10134; C12N 2730/10171; C12N 2740/14034; C12N 2740/15023; C12N 2740/15051; C12N 2740/16023; C12N 2760/00034; C12N 2760/14123; C12N 2760/16023

See application file for complete search history.

(56) References Cited

U.S. PATENT DOCUMENTS

| | | | | |
|---|---|---|---|---|
| 7,094,598 | B2 | 8/2006 | Nabel et al. | |
| 7,097,841 | B2 | 8/2006 | Carter et al. | |
| 7,608,268 | B2 | 10/2009 | Carter et al. | |
| 9,441,019 | B2 * | 9/2016 | Nabel | A61P 37/04 |
| 10,137,190 | B2 | 11/2018 | Nabel et al. | |
| 2002/0054882 | A1 | 5/2002 | Okuno et al. | |

(Continued)

FOREIGN PATENT DOCUMENTS

| | | | |
|---|---|---|---|
| EP | 1504037 | | 12/2009 |
| JP | 2015-502353 | A | 1/2015 |

(Continued)

OTHER PUBLICATIONS

Krammer et al. Current Opinion in Virology 2013, vol. 3, pp. 521-530.*
Ni et al. Biochemistry 2014, vol. 53 (5), pp. 846-854.*
Kanekiyo et al. Nature, 2013, Nature 2013, 499, 102-106.*
Benton et al. PNAS, Oct. 2018, vol. 115, No. 40, pp. 10112-10117.*
Francois Ehrenmann et al. in IMGT education, edited by Chantal Ginesteoux at p. 1-3, published on Apr. 20, 2014.*
A3KF33, UniProtKB A3KF33_I57A5, Sep. 21, 2011 [online]. [Retrieved on Feb. 26, 2013]. Retrieved from the internet <URL: http://www.uniprot.org/uniprot/A3KF33.txt?version=36>.

(Continued)

*Primary Examiner* — Bao Q Li
(74) *Attorney, Agent, or Firm* — Klarquist Sparkman, LLP

(57) ABSTRACT

Vaccines that elicit broadly protective anti-influenza antibodies. The vaccines comprise nanoparticles that display HA trimers from Group 2 influenza virus on their surface. The nanoparticles are fusion proteins comprising a monomeric subunit (e.g., ferritin) joined to stabilized stem regions of Group 2 influenza virus HA proteins. The fusion proteins self-assemble to form the HA-displaying nanoparticles. Also provided are fusion proteins, and nucleic acid molecules encoding such proteins, and assays using nanoparticles of the invention to detect anti-influenza antibodies.

15 Claims, 92 Drawing Sheets

Specification includes a Sequence Listing.

(56) References Cited

U.S. PATENT DOCUMENTS

| | | |
|---|---|---|
| 2003/0211996 A1 | 11/2003 | Gowans et al. |
| 2005/0042229 A1 | 2/2005 | Yang et al. |
| 2005/0108791 A1 | 5/2005 | Edgerton |
| 2006/0251679 A1 | 11/2006 | Carter et al. |
| 2007/0082054 A1 | 4/2007 | Mooter et al. |
| 2007/0224205 A1 | 9/2007 | Powell et al. |
| 2008/0299151 A1 | 12/2008 | Fomsgaard |
| 2009/0233377 A1 | 9/2009 | Iwahori et al. |
| 2010/0137412 A1 | 6/2010 | Zhou et al. |
| 2010/0285982 A1 | 11/2010 | Golding et al. |
| 2010/0297174 A1 | 11/2010 | Garcia-Sastre et al. |
| 2011/0038025 A1 | 2/2011 | Naitou et al. |
| 2011/0059130 A1 | 3/2011 | Yusibov |
| 2011/0177122 A1 | 7/2011 | Nabel et al. |
| 2011/0212128 A1 | 9/2011 | Galarza et al. |
| 2016/0303224 A1 | 10/2016 | Kanekiyo et al. |
| 2018/0021258 A1 | 1/2018 | Graham et al. |

FOREIGN PATENT DOCUMENTS

| | | |
|---|---|---|
| JP | 2015-519348 A | 7/2015 |
| JP | 2016-525889 A | 9/2016 |
| WO | WO 2003/094849 | 11/2003 |
| WO | WO 2009/109428 | 9/2009 |
| WO | WO 2010/036948 | 4/2010 |
| WO | WO 2010/117786 | 10/2010 |
| WO | WO 2011/035422 | 3/2011 |
| WO | WO 2011/044152 | 4/2011 |
| WO | WO 2012/162428 | 11/2012 |
| WO | WO 2013/044203 | 3/2013 |
| WO | WO 2013/044203 A2 * | 3/2013 |
| WO | WO 2013/079473 A1 | 6/2013 |
| WO | WO 2013/177444 A2 | 11/2013 |
| WO | WO 2014/191435 A1 | 12/2014 |
| WO | WO 2015/054639 | 4/2015 |
| WO | WO 2015/183969 | 12/2015 |
| WO | WO 2016/005482 A1 | 1/2016 |
| WO | WO 2016/021209 | 2/2016 |
| WO | WO 2018/005558 A1 | 1/2018 |

OTHER PUBLICATIONS

GenBank Accession No. 3EGM_A submitted Sep. 11, 2008, 2 pages.

GenBank Accession No. AAP34324, submitted May 1, 2003, 2 pages.

Bachmann, M.F., et al., "Neutralizing antiviral B cell responses," Annu Rev Immunol, 1997, 15:235-270.

Bernacchioni et al. "Loop Electrostatics Modulates the Intersubunit Interactions in Ferritin," ACS Chemical Biology, 2014, vol. 9, pp. 2517-2525.

Caton, A.J., et al., "The antigenic structure of the influenza virus A/PR/8/34 hemagglutinin (H1 subtype)," Cell, 1982, 31:417-427.

Cohen et al., "Ferritin as an Endogenous MRI Reporter for Non-invasive Imaging Neoplasia of Gene Expression in C6 Glioma Tumors," Neoplasia, Feb. 2005, 7(2):109-117.

C0LT38, UniProtKB C0LT38_9INFB, Sep. 21, 2011 [online]. [Retrieved on Feb. 26, 2013]. Retrieved from the internet <URL: http://www.uniprot.org/uniprot/C0LT38.txt?version=18>.

Corti, D., et al., "Heterosubtypic neutralizing antibodies are produced by individuals immunized with a seasonal influenza vaccine," J Clin Invest, 2010, 120:1663-1673.

Corti, D., et al., "A neutralizing antibody selected from plasma cells that binds to group 1 and group 2 influenza A hemagglutinins," Science, 2011, 333:850-856.

Dintzis, H.M. et al., "Molecular determinants of immunogenicity: the immunon model of immune response," Proc Natl Acad Sci USA, 1976, 73:3671-3675.

Ekiert, D.C., et al., "A highly conserved neutralizing epitope on group 2 influenza A viruses," Science, 2011, 333:843-850.

Ekiert, D.C., et al., "Antibody recognition of a highly conserved influenza virus epitope," Science, 2009, 324:246-251.

Greenstone et al. "Chimeric papillomavirus virus-like particles elicit antitumor immunity against the E7 oncoprotein in an HPV16 tumor model," Proc. Natl. Acad. Sci. USA, Feb. 1998, vol. 95, pp. 1800-1805.

Harrison "The Structure and Function of Ferritin," Biochemical Education, 1986, vol. 14, No. 4, pp. 154-162.

Haynes, J.R., "Influenza virus-like particle vaccines," Expert Rev Vaccines, 2009, 8:435-445.

He et al. "Presenting native-like trimeric HIV-1 antigens with self-assembling nanoparticles," Nature Communications, Jun. 2016, vol. 7, 12041, 15 pages.

Joyce et al. "Vaccine-Induced Antibodies that Neutralize Group 1 and Group 2 Influenza A Viruses," Cell, Jul. 2016, vol. 166, No. 3, pp. 609-623.

Kanekiyo, Masaru, et al., "Self-assembling influenza nanoparticle vaccines elicit broadly neutralizing H1N1 antibodies", Nature, Nature Publishing Group, United Kingdom, vol. 499, No. 7456, Jul. 4, 2013 (Jul. 4, 2013), pp. 102-106.

Kanekiyo et al. "Rational Design of an Epstein-Barr Virus Vaccine Targeting the Receptor-Binding Site," Cell, Aug. 2015, vol. 162, No. 5, pp. 1090-1100.

Kang, S.M., et al., "Influenza vaccines based on virus-like particles", Virus Research, Amsterdam, NL, vol. 143, No. 2, Aug. 1, 2009 (Aug. 1, 2009), pp. 140-146.

Kashyap, A.K., et al., "Combinatorial antibody libraries from survivors of the Turkish H5N1 avian influenza outbreak reveal virus neutralization strategies," Proc Natl Acad Sci USA, 2008, 105:5986-5991.

Kong, W.P., et al., "Protective immunity to lethal challenge of the 1918 pandemic influenza virus by vaccination," Proc Natl Acad Sci USA, 2006, 103:15987-15991.

Kossovsky et al. "Nanocrystalline Epstein-Barr virus decoys," Journal of Applied Biomaterials: An Official Journal of the Society for Biomaterials, Jan. 1991, vol. 2, No. 4, pp. 251-259.

Krause, J.C., et al., "A broadly neutralizing human monoclonal antibody that recognizes a conserved, novel epitope on the globular head of the influenza H1N1 virus hemagglutinin," J Virol, 2011, 85:10905-10908.

Lambert, L.C., et al., "Influenza vaccines for the future," N Engl J Med, 2010, 363, 2036-2044.

Lee, L.A., et al., "Adaptations of nanoscale viruses and other protein cages for medical applications", Nanomedicine: Nanotechnology, Biology and Medicine, Elsevier, NL, vol. 2, No. 3, Sep. 1, 2006 (Sep. 1, 2006), pp. 137-149.

Lee et al. "Viruses and Virus-Like Protein Assemblies—Chemically Programmable Nanoscale Building Blocks," Nano Res, 2009, vol. 2, pp. 349-364.

Li, C.Q. et al., "Ferritin nanoparticle technology: A new platform for antigen presentation and vaccine development," Industrial Biotechnol 2, 143-147 (2006).

Lopez-Sagaseta et al. "Self-assembling protein nanoparticles in the design of vaccines," Computational and Structural Biotechnology Journal, 2016, vol. 14, pp. 58-68.

Meldrum, F.C., et al., "Magnetoferritin: in vitro synthesis of a novel magnetic protein," Science, 1992, 257:522-523.

Nabel, G.J., et al., "Induction of unnatural immunity: prospects for a broadly protective universal influenza vaccine," Nat Med, 2010, 16:1389-1391.

Ni et al. "Structural Insights into the Membrane Fusion Mechanism Mediated by Influenza Virus Hemagglutinin," Biochemistry, 2014, vol. 53, pp. 846-854.

Okuno, Y., et al., "A common neutralizing epitope conserved between the hemagglutinins of influenza A virus H1 and H2 strains," J Virol, 1993, 67:2552-2558.

Pulford et al. "Expression of the Epstein-Barr Virus Envelope Fusion Glycoprotein GB85 Gene by a Recombinant Baculovirus," Journal of General Virology, Nov. 1994, vol. 75, No. 11, pp. 3241-3248.

Roldao, A., et al., "Virus-like particles in vaccine development," Expert Rev Vaccines, 2010, 9:1149-1176.

(56) References Cited

OTHER PUBLICATIONS

Ruiss et al. "A Virus-Like Particle-Based Epstein-Barr Virus Vaccine," Journal of Virology, Dec. 2011, vol. 85, No. 24, pp. 13105-13113.
Scorza et al. "Universal influenza vaccines: Shifting to better vaccines," Vaccine, Mar. 2016, vol. 34, No. 26, pp. 2926-2933.
Sheridan, C., "Flu vaccine makers upgrade technology—and pray for time," Nat Biotechnol, 2009, 27:489-491.
Steel et al. "Influenza Virus Vaccine Based on the Conserved Hemagglutinin Stalk Domain," MBIO, American Society for Microbiology, May 2010, vol. 1, No. 1, pp. e00018-10/1-9.
Sui, J., et al., "Structural and functional bases for broad-spectrum neutralization of avian and human influenza A viruses," Nat Struct Mol Biol, 2009, 16:265-273.
Treanor, J.J., et al., "Safety and immunogenicity of a recombinant hemagglutinin vaccine for H5 influenza in humans," Vaccine, 2001, 19:1732-1737.
Treanor, J.J., "Safety and immunogenicity of a baculovirus-expressed hemagglutinin influenza vaccine: a randomized controlled trial," JAMA,2007, 297:1577-1582.
Vallhov et al. "Exosomes Containing Glycoprotein 350 Released by EBV-Transformed B Cells Selectively Target B Cells through CD21 and Block EBV Infection in Vitro," The Journal of Immunology, Jan. 2011, vol. 186, No. 1, pp. 73-82.
Wang, T.T., et al., "Broadly protective monoclonal antibodies against H3 influenza viruses following sequential immunization with different hemagglutinins," PLoS Pathog, 2010, vol. 6, Issue 2, e1000796.
Wei, C.J., et al., Cross-neutralization of 1918 and 2009 influenza viruses: role of glycans in viral evolution and vaccine design. Sci Transl Med, 2010, 2, 24ra21.
Wei, C.J., et al., "Induction of broadly neutralizing H1N1 influenza antibodies by vaccination," Science, 2010, 329:1060-1064.
Wei, C.J., et al., "Comparative efficacy of neutralizing antibodies elicited by recombinant hemagglutinin proteins from avian H5N1 influenza virus," J Virol, 2008, 82:6200-6208.
Whittle, J.R., et al., "Broadly neutralizing human antibody that recognizes the receptor-binding pocket of influenza virus hemagglutinin," Proc Natl Acad Sci USA, 2011, 108:14216-14221.
Who Reference on Animal Influenza Diagnosis and Surveillance, 2002, Department of Communicable Disease Surveillance and Response, World Health Organization).
Wu, C.Y., et al., "Mammalian expression of virus-like particles for advanced mimicry of authentic influenza virus," PLoS One 5, 2010, e9784.
Xiong, A.S., et al., "PCR-based accurate synthesis of long DNA sequences," Nat Protoc, 2006, 1(2):791-797.
Yamashita, I., et al., "Ferritin in the field of nanodevices," Biochim Biophys Acta, 2010, 1800:846-857.
Yang, Z.Y., et al., "Immunization by avian H5 influenza hemagglutinin mutants with altered receptor binding specificity," Science, 2007, 317:825-828).
Yassine et al. "Hemagglutinin-stem nanoparticles generate heterosubtypic influenza protection." Nature Medicine, Sep. 2015, vol. 21, No. 9, pp. 1065-1070.
Zhang, Y., et al., "Self-Assembly in the Ferritin Nano-Cage Protein Super Family," Int. J. Mol. Sci., 2011, 12:5406-5421.
Zhang et al. "Universal Influenza Vaccines, a Dream to Be Realized Soon," Viruses, 2014, vol. 6, pp. 1974-1991.
International Preliminary Report on Patentability for International (PCT) Patent Application No. PCT/US2017/049894, dated Mar. 14, 2019 8 pages.
International Search Report and Written Opinion prepared by the European Patent Office dated Nov. 8, 2017, for International Application No. PCT/US2017/049894.
U.S. Appl. No. 13/782,381, filed Mar. 1, 2013.
U.S. Appl. No. 14/346,849, filed Mar. 24, 2014 now U.S. Pat. No. 9,441,019.
U.S. Appl. No. 15/244,321, filed Aug. 23, 2016 now U.S. Pat. No. 10,137,190.
U.S. Appl. No. 15/028,655, filed Apr. 11, 2016.
U.S. Appl. No. 15/540,898, filed Jun. 29, 2017.
Corbett et al., "Design of Nanoparticulate Group 2 Influenza Virus Hemagglutinin Stem Antigens that Activate Unmuted Ancestor B Cell Receptors of Broadly Neutralizing Antibody Lineages," *mBio 10.1*: e02810-18, Jan./Feb. 2019 (27 pages).

* cited by examiner

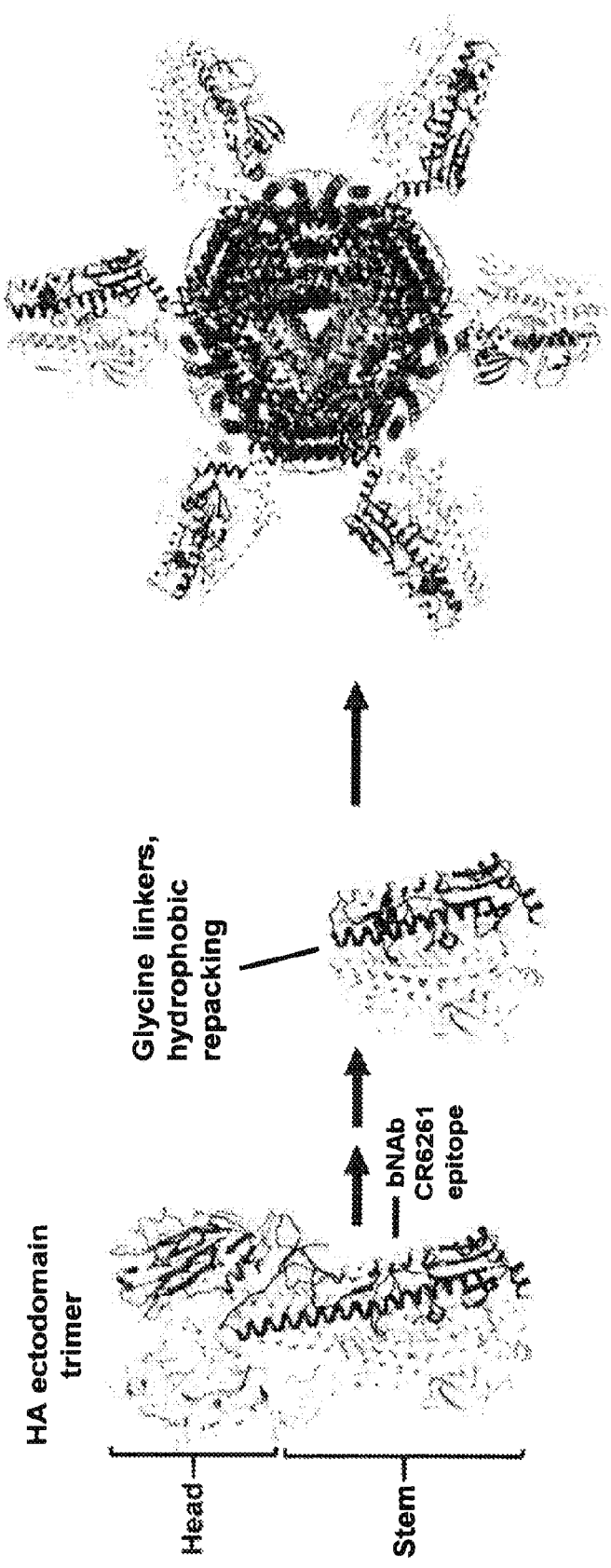

Mutations to replace head region

>H3-SS-np_231
MKTIIALSY

Mutations to replace head region

HA head replaced by disulfide-bonded loop (VF

>H3-SS-np_231
MKTIIALSYILCLVFAQKLPGNDNSTATLCLGHHAVPNGTIVK
TITNDQIEVTNATEL VPGCGV LKLATGMRNVPEKQTRGIFGA
IAGFIENGWEGMVDGWYGFRHQNSEGIGQAADLKSTQAAINQI
NG MVNRV ALMAQGPDCM AELLVAI LNQH VI DLTDSEM RKL
FERTKKQLRENAEDMGNGCFKIYHKCDNACIGSIRNGTYDHDV
YRDEALNNRFQIKSGGDIIKLLNEQVNKEMQSSNLYMSMSSWC
YTHSLDGAGLFLFDHAAEEYEHEQHISESINNIVDHAIKSKDHATF
APEHKFEGLTQIFQKAYEHEQHISESINNIVDHAIKSKDHATF
NFLQWYVAEQHEEEVLFKDILDKIELIGNENHGLYLADQYVKG
IAKSRKSGS

FIG. 4D

HA2 membrane distal region between helices A and C replaced with short linker (GGPD 3. Five residue HA2 helix A extension (ALMAQ)

>H3-SS-np_231
MKTIIALSYILCLVFAQKLPGNDNSTATLCLGHHAVPNGTIVK
TITTNDQIEVTNATEIVFPGGGVLKLATGMRNVPEKQTRGIFGA
IAGFIENGWEGMVDGWYGFRHQNSEGIGQAADLKSTQAAINQI
NGMVNRVIALMAQGGPDCMAELLVAILNQHVVIDLTDSEMRKL
FERTKKQLRENAEDMGNGCFKIYHKCDNAC

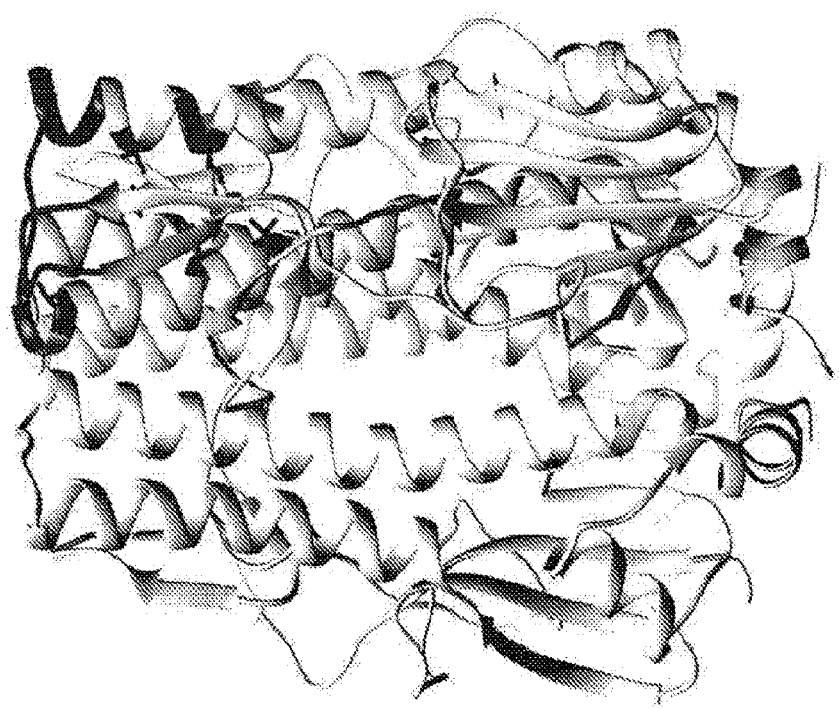

>H3-SS-np_231
MKTIIALSYILCLVFAQKLPGNDNSTATLCLGHHAVPNGTIVK
TITNDQIEVTNATEIVFPGCGVLKLATGMRNVPEKQTRGIFGA
IAGFIENGWEGMVDGWYGFRHQNSEGIGQAADLKSTQAAINQI
NGMVNRVIALMAQGGPDCMLAELLVAILNQILDLTDSEMRKL
FERTKKQLRENAEDMGNGCFKIYHKCDNACIGSIRNGTYDHDV
YRDEALNNRFQIKSGGDIIKLLNEQVNKEMQSSNLYMSMSSWC
YTHSLDGAGLFLFDHAAEEYEHEQHISESINNIVDHAIKSKDHATF
APEHKFEGLTQIFQKAYEHEEVLFKDILDKIELIGNENHGLYLADQYVKG
NFLQWYVAEQHEEEVLFKDILDKIELIGNENHGLYLADQYVKG
IAKSRKSGS

Negative stain EM 2D class averages

| mAb | EC50 (ug/ml) | |
|---|---|---|
| | H1-SS-np | H3-SS-np_231 |
| D25 | --- | --- |
| CR8020 | 15.56 | 0.02 |
| CT149 | 0.03 | 0.03 |
| F16 | 0.14 | 0.08 |

| Fab | $K_D$ (M) | $K_D$ Error | $k_{on}$(1/Ms) |
|---|---|---|---|
| CT149 | 2.69E-09 | 2.66E-10 | 1.06E+06 |
| CR9114 | 6.41E-11 | 1.29E-09 | 2.00E+05 |

231 FIG. 11A
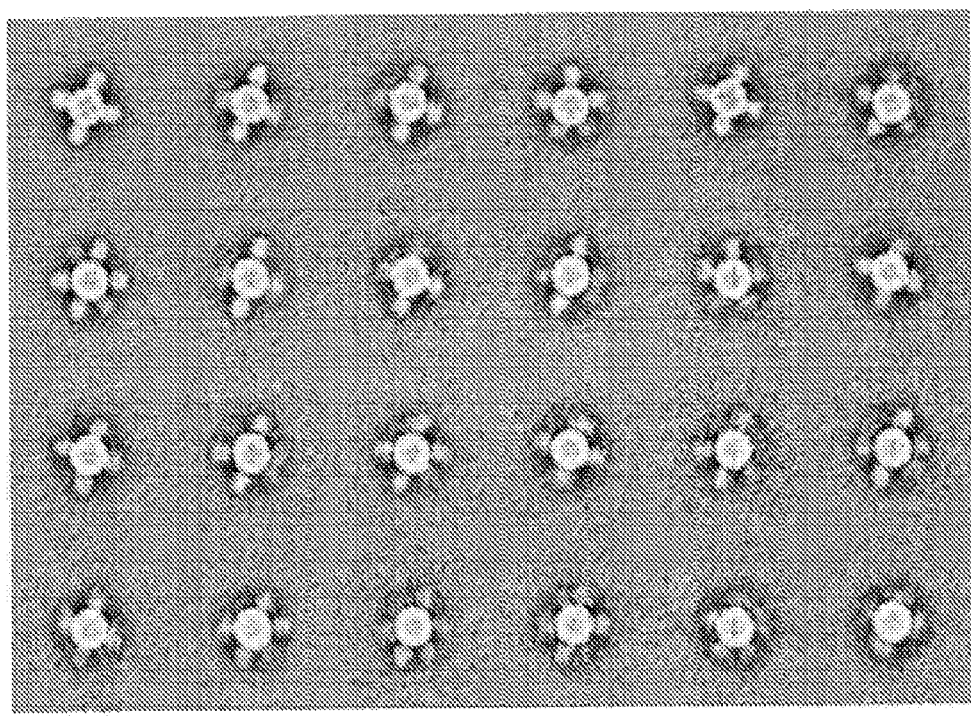
249 FIG. 11B
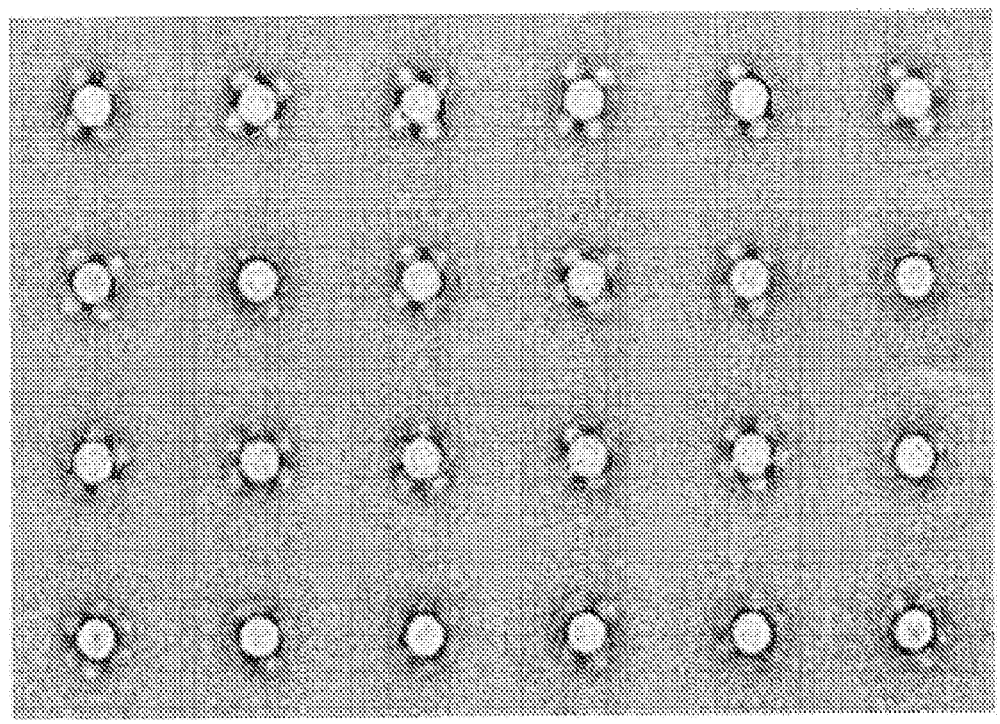

256

258

262 FIG. 11E
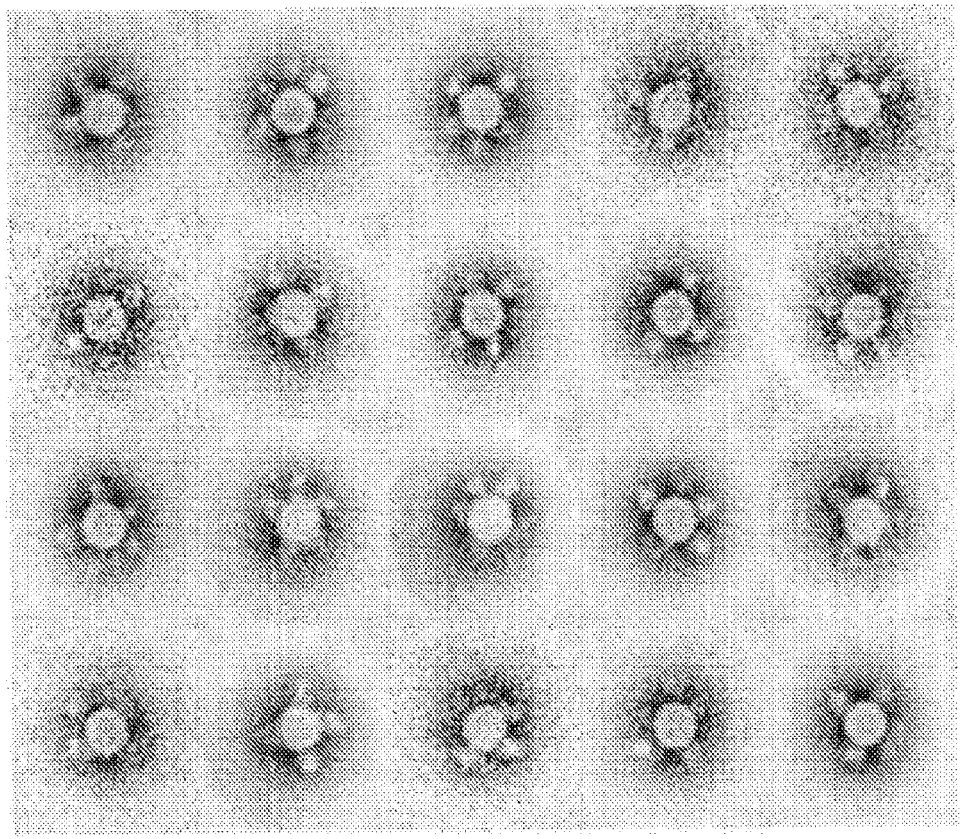
264 FIG. 11F
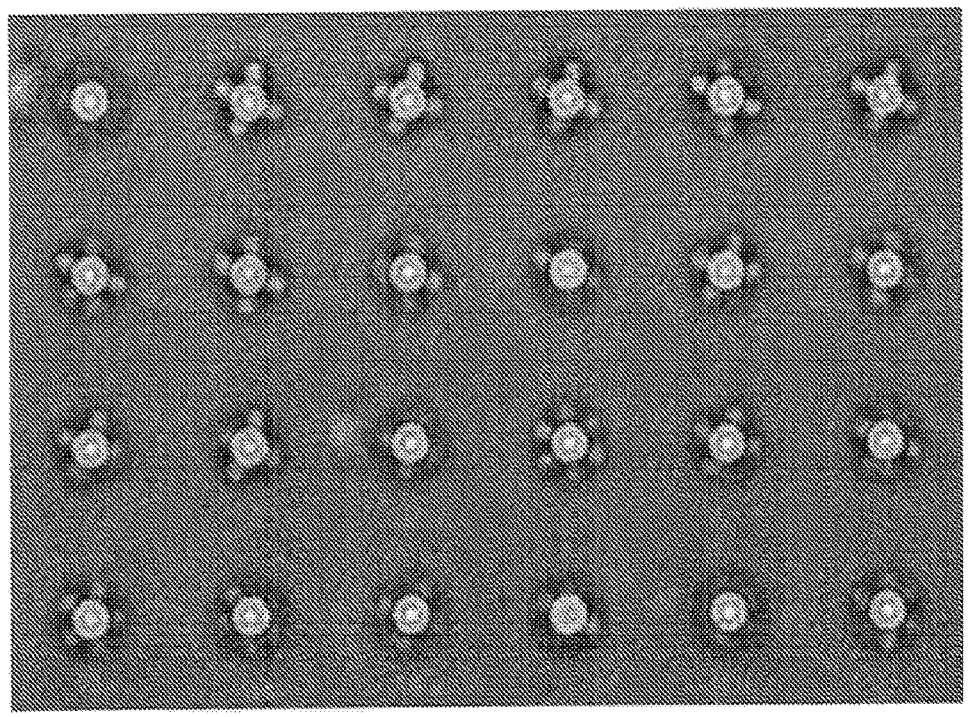

| H3-SS-np# | Antibody EC$_{50}$ (µg/ml) | | |
|---|---|---|---|
| | CR8020 | CT149 | FI6 |
| 249 | 0.036 | 0.013 | 0.024 |
| 256 | 0.050 | 0.020 | 0.022 |
| 258 | 0.060 | 0.140 | 0.028 |
| 262 | 0.039 | 0.019 | 0.022 |
| 264 | 0.041 | 0.010 | 0.026 |

ELISA characterization of H3-SS-np designs 235-265

ELISA Plate key

| | | 1 | 2 | 3 | 4 | 5 | 6 | 7 | 8 | 9 | 10 | 11 | 12 |
|---|---|---|---|---|---|---|---|---|---|---|---|---|---|
| | A | neg. ctrl | FL H3 Np | H1-SS-np | | | | | | | | | |
| ELISA Plate key | B | 242 | 243 | 244 | 190 | 231 | 235 | 236 | 237 | 238 | 239 | 240 | 241 |
| | C | 254 | 255 | 256 | 245 | 246 | 247 | 248 | 249 | 250 | 251 | 252 | 253 |
| | D | empty np | FL H3 Np | H1-SS-np | 257 | 258 | 259 | 260 | 261 | 262 | 263 | 264 | 265 |
| | | | | | 231 | | | | | | | | |

96-well transfection Test - H3SSnp constructs #235 - #265 - ELISA Plate Key

| | | 1 | 2 | 3 | 4 | 5 | 6 | 7 | 8 | 9 | 10 | 11 | 12 |
|---|---|---|---|---|---|---|---|---|---|---|---|---|---|
| D25 (neg. ctrl) | A | 0.28 | -0.05 | 0.41 | 0.00 | 0.20 | 0.28 | 0.22 | 0.53 | 0.45 | 0.20 | 0.57 | -

ELISA characterization of H3-SS-np designs 266-296

| Key | | 1 | 2 | 3 | 4 | 5 | 6 | 7 | 8 | 9 | 10 | 11 | 12 |
|---|---|---|---|---|---|---|---|---|---|---|---|---|---|
| | A | neg. ctrl | H1-SS-np | 231 | 266 | 267 | 268 | 269

FIG. 16D

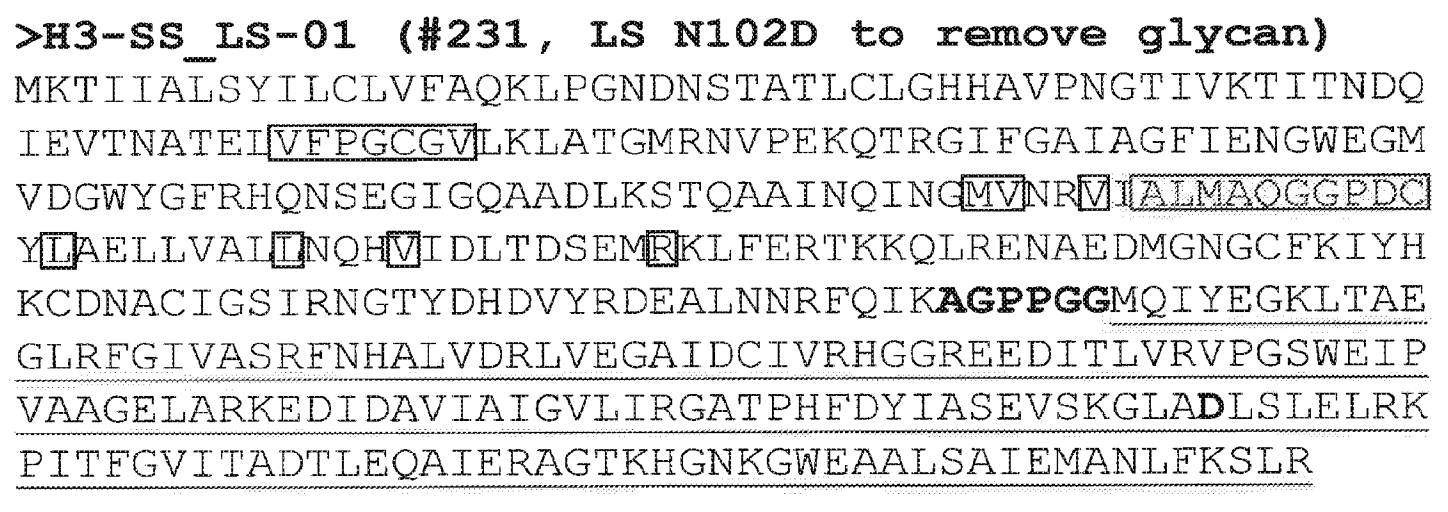

>H3-SS_LS-01 (#231, LS N102D to remove glycan)

MKTIIALSYILCLVFAQKLPGNDNSTATLCLGHHAVPNGTIVKTITNDQ
IEVTNATEIVFPGCGVLKLATGMRNVPEKQTRGIFGAIAGFIENGWEGM
VDGWYGFRHQNSEGIGQAADLKSTQAAINQINGMVNRVIALMAQGGPDC
YLAELLVALLNQHVIDLTDSEMRKLFERTKKQLRENAEDMGNGCFKIYH
KCDNACIGSIRNGTYDHDVYRDEALNNRFQIKAGPPGGMQIYEGKLTAE
GLRFGIVASRFNHALVDRLVEGAIDCIVRHGGREEDITLVRVPGSWEIP
VAAGELARKEDIDAVIAIGVLIRGATPHFDYIASEVSKGLADLSLELRK
PITFGVITADTLEQAIERAGTKHGNKGWEAALSAIEMANLFKSLR

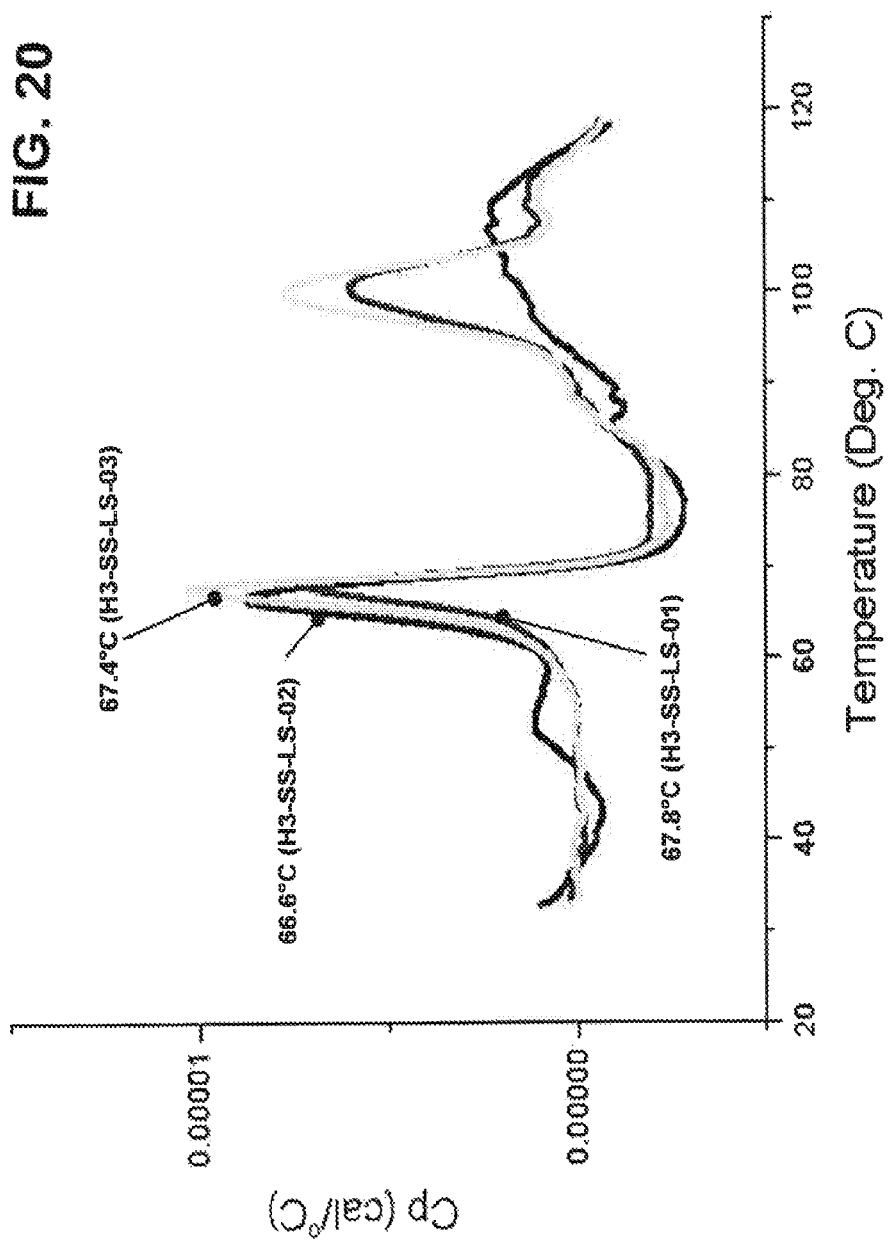

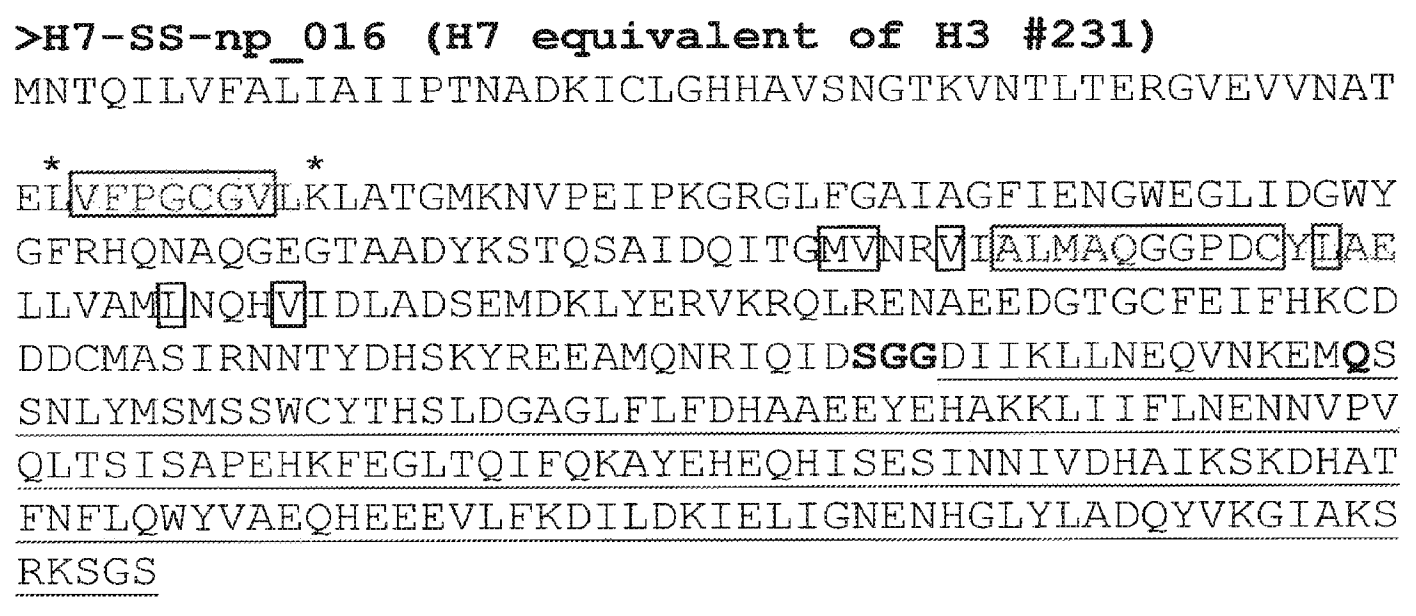

>H7-SS-np_016 (H7 equivalent of H3 #231)

MNTQILVFALIAIIPTNADKICLGHHAVSNGTKVNTLTERGVEVVNAT

*         *
EILVFPGCGVLKLATGMKNVPEIPKGRGLFGAIAGFIENGWEGLIDGWY
GFRHQNAQGEGTAADYKSTQSAIDQITGMVNRVIALMAQGGPDCYLAE
LLVAMINQHVIDLADSEMDKLYERVKRQLRENAEEDGTGCFEIFHKCD
DDCMASIRNNTYDHSKYREEAMQNRIQIDSGGDIIKLLNEQVNKEMQS
SNLYMSMSSWCYTHSLDGAGLFLFDHAAEEYEHAKKLIIFLNENNVPV
QLTSISAPEHKFEGLTQIFQKAYEHEQHISESINNIVDHAIKSKDHAT
FNFLQWYVAEQHEEEVLFKDILDKIELIGNENHGLYLADQYVKGIAKS
RKSGS

H1-SS-np (control) FIG. 25A
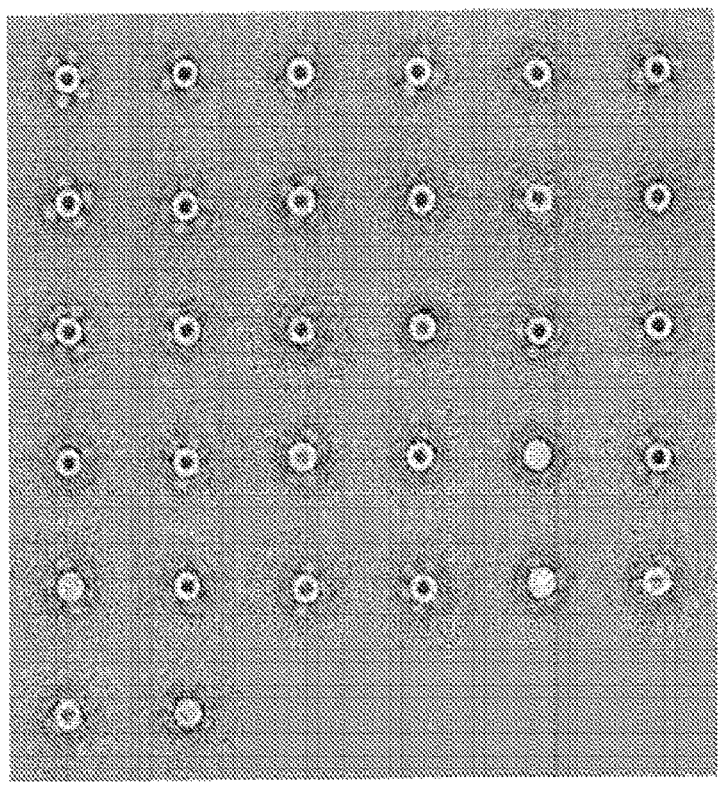
H7-SS-16 FIG. 25B
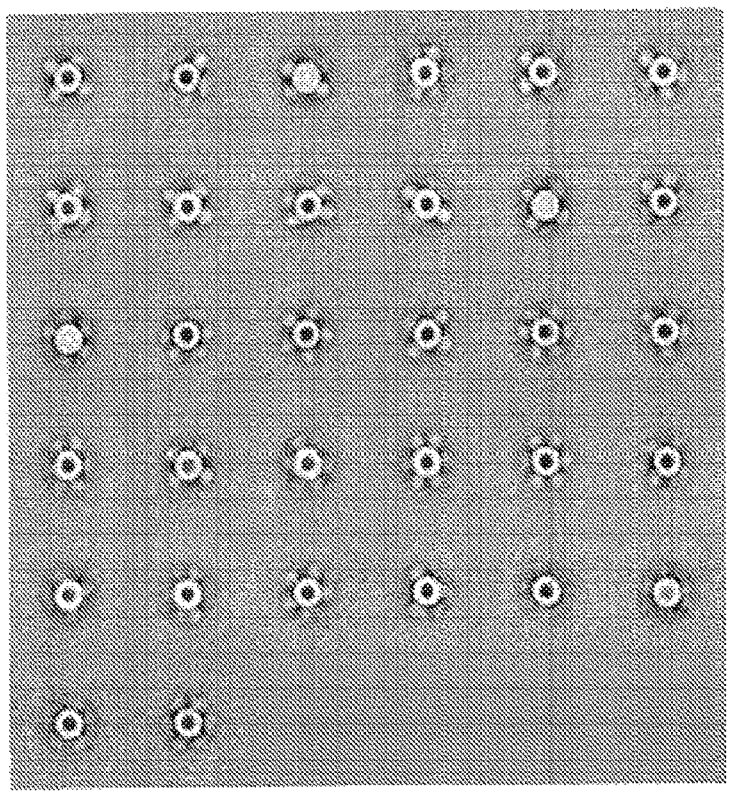

H7-SS-18

H7-SS-20

H7-SS-21   FIG. 25E
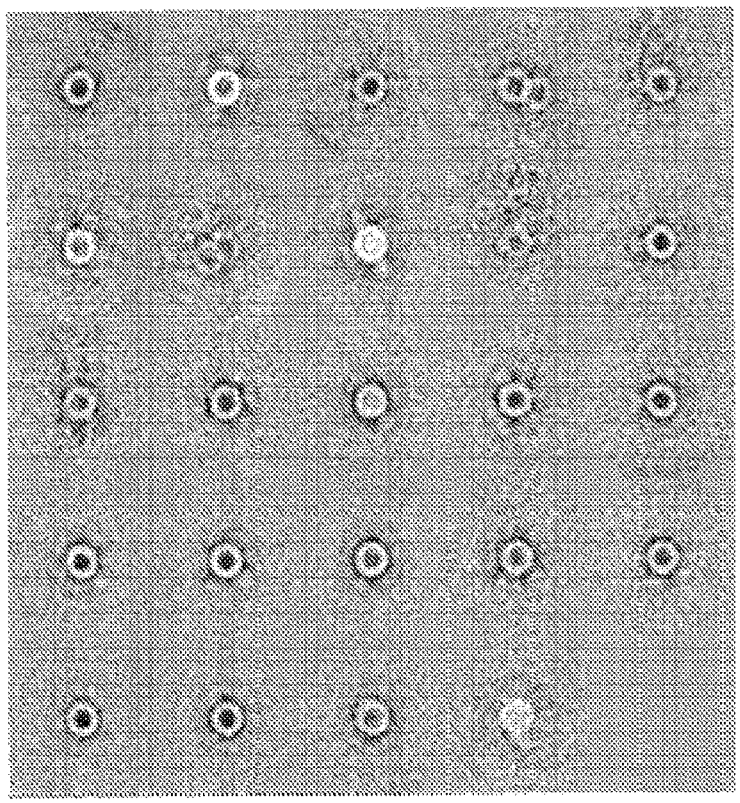
H7-SS-23   FIG. 25F
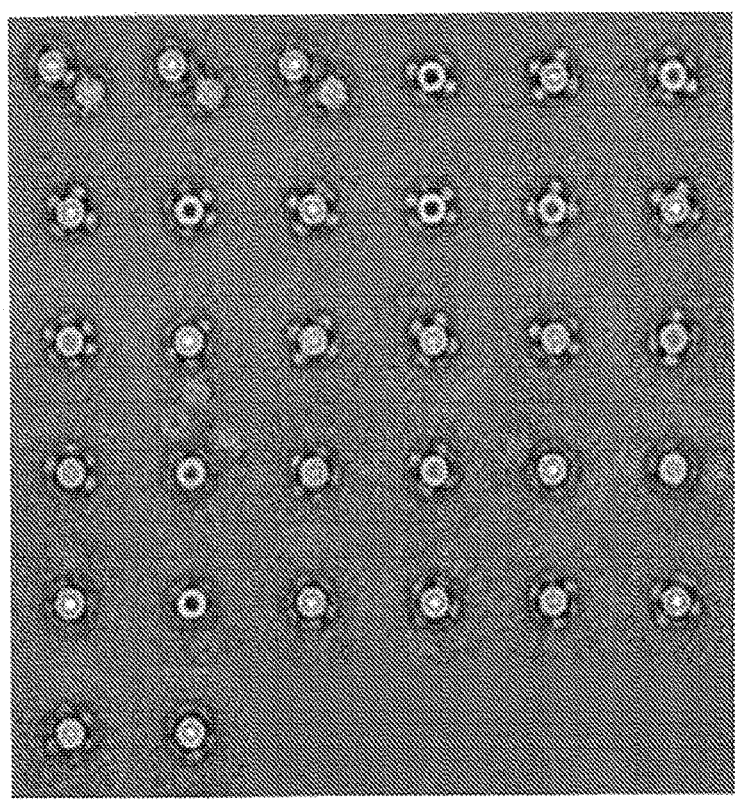

H7-SS-25

H7-SS-26

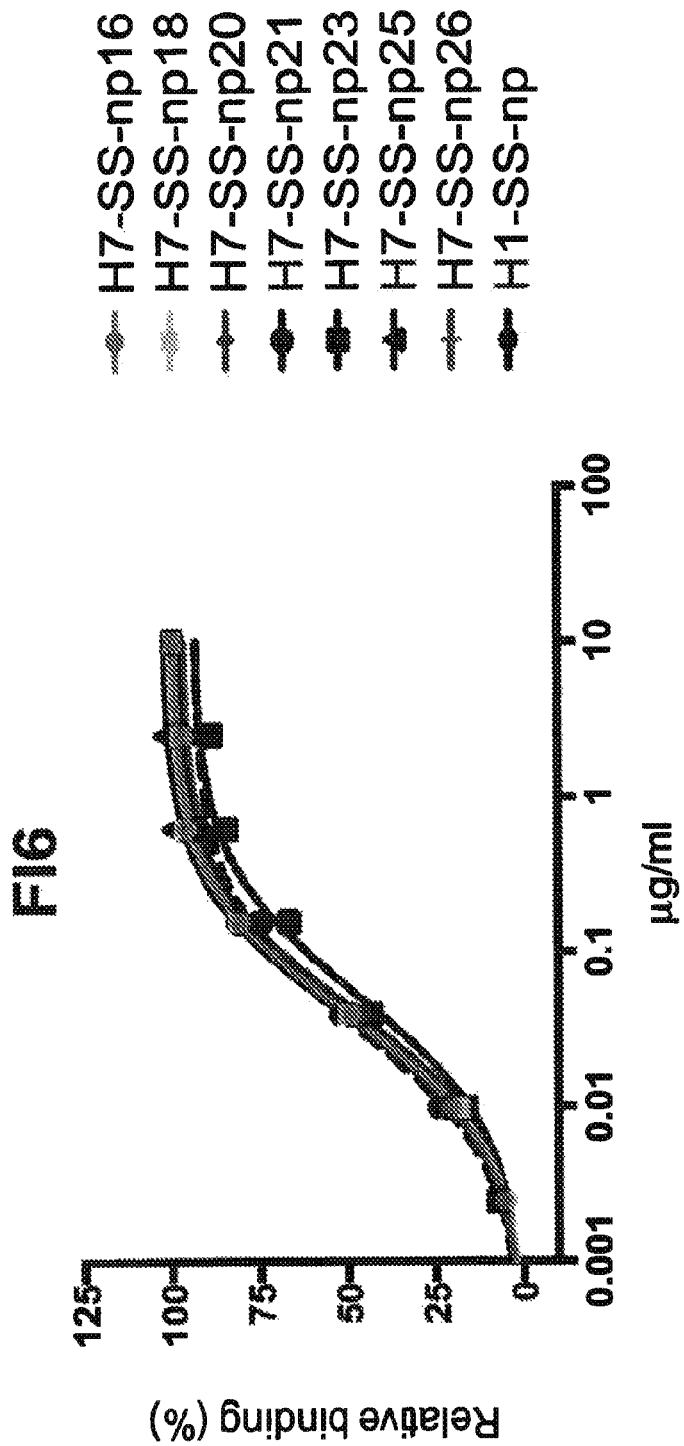

FIG. 26B

| | Antibody $IC_{50}$ (µg/ml) | | |
|---|---|---|---|
| design | FI6 | CT149 | CR8020 |
| H7-SS-np16 | 0.039 | 0.024 | 0.089 |
| H7-SS-np18 | 0.039 | 0.024 | 0.069 |
| H7-SS-np20 | 0.045 | 0.024 | 0.084 |
| H7-SS-np21 | 0.038 | 0.024 | 0.101 |
| H7-SS-np23 | 0.052 | 0.022 | 0.135 |
| H7-SS-np25 | 0.039 | 0.070 | 0.086 |
| H7-SS-np26 | 0.038 | 0.096 | 0.071 |
| H1-SS-np | 0.032 | 0.037 | ND |

Antigen: H1 HA NC99

Antigen: H5 HA VN04

>H10N8-SS-np_02 (H10ssF_2) (SEQ ID NO:103)
MYKIVVIALLGAVKGLDKICLGHHAVANGTIVKTLTNEQEEVTNATELVFPGCVMLATGMRNVPELIQGRGLFGAIAGPLENGWEGMVDGWY
GFRHQNAQGTGQAADYKSTQAAIDQITGMVNRMAIMAQGGPDMQAELLVAMNQHVDMADSEMVIDMADSEMNLYERVRKQLRQNAEEDGKGCFEIYHA
CDDSCMESIRNNTYDHSQYREEALLNRLNINSGGDIKLLNEQVNKEMQSSNLYMSMSSWCYTHSLDGAGLFLFDHAAEEYEHAKLLIFLNEN
NVPVQLTSAPEHKFEGLTQIFQKAYEHEQHISESINNIVDHAIKSKDHATFNFLQWYVAEQHEEVLFKDILDKIELIGNENHGLYLADQYV
KGIAKSRKSGS

>H10N8-SS-np_03 (H10ssF_3) (SEQ ID NO:104)
MYKIVVIALLGAVKGLDKICLGHHAVANGT

Average Core Size: 13.5 ± 0.3 nm
Average Spike Size: 6.5 ± 0.4 nm

Average Core Size: 13.5 ± 0.5 nm
Average Spike Size: 7.1 ± 0.8 nm

Average Core Size: 14.4 ± 0.3 nm
Average Spike Size: 6.6 ± 0.5 nm

Average Core Size: 13.9 ± 0.3 nm
Average Spike Size: 6.4 ± 0.7 nm

Average Core Size: 13.2 ± 0.7 nm
Average Spike Size: 6.8 ± 0.5 nm

FI6
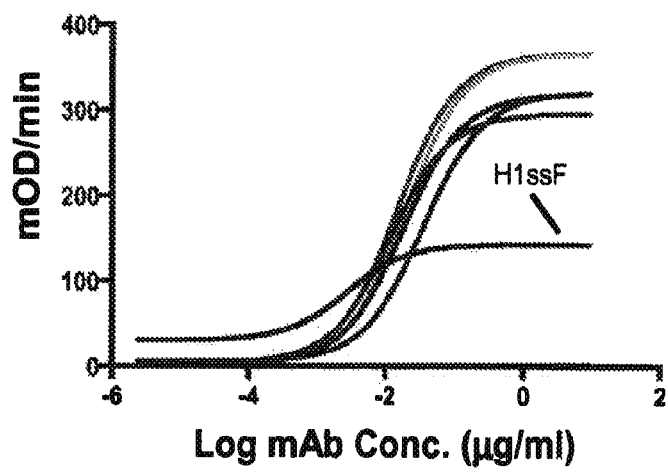
FIG. 34A
CT149
FIG. 34B
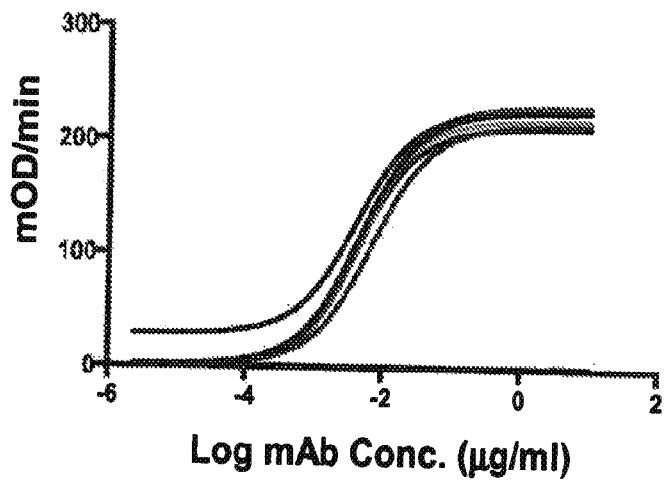

CR8020

| Nanoparticle | Antibody IC$_{50}$ (mg/ml) | | |
|---|---|---|---|
| | FI6 | CT149 | CR8020 |
| Empty | ND | ND | ND |
| H1ssF | 0.002 | 0.004 | ND |
| H7ssF26 | 0.01 | 0.007 | 0.02 |
| H10ssF2 | 0.02 | 0.004 | 0.01 |
| H10ssF3 | 0.02 | 0.004 | 0.01 |
| H10ssF4 | 0.01 | 0.005 | 0.01 |
| H10ssF5 | 0.02 | 0.004 | 0.01 |

ND, not detected

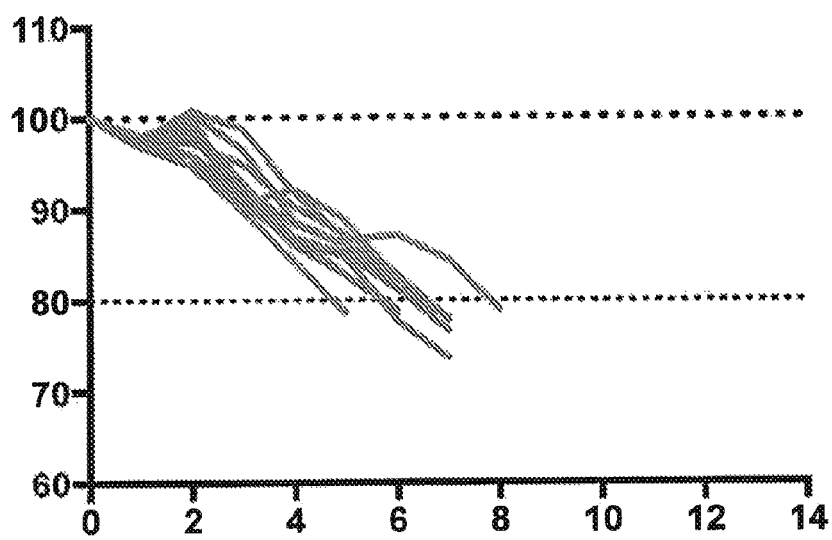
FIG. 36A Empty NP
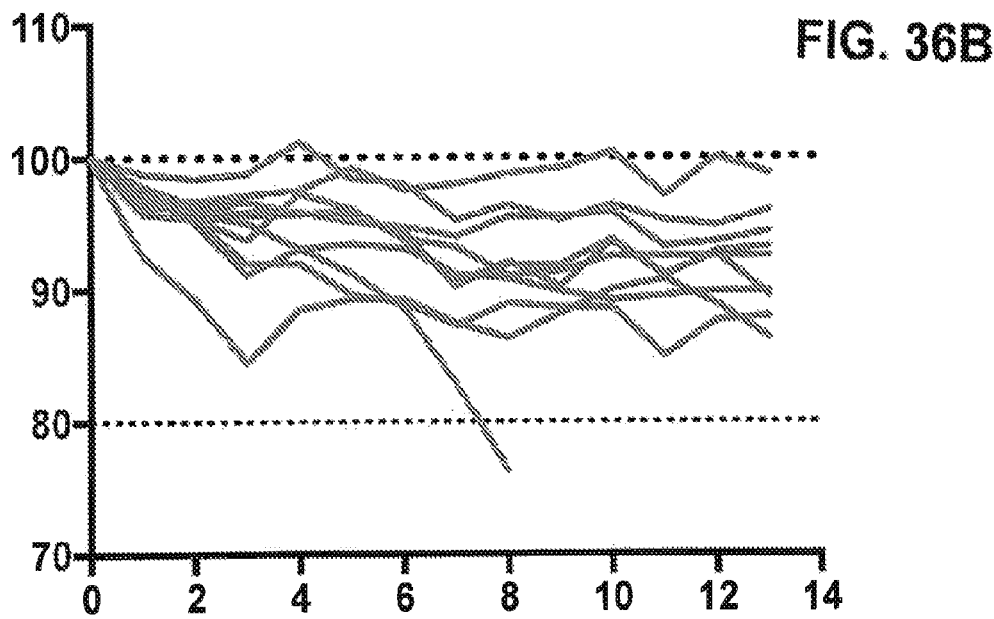
FIG. 36B H10ssF 4

>H3-SS-np_231 SEQ ID NO:46
MKTIIALSYILCLVFAQKLPGNDNSTATLCLGHHAVPNGTIVKTITNDQIEVTNATEIVFPGGCGVKLATGMRNVPEKQTRGIFGAIAGFIENGWEGMVDGWY
GFRHQNSEGIGQAADLKSTQAAINQINGKVNIVALMAQGGPDCIDLTDSEMKLFERTKKQLRENAEDMGNGCFKIYHKCDNACIGSI
RNGTYDHDVYRDEALNNRFQIKSGQDIIKLLNEQVNKEMGSNLYMSMSSWCYTHSLDGAGLFLFDHAAEEYEHAKKLIIFLNENNVPVQLTSISAPEHKF
LTQIFQKAYEHEQHISESINNIVDHAIKSKDHATFNPLQWYAEQHEEEVLFKDIILDKIELIGNENHGLYLADQYVKGIAKSRKSGS

>H3-SS-np_249 SEQ ID N

>H7-SS-np_020 (H7ssF_20)  SEQ ID NO:93
MNTQILVFALIAIIPTNADKICLGHHAVSNGTKVNTLTERGVEVVNATELVFPGCGVKLATGMKNVPEIPKGRGLFGAIAGFIENGWEGLIDGW
YGFRHQNAQGEGTAADYKSTQSAIDQITGMVNALMAQGGPDCAELLVAMNQHMDLADSEMDKLYERVKRQLFEDHAAEEYEHAKKLIFLNE
KCDDDCMASIRNNTYDHSKYREEAMQNRIQIDSGGDIIKLLNEQVNKEMSNLYMSMSSWCYTHSLDGAGLFEDILDKIELIGNERHGLYLADQY
NNVPVQLTSISAPE

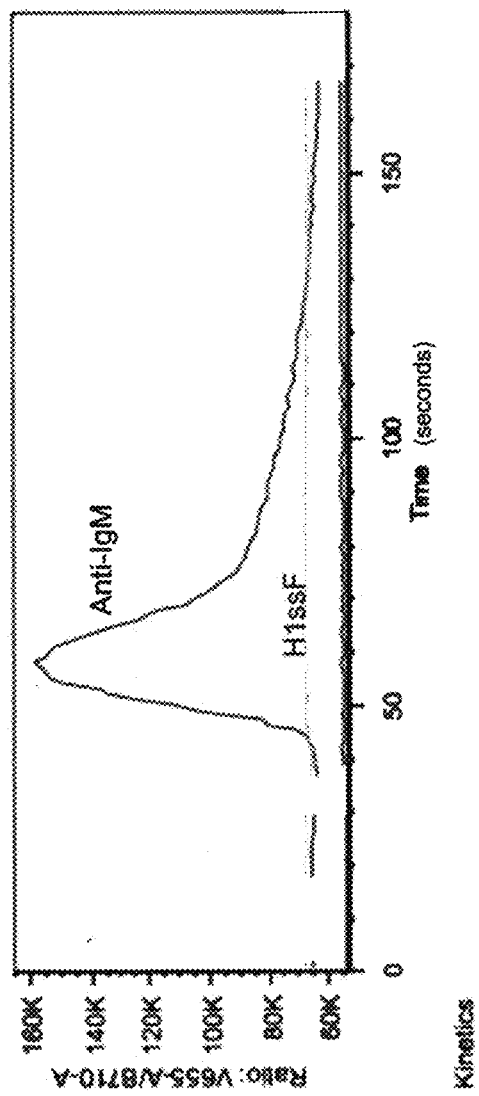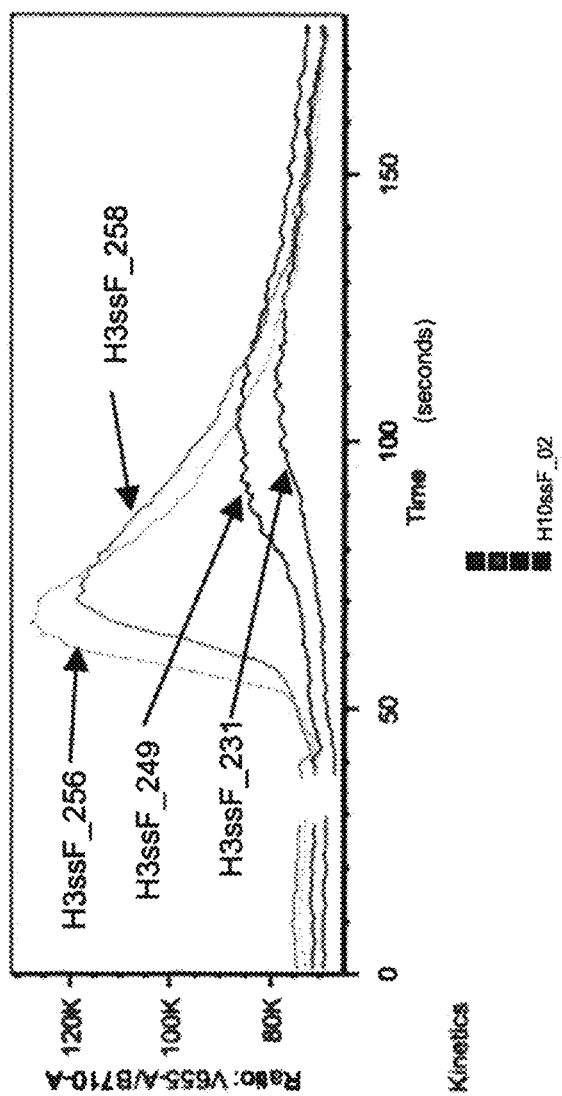

>H3-SS-np_256 (H3ssF_256) SEQ ID NO:48
MKTIIALSYILCLVFAQKLPGNDNSTATLCLGHHAVPNGTIVKTITNDQIEVTNATELVFPGCGVLKLATGMRNVPEKQTRGIFGAIAGFIENGWEGMVDGWY
GFRHQNSEGIGQAADLKSTQAAINQINGMVNRVIELMEQGGPDCYLAELLVALLNQHVIDLTDSEMRKLFERTKKQLRENAEDMGNGCFKIYHKCDNACIGSI
RNGTYDHDVYRDEALNNRFQIK

>H3-SS-np_258 (H3ssF_258) SEQ ID NO:49
MKTIIALSYILCLVFAQKLPGNDNSTATLCLGHHAVPNCTIVKTITNDQIEVTNATELVFPGCGVLKLATGMRCVPEKQTRGIFGAIAGFIENGWEGMVDGWY
GFRHQNSEGIGQAADLKSTQAAINQINGMVNRVIELMEQGGPDCYLAELLVALLNQHVIDLTDSEMRKLFERTKKQLRENAEDMGNGCFKIYHKCDNACIGSI
RNGTYDHDVYRDEALNNRFQIK

>H7-SS-np_026 (H7ssF_26) SEQ ID NO:97
MNTQILVFALIAIIPTNADKICLGHHAVSNGTKVNTLTERGVEVVNATELVFPGCGVLKLATGMKNVPEIPKGRGLFGAIAGFIENGWEGLIDGWY
GFRHQNAQGEGTAADYKSTQSAIDQITGMVNRVIELMEQGGPDCYLAELLVAMLNQHVIDLADSEMDKLYERVKRQLRENAEEDGTGCFEIFHKCD
DDCMASIRNNTYDHSKYREEAMQNRIQID

>H10N8-SS-np_02 (H10ssF_2) (SEQ ID NO:103)
MYKIVVIIALLGAVKGLDKICLGHHAVANGTIVKTLTNEQEEVTNATELVFPGCVIMLATGMRNVPELIQGRGLFGAIAGFLENGWEGMVDGWY
GFRHQNAQGTGQAADYKSTQAAIDQITGMVNRVVALMAQGGPDCYLAELLVAMLNQHVIDMADSEMRNLYERVRKQLRQNAEEDGKGCFEIYHA
CDDSCMESIRNNTYDHSQYREEALLNRLNIN

>H10N8-SS-np_03 (H10ssF_3) (SEQ ID NO:104)
MYKIVVIIALLGAVKGLDKICLGHHAVANGTIVKTLTNEQEEVTNATELVFPCGVLMLATGMRNVPELIQGRGLFGAIAGFLENGWEGMVDGWY
GFRHQNAQGTGQAADYKSTQAAIDQITGMVNRVVALMAQGGPDCYLAELLVAMLNQHVIDMADSEMRNLYERVRKQLRQNAEEDGKGCFEIYHA
CDDSCMESIRNNTYDHSQYREEALLNRLNIN

>H10N8-SS-np_04 (H10ssF_4) (SEQ ID NO:105)
MYKIVVIIALLGAVKGLDKICLGHHAVANGTIVKTLTNEQEEVTNATELVFPGCGVLMLATGMRNVPELIQGRGLFGAIAGFLENGWEGMVDGWY
GFRHQNAQGTGQAADYKSTQAAIDQITGMVNRVVELMEQGGPDCYLAELLVAMLNQHVIDMADSEMRNLYERVRKQLRQNAEEDGKGCFEIYHAC
DDSCMESIRNNTYDHSQYREEALLNRLNIN

FIG. 41

STABILIZED GROUP 2 INFLUENZA HEMAGGLUTININ STEM REGION TRIMERS AND USES THEREOF

CROSS REFERENCE TO RELATED APPLICATION

This application is a national stage application under 35 U.S.C. 371 of PCT Application No. PCT/US2017/049894 having an international filing date of Sep. 1, 2017, which designated the United States, which PCT application claimed the benefit of U.S. Provisional Patent Application Ser. No. 62/383,267 filed on Sep. 2, 2016, the disclosures of each of which are incorporated herein by reference in their entireties.

REFERENCE TO SEQUENCE LISTING

This application contains a Sequence Listing submitted as an electronic text file named "Sequence_Listing_ST25.txt", having a size in bytes of 452 KB, and created on May 18, 2021. The information contained in this electronic file is hereby incorporated by reference in its entirety pursuant to 37 CFR § 1.52(e)(5).

BACKGROUND

Protective immune responses induced by vaccination against influenza viruses are primarily directed to the viral HA protein, which is a glycoprotein on the surface of the virus responsible for interaction of the virus with host cell receptors. HA proteins on the virus surface are trimers of HA protein monomers that are enzymatically cleaved to yield amino-terminal HA1 and carboxyl-terminal HA2 polypeptides. The globular head consists exclusively of the major portion of the HA1 polypeptide, whereas the stem that anchors the HA protein into the viral lipid envelope is comprised of HA2 and part of HA1. The globular head of a HA protein includes two domains: the receptor binding domain (RBD), an ~148-amino acid residue domain that includes the sialic acid-binding site, and the vestigial esterase domain, a smaller ~75-amino acid residue region just below the RBD. The globular head includes several antigenic sites that include immunodominant epitopes. Examples include the Sa, Sb, $Ca_1$, $Ca_2$ and Cb antigenic sites (see, for example, Caton, et al, 1982, Cell 31, 417-427). The RBD-A region includes the Sa antigenic site and part of the Sb antigenic site.

Antibodies against influenza often target variable antigenic sites in the globular head of HA, which surround a conserved sialic acid binding site, and thus, neutralize only antigenically closely related viruses. The variability of the HA head is due to the constant antigenic drift of influenza viruses and is responsible for seasonal endemics of influenza. In contrast, the HA stem is highly conserved and experiences little antigenic drift. Unfortunately, unlike the immunodominant head, the conserved HA stem is not very immunogenic. Furthermore, gene segments of the viral genome can undergo reassortment (antigenic shift) in host species, creating new viruses with altered antigenicity that are capable of becoming pandemics [Salomon, R. et al. *Cell* 136, 402-410 (2009)]. Until now, each year, influenza vaccine is updated to reflect the predicted HA and neuraminidase (NA) for upcoming circulating viruses.

Recently, an entirely new class of broadly neutralizing antibodies against influenza viruses was isolated that recognize the highly conserved HA stem [Corti, D. et al. *J Clin Invest* 120, 1663-1673 (2010); Ekiert, D. C. et al. *Science* 324, 246-251 (2009); Kashyap, A. K. et al. *Proc Natl Acad Sci USA* 105, 5986-5991 (2008); Okuno, Y. et al. *J Virol* 67, 2552-2558 (1993); Sui, J. et al. *Nat Struct Mol Biol* 16, 265-273 (2009); Ekiert, D. C. et al. *Science* 333, 843-850 (2011); Corti, D. et al. *Science* 333, 850-856 (2011)]. Unlike strain-specific antibodies, those antibodies are capable of neutralizing multiple antigenically distinct viruses, and hence inducing such antibodies has been a focus of next generation universal vaccine development [Nabel, G. J. et al. *Nat Med* 16, 1389-1391 (2010)]. However, robustly eliciting these antibodies with such heterologous neutralizing profile by vaccination has been difficult [Steel, J. et al. *M Bio* 1, e0018 (2010); Wang, T. T. et al. *PLoS Pathog* 6, e1000796 (2010); Wei, C. J. et al. *Science* 329, 1060-1064 (2010)]. Removal of the immunodominant head region of HA (which contains competing epitopes) and stabilization of the resulting stem domain through genetic manipulation is one potential way to improve the elicitation of these broadly neutralizing stem antibodies.

Current vaccine strategies for influenza use either a chemically inactivated or a live attenuated influenza virus. Both vaccines are generally produced in embryonated eggs which present major manufacturing limitations due to the time consuming process and limited production capacity. Another more critical limitation of current vaccines is its highly strain-specific efficacy. These challenges became glaring obvious during emergence of the 2009 H1N1 pandemic, thus validating the necessity for new vaccine platforms capable of overcoming these limitations. Virus-like particles represent one of such alternative approaches and are currently being evaluated in clinical trials [Roldao, A. et al. *Expert Rev Vaccines* 9, 1149-1176 (2010); Sheridan, C. *Nat Biotechnol* 27, 489-491 (2009)]. Instead of embryonated eggs, VLPs that often comprise HA, NA and matrix protein 1 (M1) can be mass-produced in mammalian or insect cell expression systems [Haynes, J. R. *Expert Rev Vaccines* 8, 435-445 (2009)]. The advantages of this approach are its particulate, multivalent nature and the authentic display of properly folded, trimeric HA spikes that faithfully mimic the infectious virion. In contrast, by the nature of its assembly, the enveloped VLPs contain a small but finite host cell component that may present potential safety, immunogenicity challenges following repeated use of this platform [Wu, C. Y. et al. *PLoS One* 5, e9784 (2010)]. Moreover, the immunity induced by the VLPs is essentially the same as current vaccines, and thus, will not likely significantly improve both potency and breadth of vaccine-induced protective immunity. In addition to VLPs, a recombinant HA protein has also been evaluated in humans [Treanor, J. J. et al. *Vaccine* 19, 1732-1737 (2001); Treanor, J. J. *JAMA* 297, 1577-1582 (2007)], though the ability to induce protective neutralizing antibody titers are limited. The recombinant HA proteins used in those trials were produced in insect cells and might not form native trimer preferentially [Stevens, J. *Science* 303, 1866-1870 (2004)].

Despite several alternatives to conventional influenza vaccines, advances in biotechnology in past decades have allowed engineering of biological materials to be exploited for the generation of novel vaccine platforms. Ferritin, an iron storage protein found in almost all living organisms, is an example which has been extensively studied and engineered for a number of potential biochemical/biomedical purposes [Iwahori, K. U.S. Patent 2009/0233377 (2009); Meldrum, F. C. et al. *Science* 257, 522-523 (1992); Naitou, M. et al. U.S. Patent 2011/0038025 (2011); Yamashita, I. *Biochim Biophys Acta* 1800, 846-857 (2010)], including a potential vaccine platform for displaying exogenous epitope peptides [Carter, D. C. et al. U.S. Patent 2006/0251679 (2006); Li, C. Q. et al. *Industrial Biotechnol* 2, 143-147 (2006)]. Its use as a vaccine platform is particularly interesting because of its self-assembly and multivalent presentation of antigen which induces stronger B cell responses than monovalent form as well as induce T-cell independent antibody responses [Bachmann, M. F. et al. *Annu Rev Immunol* 15, 235-270 (1997); Dintzis, H. M. et al. *Proc Natl Acad Sci USA* 73, 3671-3675 (1976)]. Further, the molecular architecture of ferritin, which consists of 24 subunits assembling into an octahedral cage with 432 symmetry has the potential to display multimeric antigens on its surface.

Previous work has shown that the stem regions of Group 1 hemagglutinin proteins could be modified to form to a stabilized HA stem protein, the conformation of which is very similar to the pre-fusion conformation of full-length, wild-type (wt) influenza hemagglutinin protein. Additionally, when such modified stabilized stem (SS) HA proteins were joined to a monomeric subunit protein, such as ferritin, the resulting fusion protein formed nanoparticles, the surfaces of which displayed trimers of the SS-HA protein. Moreover, such nanoparticles were able to elicit an immune response Group 1 influenza viruses, indicating that the SS-HA protein trimers displayed by the nanoparticles had conformation similar to that of wt influenza HA protein. Such constructs are disclosed in International Patent Application No. PCT/US2015/032695, the content of which are incorporated herein in their entirety by reference. However, the antibodies elicited by the aforementioned nanoparticles were more protective against Group 1 influenza viruses than they were against Group 2 influenza viruses.

Thus, there remains a need for an efficacious influenza vaccine that provides robust protection against Group 2 influenza viruses. Further, there also remains a need for an influenza vaccine that protects individuals from heterologous strains of influenza virus, including evolving seasonal and pandemic influenza virus strains of the future. The present invention meets this need by providing a novel nanoparticle-based vaccine consisting of a novel Group 2 HA stabilized stem (SS) lacking the variable immunodominant head region, fused to the surface of nanoparticles, resulting in an influenza vaccine that is easily manufactured, potent, and elicits antibodies that are broadly heterosubtypic protective.

SUMMARY OF THE INVENTION

Accordingly, this disclosure provides recombinant proteins comprising a Group 2 influenza hemagglutinin (HA) protein, wherein the amino acid sequence of the head region is replaced with a linker comprising less than 5 contiguous amino acids from the head region of an influenza HA protein. Following administration of these recombinant proteins to a mammal, these recombinant proteins elicit an immune response to a Group 2 influenza HA protein in the mammal.

The recombinant proteins may comprise a first amino acid sequence from the stem region of a Group 2 influenza virus hemagglutinin (HA) protein, and a second amino acid sequence from the stem region of a Group 2 influenza virus hemagglutinin (HA) protein, wherein the first and second amino acid sequences are covalently joined by the linker sequence, and wherein the first amino acid sequence comprises at least 20 contiguous amino acid residues from the amino acid sequence upstream of the amino-terminal end of the head region sequence, and wherein the second amino acid sequence comprises at least 20 contiguous amino acid residues from the amino acid sequence downstream of the carboxyl-terminal end of the head region sequence. In this recombinant protein construct, the first amino acid sequence may comprise at least 20 contiguous amino acids from the upstream polypeptide sequence immediately adjacent to the amino terminal end of the head region. Alternatively or additionally, the first amino acid sequence may comprise at least 20 contiguous amino acids from SEQ ID NO:27, SEQ ID NO: 28 or SEQ ID NO: 29. Alternatively or additionally, the second amino acid sequence may comprise at least 20 contiguous amino acids from the downstream polypeptide sequence immediately adjacent to the carboxyl-terminal end of the head region. Alternatively or additionally, the first amino acid sequence may comprise at least 20 contiguous amino acids from SEQ ID NO: 31, SEQ ID NO:32 or SEQ ID NO:33.

The recombinant proteins may comprise an amino-terminal end of helix C (i.e., the membrane distal end of helix C) that is joined to the head region sequence modified to contain a first cysteine amino acid, and a linker sequence comprising a second cysteine amino acid such that the first and second cysteine form a disulfide bond.

The recombinant proteins may comprise an inter-helix region (i.e., the amino acid sequence connecting the N-terminal end of helix C to the carboxyl-terminal end of helix A (i.e., the membrane distal end of helix A)) that is modified so that the three-dimensional structure of the recombinant HA stem protein approximates the three-dimensional structure of the HA stem region in a native Group 2 HA protein. The recombinant proteins may comprise an amino acid linker sequence that is less than eight amino acids in length, and replaces the inter-helix region.

The recombinant proteins may comprise a membrane distal end of helix A that is extended by the addition of amino acids.

The recombinant proteins may comprise a third amino acid linker that is joined to the carboxyl-terminus of the amino acid sequence forming helix A and forms a helix that extends the length of helix A. The distal end of helix C may be linked to the carboxyl end of the third linker by the linker peptide. The linker peptide is preferably less than eight amino acids in length.

These recombinant proteins may comprise one or more mutations that increase the stability of the protein. These stabilizing mutations are preferably located in the amino acid sequences forming at least one of helix A and helix C.

These recombinant proteins may be joined to a monomeric subunit from ferritin or lumazine synthase.

Exemplary recombinant proteins of this disclosure may comprise an amino acid sequence that is at least 80% identical, or at least 85% identical, or at least 90% identical, or at least 95% identical, or at least 97% identical, or at least 99% identical to an amino acid sequence selected from the group consisting of SEQ ID NOs: 47-159.

Exemplary recombinant proteins of this disclosure may comprise an amino acid sequence selected from the group consisting of SEQ ID NOs: 47-159.

This disclosure also provides a nanoparticle comprising at least one recombinant protein of this disclosure.

This disclosure also provides immunogenic compositions comprising at least one protein that comprises an amino acid sequence at least 95% identical to these recombinant proteins. These immunogenic compositions may comprise a protein comprising an amino acid sequence selected from the group consisting of SEQ ID NOs: SEQ ID NOs: 47-1598. These immunogenic compositions may comprise a protein consisting of an amino acid sequence selected from the group consisting of SEQ ID NOs:47-159. Thus, this disclosure also provides vaccine compositions comprising these immunogenic compositions, and an adjuvant.

This disclosure also provides methods of preventing or reducing the pathological effects of an influenza virus infection in a human comprising administering to a human in need thereof an immunologically effective dose of a vaccine composition of this disclosure.

Also provided are nucleic acids encoding the recombinant proteins of this disclosure. Preferably, the nucleic acid is DNA. Also provided are vectors comprising these nucleic acids. Also provided are host cells comprising these vectors. These host cells may be bacterial cells, yeast cells, or mammalian cells. These host cells may be inactivated.

This disclosure also provides pharmaceutical compositions comprising the recombinant proteins of this disclosure. Similarly, these compositions may be a vaccine comprising the recombinant proteins of this disclosure, in combination with a physiologically acceptable carrier.

This disclosure also provides methods of vaccination, comprising administering a prophylactically or therapeutically effective amount of a recombinant protein of this disclosure to a subject.

This disclosure also provides a method of treatment of an influenza-associated disease, comprising administering a prophylactically or therapeutically effective amount of a recombinant protein of this disclosure to a subject in need thereof. Preferably, the subject is a human.

BRIEF DESCRIPTION OF THE FIGURES

FIGS. 1A-1C provide a summary of prior art. FIG. 1A is a ribbon diagram depicting the design of full length HA-ferritin nanoparticles. FIG. 1B is a ribbon diagram depicting the design of HA stem-ferritin nanoparticles stabilized by a HIV gp41 trimerization domain. Both designs are described in detail in patent application PCT/US12/56822, which is incorporated herein by reference. FIG. 1C is a ribbon diagram depicting the design of group 1 HA stabilized stem nanoparticles disclosed in PCT patent application No. PCT/US15/32695, which is incorporated herein by reference.

FIG. 3A is a ribbon diagram depicting a model of a group 2 H3N2 stabilized HA stem trimer based on PDB ID 2YP2 . . . . Regions of mutations in the helices are shown in dark gray. FIG. 3B shows the sequence of H3 design #231 (SEQ ID NO: 47; based on the HA stem of A/Denmark35/2005 H3N2, GenBank ABU92694). Mutations made to the sequence are boxed. For reference, the C-terminal SGG linker is bolded, the C-terminal ferritin is underlined and a Asn to Gln ferritin mutation to remove an N-linked glycan is bolded.

FIGS. 4A-4D show mutations in H3N2 design 231 in the loop that replaces the HA1 head. FIG. 4A shows a ribbon diagram depicting a model of a group 2 H3N2 stabilized HA stem trimer based on PDB ID 2YP2. The seven mutations in the loop that replaces the HA1 head region, and the additional cysteine in helix C that forms a disulfide with the aforementioned loop are indicated. All other mutations in the helix regions are shown in dark grey. FIG. 4B depicts the mutated loop (indicated as replacing the head region in FIG. 4A) with side chains represented by stick models. FIG. 4C shows variants of the loop sequence. The sequences are TELVFPGCGVLKL (residues 56-68 of SEQ ID NO: 47), TELVFPGCVLKL (residues 56-67 of SEQ ID NO: 51), TELVFPCGVLKL (residues 56-67 of SEQ ID NO: 52), TELVFPNCGVLKL (residues 56-68 of SEQ ID NO: 71), and TELCFNGICLKL (residues 56-67 of SEQ ID NO: 48). FIG. 4D shows the sequence of H3 design #231 (SEQ ID NO: 47). The mutations in the head and helix regions, which are illustrated in FIGS. 4A-4C, are boxed. For reference, the C-terminal SGG linker is bolded, the C-terminal ferritin is underlined and a Asn to Gln ferritin mutation to remove an N-linked glycan is bolded.

FIGS. 5A-5C show mutations in H3N2, design 231, in the loop that connects HA2 helices A and C. FIG. 5A is a ribbon diagram depicting a model of a group 2 H3N2 stabilized HA stem trimer based on PDB ID 2YP2. The four residues that connect HA2 helices A and C are indicated. Mutations in the helices are in dark grey. FIG. 5B shows a close-up of the loop (indicated region in FIG. 5A) with side chains represented by stick models. FIG. 5C shows the sequence of H3 design #231 (SEQ ID NO: 47). The mutations in the helices, and the amino acids making up the short linker, which are illustrated in FIGS. 5A and 5B, are boxed. For reference, the C-terminal SGG linker is bolded, the C-terminal ferritin is underlined and a Asn to Gln ferritin mutation to remove an N-linked glycan is bolded.

FIG. 6A shows a ribbon diagram depicting a model of a group 2 H3N2 stabilized HA stem trimer based on PDB ID 2YP2. The five-residue extension of helix A is indicated. Mutations in the helices are in dark grey. FIG. 6B shows a close-up of the helical extension (also indicated in FIG. 6A) with side chains represented by stick models. FIG. 6C shows the sequence of H3 design #231 (SEQ ID NO: 47). Mutations in the helices, and the acids making up the five residue extension, are boxed. For reference, the C-terminal SGG linker is bolded, the C-terminal ferritin is underlined and a Asn to Gln ferritin mutation to remove an N-linked glycan is bolded.

FIGS. 7A and 7B show cavity-filling mutations in H3N2 design 231. FIG. 7A shows a ribbon diagram depicting a model of a group 2 H3N2 stabilized HA stem trimer based on PDB ID 2YP2. The seven cavity-filling mutations are in dark grey with side chains represented by stick models. FIG. 7B shows the sequence of H3 design #231 (SEQ ID NO: 47). Mutations to the helices and head region are boxed. For reference, the C-terminal SGG linker is bolded, the C-terminal ferritin is underlined and a Asn to Gln ferritin mutation to remove an N-linked glycan is bolded.

FIG. 8A shows a gel filtration elution profile for H3-SS-np_231 with a single peak at the expected elution volume. The expression yield for H3-SS-np_231 from Expi293 cells after gel filtration was 7.7 mg/L. FIG. 8B shows negative stain electron microscopy 2D class averages of H3-SS-np_231 revealing the formation of particles with a visible arrangement of HA stems projecting from hollow spheres.

FIG. 9A lists the $EC_{50}$ values from a kinetic ELISA H3-SS-np_231 recognition assay by three HA stem antibodies. The values for the recognition of H1-SS-np are also shown as a control. In both cases the nanoparticle was immobilized on the plate. FIG. 9B shows biolayer interferometry (BLI, from Octet) binding curves for CT149 recognition of H3-SS-np_231 (upper panel) and BLI kinetic constants for HA stem antibodies CT149 and CR9114 (lower panel).

FIGS. 11A-11F show electron microscopy of H3-SS-np nanoparticles variants. Negative stain electron microscopy 2D class averages of H3-SS-np variants revealing the formation of particles with a visible arrangement of HA stems projecting from hollow spheres. Images for the H3-SS-np_231 particle (upper left panel) are shown as a positive control.

FIGS. 12A-12C show the kinetic ELISA curves for FI6 (FIG. 12A), CT149 (FIG. 12B), and CR8020 (FIG. 12C) recognition of H3-SS-np_231 variants 249, 256, 258, 262 and 264. FIG.

Figure 26B:
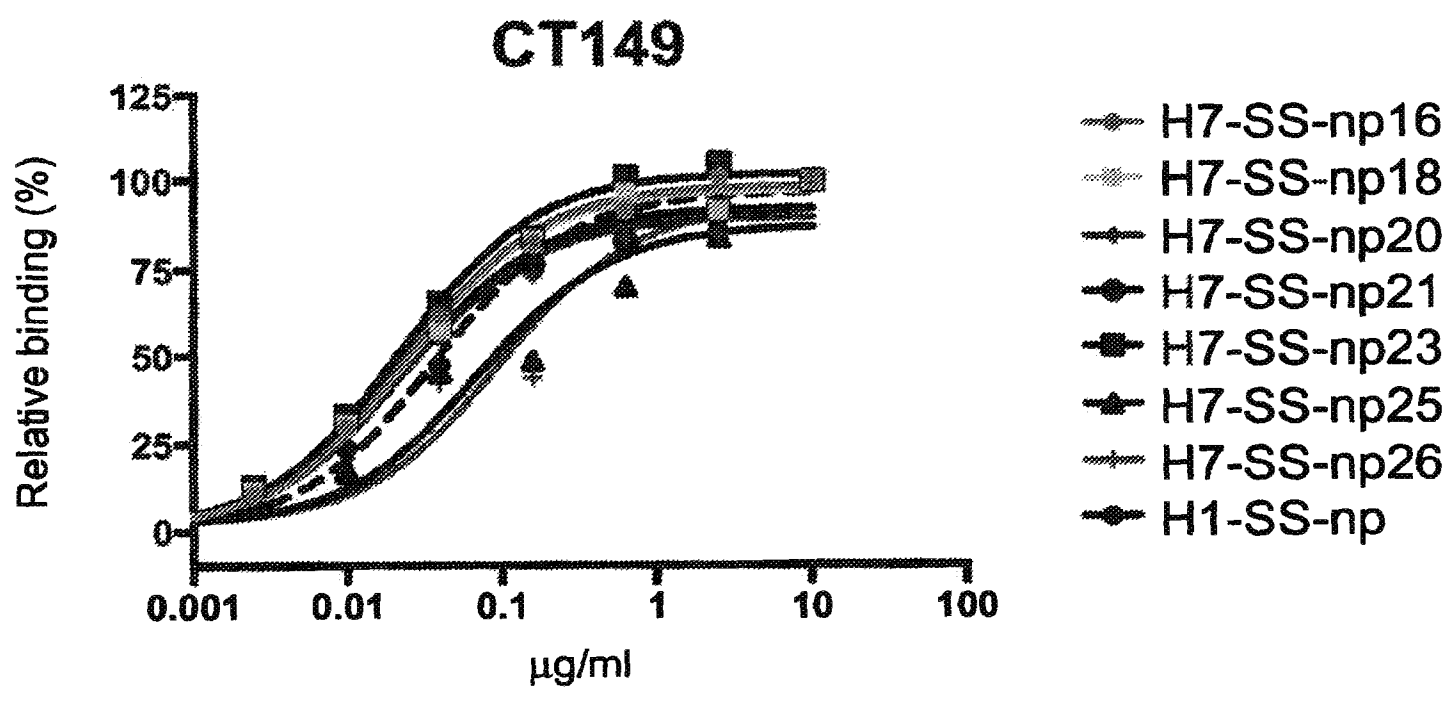

FIGS. 26A-26D show kinetic ELISA results for variants of H7-SS-np. FIGS. 26A-26C show the kinetic ELISA curves for FI6 (FIG. 26A), CT149 (FIG. 26B) and CR8020 (FIG. 26C) recognition of H7-SS-np variants 16, 18, 20, 21, 23, 25, 26 and an H1-SS-np positive control. FIG. 26D lists the $EC_{50}$ values from the curves in FIGS. 26A-26C shown. ND, not determined.

Figures 30A, 30B:
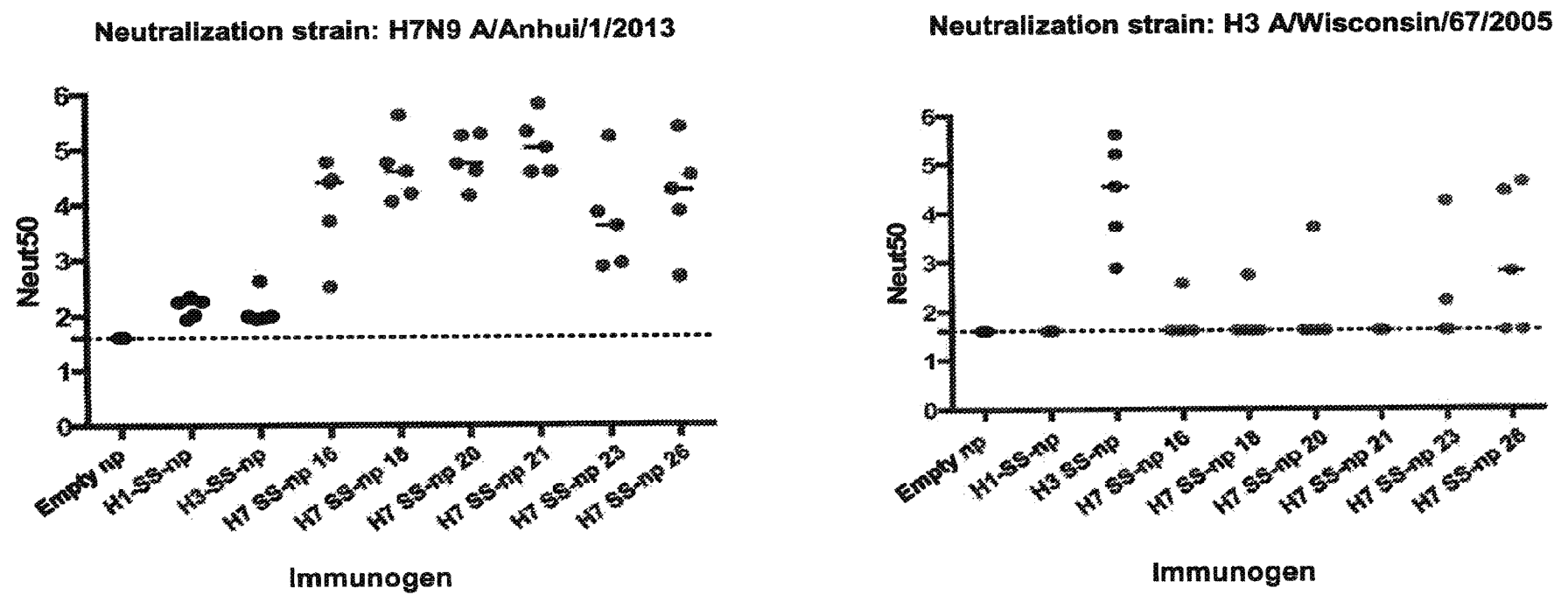

FIGS. 30A and 30B show neutralizing sera responses of H7-SS-np-immunized mice to H3N2 and H7N9. Pseudovirus neutralization titers of sera from BALB/c mice (n=5) immunized 3× with six different versions of SAS-adjuvanted H7-SS-np. FIG. 30A shows neutralization to A/Anhui/1/2013 (H7N9). FIG. 30B shows neutralization of A/Wisconsin/67/2005 (H3N2). Sera from mice immunized with empty ferritin nanoparticle, H1-SS-np and H3-SS-np (#231) serve as controls. Geometric mean titers are shown by horizontal lines. Horizontal dotted lines indicate the baseline titer of 50.

FIG. 31 shows the sequence of four different examples of protein constructs of the invention, based on the sequence of the influenza subtype 10 HA (H10) protein. Mutations made to the influenza HA sequences are boxed. For reference, the C-terminal SGG linker is bolded, and the C-terminal ferritin sequence is underlined.

FIGS. 34A-34D show kinetic ELISA results for H10ssF variants 2-5. FIGS. A-C. show ELISA curves. FIG. D. shows IC50 values calculated from the curves. Supernatants from HEK293T cells expressing design immunogens were plated and detected by above antibodies

FIGS. 36A-36D show the responses of H10ssF-immunized mice to a lethal H3N2 challenge. FIGS. 36A-C. shows weight loss curves for BALB/c mice (n=10) immunized with empty nanoparticles (FIG. 36A), H10ssF_4 (FIG. 36B), or H10ssF_5 (FIG. 36C), and then challenged with a lethal dose of A/Philippines/1982 (H3N2) influenza. FIG. 36D. shows survival curves for the same mice as in A. Mice immunized with ferritin nanoparticle alone (empty np) serve as a negative control.

FIG. 37A. shows survival curves for H10ssF-immunized BALB/c mice (n=10) challenged with a lethal dose of A/Shanghai/2/2013-like (H7N9) influenza. Mice immunized with ferritin nanoparticle alone (empty np) serve as a negative control. FIG. 37B shows weight loss six days post challenge for the same mice as in FIG. 37A. FIGS. 37C-G show weight loss over 12 days post challenge for the same mice as in FIGS. 37A & 3B7.

FIG. 38 shows the sequence of four different examples of protein constructs of the invention, based on the sequence of the influenza subtype 3 HA (H3) protein. Mutations made to the influenza HA sequences are boxed. For reference, the C-terminal SGG linker is bolded, and the C-terminal ferritin sequence is underlined. Also, a Asn to Gln ferritin mutation that removes an N-linked glycan is boxed and bolded.

FIG. 39 shows the sequence of four different examples of protein constructs of the invention, based on the sequence of the influenza subtype 7 HA (H7) protein. Mutations made to the influenza HA sequences are boxed. For reference, the C-terminal SGG linker is bolded, and the C-terminal ferritin sequence is underlined. Also, a Asn to Gln ferritin mutation that removes an N-linked glycan is boxed and bolded.

FIG. 41 shows the sequence of HA portion of protein constructs that exhibited activity in the B-cell activation assay illustrated in FIGS. 40A-C. Mutations made to the influenza HA sequences are boxed.

DETAILED DESCRIPTION OF THE INVENTION

Figure 1A:
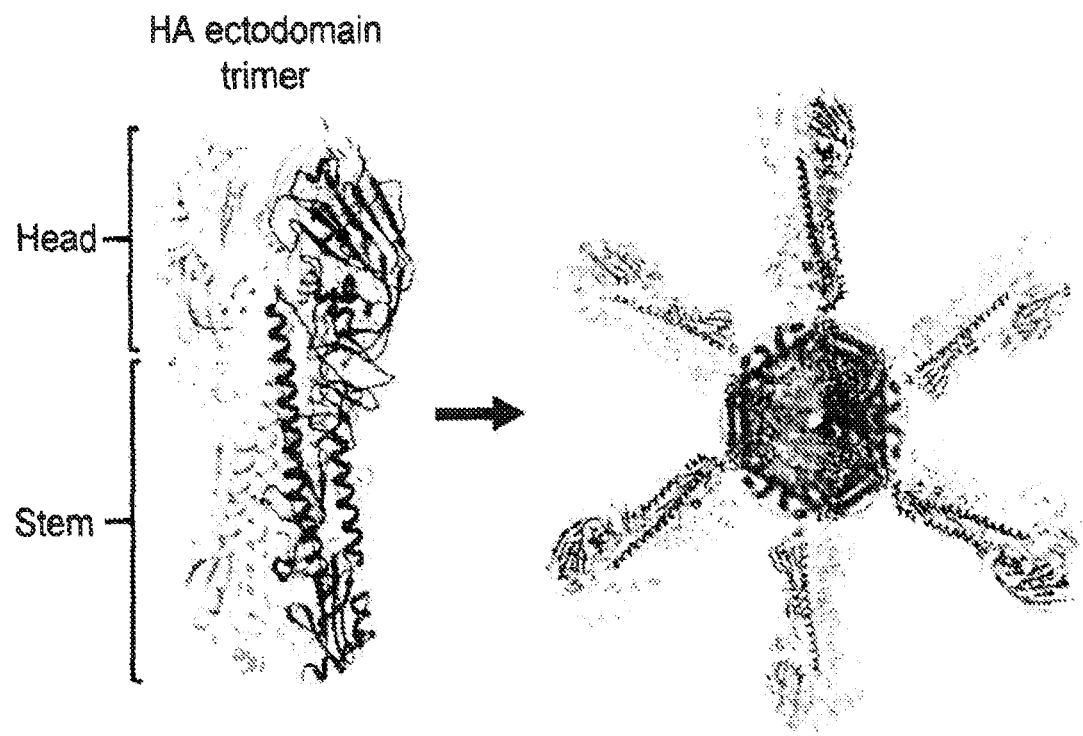
Figure 1B:
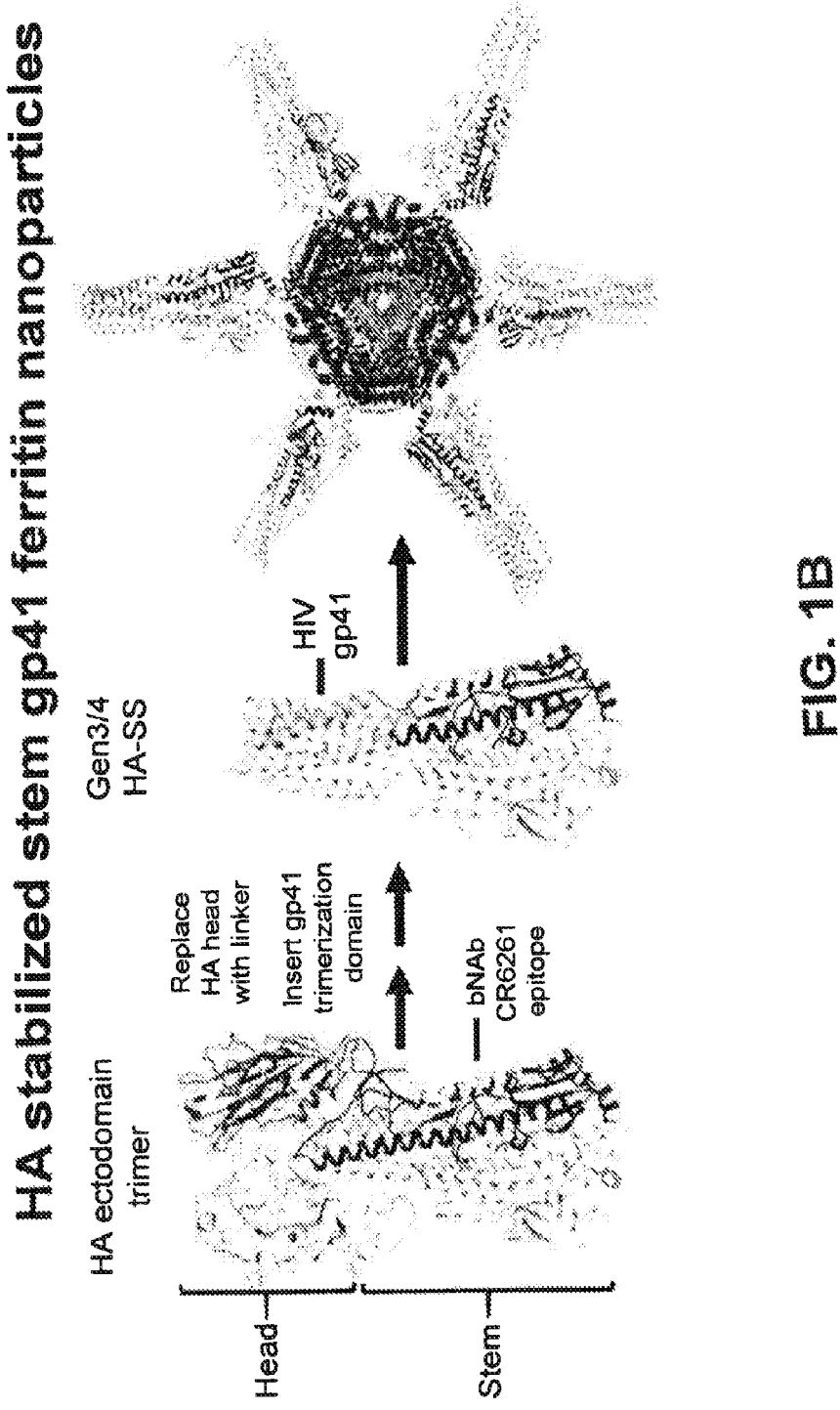
Figure 2:
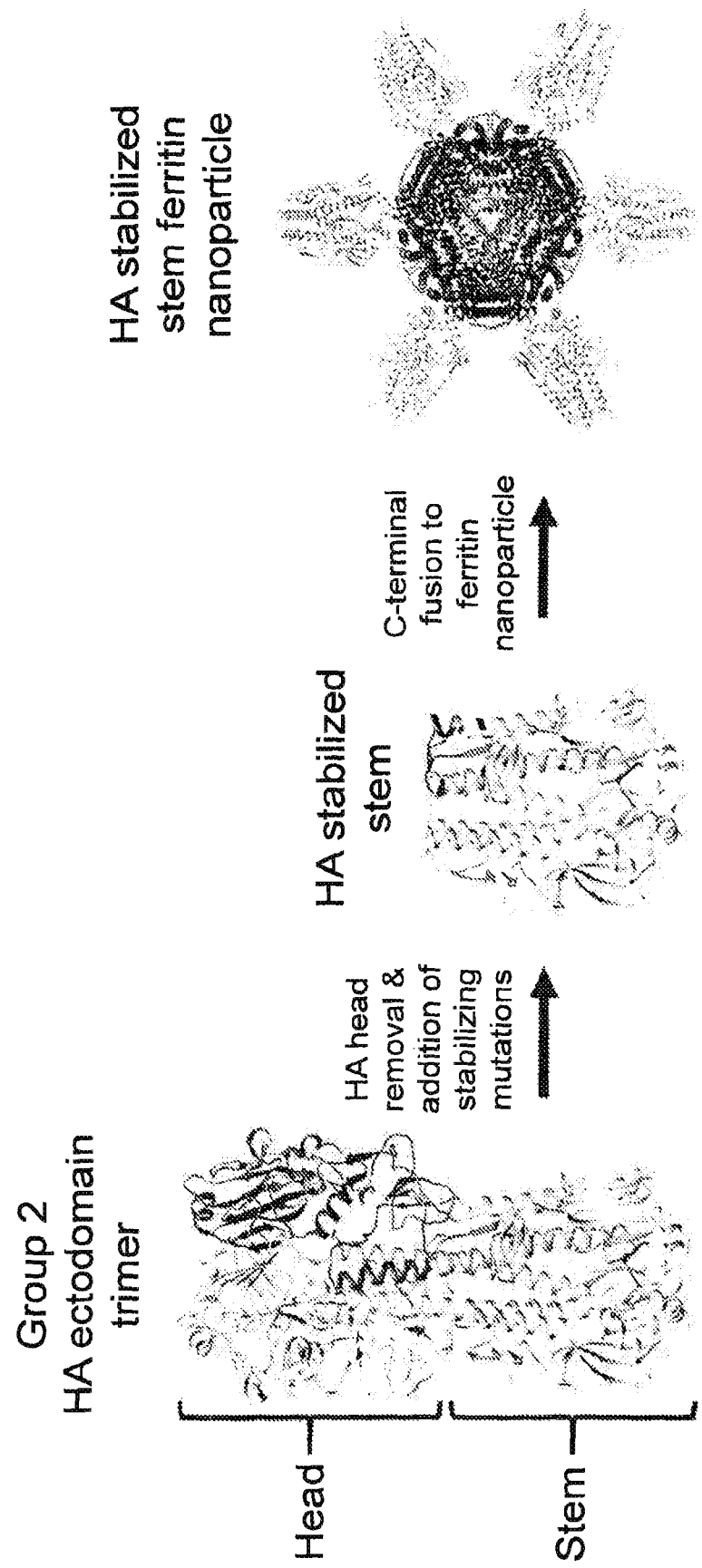
FIG. 2 depicts the creation of self-assembling group 2 HA stem nanoparticles. Ribbon diagrams depict (from left to right) the design of group 2 HA stabilized stem nanoparticles. The head region of one HA monomer is represented in dark gray. The stem region of that same monomer is shown in a medium grey. The other two monomers are shown in light gray.
Figures 3A, 3B:
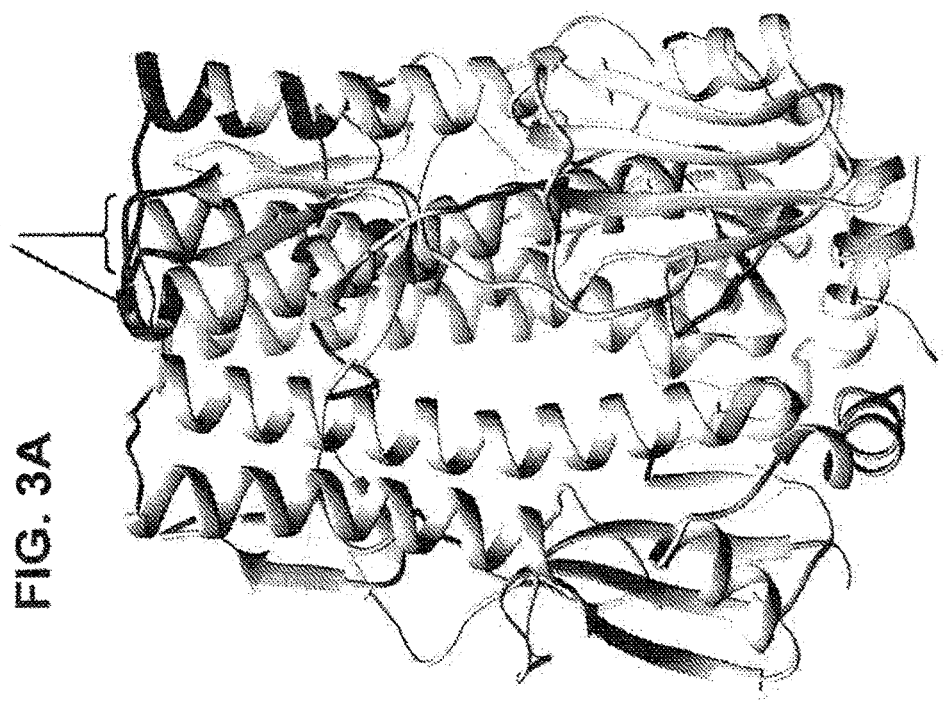
FIGS. 3A and 3B show mutations in H3N2 design 231 that enable the formation of group 2 HA stabilized stem nanoparticles.
Figures 4A, 4B:
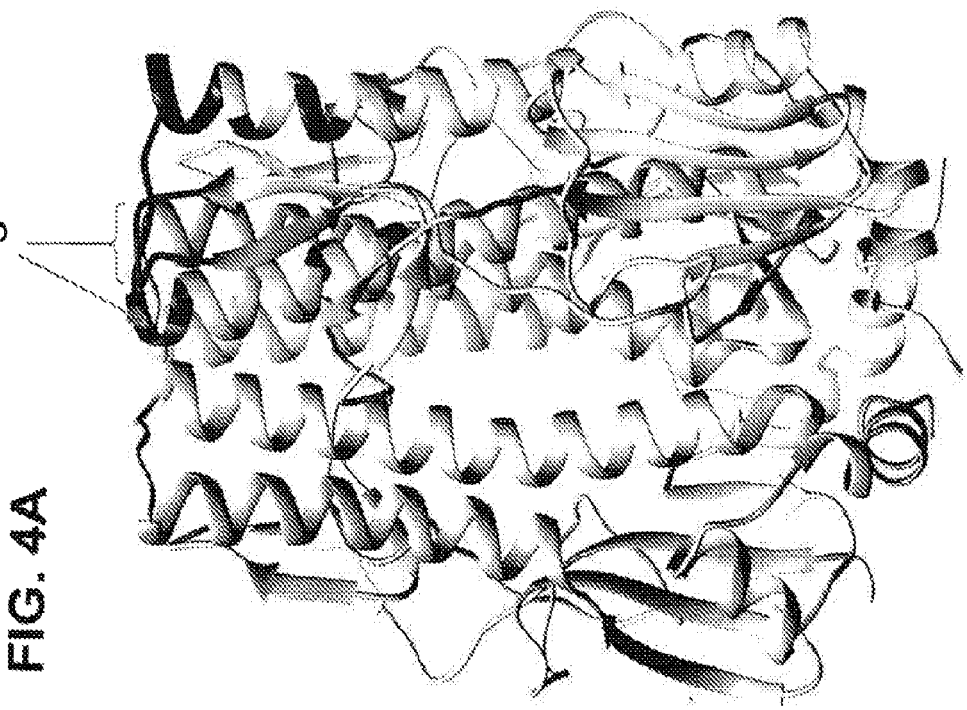
Figure 5B:
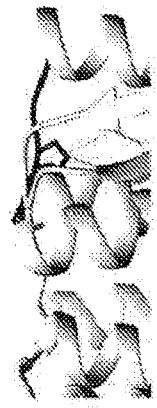
Figures 6A, 6B, 6C:
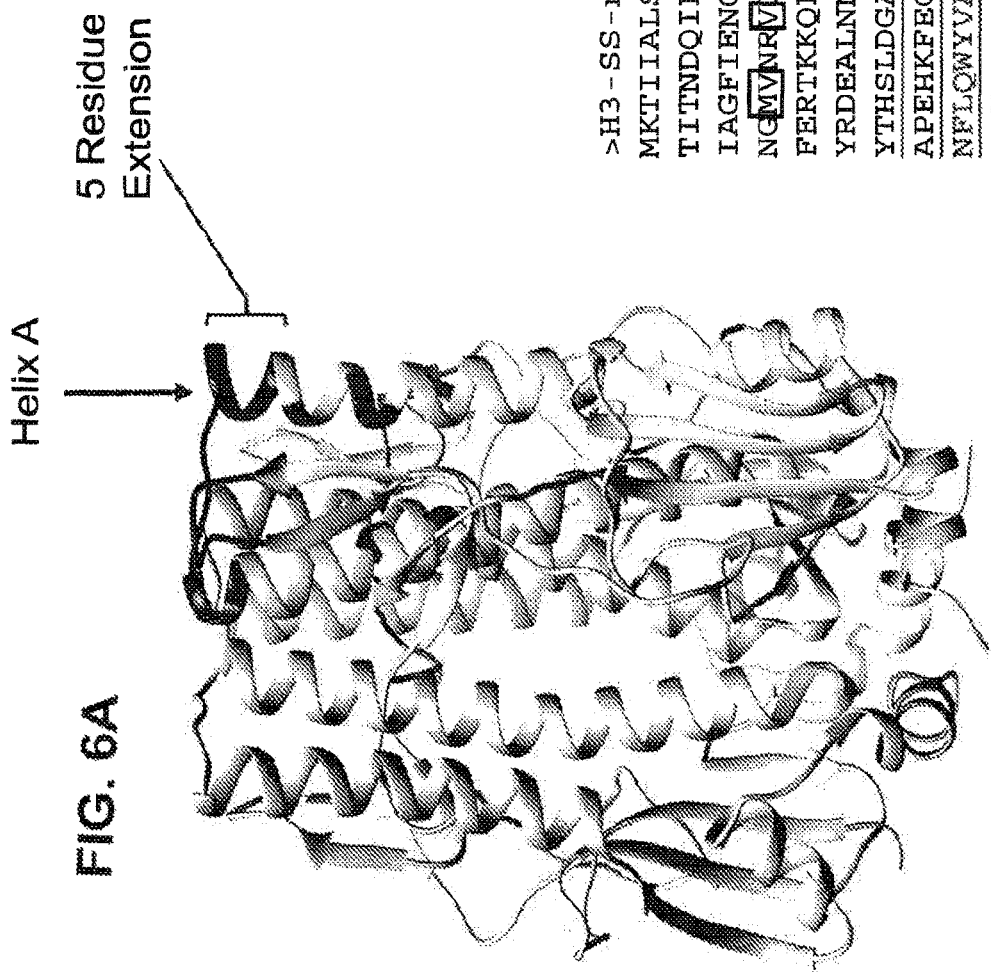
FIGS. 6A-6C show mutations in H3N2, design 231, in the C-terminal extension of helix A.
Figure 8A:
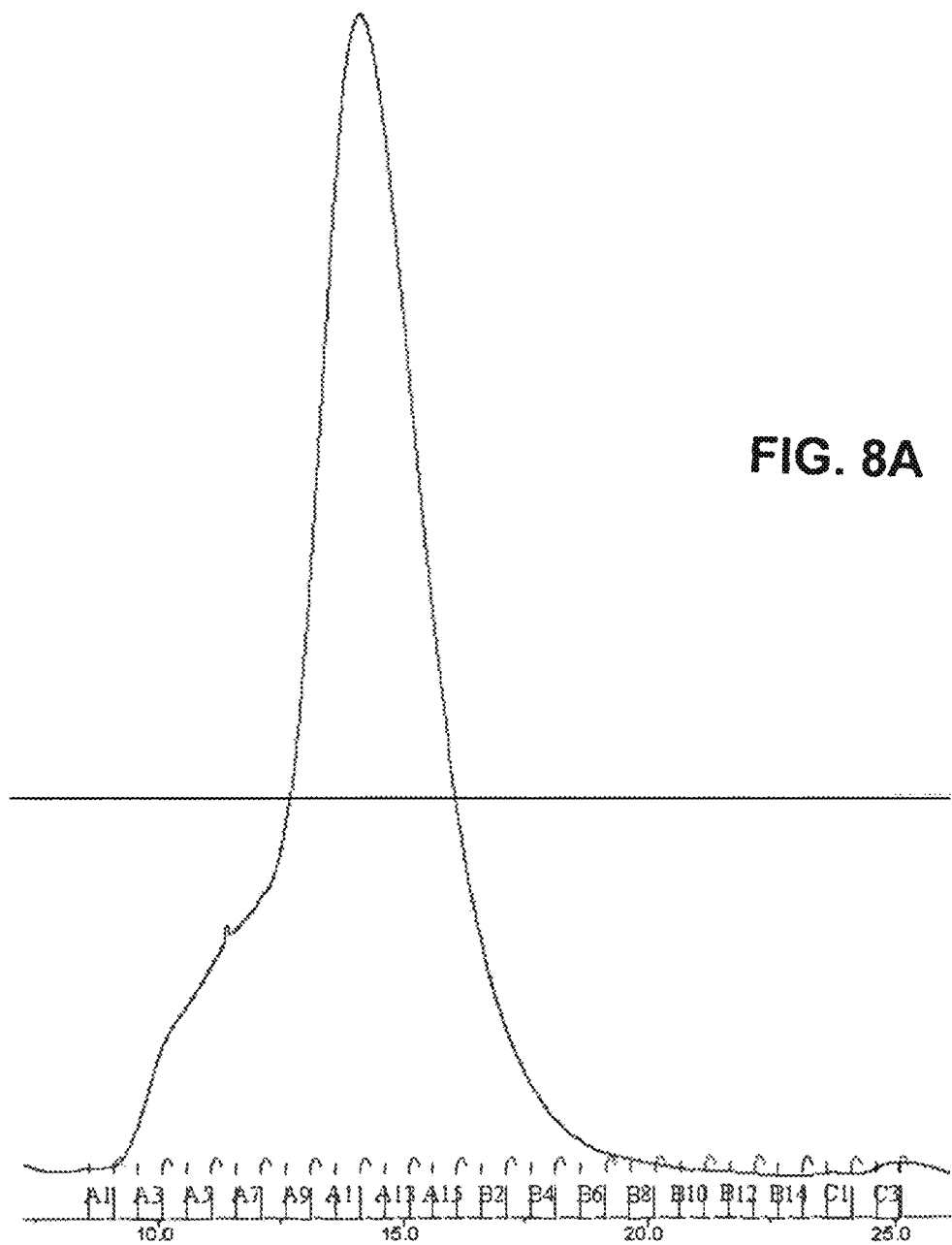
FIGS. 8A and 8B show the expression and characterization of H3 stabilized stem ferritin nanoparticle 231 (H3-SS-np_231).
Figure 8B:
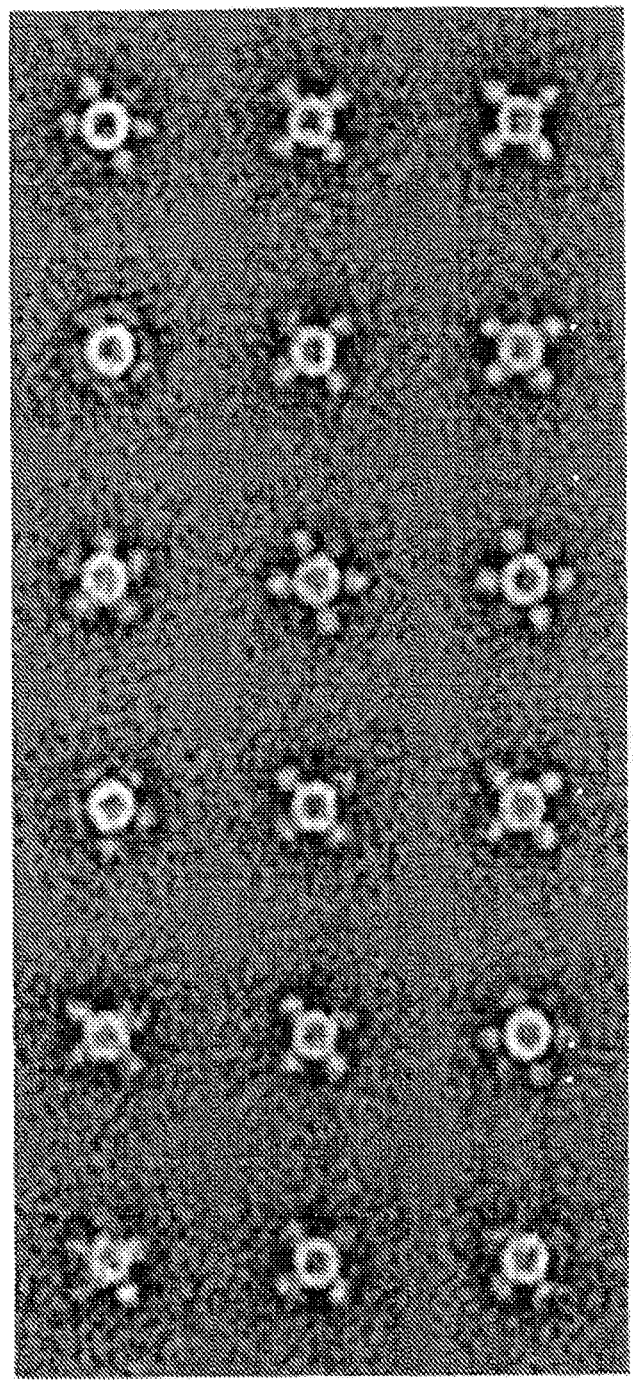
Figures 9A, 9B:
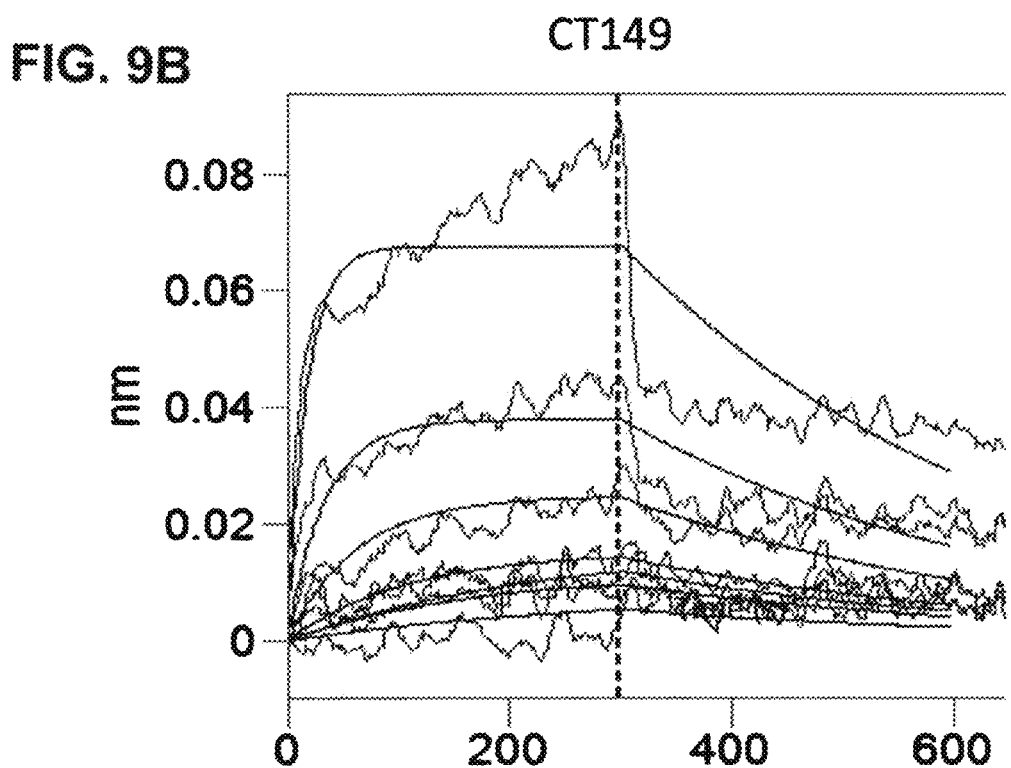
FIGS. 9A and 9B show HA stem antibody recognition of H3-SS-np_231.
Figure 10A:
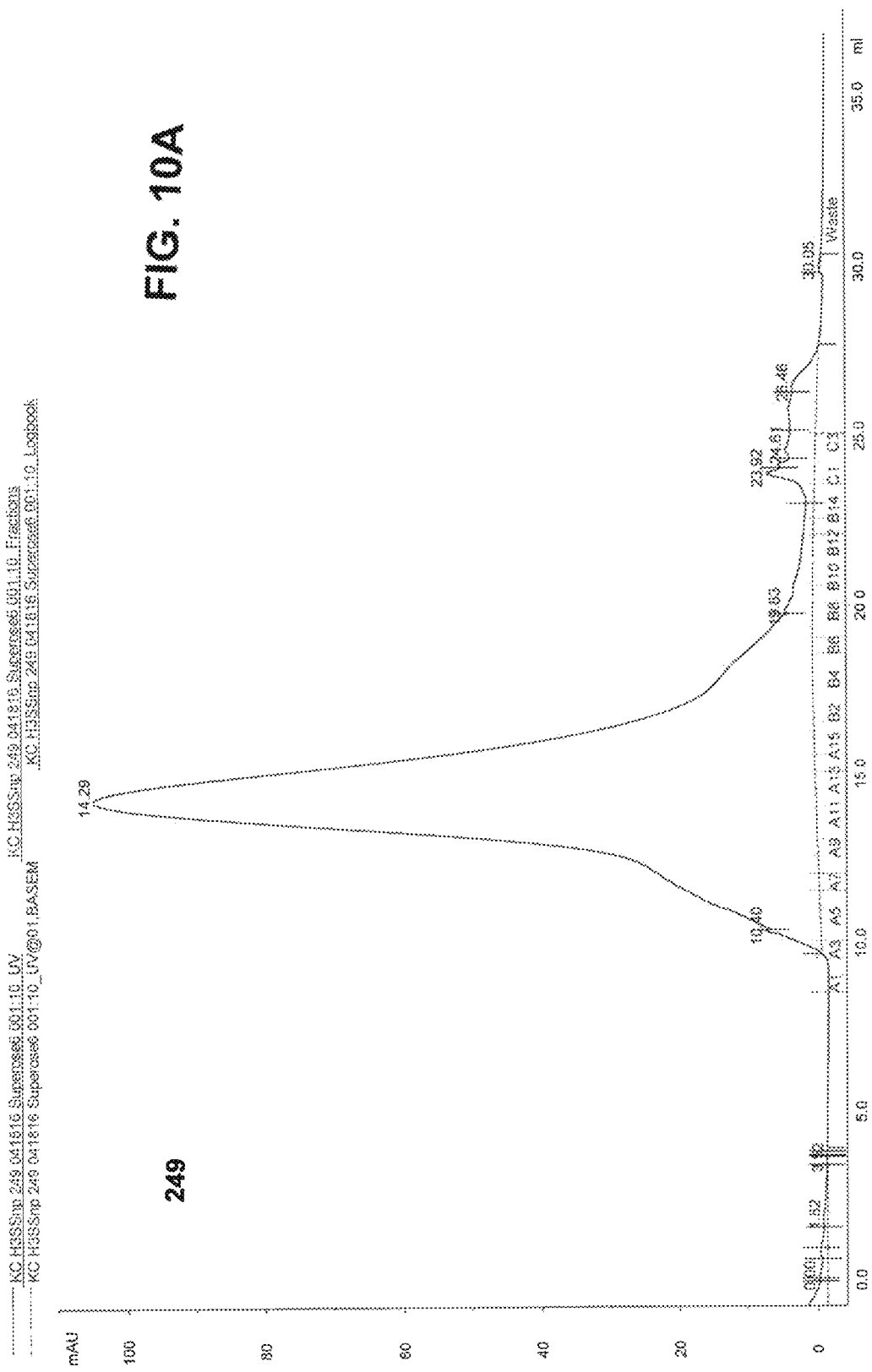
FIGS. 10A-10E show gel filtration profiles for five variants of H3-SS-np_231. Gel filtration Superose 6 10/30 profiles for H3-SS-np_231 variants, 249 (FIG. 10A), 256 (FIG. 10B), 258 (FIG. 10C), 262 (FIG. 10D) and 264 (FIG. 10E). In each case a single peak was eluted at a volume of approximately 14.5 mls. The final yields from Expi293 cells after gel filtration were 6-8 mg/L of culture.
Figure 10B:
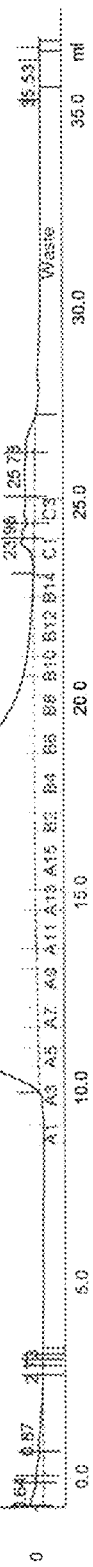
Figure 10C:
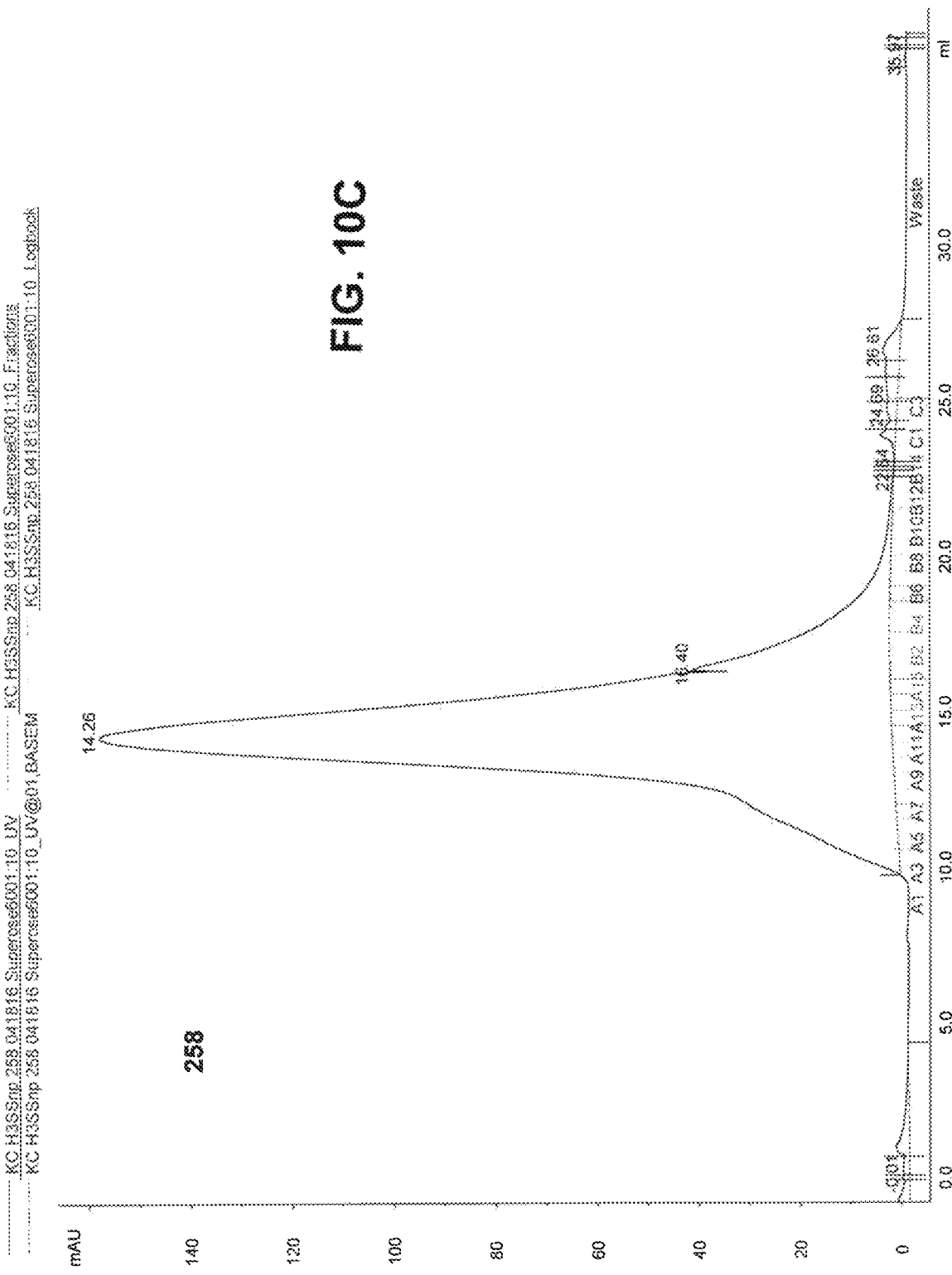
Figure 10D:
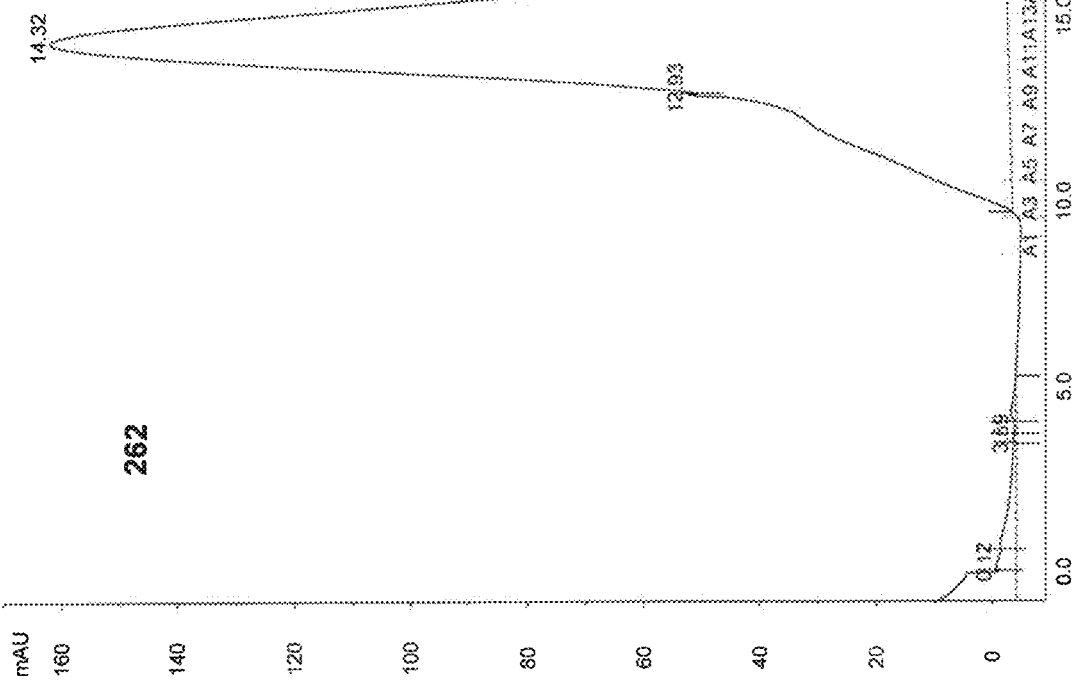
Figure 10E:
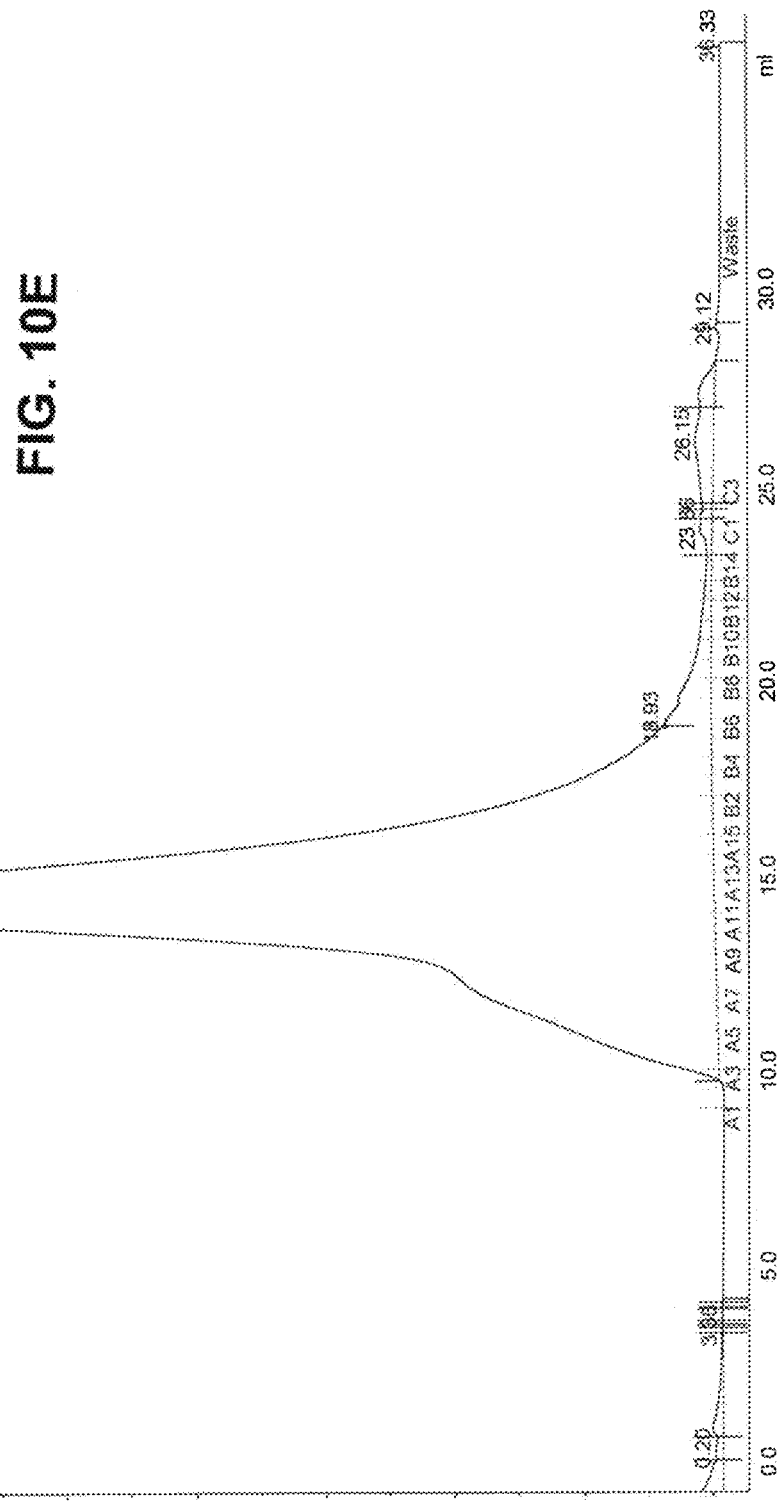
Figure 11C:
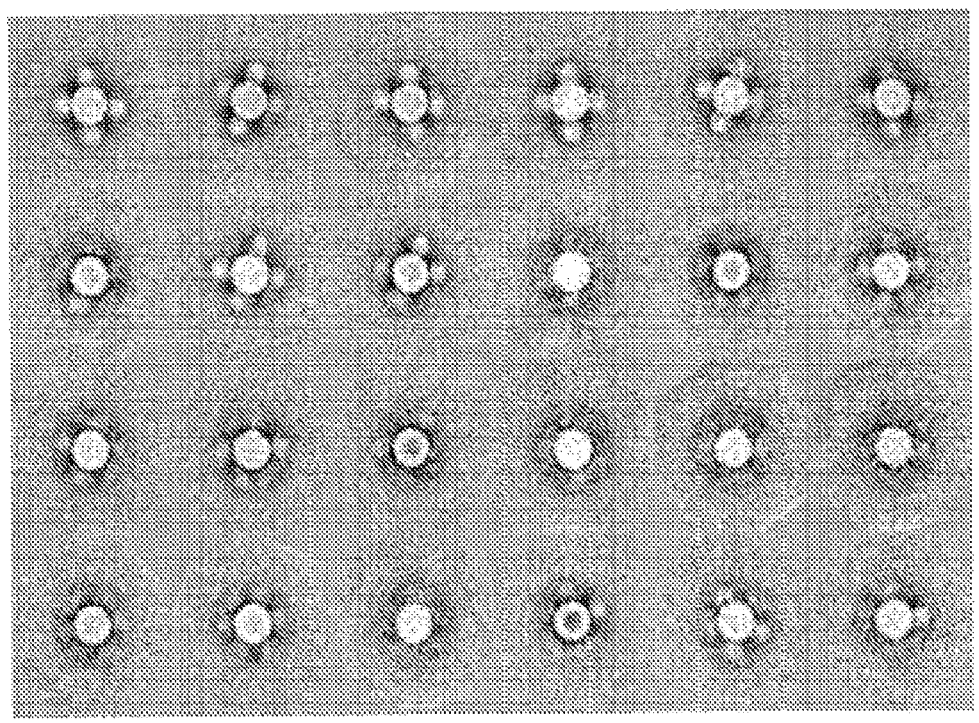
Figure 11D:
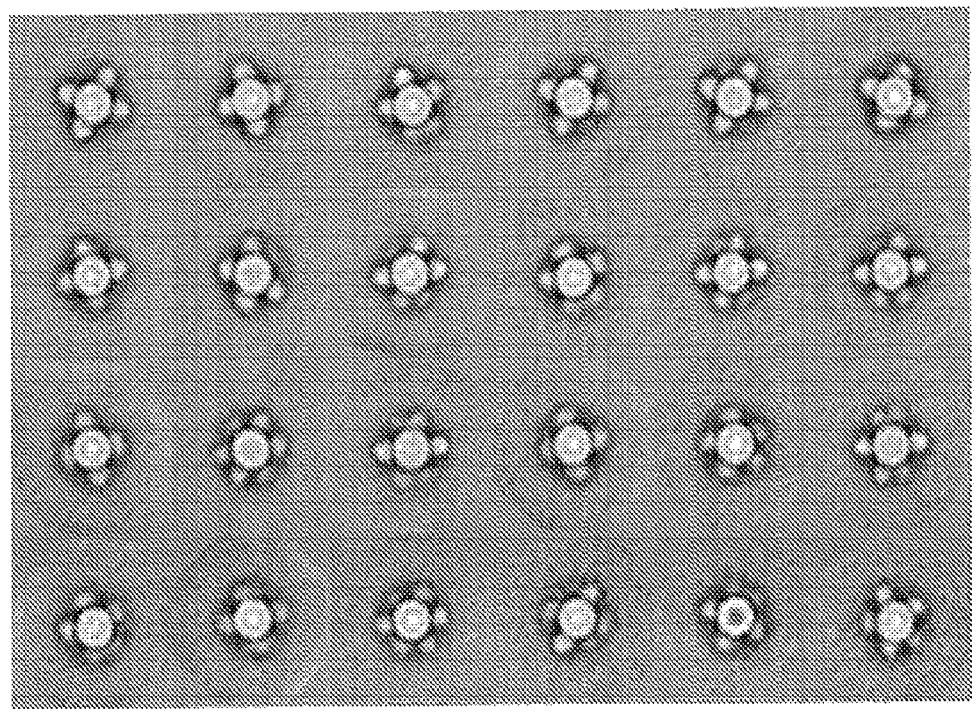
Figure 12A:
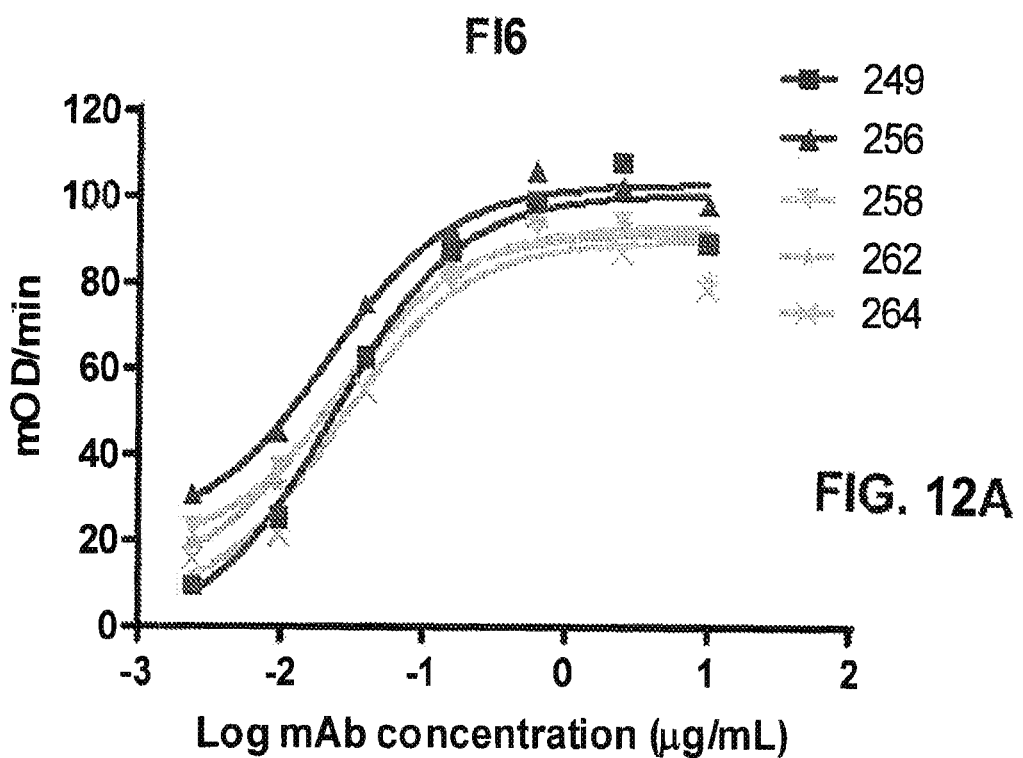
FIGS. 12A-12D show kinetic ELISA results for five variants of H3-SS-np_231.
Figure 12B:
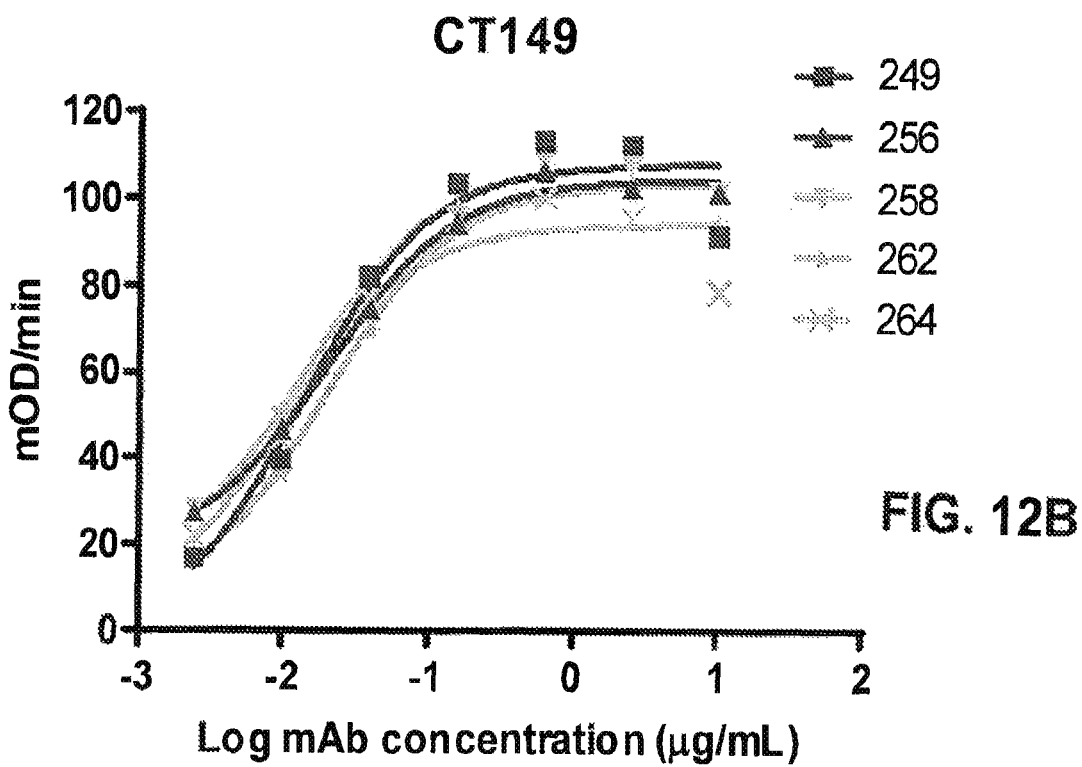
Figures 12C, 12D:
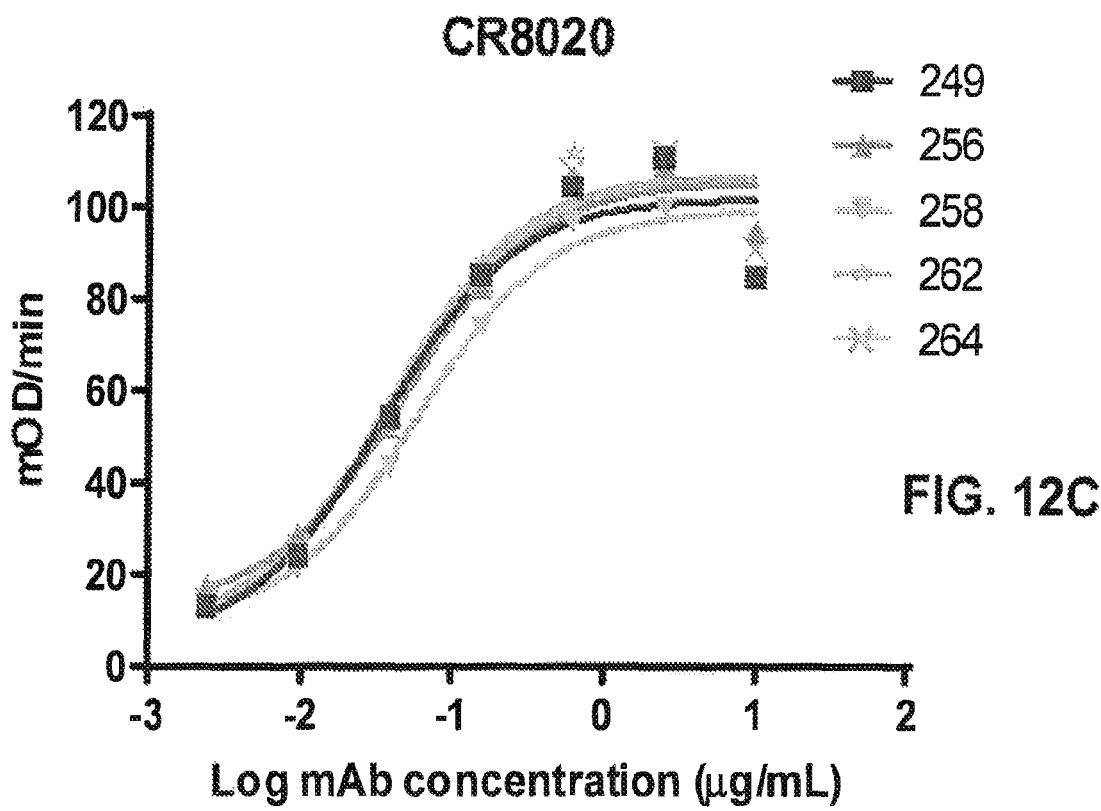
Figure 14:
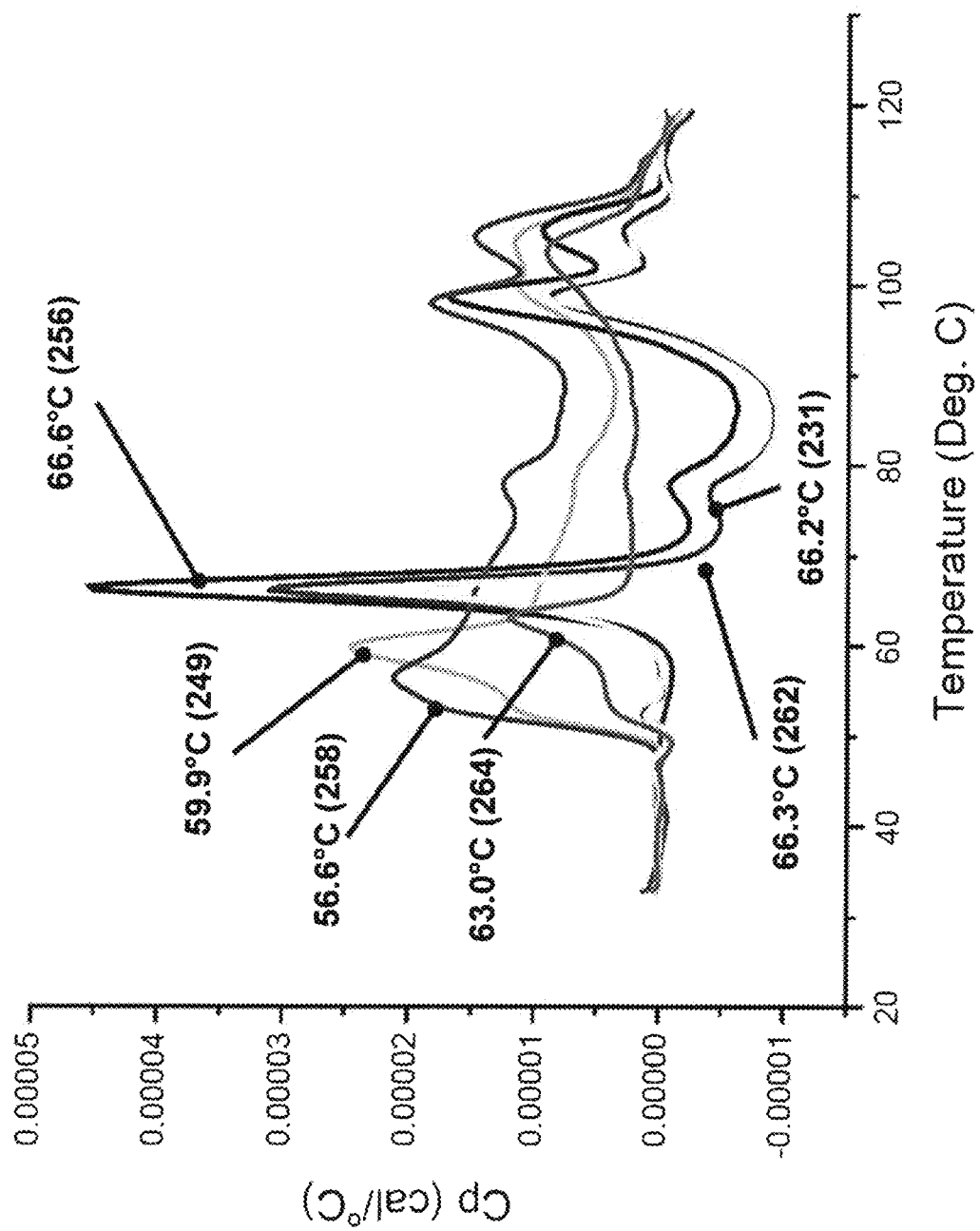
Figure 15A:
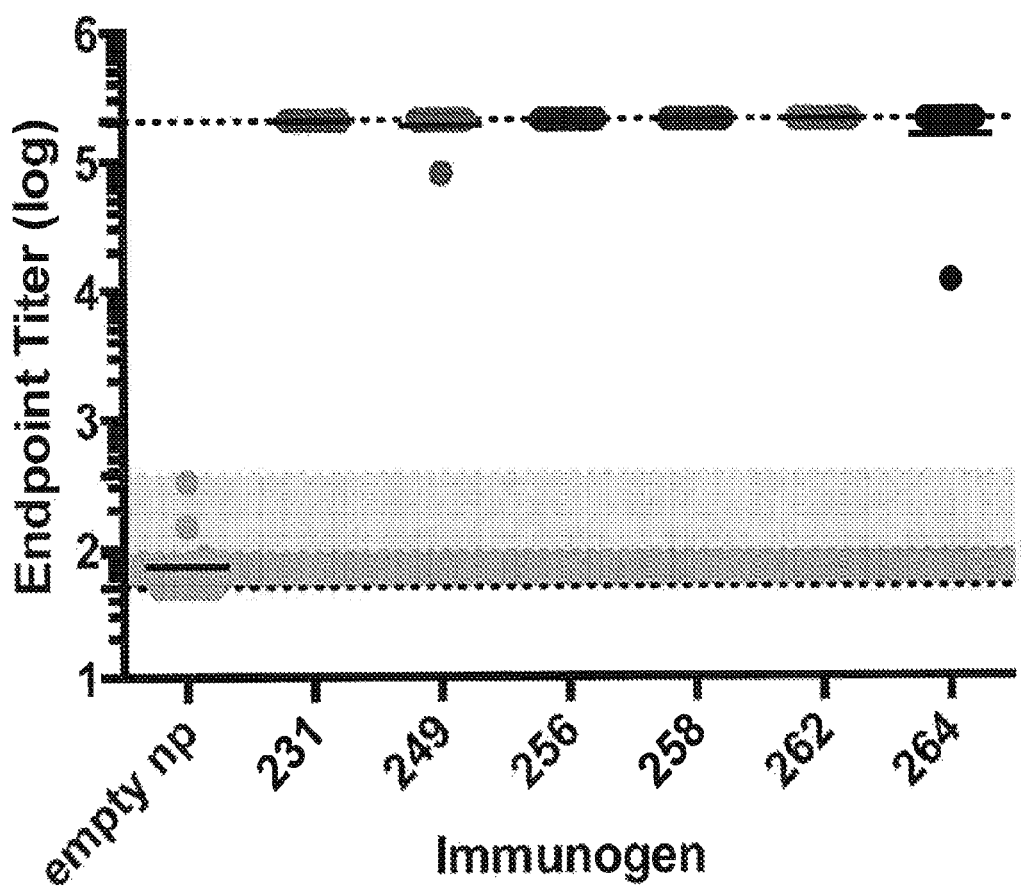
Figure 15B:
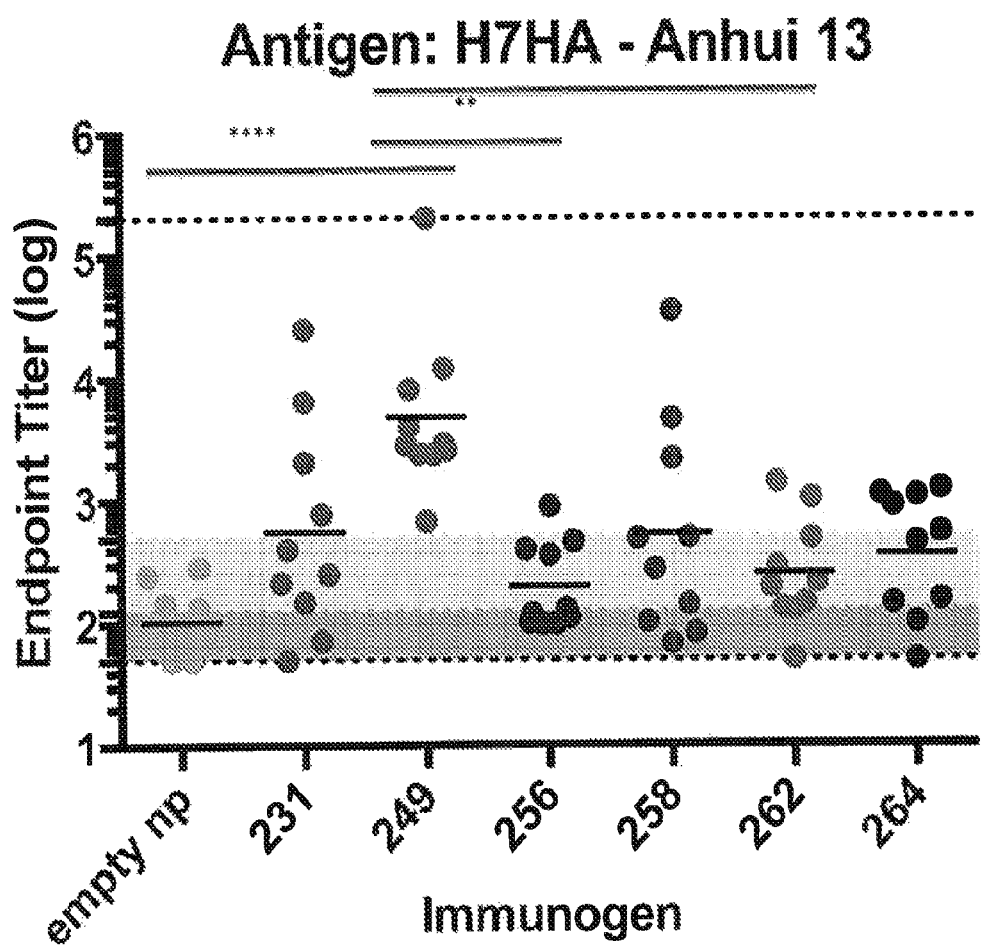
Figure 16A:
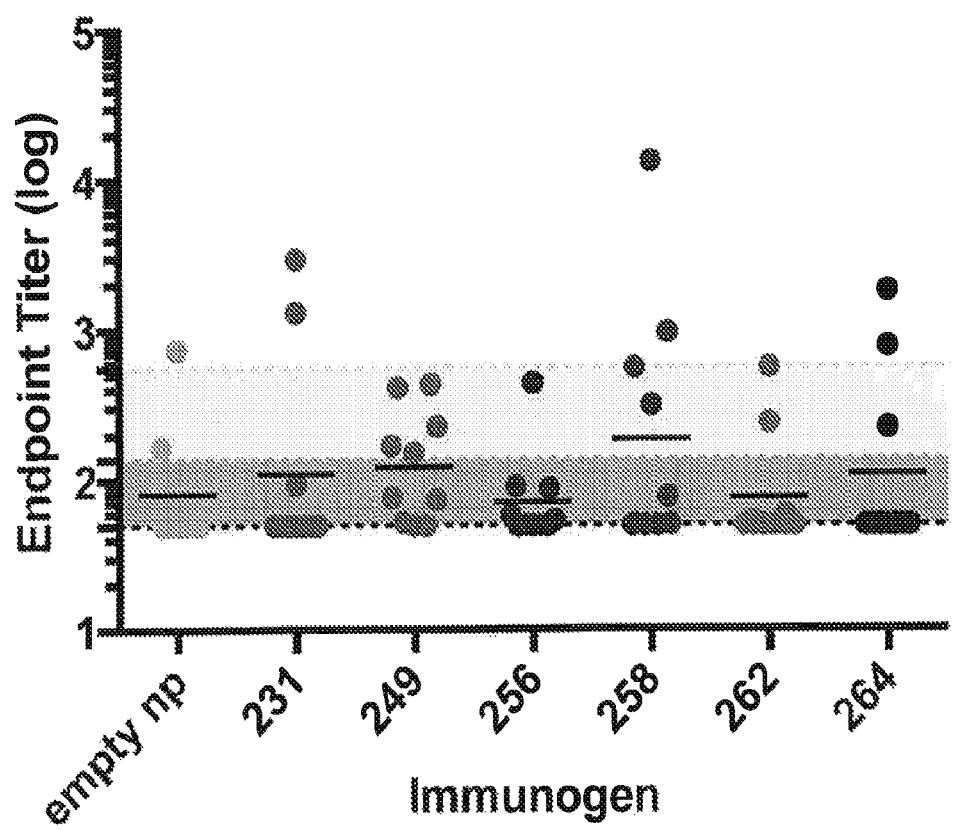
Figure 16B:
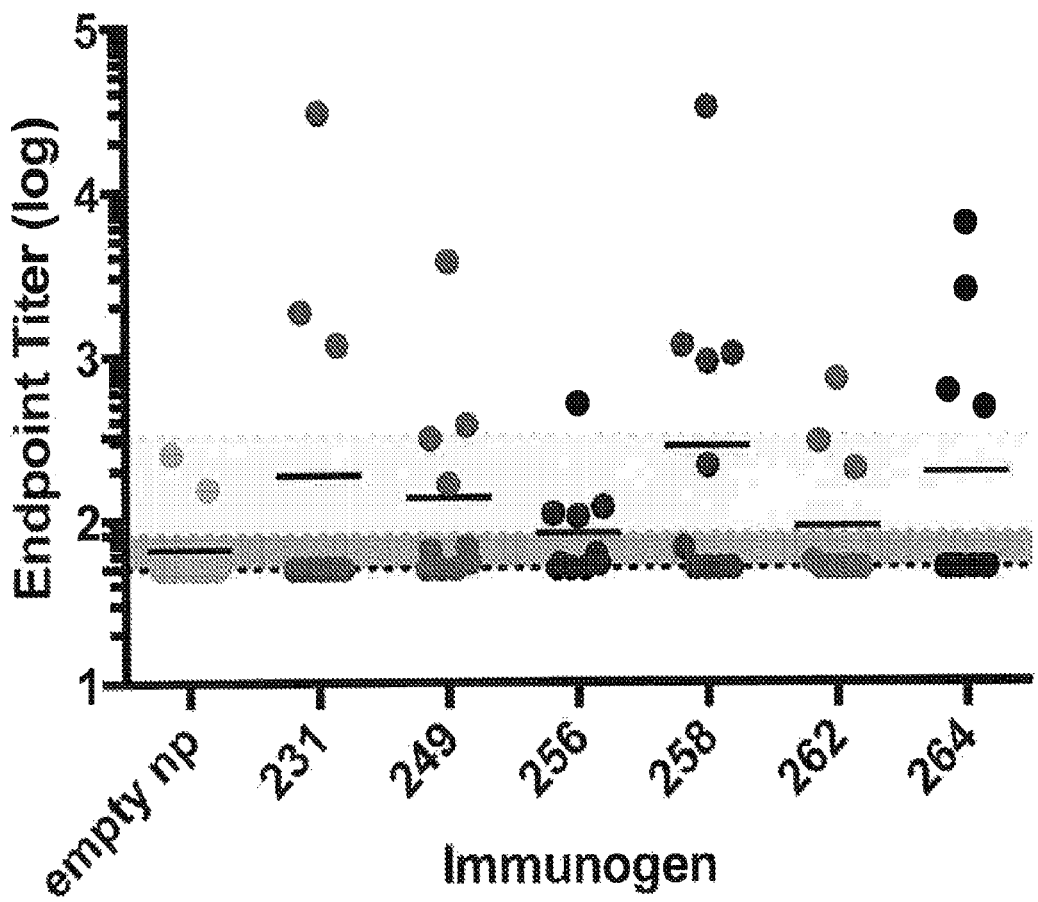
Figure 16C:
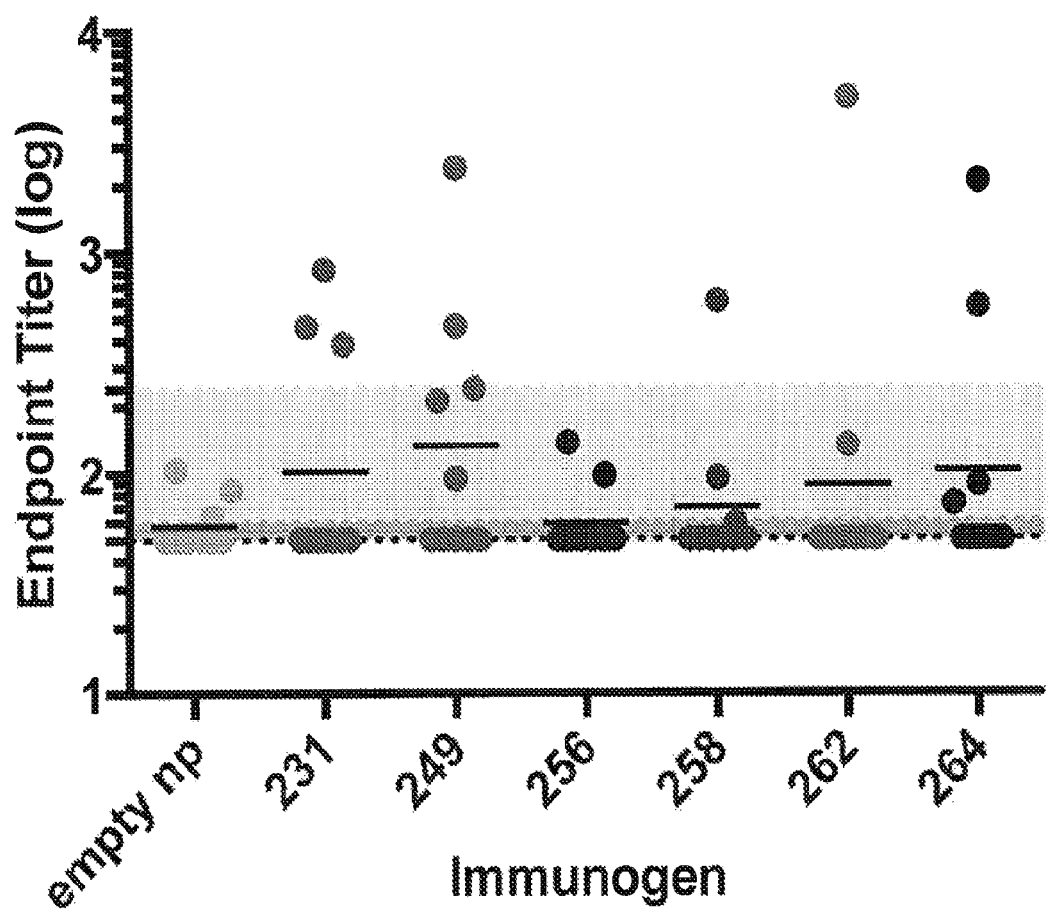
Figure 18A:
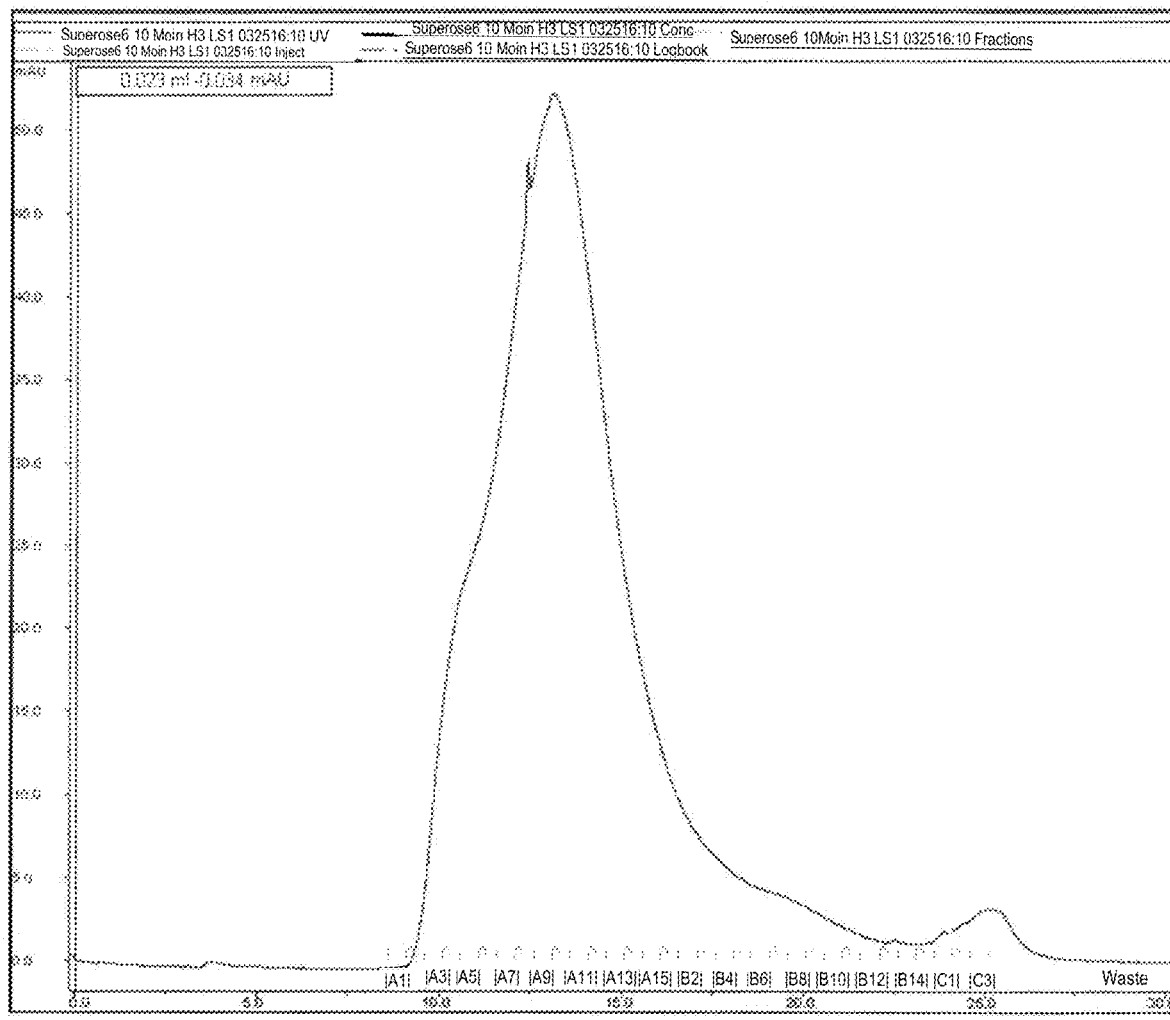
Figure 18B:
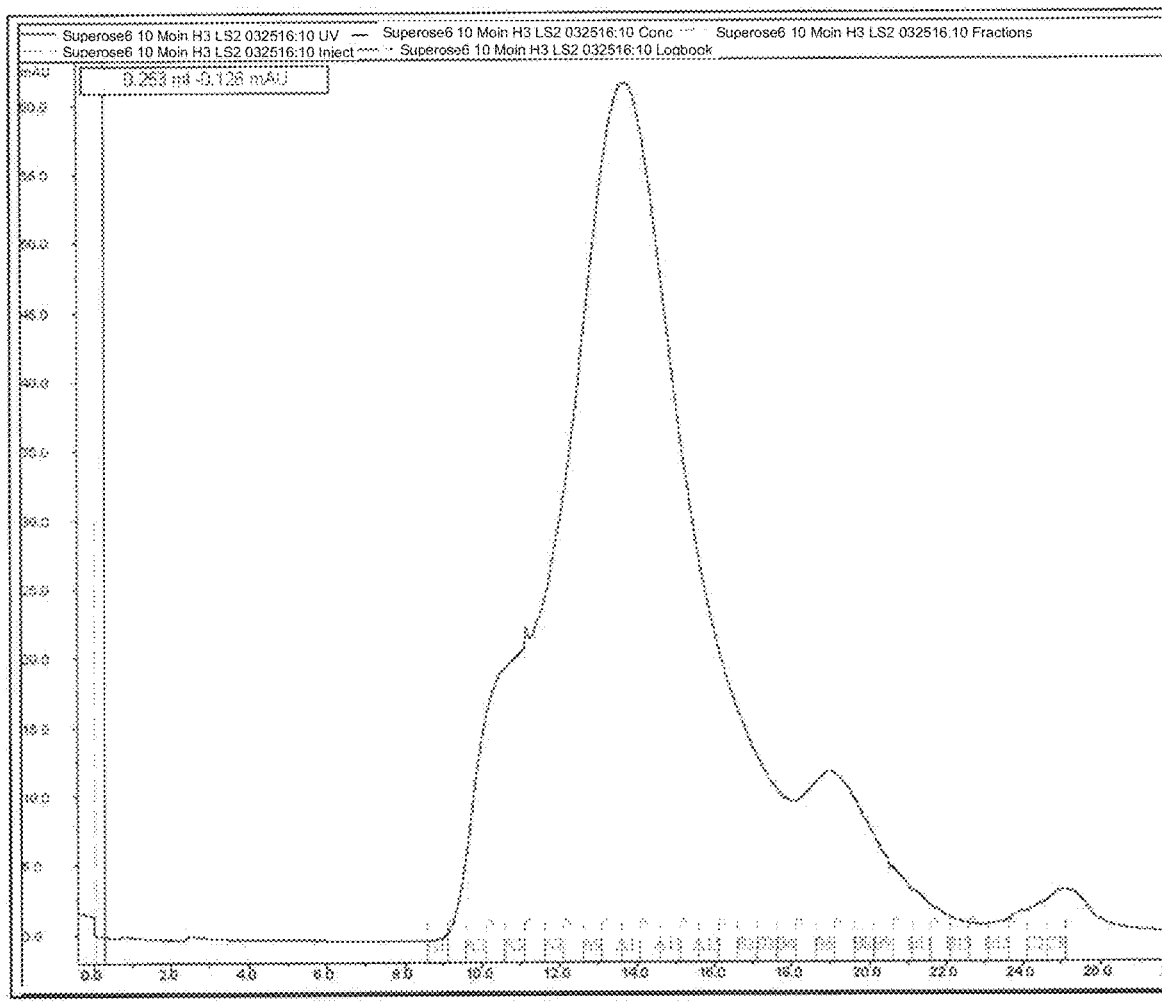
Figure 18C:
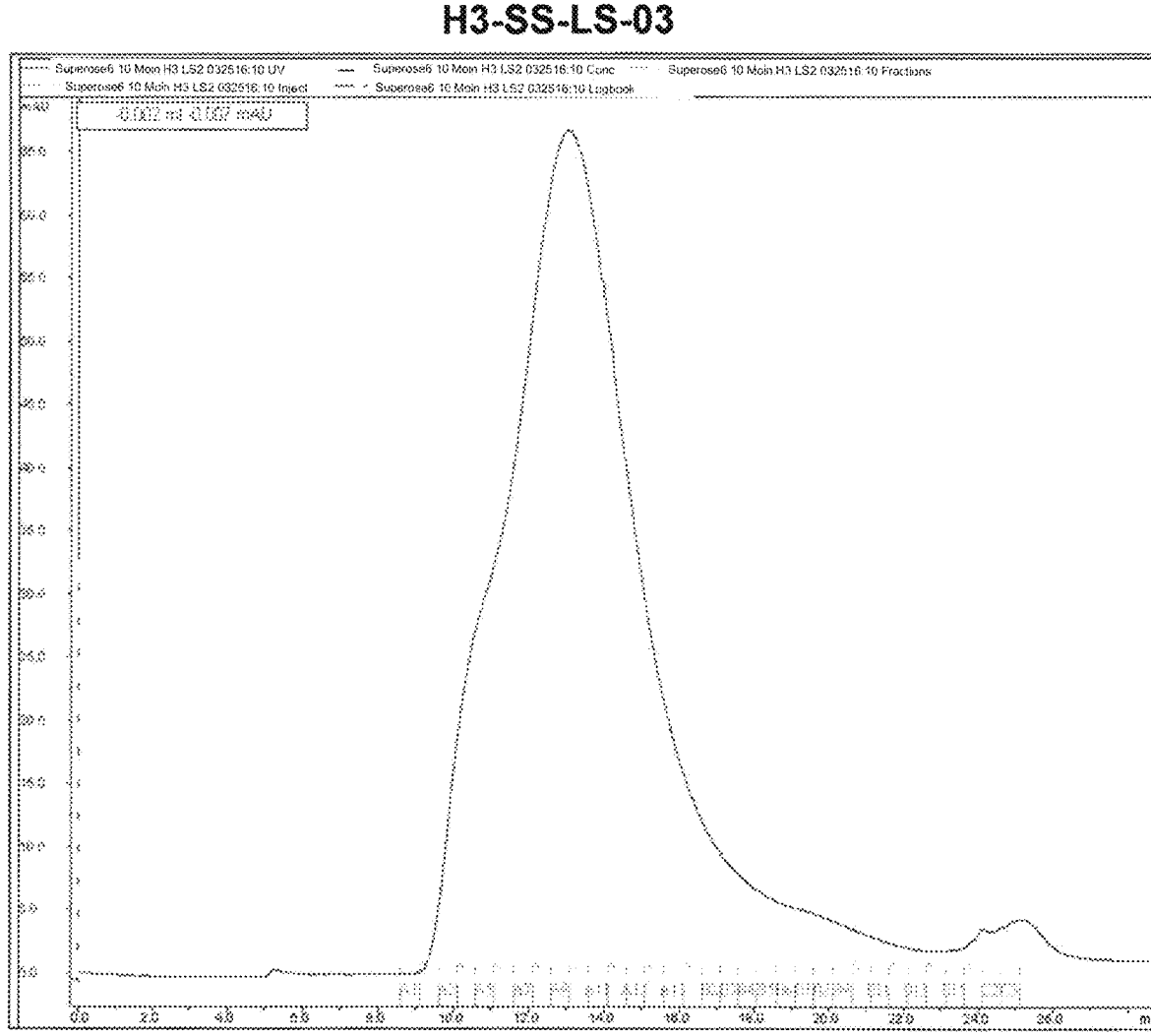
Figure 18D:
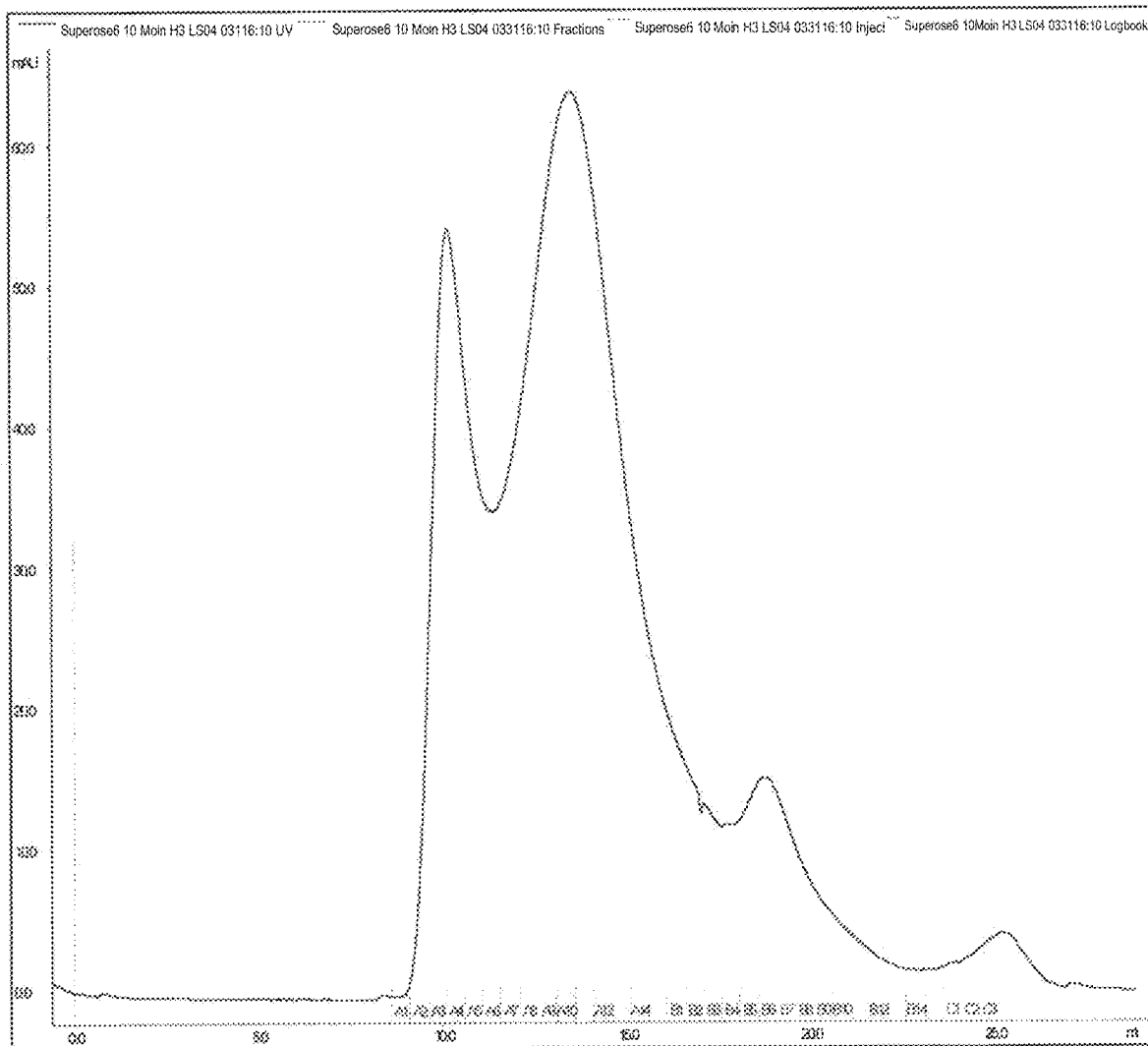
Figure 18E:
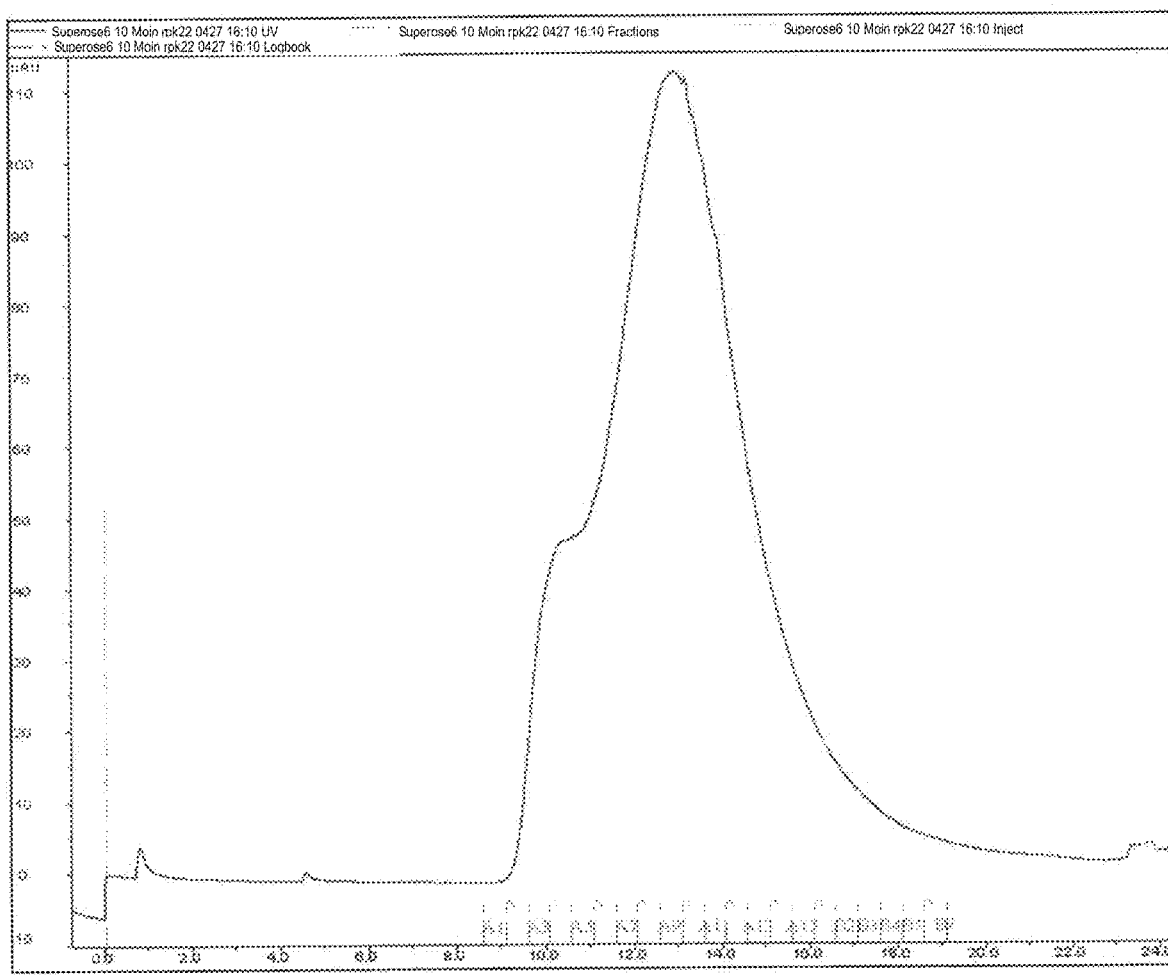
Figure 18F:
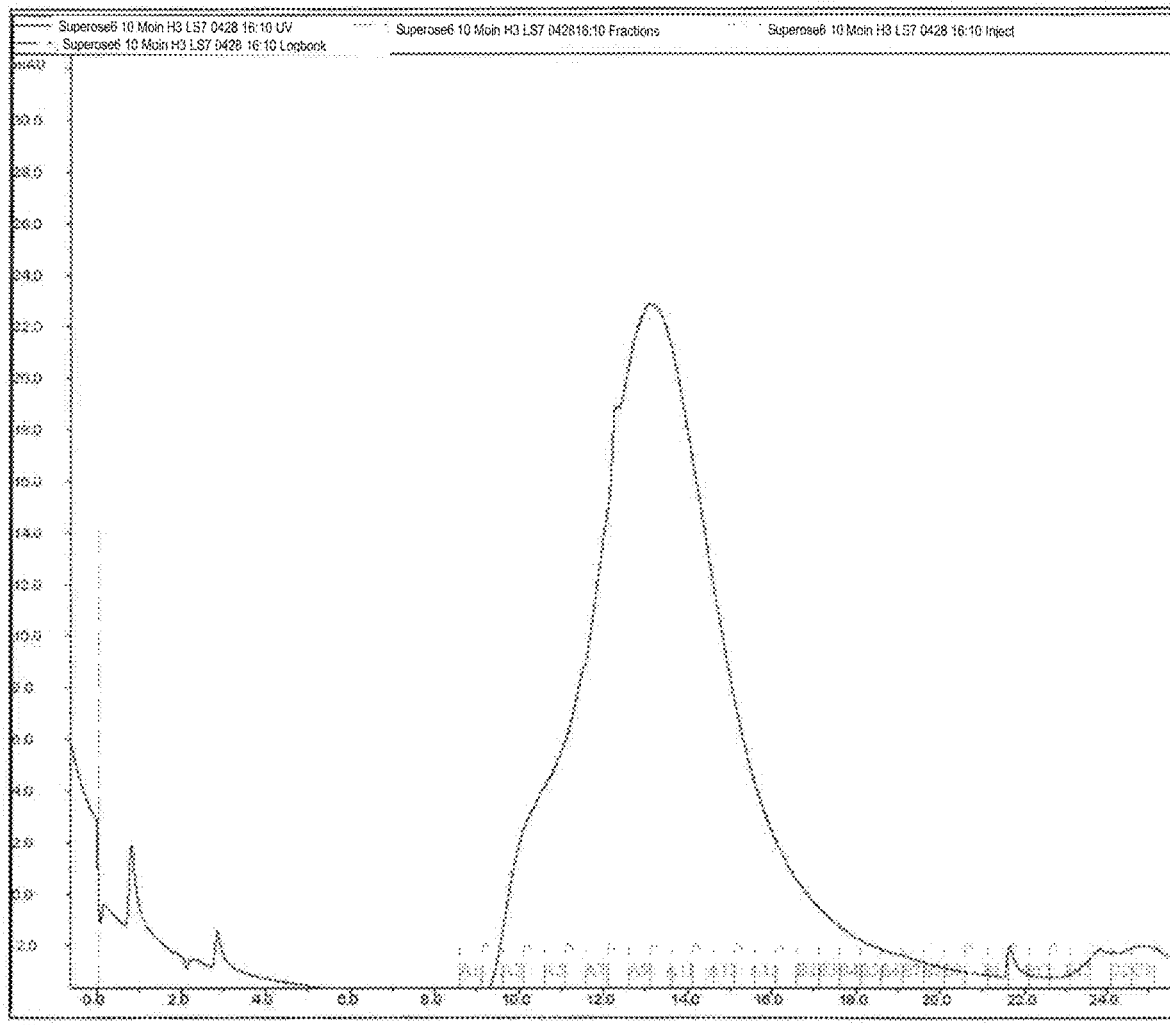
Figure 19A:
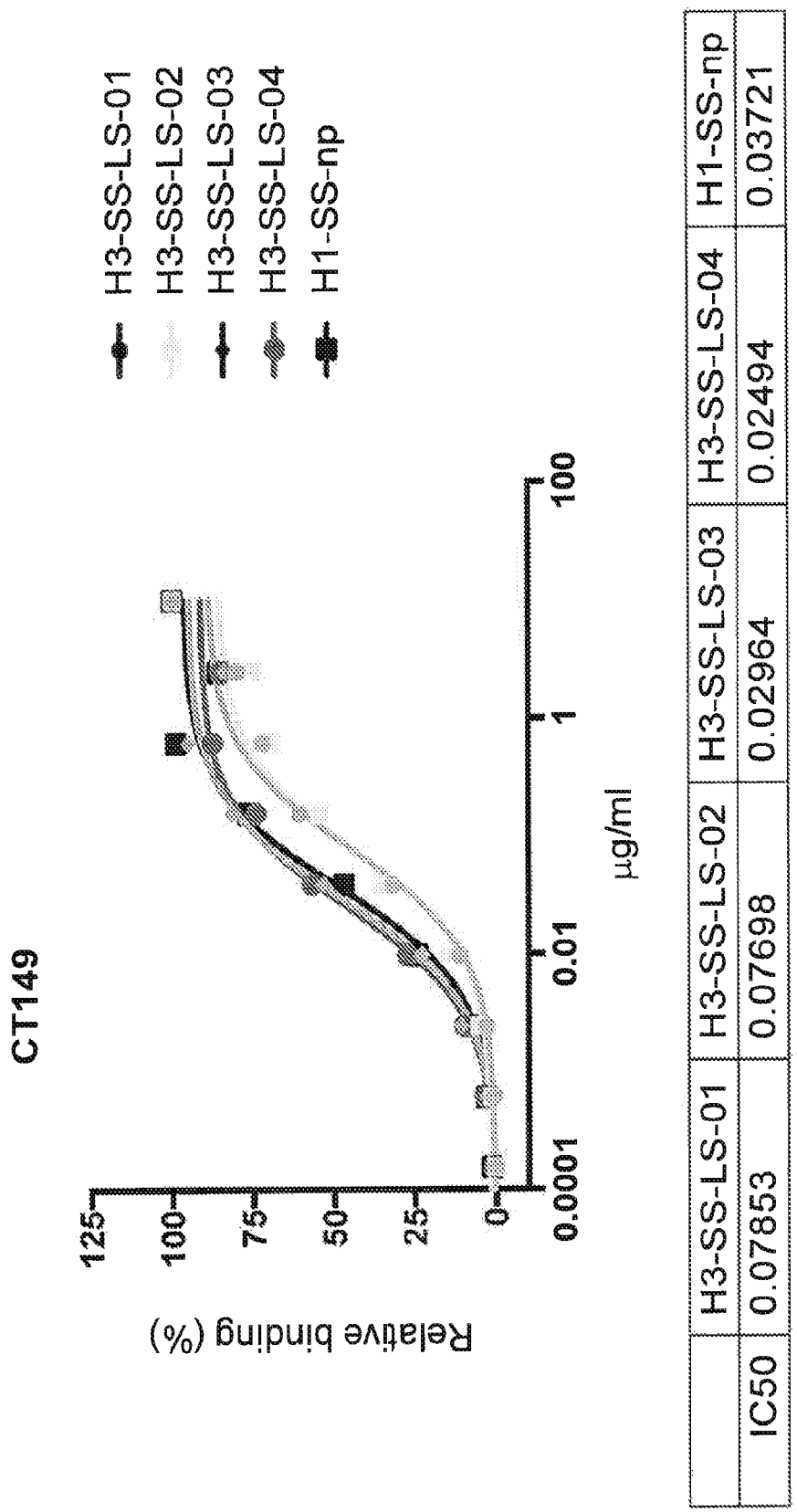
Figure 19B:
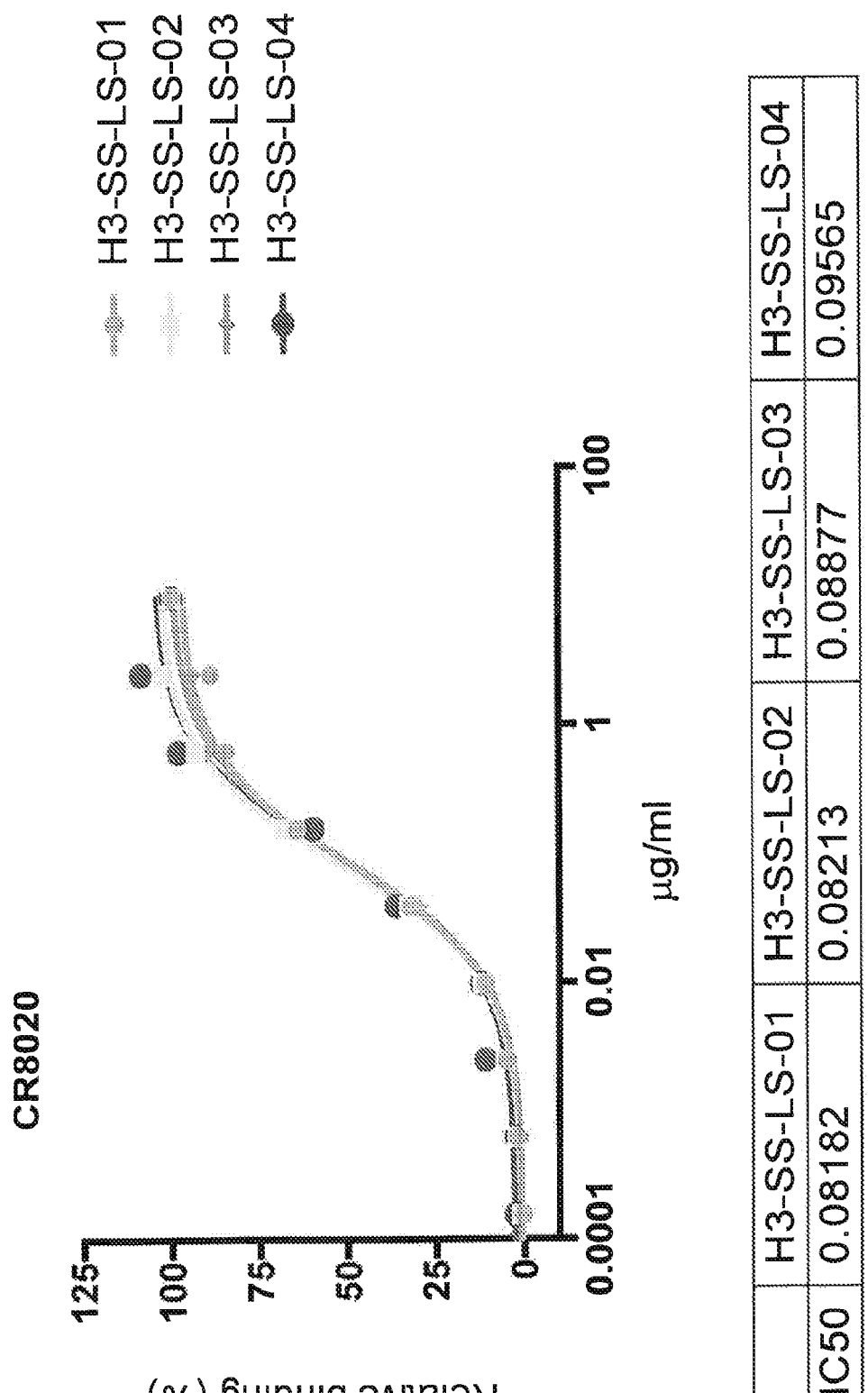
Figure 21A:
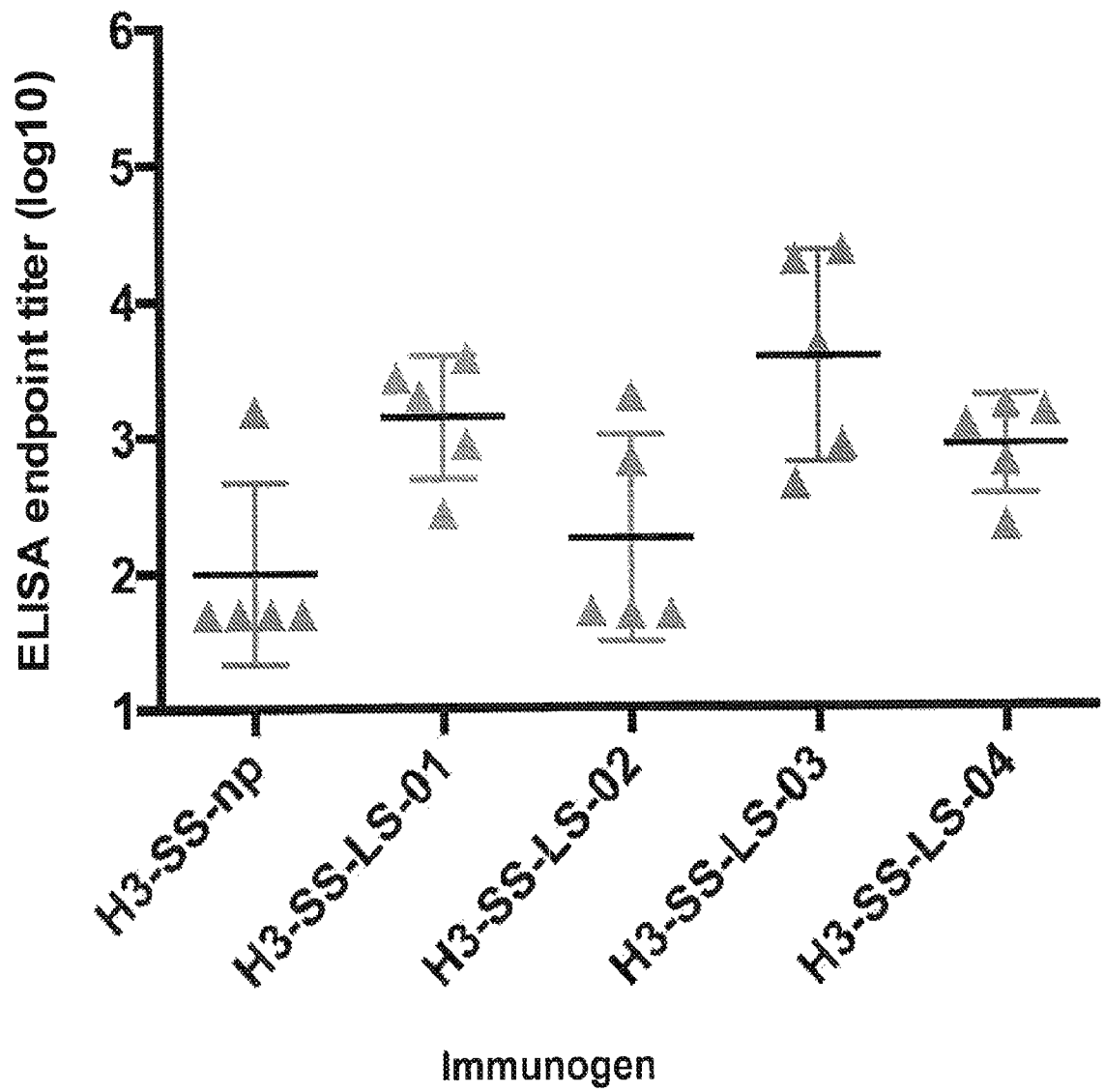
Figure 21B:
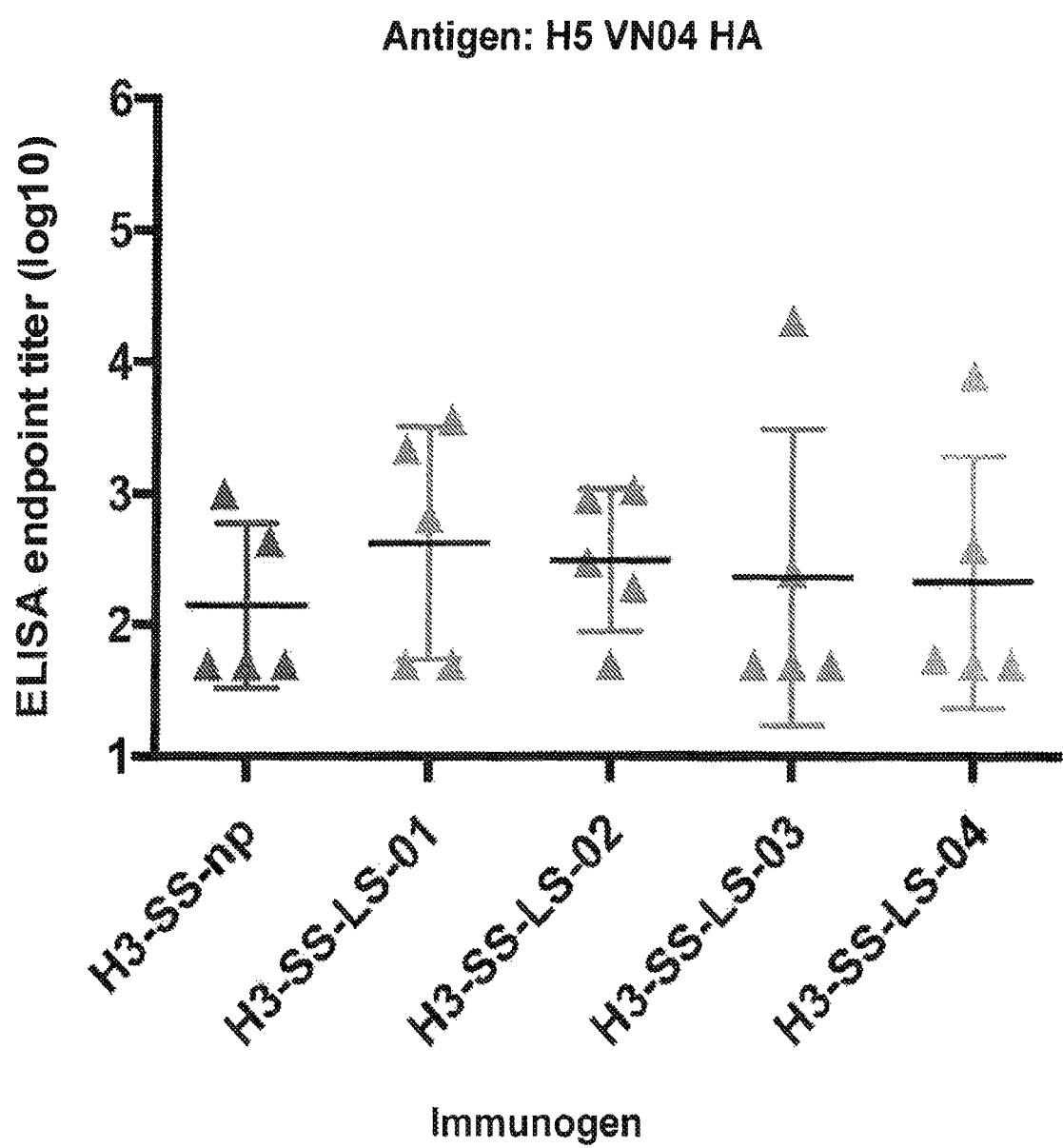
Figure 21C:
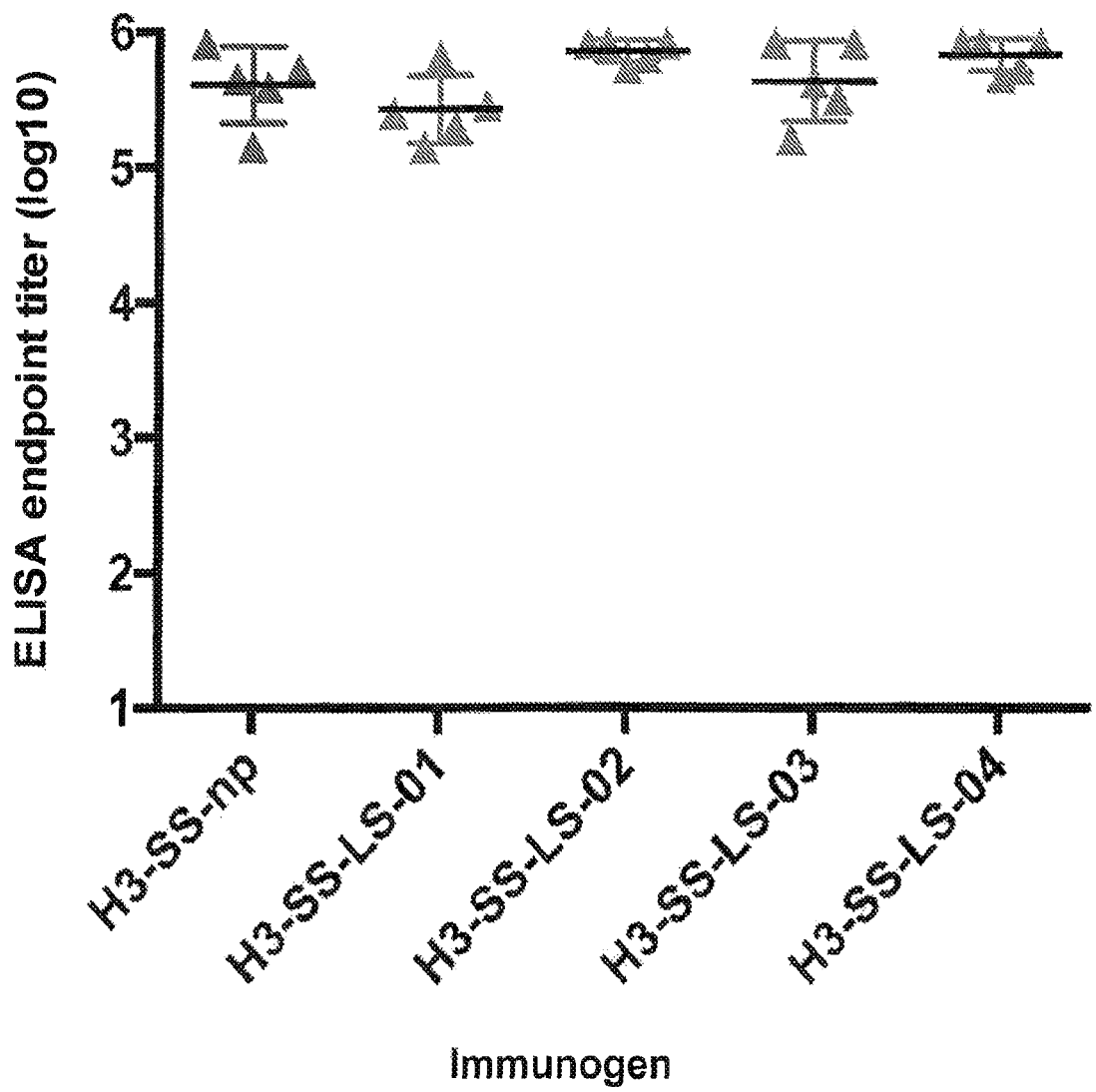
Figure 21D:
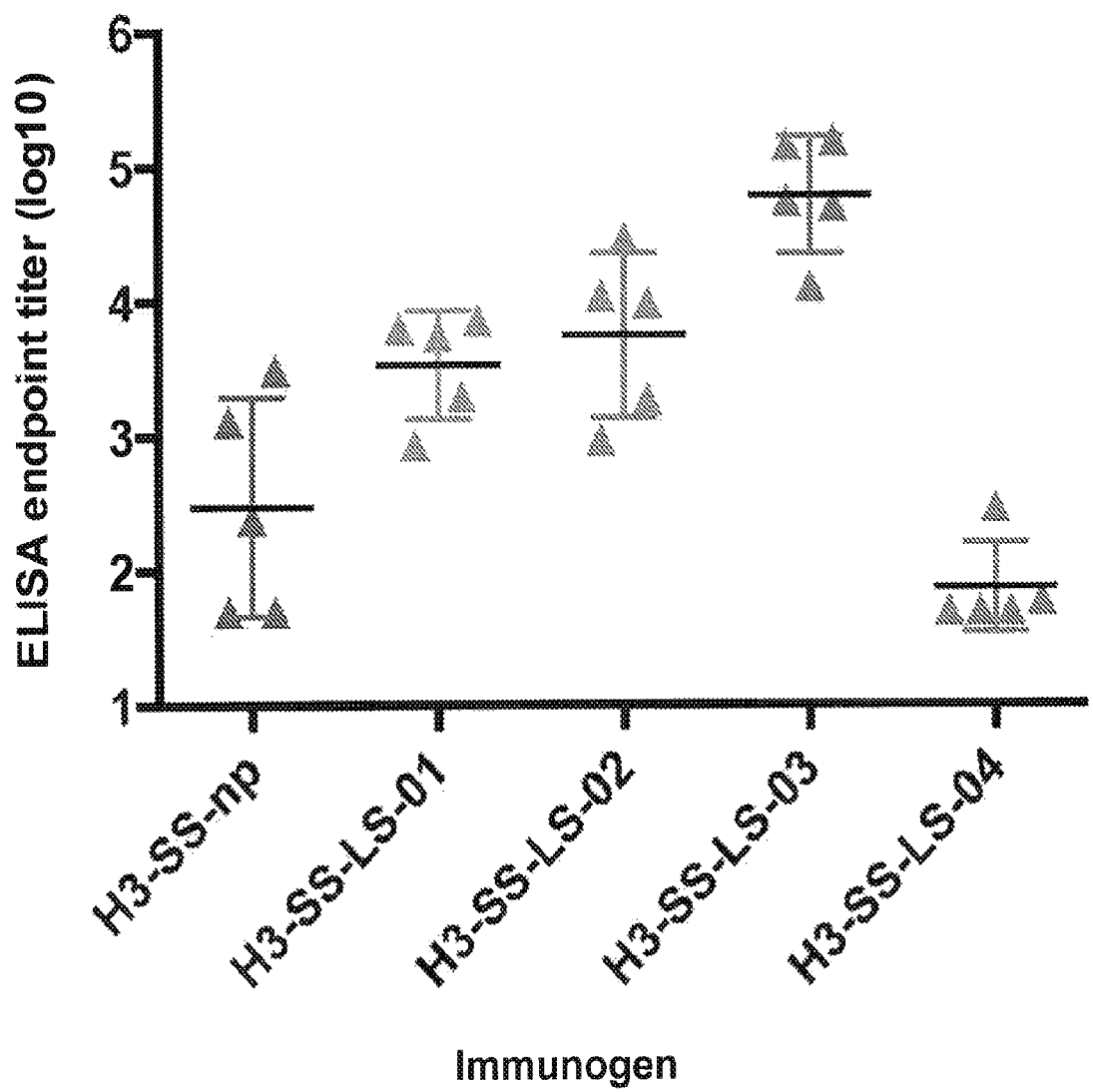
Figure 22A:
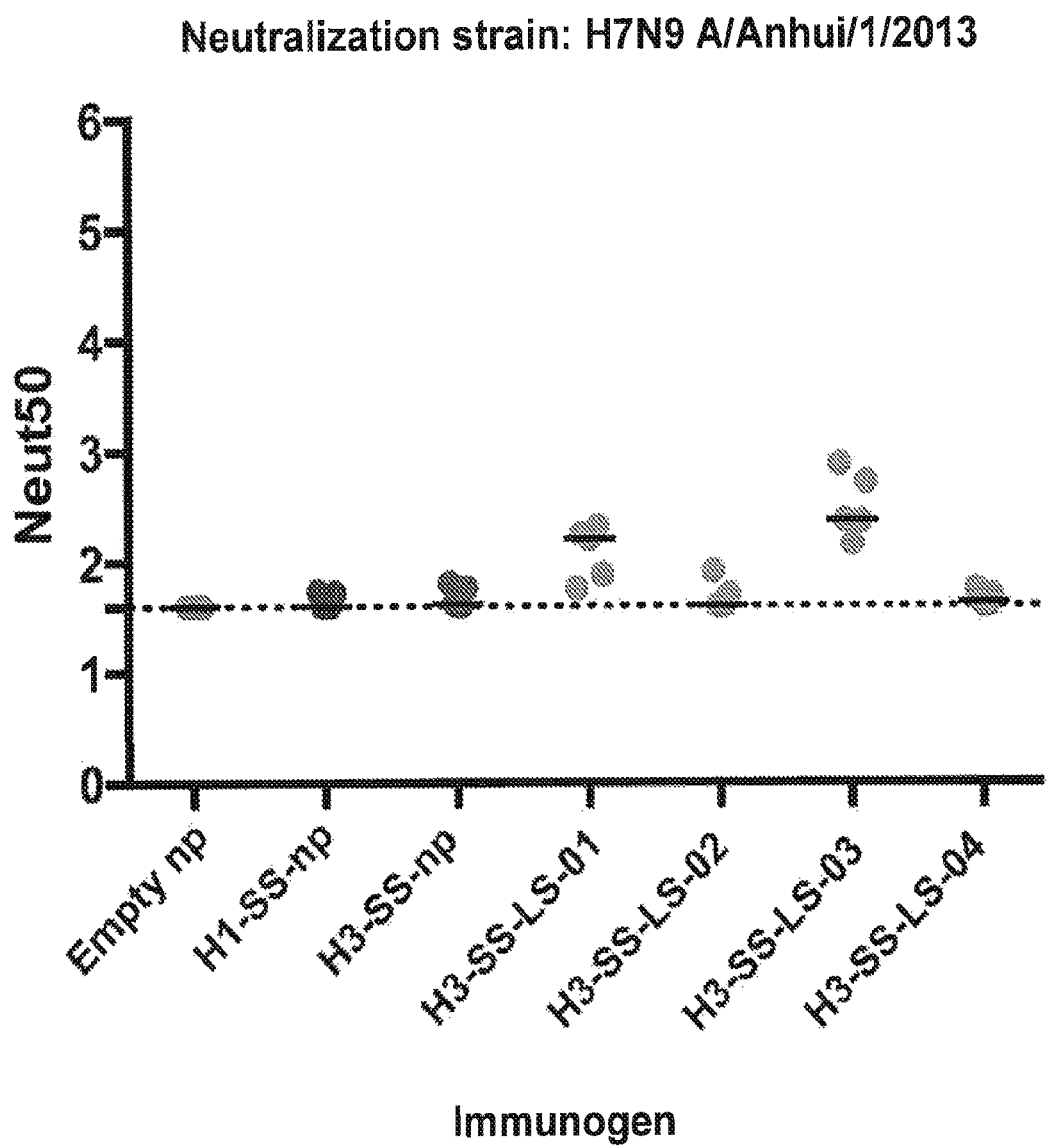
Figure 22B:
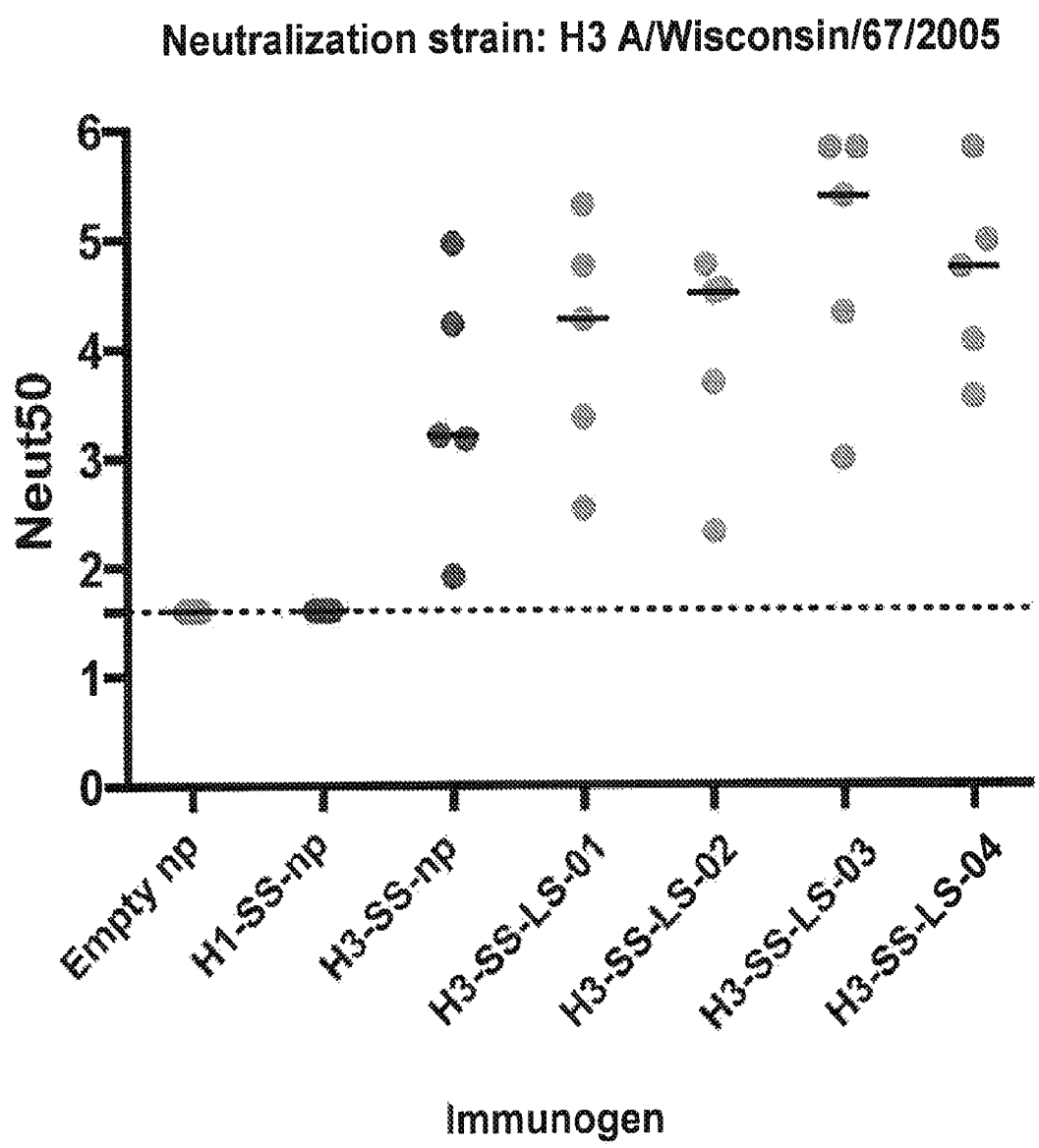
Figure 24A:
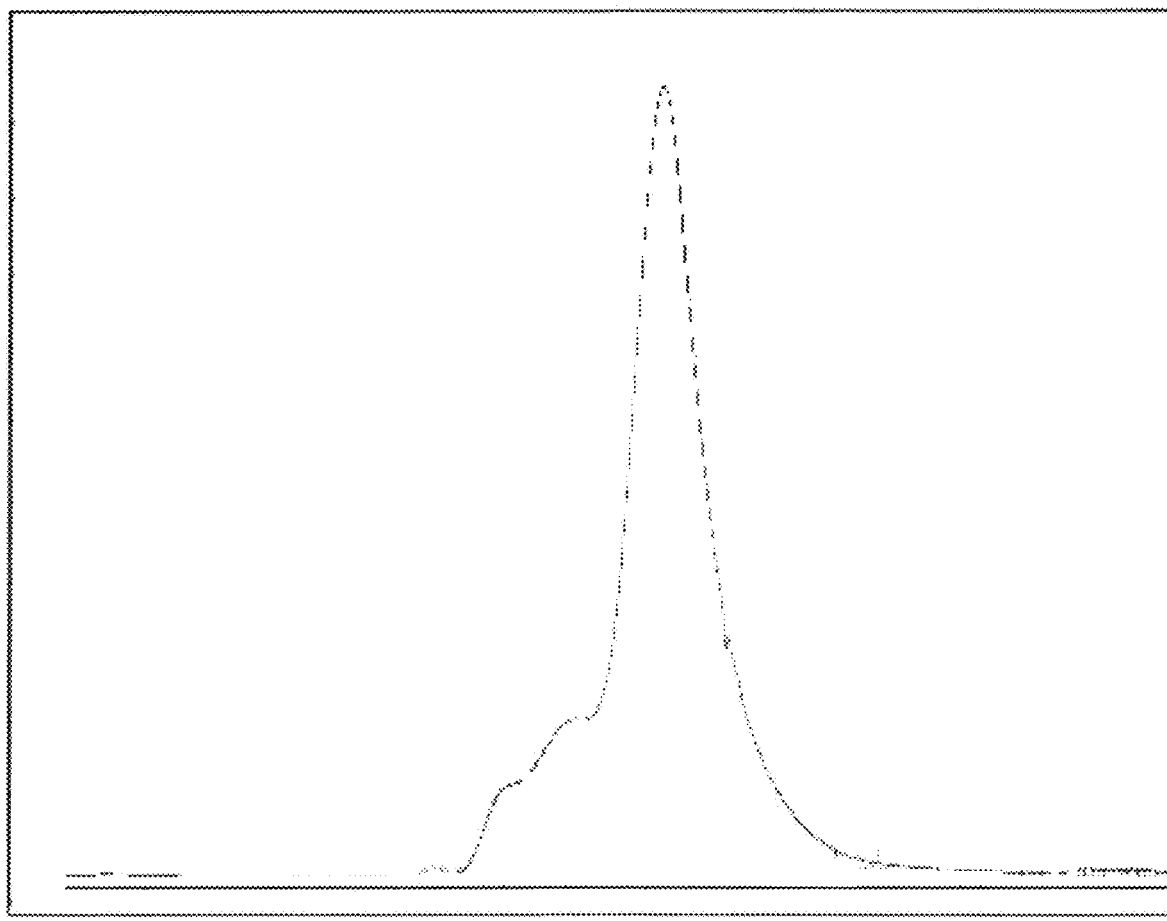
Figure 24B:
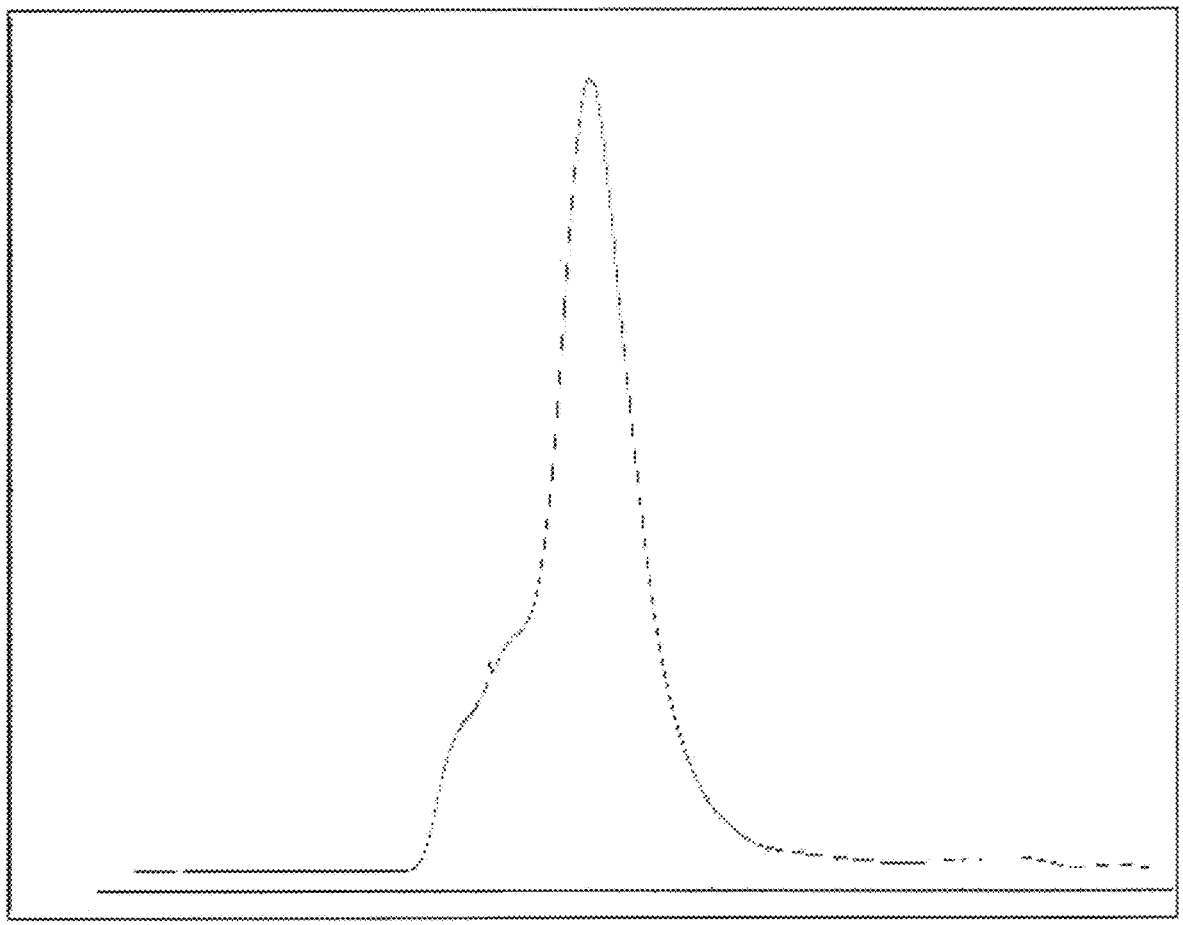
Figure 24C:
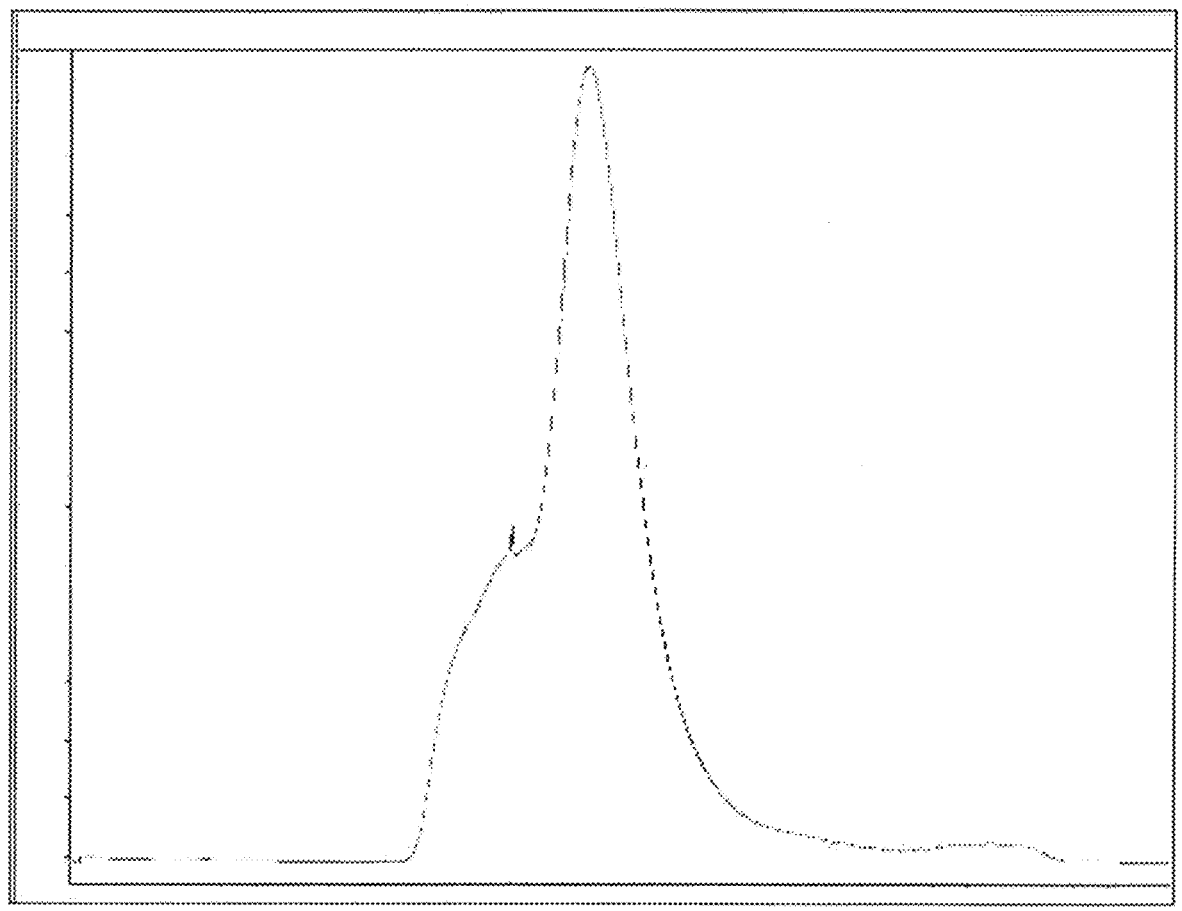
Figure 24E:
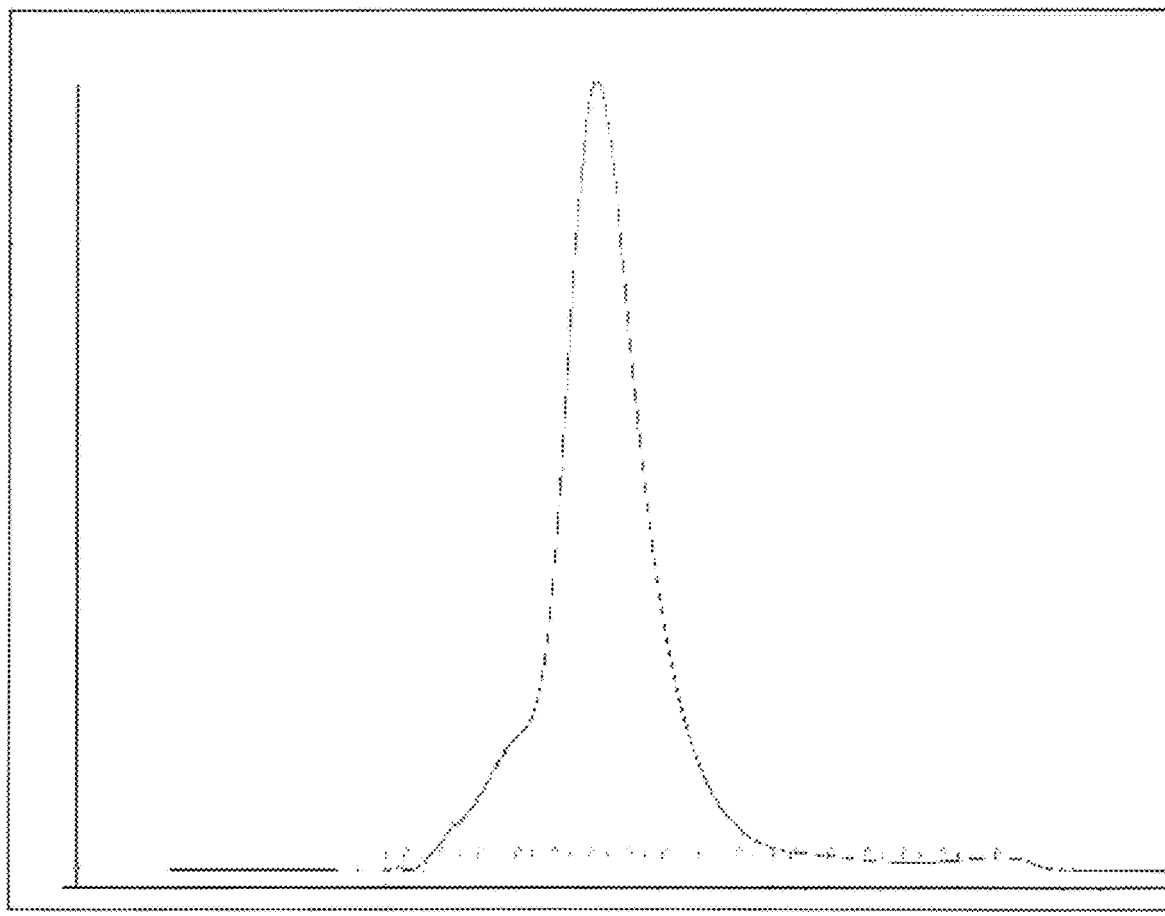
Figure 24F:
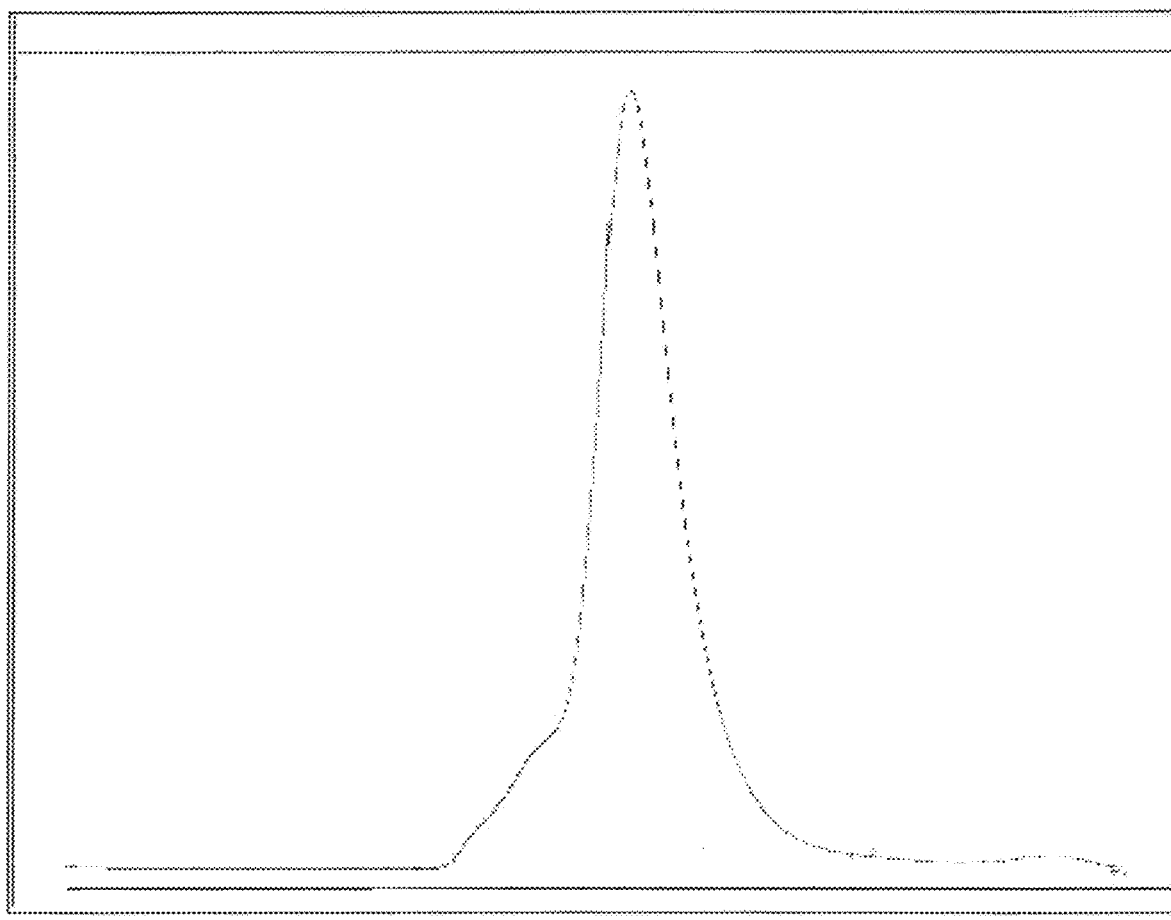
Figure 25C:
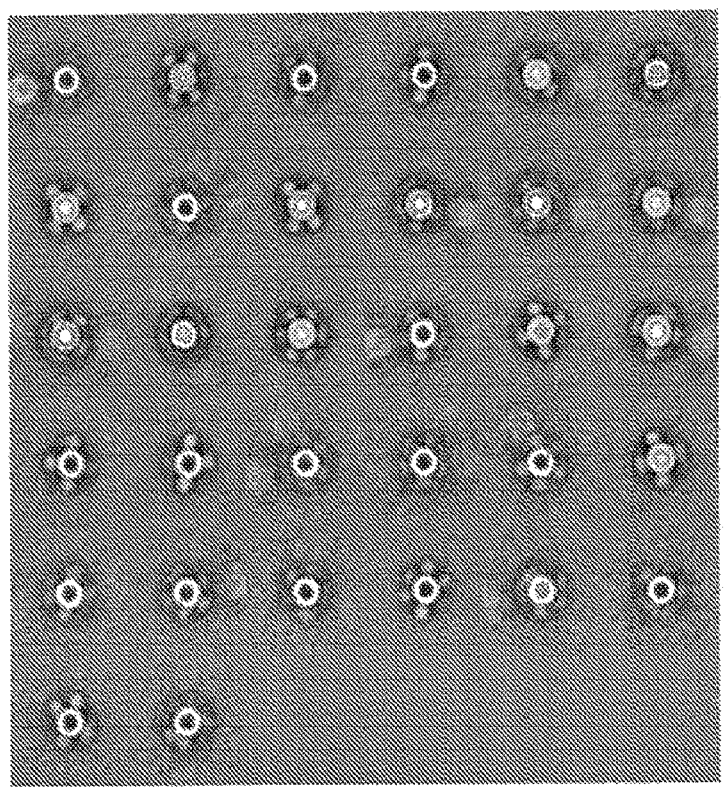
FIG. 25 shows electron microscopy of H7-SS-np. Negative stain electron microscopy 2D class averages of H7-SS-np variants revealing the formation of particles with a visible arrangement of HA stems projecting from hollow spheres. Images for an H1-SS-np particle (upper left panel) are shown as a positive control.
Figure 25D:
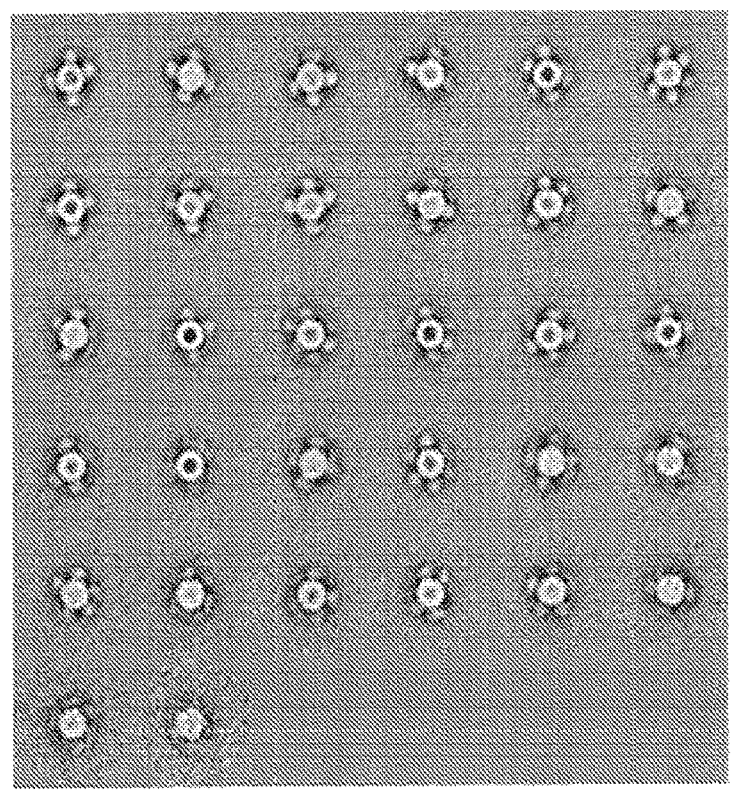
Figure 25G:
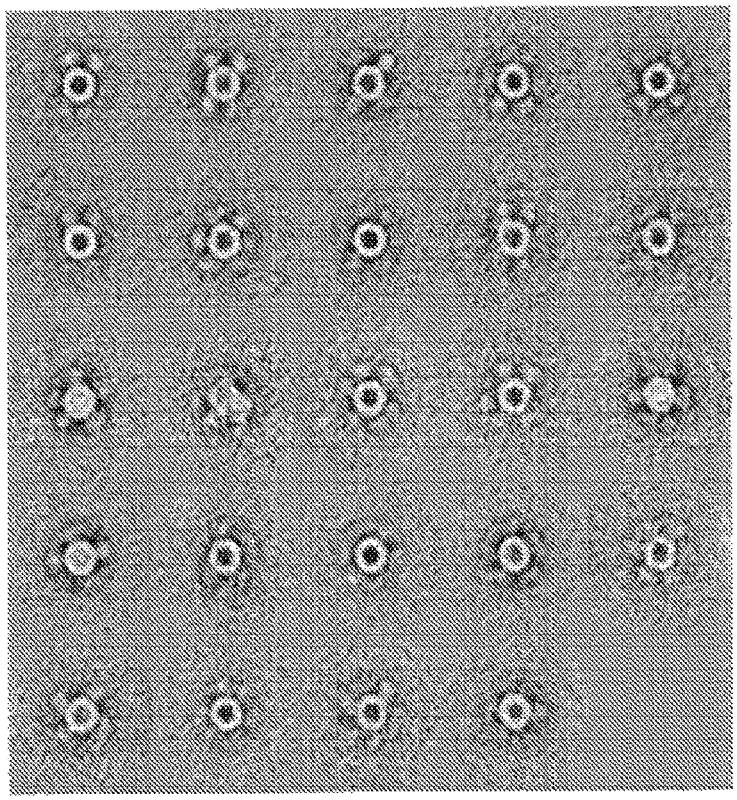
Figure 25H:
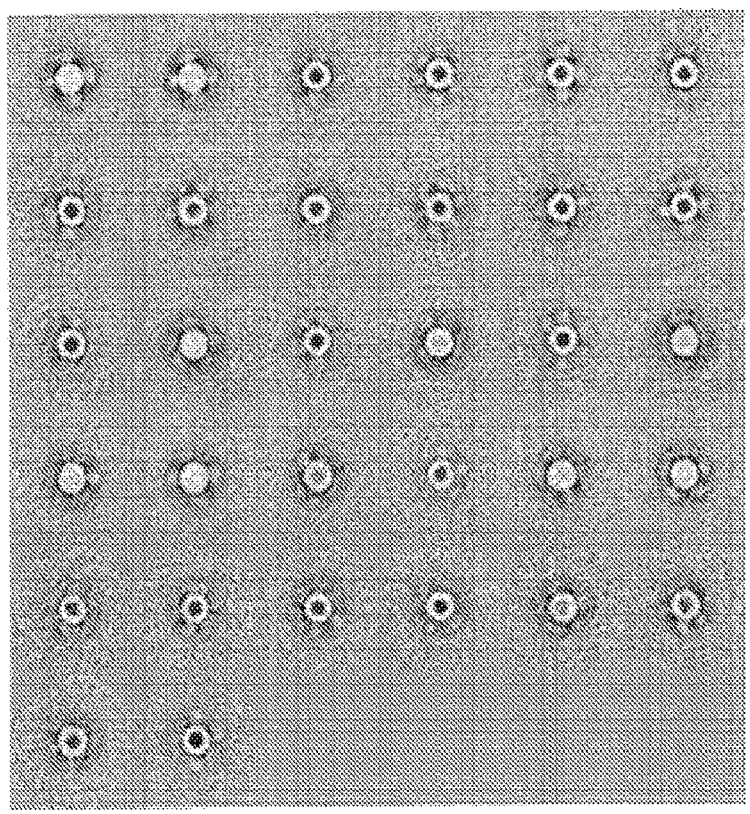
Figure 26C:
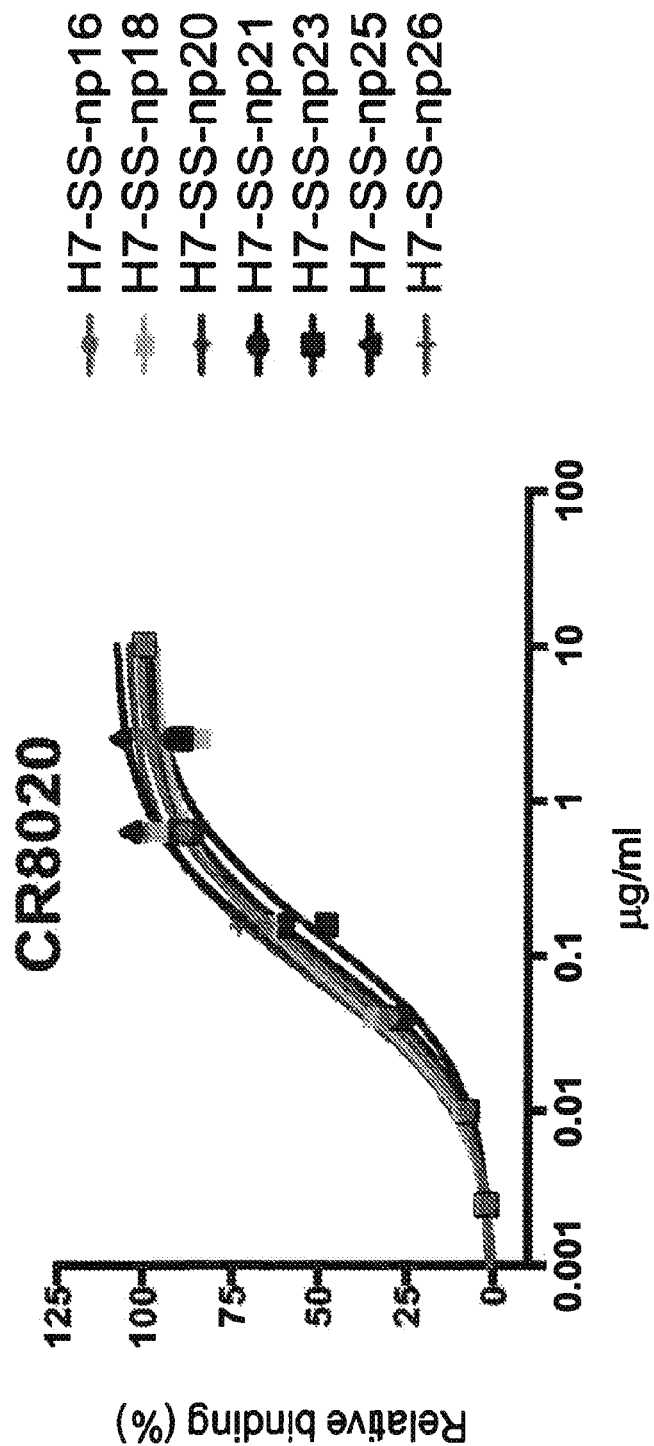
Figure 27B:
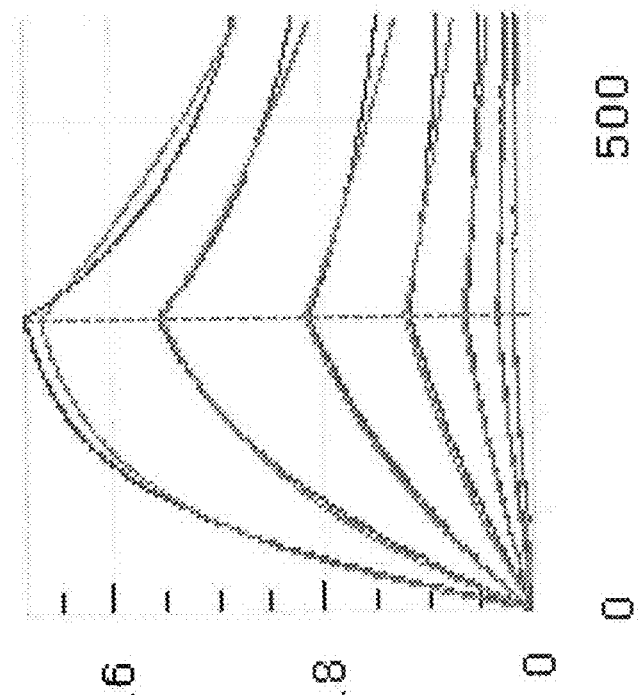
FIG. 27B: H7-SS-18.
Figure 27A:
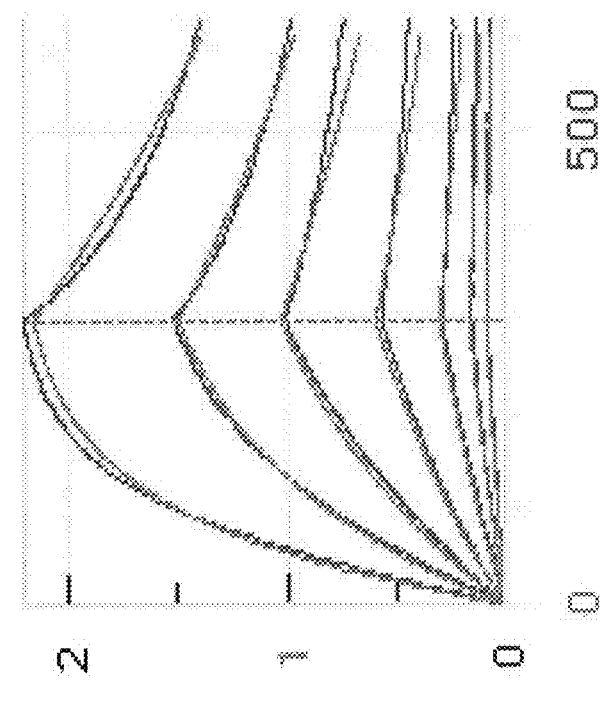
FIG. 27 shows HA stem antibody recognition of H7-SS-np. Biolayer interferometry binding curves for CT149 recognition of six H7-SS-np variants (FIG. 27A: H7-SS-16.
FIG. 27C: H7-SS-21.
FIG. 27D: H7-SS-23.
FIG. 27E: H7-SS-25.
FIG. 27F: H7-SS-26) are shown with the kinetic constants listed to the right of each curve set. Nanoparticles were immobilized to the sensor tip by amine coupling and incubated in various concentrations of antibody Fabs.
Figure 27D:
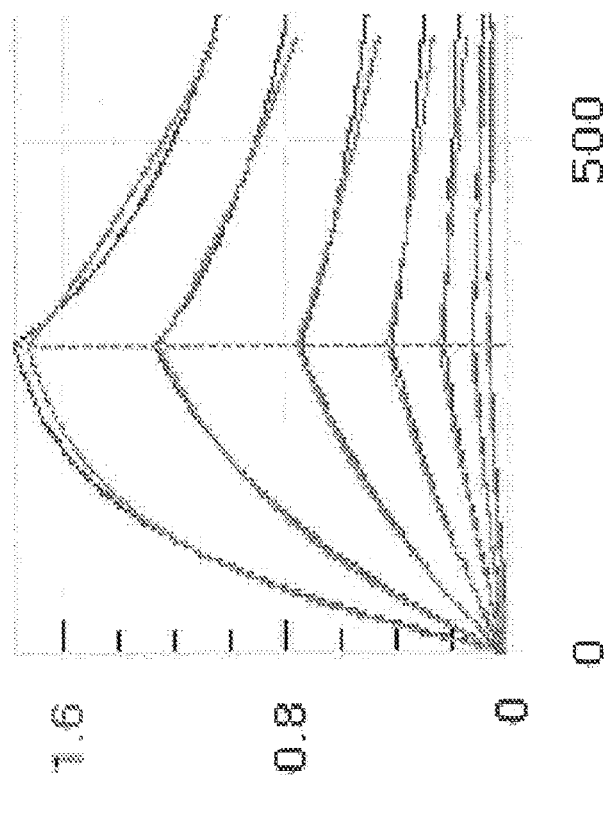
Figure 27C:
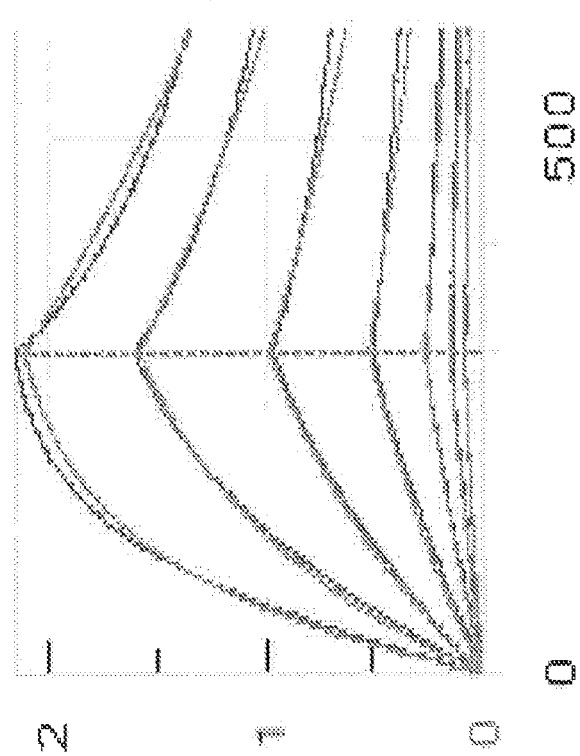
Figure 27F:
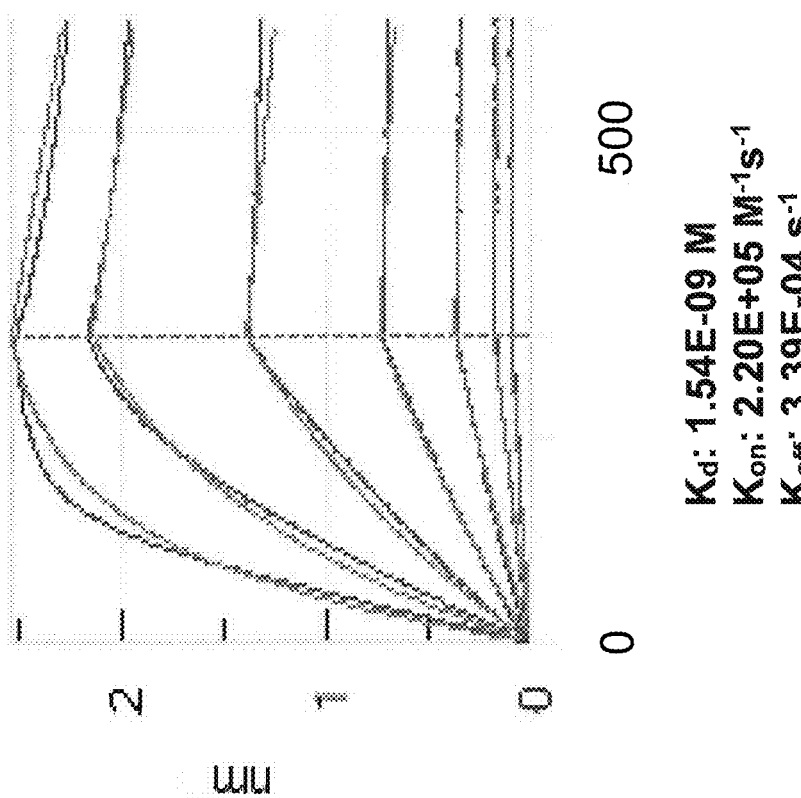
Figure 27E:
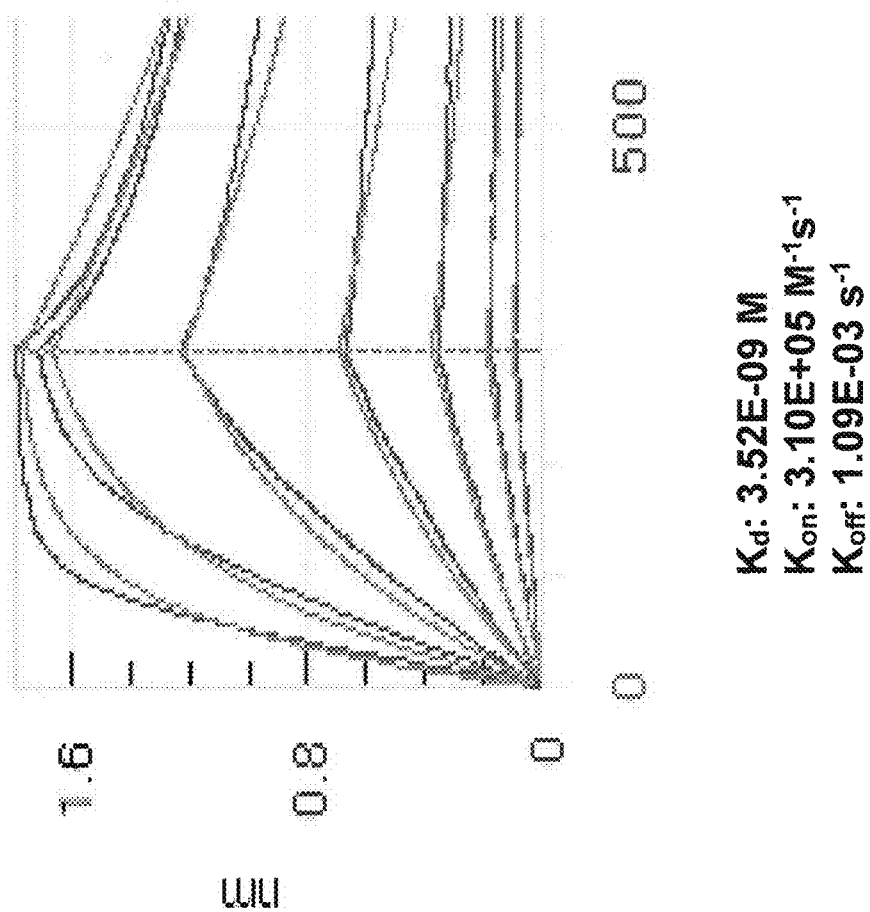
Figure 28:
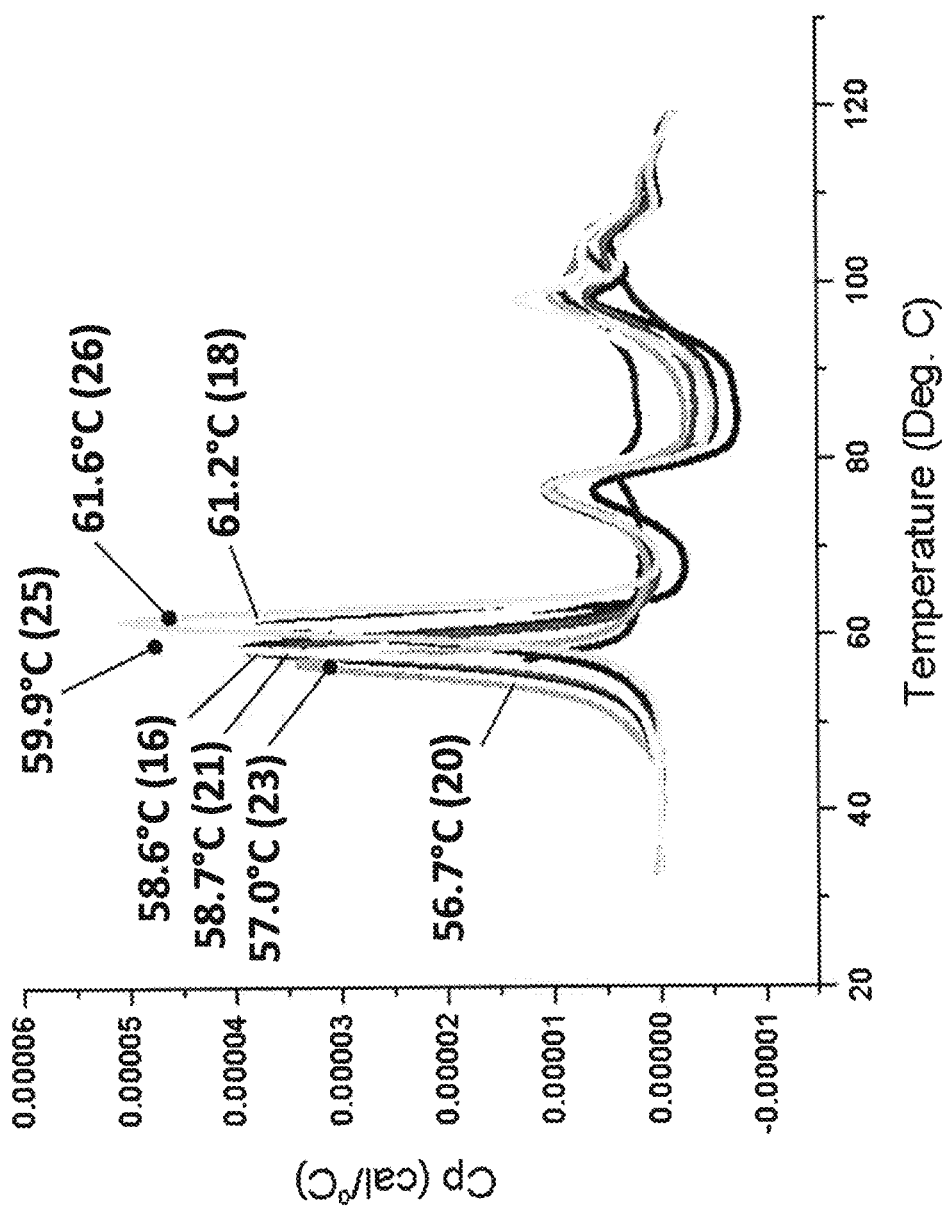
FIG. 28 shows dynamic scanning calorimetry (DSC) plots for seven H7-SS-np variants. Plots of heat capacity (Cp) versus temperature depicts melting transitions for each protein. The earliest melting points (TMs) for each protein are noted and color-coded to match the associated curve. The H7-SS-np design number is shown for each in parentheses. In this diagram, the Cp values on the Y-axis are shown with an arbitrary scale.
Figure 29A:
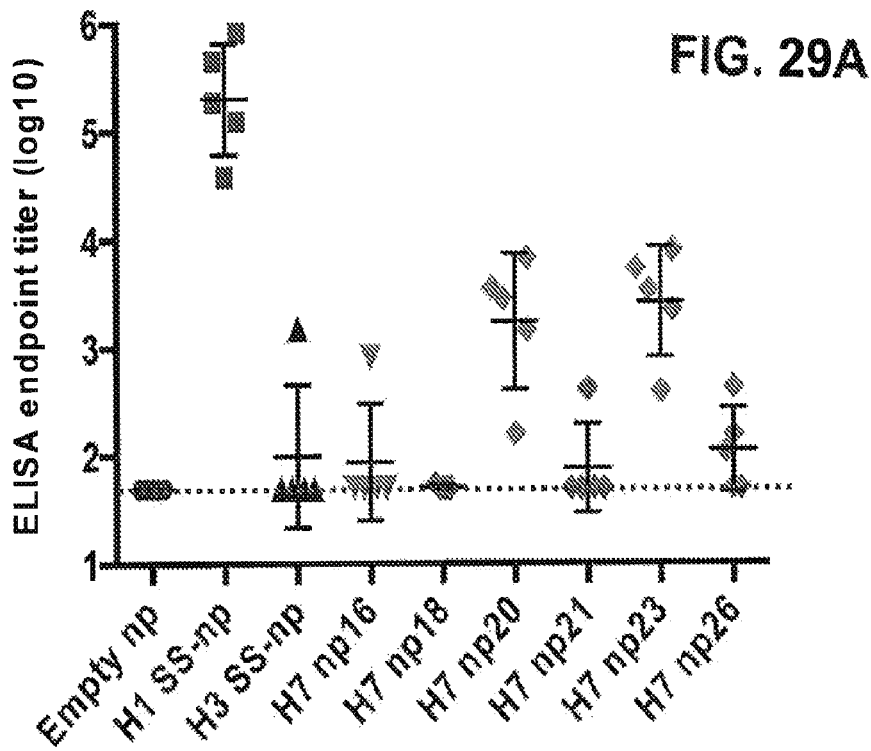
FIGS. 29A-29D show immune responses of H7-SS-np-immunized mice to diverse HAs. ELISA antibody endpoint titers of sera from BALB/c mice (n=5) immunized 3× with six different versions of SAS-adjuvanted H7-SS-np to plated A/New Caledonia/20/1999 (H1N1) HA (FIG. 29A), A/Vietnam/1203/2004 (H5N1) (FIG. 29B), A/Hong Kong/1/1968 (H3N2) (FIG. 29C) and A/Anhui/1/2013 (H7N9) (FIG. 29D). Sera from mice immunized with empty ferritin nanoparticle, H1-SS-np and H3-SS-np (#231) serve as controls. Geometric mean titers are shown by horizontal lines. Horizontal dotted lines indicate the baseline titer of 50.
Figure 29B:
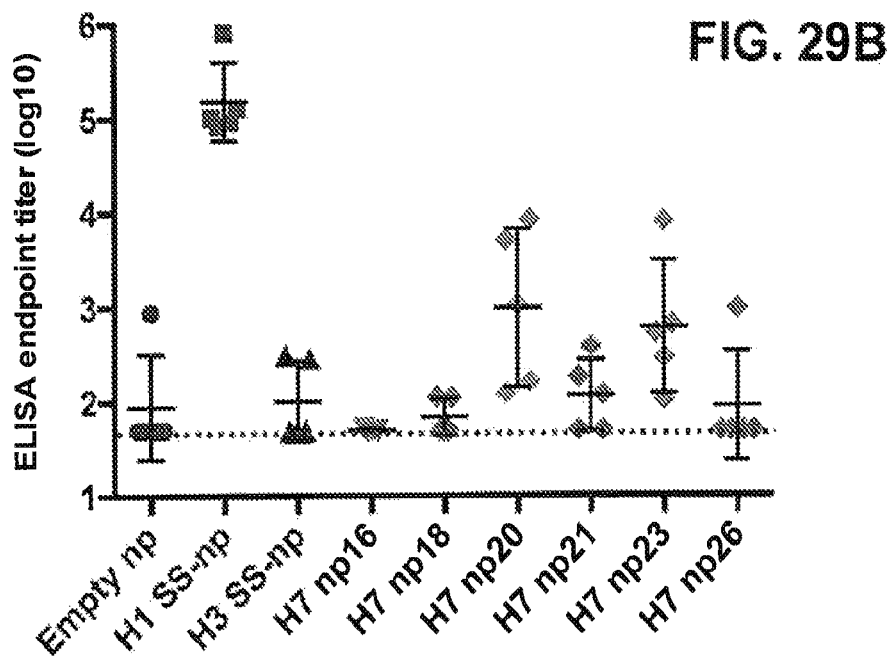
Figure 29C:
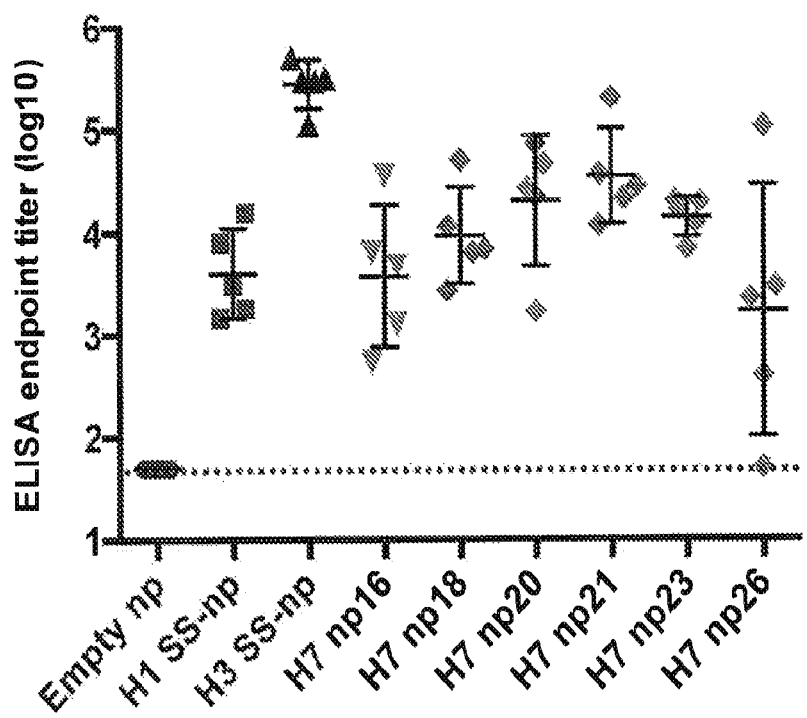
Figure 29D:
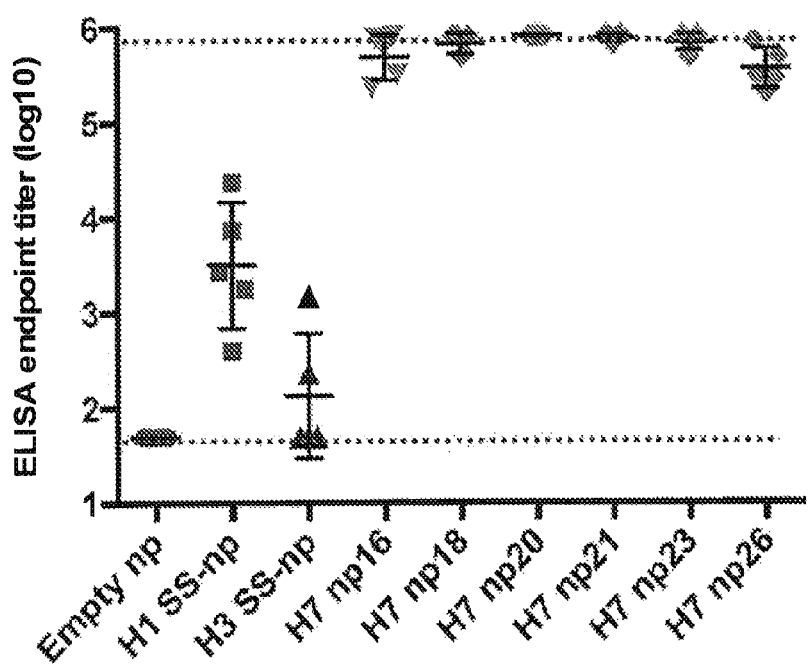
Figure 32A:
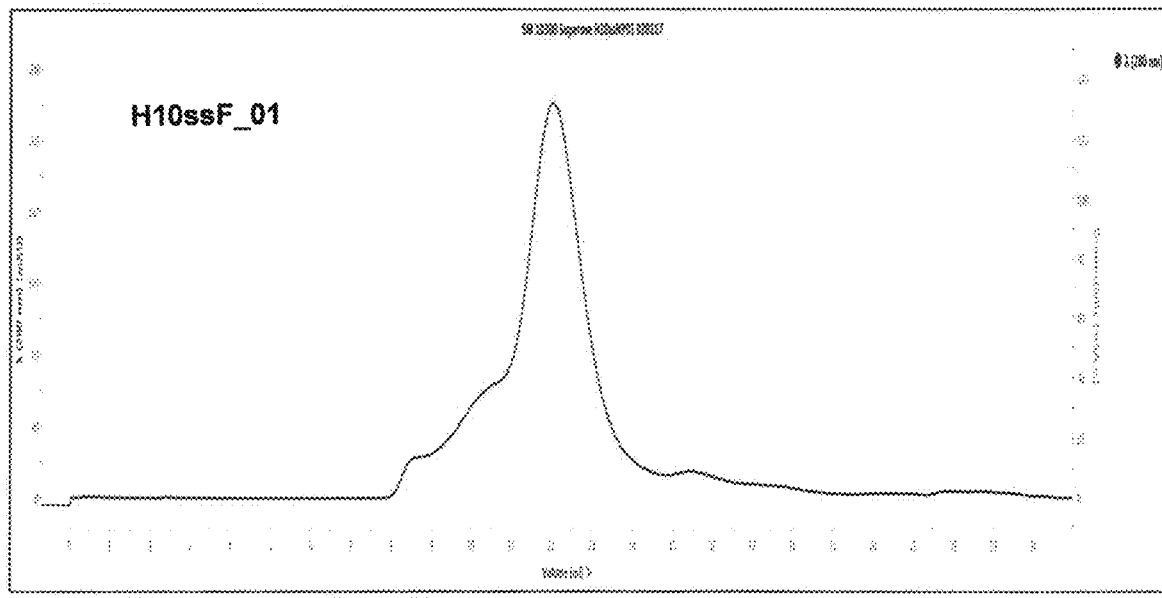
FIGS. 32A-32E show gel filtration Superdex 200 10/30 profiles for H10ssF variants 1 (FIG. 32A), 2 (FIG. 32B) 3 (FIG. 32C), 4 (FIG. 32D) and 5 (FIG. 32E). In each case a single peak was eluted at a volume of approximately 12.5 mls. The final yields from Expi293 cells after gel filtration were 6-8 mg/L of culture.
Figure 32B:
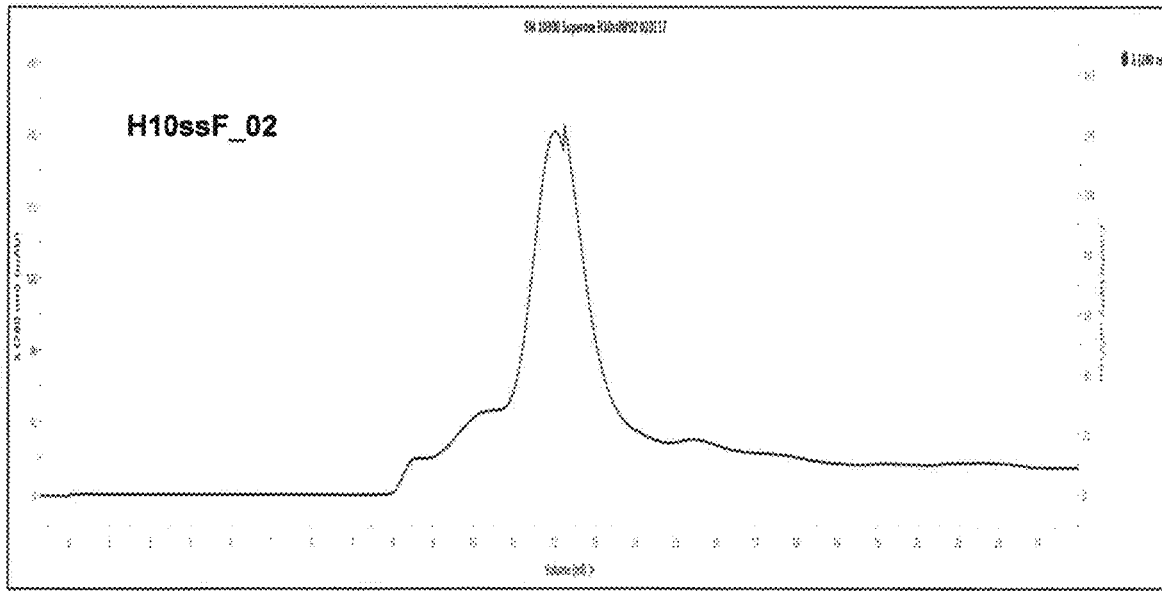
Figure 32C:
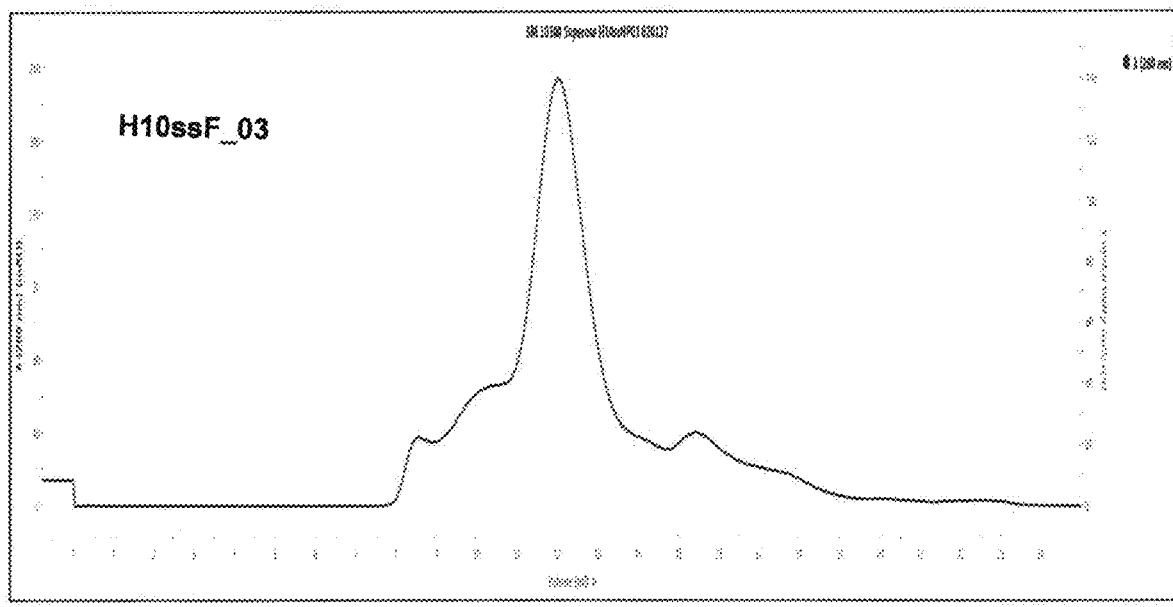
Figure 32D:
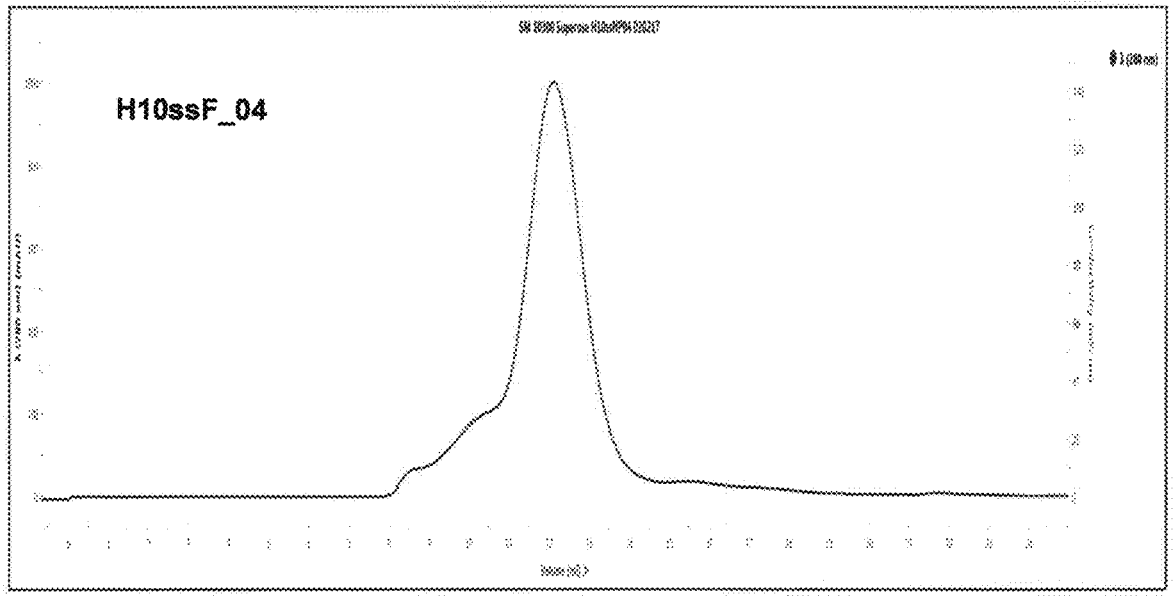
Figure 32E:
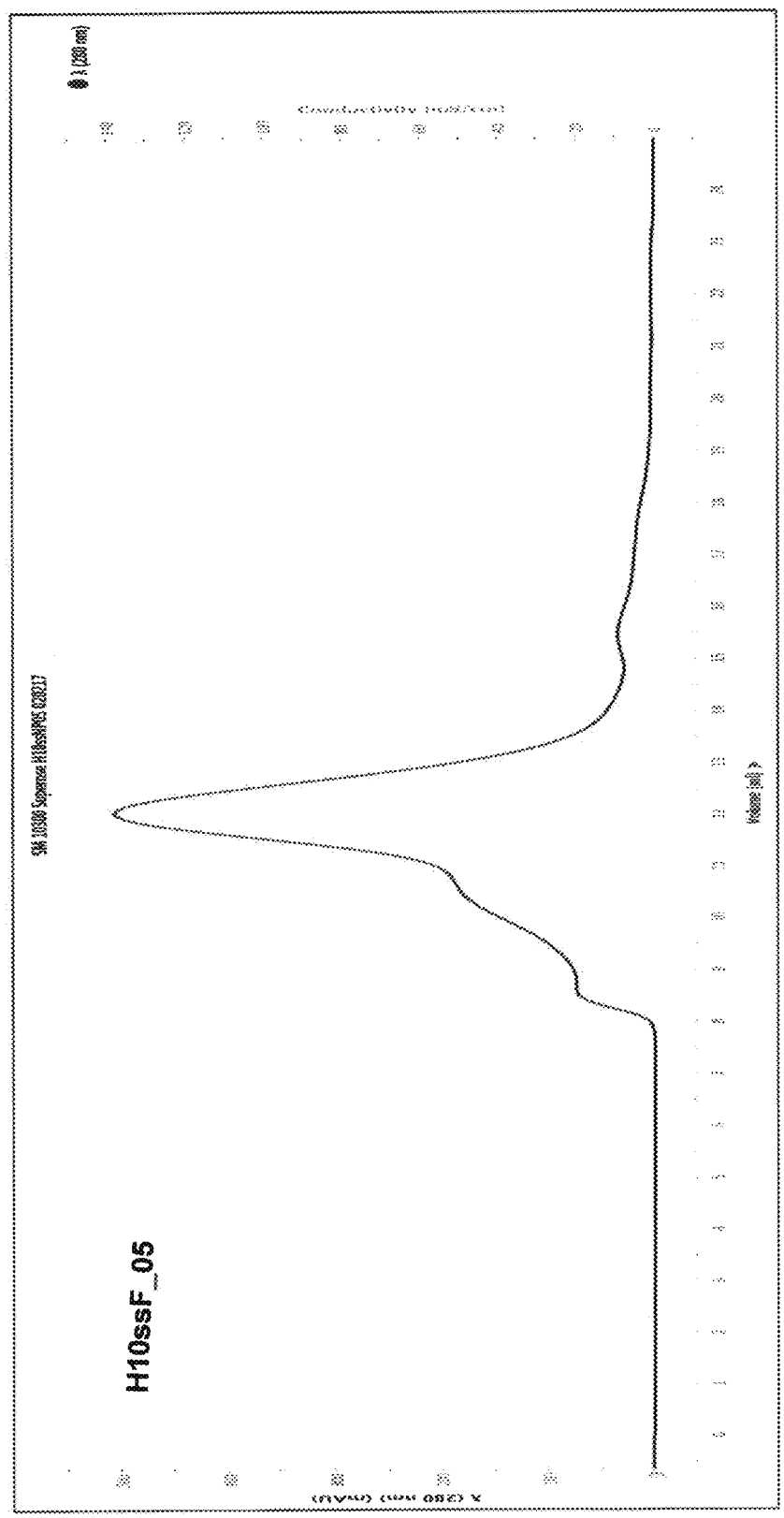
Figure 33A:
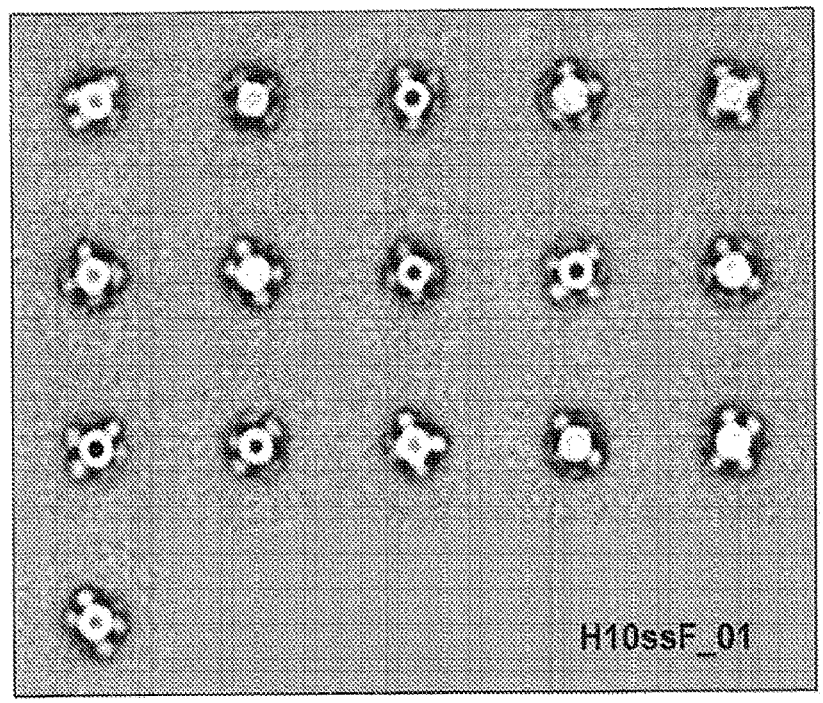
FIG. 33. Electron microscopy of H10ssF nanoparticles variants. Negative stain electron microscopy 2D class averages of H10ssF variants revealing the formation of particles with a visible arrangement of HA stems projecting from hollow spheres.
Figure 33B:
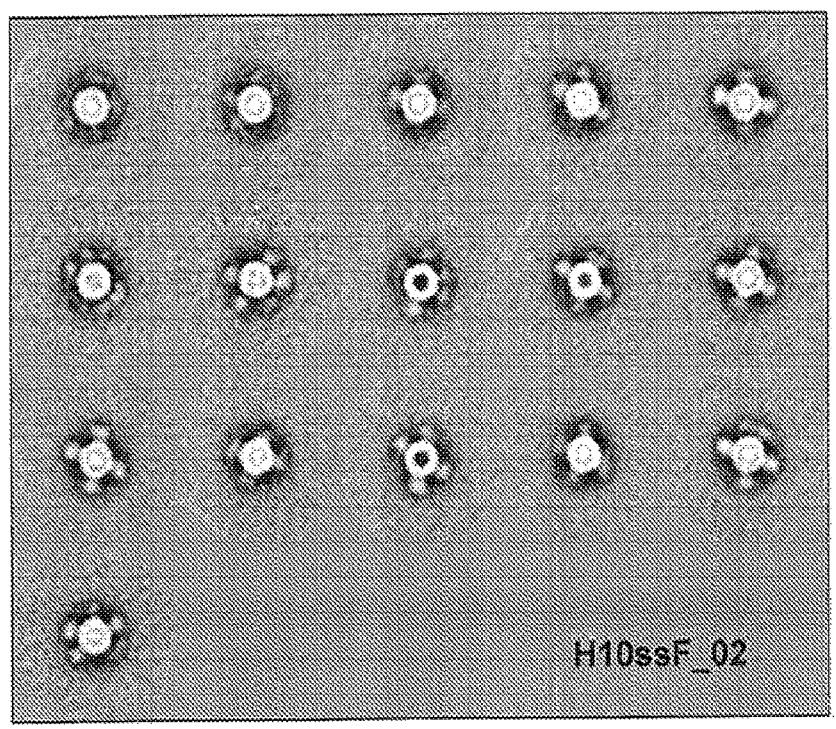
Figure 33C:
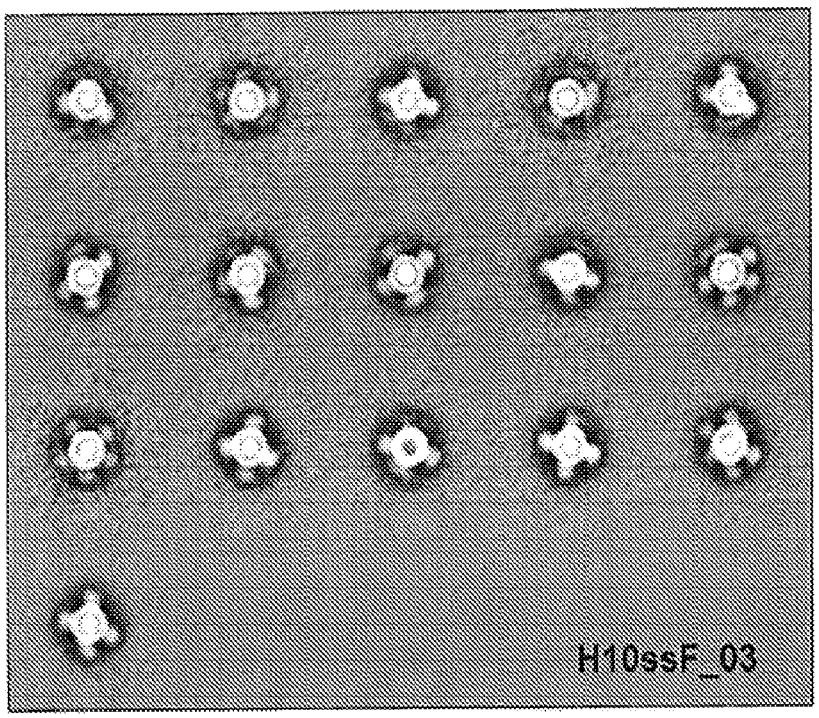
Figure 33D:
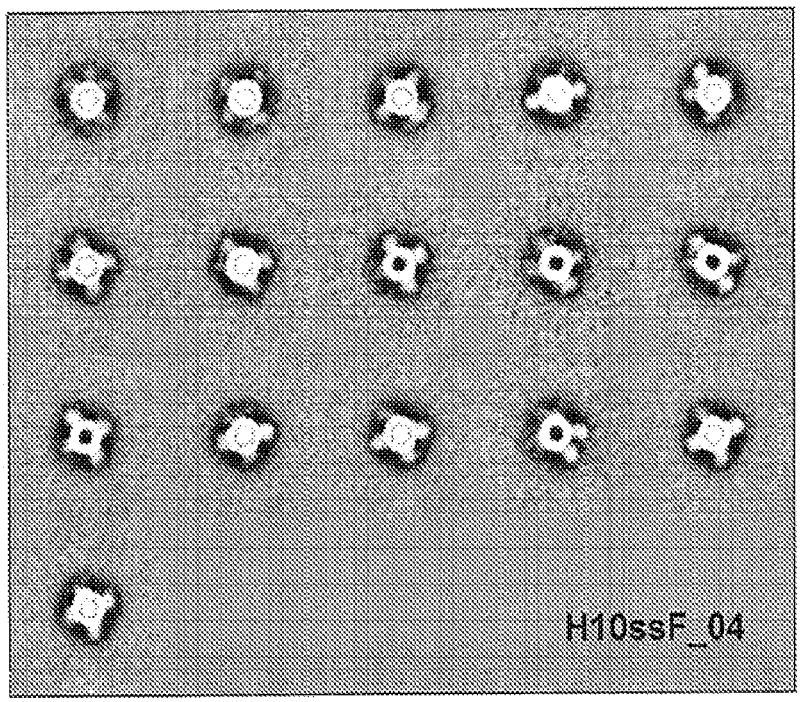
Figure 33E:
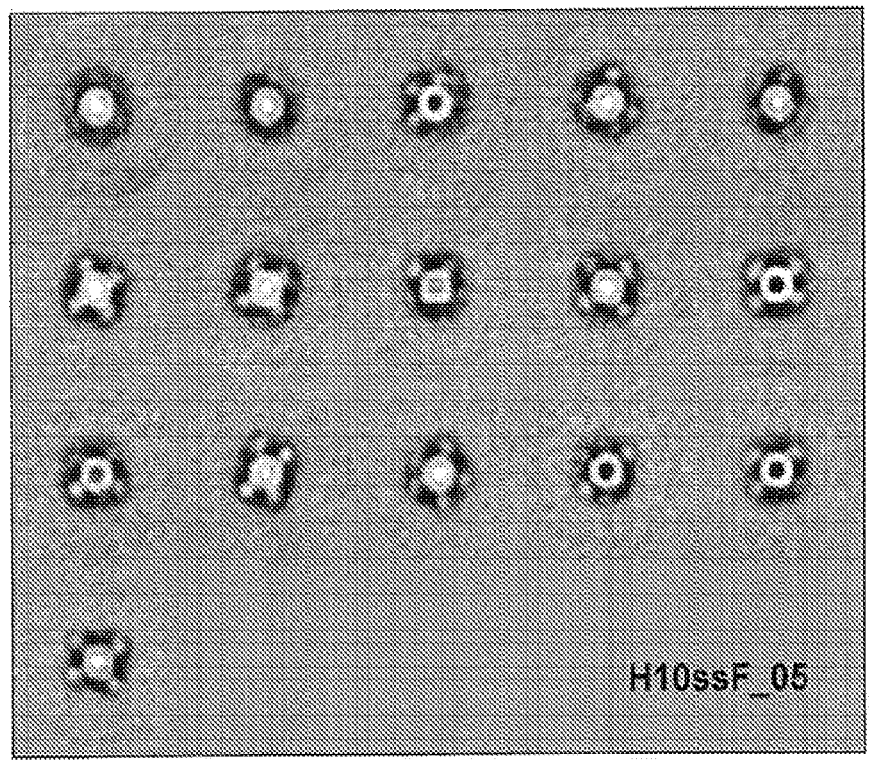
Figures 34C, 34D:
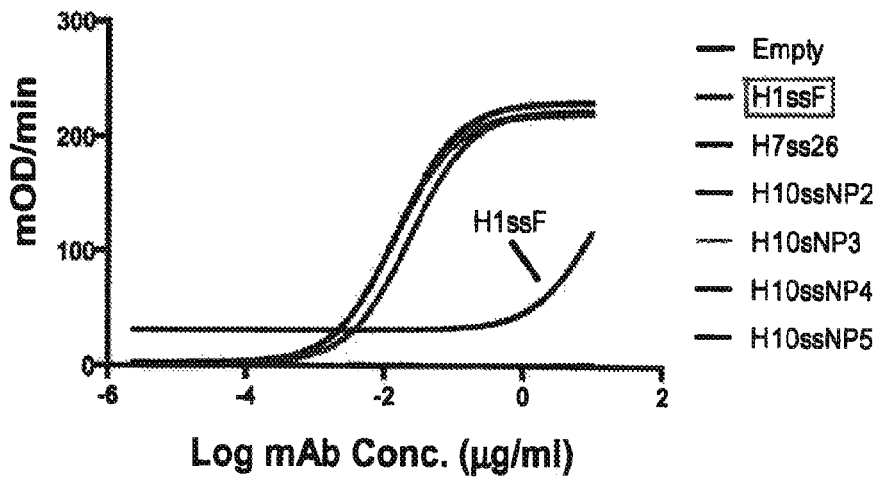

The present invention relates to a novel vaccine for influenza virus. More specifically, the present invention relates to novel, Group 2 influenza HA protein-based vaccines that elicit an immune response against the stem region of the HA protein from a broad range of influenza viruses. It also relates to self-assembling nanoparticles that display immunogenic portions of the pre-fusion conformation of the stem region from the Group 2 influenza HA protein on their surface. Such nanoparticles are useful for vaccinating individuals against influenza virus. Accordingly, the present invention also relates to protein constructs for producing such nanoparticles and nucleic acid molecules encoding such proteins. Additionally, the present invention relates to methods of producing nanoparticles of the present invention, and methods of using such nanoparticles to vaccinate individuals.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly, the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

For convenience, certain abbreviations can be used to refer to protein constructs, and portions thereof, of the invention. For example, HA can refer to influenza hemagglutinin protein, or a portion thereof. HA-SS refers to a stabilized stem region, or a portion of the stem region, from an influenza HA protein. Typically the HA portion of such a designation will refer to the subtype of the hemagglutinin protein. For example, a stabilized stem region from a subtype 3 hemagglutinin can be referred to as H3-SS. A protein construct comprising a HA-SS (e.g., H3-SS) joined to an influenza HA protein transmembrane domain can be referred to as HA-SS-TM (e.g., H3-SS-TM). A protein constructs comprising a HA-SS joined to a ferritin monomeric subunit can be referred to as HA-SS-np. Such a designation may also be followed by a number that indicates a particular construct containing specific alterations (e.g., H3-SS-np_231 (SEQ ID NO:47)). It should be noted that such a construct can also be referred to HAssF (e.g., H3ssF_231). In certain aspects of the invention, a HA-SS is joined to other monomeric subunits, such as, for example, lumazine synthase. Such a construct can be referred to by the designation HA-SS-LS (e.g., H3-SS_LS-01 (SEQ ID NO:83)) or HAssL (e.g., H3ssLS-01 (SEQ ID NO:83)).

In addition to the above, unless specifically defined otherwise, the following terms and phrases, which are common to the various embodiments disclosed herein, are defined as described below.

As used herein, a protein construct is a protein made by the hand of man, in which the amino acid sequence of a protein is modified so that the resulting modified protein comprises a sequence that is not found in nature. Protein constructs include protein in which two or more amino acid sequences have been covalently joined in a way not found in nature. The amino acid sequences being joined can be related or unrelated. As used herein, polypeptide sequences are unrelated, if their amino acid sequences are not normally found joined together via a covalent bond in their natural environment(s) (e.g., inside a cell). For example, the amino acid sequence of a ferritin monomeric subunit, and the amino acid sequence of a Group 2 influenza HA protein are not normally found joined together via a covalent bond. Thus, such sequences are considered unrelated.

Protein constructs can also comprise related amino acid sequences. For example, the structure of the influenza HA protein is such that the head region amino acid sequence is flanked on both ends by stem region amino acid sequences. Through genetic means, it is possible to create a modified version of an HA protein by removing amino acid residues from the middle of the head region, while maintaining a portion of the head region flanked by stem regions sequences. While the order of the sequences in the final molecule would remain the same, the spatial relationship between the amino acids would differ from the natural protein. Thus, such a molecule would be considered a protein construct. According to the present invention, protein constructs may also be referred to as fusion proteins.

Amino acid sequences in a protein construct can be joined directly to each other or they can be joined using a linker. A linker, linker sequence, linker peptide, and the like, is a short (e.g., 2-20) amino acid sequence used to connect two proteins having a desired characteristic (e.g., structure, epitope, immunogenicity, activity, etc.). A linker sequence typically does not have its own activity and is usually used to connect other parts of the protein construct, thereby allowing them to assume a desired conformation. Linker sequences are typically made from small amino acid residues and/or runs thereof, such as, for examples, serine, alanine and glycine, although the use of other amino acid residues is not excluded. For example, it may be desirable to include an amino acid that can form a covalent bond, such as a cysteine residue, in the linker sequence.

As used herein, the term immunogenic refers to the ability of a specific protein, or a specific region thereof, to elicit an immune response to the specific protein, or to proteins comprising an amino acid sequence having a high degree of identity with the specific protein. According to the present invention, two proteins having a high degree of identity have amino acid sequences at least 80% identical, at least 85% identical, at least 87% identical, at least 90% identical, at least 92% identical, at least 93% identical, at least 94% identical, at least 95% identical, at least 96% identical, at least 97% identical, at least 98% identical or at least 99% identical. Methods of determining the percent identity between two amino acid or nucleic acid sequence are known in the art.

As used herein, an immune response to a vaccine, or nanoparticle, of the present invention is the development in a subject of a humoral and/or a cellular immune response to a Group 2 HA protein present in the vaccine. For purposes of the present invention, a "humoral immune response" refers to an immune response mediated by antibody molecules, including secretory (IgA) or IgG molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+ T-cells.

Thus, an immunological response may be one that stimulates CTLs, and/or the production or activation of helper T-cells. The production of chemokines and/or cytokines may also be stimulated. The vaccine may also elicit an antibody-mediated immune response. Hence, an immunological response may include one or more of the following effects: the production of antibodies (e.g., IgA or IgG) by B-cells; and/or the activation of suppressor, cytotoxic, or helper T-cells and/or T-cells directed specifically to a Group 2 HA protein present in the vaccine. These responses may serve to neutralize infectivity (e.g., antibody-dependent protection), and/or mediate antibody-complement, or antibody dependent cell cytotoxicity (ADCC) to provide protection to an immunized individual. Such responses can be determined using standard immunoassays and neutralization assays, well known in the art.

As used herein, the term antigenic, antigenicity, and the like, refers to a protein that is bound by an antibody or a group of antibodies. Similarly, an antigenic portion of a protein is any portion that is recognized by an antibody or a group of antibodies. According to the present invention, recognition of a protein by an antibody means the antibody selectively binds to the protein. As used herein, the phrase selectively binds, selective binding, and the like, refer to the ability of an antibody to preferentially bind an HA protein as opposed to binding proteins unrelated to HA, or non-protein components in the sample or assay. An antibody that preferentially binds HA is one that binds HA but does not significantly bind other molecules or components that may be present in the sample or assay. Significant binding is considered, for example, binding of an anti-HA antibody to a non-HA molecule with an affinity or avidity great enough to interfere with the ability of the assay to detect and/or determine the level of anti-influenza antibodies, or HA protein, in the sample. Examples of other molecules and compounds that may be present in the sample, or the assay, include, but are not limited to, non-HA proteins, such as albumin, lipids and carbohydrates. According to the present invention, a non-HA protein is a protein having an amino acid sequence sharing less than 60% identity with the sequence of an influenza HA protein disclosed herein. In some embodiments, the antibody or antibodies provide broad heterosubtypic protection. In some embodiments, the antibody or antibodies are neutralizing.

As used herein, neutralizing antibodies are antibodies that prevent influenza virus from completing one round of replication. As defined herein, one round of replication refers the life cycle of the virus, starting with attachment of the virus to a host cell and ending with budding of newly formed virus from the host cell. This life cycle includes, but is not limited to, the steps of attaching to a cell, entering a cell, cleavage and rearrangement of the HA protein, fusion of the viral membrane with the endosomal membrane, release of viral ribonucleoproteins into the cytoplasm, formation of new viral particles and budding of viral particles from the host cell membrane. According to the present invention, a neutralizing antibody is one that inhibits one or more such steps.

As used herein, broadly neutralizing antibodies are antibodies that neutralize more than one type, subtype and/or strain of influenza virus. For example, broadly neutralizing antibodies elicited against an HA protein from a Type A influenza virus may neutralize a Type B or Type C virus. As a further example, broadly neutralizing antibodies elicited against an HA protein from Group 2 influenza virus may neutralize a Group 1 virus. As an additional example, broadly neutralizing antibodies elicited against an HA protein from one sub-type or strain of virus, may neutralize another sub-type or strain of virus. For example, broadly neutralizing antibodies elicited against an HA protein from an H3 influenza virus may neutralize viruses from one or more sub-types selected from the group consisting of H1, H2, H4, H5, H6, H7, H8, H8, H10, H11, H12, H13, H14, H15, H16, H17 or H18.

According to the present invention all nomenclature used to classify influenza virus is that commonly used by those skilled in the art. Thus, a Type, or Group, of influenza virus refers to influenza Type A, influenza Type B or influenza type C. It is understood by those skilled in the art that the designation of a virus as a specific Type relates to sequence difference in the respective M1 (matrix) protein or NP (nucleoprotein). Type A influenza viruses are further divided into Group 1 and Group 2. These Groups are further divided into subtypes, which refers to classification of a virus based on the sequence of its HA protein. Examples of current commonly recognized subtypes are H1, H2, H3, H4, H5, H6, H7, H8, H8, H10, H11, H12, H13, H14, H15, H16, H17 or H18. Group 1 influenza subtypes are H1, H2, H5, H6, H8, H9, H11, H12, H13, H16, H17 and H18. Group 2 influenza subtypes are H3, H4, H7, H10, H14, and H15. Finally, the term strain refers to viruses within a subtype that differ from one another in that they have small, genetic variations in their genome.

As used herein, an influenza hemagglutinin protein, or HA protein, refers to a full-length influenza hemagglutinin protein or any portion thereof, that is useful for producing protein constructs and nanoparticles of the invention or that are capable of eliciting an immune response. Preferred HA proteins are those that are capable of forming a trimer. An epitope of a full-length influenza HA protein refers to a portion of such protein that can elicit an antibody response against the homologous influenza strain, i.e., a strain from which the HA is derived. In some embodiments, such an epitope can also elicit an antibody response against a heterologous influenza strain, i.e., a strain having an HA that is not identical to that of the HA of the immunogen. In some embodiments, the epitope elicits a broadly heterosubtypic protective response. In some embodiments, the epitope elicits neutralizing antibodies.

As used herein, a variant refers to a protein, or nucleic acid molecule, the sequence of which is similar, but not identical to, a reference sequence, wherein the activity of the variant protein (or the protein encoded by the variant nucleic acid molecule) is not significantly altered. These variations in sequence can be naturally occurring variations or they can be engineered through the use of genetic engineering technique known to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as the resulting variant protein retains the ability to elicit neutralizing or non-neutralizing antibodies against an influenza virus. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxyl terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein. In variants into which insertions have been made, the inserted amino acids may be referred to by referencing the amino acid residue after which the insertion was made. For example, an insertion of four amino acid residues after amino acid residue 402 could be referred to as 402a-402d. Moreover, if one of those inserted amino acids are later substituted with another amino acid, such a change can be referred to by reference to the letter position. For example, substitution of an inserted glycine (in the further position of the insert) with a threonine can be referred to as S402dT.

As noted, variant proteins of the present invention can contain amino acid substitutions relative to the influenza HA proteins disclosed herein. Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:
1) hydrophobic: Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological invention, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the HA protein, or to increase or decrease the immunogenicity, solubility or stability of the HA proteins described herein. Exemplary amino acid substitutions are shown below in Table 1.

TABLE 1

Amino Acid Substitutions

| Original Amino Acid | Exemplary Substitutions |
| --- | --- |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase "significantly affect a protein activity" refers to a decrease in the activity of a protein by at least 10%, at least 20%, at least 30%, at least 40% or at least 50%. With regard to the present invention, such an activity may be measured, for example, as the ability of a protein to elicit protective antibodies against an influenza virus. Such activity may be measured by measuring the titer of such antibodies against influenza virus, the ability of such antibodies to protect against influenza infection or by measuring the number of types, subtypes or strains neutralized by the elicited antibodies. Methods of determining antibody titers, performing protection assays and performing virus neutralization assays are known to those skilled in the art. In addition to the activities described above, other activities that may be measured include the ability to agglutinate red blood cells and the binding affinity of the protein for a cell. Methods of measuring such activities are known to those skilled in the art.

The terms individual, subject, and patient are well-recognized in the art, and are herein used interchangeably to refer to any human or other animal susceptible to influenza infection. Examples include, but are not limited to, humans and other primates, including non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European. An infected subject is a subject that is known to have influenza virus in their body.

As used herein, a vaccinated subject is a subject that has been administered a vaccine that is intended to provide a protective effect against an influenza virus.

As used herein, the terms exposed, exposure, and the like, indicate the subject has come in contact with a person of animal that is known to be infected with an influenza virus.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

One embodiment of the present invention is a protein construct comprising a Group 2 influenza HA protein wherein the head region of the Group 2 influenza HA protein has been replaced with an amino acid sequence comprising less than 5 contiguous amino acid residues from the head region of an influenza HA protein. As used herein, a Group 2 HA protein, refers to a full-length influenza HA protein from a Group 2 influenza virus, or any portion/portions and/or variants thereof, that is/are useful for producing protein constructs and nanoparticles of the invention. Accordingly, the present invention is drawn to molecules that are capable of eliciting an immune response to the stem region of a Group 2 influenza HA protein. In some embodiments, the sequence of the HA protein construct has been further altered (i.e., mutated) to stabilize the stem region of the protein in a form that can be presented to the immune system. Examples of Group 2 influenza HA proteins useful for practicing the invention, and protein constructs made therefrom, are shown in Table 2, below.

TABLE 2

| PCT SEQ ID NO | Comments |
|---|---|
| | Monomeric Subunit Proteins |
| 1 | Amino acid sequence of ferritin monomeric subunit protein from *H. pylori*,<br>MLSDIIKLLNEQVNKEMQSSNLYMSMSSWCYTHSLDGAGLFLFDHAAEEYE<br>HAKKLIIFLNENNVPVQLTSISAPEHKFEGLTQIFQKAYEHEQHISESINN<br>IVDHAIKSKDHATFNFLQWYVAEQHEEEVLFKDILDKIELIGNENHGLYLA<br>DQYVKGIAKSRKSGS |
| 2 | amino acids 4-168 from SEQ ID NO: 2; Asn19 has been replaced with Gln,<br>DIIKLLNEQVNKEMQSSNLYMSMSSWCYTHSLDGAGLFLFDHAAEEYEHAK<br>KLIIFLNENNVPVQLTSISAPEHKFEGLTQIFQKAYEHEQHISESINNIVD<br>HAIKSKDHATFNFLQWYVAEQHEEEVLFKDILDKIELIGNENHGLYLADQY<br>VKGIAKSRKSGS |
| 3 | Amino acid sequence of lumazine synthase from aquifex aeolicus,<br>MQIYEGKLTAEGLRFGIVASRFNHALVDRLVEGAIDCIVRHGGREEDITLV<br>RVPGSWEIPVAAGELARKEDIDAVIAIGVLIRGATPHFDYIASEVSKGLAD<br>LSLELRKPITFGVITADTLEQAIERAGTKHGNKGWEAALSAIEMANLFKSL<br>R |

TABLE 2-continued

| PCT SEQ ID NO | Comments |
|---|---|
| | FULL LENGTH HA |
| 4 | amino acid sequence of hemagglutinin protein from influenza A virus (A/Denmark/35/2005 (H3N2)); GenBank: ABU92694.1 |
| 5 | amino acid sequence of hemagglutinin protein from influenza A virus (A/Bangladesh/558/2012 (H3N2)); Accession: AJB43527.1 |
| 6 | amino acid sequence of hemagglutinin protein from influenza A virus (A/Sao Paulo/89403/2010 (H3N2)); Accession: AET10116.1 |
| 7 | amino acid sequence of hemagglutinin protein from influenza A virus (A/Bangladesh/541/2012 (H3N2)); Accession: AJB43525.1 |
| 8 | amino acid sequence of hemagglutinin protein from influenza A virus (A/Bangladesh/542/2012(H3N2)); Accession: AJB43524.1 |
| 9 | amino acid sequence of hemagglutinin protein from influenza A virus (A/Tocantins/979/2010 (H3N2)); Accession: AET10115.1 |
| 10 | amino acid sequence of hemagglutinin protein from influenza A virus (A/Tunisia/17332/2011 (H3N2)); Accession: AFV68725.1 |
| 11 | amino acid sequence of hemagglutinin protein from influenza A virus (A/Norway/88/2003 (H3N2)); Accession: ABR14669.1 |
| 12 | amino acid sequence of hemagglutinin protein from influenza A virus (A/Japan/AF2844/2012 (H3N2)); Accession: AFH57071.1 |
| 13 | amino acid sequence of hemagglutinin protein from influenza A virus (A/Texas/2977/2012(H3N2)); Accession: AFM45466.1 |
| 14 | amino acid sequence of hemagglutinin protein from influenza A virus (A/North Carolina/AF2716/2011 (H3N2)); Accession: ADY05375.1 |
| 15 | amino acid sequence of hemagglutinin protein from influenza A virus (A/Norway/70/2005 (H3N2)); Accession: ABI22080.1 |
| 16 | amino acid sequence of hemagglutinin protein from influenza A virus (A/duck/Chiba/24-203-44/2012 (H7N1)); Accession: BAN16716.1 |
| 17 | amino acid sequence of hemagglutinin protein from influenza A virus (A/chicken/Germany/2003 (H7N7)); Accession: CAG28959.1 |
| 18 | amino acid sequence of hemagglutinin protein from influenza A virus (A/chicken/Italy/444/1999 (H7N1)); Accession: CAG28956.1 |
| 19 | amino acid sequence of hemagglutinin protein from influenza A virus (A/mallard/Italy/4810-7/2004 (H7N7)); Accession: ABG57092.1 |
| 20 | amino acid sequence of hemagglutinin protein from influenza A virus (A/Anhui/DEWH72-03/2013 (H7N9)); Accession: AHZ39710.1 |
| 21 | amino acid sequence of hemagglutinin protein from influenza A virus (A/Shanghai/JS01/2013 (H7N9)); Accession: AGW82612.1 |
| 22 | amino acid sequence of hemagglutinin protein from influenza A virus (A/Guangdong/02/2013 (H791)); Accession: AHD25003.1 |
| 23 | amino acid sequence of hemagglutinin protein from influenza A virus (A/Shenzhen/SP44/2014 (H7N9)); Accession: AJJ91957.1 |
| 24 | amino acid sequence of hemagglutinin protein from influenza A virus (A/Beijing/3/2013 (H7N9)); Accession: AHM24224.1 |
| 25 | amino acid sequence of hemagglutinin protein from influenza A virus (A/Hong Kong/470129/2013 (H7N9)); Accession: AHF20528.1 |
| 26 | amino acid sequence of hemagglutinin protein from influenza A virus (A/Jiangxi/IPB13/2013 (H10N8; Accession: AHK10761.1) |

TABLE 2-continued

| PCT SEQ ID NO | Comments |
|---|---|
| | Flanking Sequences |
| 27 | Amino acid sequence flanking amino-terminal end of head region from influenza virus A (Denmark/35/2005 (H3N2))-full(aa1-59)<br>MKTIIALSYILCLVFAQKLPGNDNSTATLCLGHHAVPNGTIVKTITNDQIE VTNATELV |
| 28 | Amino acid sequence flanking amino-terminal end of head region from influenza virus A (Denmark/35/2005 (H3N2))-partial (40 aa's)<br>PGNDNSTATLCLGHHAVPNGTIVKTITNDQIEVTNATELV |
| 29 | Amino acid sequence flanking amino-terminal end of head region from influenza virus A (Denmark/35/2005 (H3N2))-partial (25 aa's)<br>AVPNGTIVKTITNDQIEVTNATELV |
| 30 | Amino acid sequence of stem region flanking carboxyl-terminal end of head region from influenza virus A (Denmark/35/2005 (H3N2))<br>LKLATGMRNVPEKQTRGIFGAIAGFIENGWEGMVDGWYGFRHQNSEGIGQA ADLKSTQAAINQINGKLNRLIGKTNEKFHQIEKEFSEVEGRIQDLEKYVED TKVDLWSYNAELLVALENQHTIDLTDSEMNKLFERTKKQLRENAEDMGNGC FKIYHKCDNACIGSIRNGTYDHDVYRDEALNNRFQIK |
| 31 | Amino acid sequence of stem region flanking carboxyl-terminal end of head region from influenza virus A (Denmark/35/2005 (H3N2))-partial-66 aa's<br>LKLATGMRNVPEKQTRGIFGAIAGFIENGWEGMVDGWYGFRHQNSEGIGQA ADLKSTQAAINQING |
| 32 | Amino acid sequence of stem region flanking carboxyl-terminal end of head region from influenza virus A (Denmark/35/2005 (H3N2))-partial-50 aa's<br>LKLATGMRNVPEKQTRGIFGAIAGFIENGWEGMVDGWYGFRHQNSEGIGQ |
| 33 | Amino acid sequence of stem region flanking carboxyl-terminal end of head region from influenza virus A (Denmark/35/2005 (H3N2))-partial-25 aa's<br>LKLATGMRNVPEKQTRGIFGAIAGF |
| | Linker Sequences |
| 34 | VFPGCGV-head linker |
| 35 | CFNGIC-head linker |
| 36 | Helix A extension sequence-ALMAQ |
| 37 | Helix A extension sequence-ELMEQ |
| 38 | Inter-helix region-GKTNEKFHQIEKEFSEVEGRIQDLEKYVEDTKVDLW |
| 39 | Inter-helix linker-GGPD |
| | Head region carboxyl flank (inter-helix region replaced with linker) |
| 40 | DLKSTQAAINQINGKLNRLIALMAQGGPDSYNAELLVALENQHTIDLTD |
| 41 | NSEGIGQAADLKSTQAAINQINGKLNRLIALMAQGGPDSYNAELLVALE NQHTIDLTDSEMNKLFERT |
| 42 | NSEGIGQAADLKSTQAAINQINGKLNRLIALMAQGGPDSYNAELLVALE NQHTIDLTDSEMNKLFERTKKQLRENAEDMGNGCFKIYH |
| 43 | LKLATGMRNVPEKQTRGIFGAIAGFIENGWEGMVDGWYGFRHQNSEGIG QAADLKSTQAAINQINGKLNRLIALMAQGGPDSYNAELLVALENQHTID LTDSEMNKLFERTKKQLRENAEDMGNGCFKIYHKCDNACIGSIRNGTYD HDVYRDEALNNRFQIK |
| | Inter-helix carboxyl flank-goes all the way to end of stem; does not include TM domain |
| 44 | SYNAELLVALENQHTIDLTDSEMNKLFERTKKQLRENAEDMG |
| 45 | SYNAELLVALENQHTIDLTDSEMNKLFERTKKQLRENAEDMGNGCFKIY HKCDNACIGSIRN |

TABLE 2-continued

| PCT SEQ ID NO | Comments |
|---|---|
| 46 | SYNAELLVALENQHTIDLTDSEMNKLFERTKKQLRENAEDMGNGCFKIYHKCDNACIGSIRNGTYDHDVYRDEALNNRFQIK |
| | Protein Constructs With HA Joined to Monomeric Subunit |
| 47 | Amino acid sequence of H3-SS-np_231; (H3ssF_231) |
| 48 | Amino acid sequence of H3-SS-np_249; (H3ssF_249) |
| 49 | Amino acid sequence of H3-SS-np_256; (H3ssF_256) |
| 50 | Amino acid sequence of H3-SS-np_258; (H3ssF_258) |
| 51 | Amino acid sequence of H3-SS-np_262; (H3ssF_262) |
| 52 | Amino acid sequence of H3-SS-np_264; (H3ssF_264) |
| 53 | Amino acid sequence of H3-SS-np_265; (H3ssF_265) |
| 54 | Amino acid sequence of H3-SS-np_266; (H3ssF_266) |
| 55 | Amino acid sequence of H3-SS-np_267; (H3ssF_267) |
| 56 | Amino acid sequence of H3-SS-np_268; (H3ssF_268) |
| 57 | Amino acid sequence of H3-SS-np_269; (H3ssF_269) |
| 58 | Amino acid sequence of H3-SS-np_270; (H3ssF_270) |
| 59 | Amino acid sequence of H3-SS-np_271; (H3ssF_271) |
| 60 | Amino acid sequence of H3-SS-np_272; (H3ssF_272) |
| 61 | Amino acid sequence of H3-SS-np_279; (H3ssF_279) |
| 62 | Amino acid sequence of H3-SS-np_281; (H3ssF_281) |
| 63 | Amino acid sequence of H3-SS-np_287; (H3ssF_287) |
| 64 | Amino acid sequence of H3-SS-np_288; (H3ssF_288) |
| 65 | Amino acid sequence of H3-SS-np_289; (H3ssF_289) |
| 66 | Amino acid sequence of H3-SS-np_291; (H3ssF_291) |
| 67 | Amino acid sequence of H3-SS-np_292; (H3ssF_292) |
| 68 | Amino acid sequence of H3-SS-np_293; (H3ssF_293) |
| 69 | Amino acid sequence of H3-SS-np_294; (H3ssF_294) |
| 70 | Amino acid sequence of H3-SS-np_295; (H3ssF_295) |
| 71 | Amino acid sequence of H3-SS-np_296 (based on H7 #21); (H3ssF_296) |
| 72 | Amino acid sequence of H3-SS-np_297 (based on H7 #23); (H3ssF_297) |
| 73 | Amino acid sequence of H3-SS-np_298 (based on #249 and H7 #23); (H3ssF_298) |
| 74 | Amino acid sequence of H3-SS-np_299 (based on #249 and #258); (H3ssF_299) |
| 75 | Amino acid sequence of H3-SS-np_231_HK68; (H3ssF_231_HK68) |
| 76 | Amino acid sequence of H3-SS-np_231_BK79; (H3ssF_231_BK79) |
| 77 | Amino acid sequence of H3-SS-np_231_Wyo03; (H3ssF_231_Wyo03) |
| 78 | Amino acid sequence of H3-SS-np_231_Switz13; (H3ssF_231_Switz13) |
| 79 | Amino acid sequence of H3-SS-np_262_HK68; (H3ssF_262_HK68) |
| 80 | Amino acid sequence of H3-SS-np_262_BK79; (H3ssF_262_BK79) |
| 81 | Amino acid sequence of H3-SS-np_262_Wyo03; (H3ssF_262_Wyo03) |
| 82 | Amino acid sequence of H3-SS-np_262_Switz13; (H3ssF_262Switz13) |

TABLE 2-continued

| PCT SEQ ID NO | Comments |
|---|---|
| 83 | Amino acid sequence of H3-SS_LS-01 (based on #231, N298D, Linker extension); (H3ssLS-01) |
| 84 | Amino acid sequence of H3-SS_LS-02 (based on #231, M197C, I244C, N298D, linker extension, added glutamates); (H3ssLS-02) |
| 85 | Amino acid sequence of H3-SS_LS-03 (based on #231, N298D, linker extension, added glutamates); (H3ssLS-03) |
| 86 | Amino acid sequence of H3-SS_LS-04 (based on #231, M197, I244C, N298D, linker extension, added glutamates); (H3ssLS-04) |
| 87 | Amino acid sequence of H3-SS_LS-05 (based on #266, S300A, linker extension); (H3ssLS-05) |
| 88 | Amino acid sequence of H3-SS_LS-06 (based on #266, N298D, linker extension); (H3ssLS-06) |
| 89 | Amino acid sequence of H3-SS_LS-07 (based on #274, N298D, linker extension); (H3ssLS-07) |
| 90 | Amino acid sequence of H3-SS-SA_01 |
| 91 | Amino acid sequence of H3-SS_SA_02 |
| 92 | Amino acid sequence of H7-SS-np_016 (based on H3 #231); (H7ssF_016) |
| 93 | Amino acid sequence of H7-SS-np_018 (based on H3 #262); (H7ssF_018) |
| 94 | Amino acid sequence of H7-SS-np_020 (based on H3 #264); (H7ss_F020) |
| 95 | Amino acid sequence of H7-SS-np_021 (based on a variation of H3 #231); (H7ssF_021) |
| 96 | Amino acid sequence of H7-SS-np_023 (based on a variation of H3 #231); (H7ssF_023) |
| 97 | Amino acid sequence of H7-SS-np_025 (based on H3 #265); (H7ssF_025) |
| 98 | Amino acid sequence of H7-SS-np_026 (based on H3 #256); (H7ssF_026) |
| 99 | Amino acid sequence of H7-SS-np_027 (based on H3 #249); (H7ssF_027) |
| 100 | Amino acid sequence of H7-SS-np_028 (combine H7 #20 and #23); (H7ssF_028) |
| 101 | Amino acid sequence of H7-SS-SA_01 (from H7-SS-np #16); (H7ssSA_01) |
| 102 | Amino acid sequence of H7-SS-SA_02 (from H3-ss np #18); (H7ssSA_02) |
| 103 | Amino acid sequence of H10N8-SS-NP_01 (similar to H3 231, H7 16); (H10ssF_01) |
| 104 | Amino acid sequence of H10N8-SS-np_02 (similar to H3 262, H7 18); (H10ssF_02) |
| 105 | Amino acid sequence of H10N8-SS-np_03 (similar to H3 264, H7 20); (H10ssF_03) |
| 106 | Amino acid sequence of H10N8-SS-np_04 (similar to H3 256, H7 26); (H10ssF_04) |
| 107 | Amino acid sequence of H10N8-SS-np_05 (similar to H7 23); (H10ssF_05) |
| 108 | Amino acid sequence of H10N8-SS-np_06 (similar to H3 249, H7 27); (H10ssF_06) |
| | Protein Constructs With HA Joined to Transmembrane Domain |
| 109 | Amino acid sequence of H3-SS-TM_231_HK68 |
| 110 | Amino acid sequence of H3-SS-TM_231_BK79 |
| 111 | Amino acid sequence of H3-SS TM_231_Wyo03 |
| 112 | Amino acid sequence of H3-SS-TM_231_Switz13 |
| 113 | Amino acid sequence of H3-SS-TM_256_Den05 |
| 114 | Amino acid sequence of H3-SS-TM_262_Den05 |

TABLE 2-continued

| PCT SEQ ID NO | Comments |
|---|---|
| 115 | Amino acid sequence of H3-SS-TM_264_Den05 |
| 116 | Amino acid sequence of H3-SS-TM_262_HK68 |
| 117 | Amino acid sequence of H3-SS-TM_262_BK79 |
| 118 | Amino acid sequence of H3-SS-TM_262_Wyo03 |
| 119 | Amino acid sequence of H3-SS-TM_262_Switz13 |
| 120 | Amino acid sequence of H7-SS-TM_016 |
| 121 | Amino acid sequence of H7-SS-TM_018 |
| 122 | Amino acid sequence of H7-SS-TM_020 |
| 123 | Amino acid sequence of H7-SS-TM_021 |
| 124 | Amino acid sequence of H7-SS-TM_023 |
| 125 | Amino acid sequence of H7-SS-TM_024 |
| 126 | Amino acid sequence of H7-SS-TM_025 |
| 127 | Amino acid sequence of H7-SS-TM_026 |
| 128 | Amino acid sequence of H7-SS_TM_027 (#16 with H7N7 A/England/268/1996) |
| 129 | Amino acid sequence of H7-SS_TM_028 (#16 with H7N7 A/Netherlands/219/2003) |
| 130 | Amino acid sequence of H3-SS-TM_256_HK68 |
| 131 | Amino acid sequence of H3-SS-TM_258_HK68 |
| | Protein Constructs With HA Joined to Monomeric Subunit |
| 132 | Amino acid sequence of H3-SS-np_300 (based on 231 with glycan at N38 removed); (H3ssF_300) |
| 133 | Amino acid sequence of H3-SS-np_301 (Delta cleavage loop; based on 231); (H3ssF_301) |
| 134 | Amino acid sequence of H3-SS-np_302 (Delta cleavage loop; based on 258); (H3ssF_302) |
| 135 | Amino acid sequence of H3-SS-np_303 (Delta cleavage loop; based on 231); (H3ssF_303) |
| 136 | Amino acid sequence of H3-SS-np_304 (Delta cleavage loop; based on 231); (H3ssF_304) |
| 137 | Amino acid sequence of H3-SS-np_305 (Delta cleavage loop; based on 231); (H3ssF_305) |
| 138 | Amino acid sequence of H3-SS-np_306 (Glycan addition; based on 231); (H3ssF_306) |
| 139 | Amino acid sequence of H3-SS-np_307 (Glycan addition; based on 231); (H3ssF_307) |
| 140 | Amino acid sequence of H3-SS-np_308 (Glycan addition; based on 231); (H3ssF_308) |
| 141 | Amino acid sequence of H3-SS-np_309 (Glycan addition; based on 231); (H3ssF_309) |
| 142 | Amino acid sequence of H3-SS-np_310 (Glycan addition; based on 231); (H3ssF_310) |
| 143 | Amino acid sequence of H3-SS-np_311 (Glycan addition; based on 231); (H3ssF_311) |
| 144 | Amino acid sequence of H3-SS-np_312 (Glycan addition; based on 231); (H3ssF_312) |
| 145 | Amino acid sequence of H3-SS-np_313 (Glycan addition; based on 231); (H3ssF_313) |
| 146 | Amino acid sequence of H3-SS-np_314 (Glycan addition; based on 231); (H3ssF_314) |
| 147 | Amino acid sequence of H3-SS-LS_08 (based on 249); (H3ssL_08) |
| 148 | Amino acid sequence of H3-SS-LS_09 (based on 249 + 256); (H3ssL_09) |

TABLE 2-continued

| PCT SEQ ID NO | Comments |
|---|---|
| 149 | Amino acid sequence of H3-SS-LS_10 (based on 249 + 258); (H3ssL_10) |
| 150 | Amino acid sequence of H3-SS-LS_11 (based on 256); (H3ssL_11) |
| 151 | Amino acid sequence of H3-SS-LS_12 (based on 258); (H3ssL_12) |
| 152 | Amino acid sequence of H7-SS-LS_01 (based on H3 258); (H7ssL_01) |
| 153 | Amino acid sequence of H7-SS-LS_02 (based on H3 249); (H7ssL_02) |
| 154 | Amino acid sequence of H7-SS-LS_03 (based on H3 249 & 258); (H7ssL_03) |
| 155 | Amino acid sequence of H7-SS-LS_04 (H7 20 + 26); (H7ssL_04) |
| 156 | Amino acid sequence of H7-SS-LS_05 (H7 23 + 26); (H7ssL05) |
| 157 | Amino acid sequence of H7-SS-LS_06 (H7 20 + 23 + 26); (H7ssL06) |
| 158 | Amino acid sequence of H3-SS-np_256_HK68; (H3ssF_256) |
| 159 | Amino acid sequence of H3-SS-np_258_HK68; (H3ssF_258) |

The influenza viruses, and the sequences there from, listed above are exemplary, and any other Group 2 influenza virus, and sequences and proteins therefrom can be used to practice the invention.

The trimeric HA protein on the surface of the virus comprises a globular head region and a stem, or stalk, region, which anchors the HA protein into the viral lipid envelope. The head region of influenza HA is formed exclusively from a major portion of the HA1 polypeptide, whereas the stalk region is made from segments of HA1 and HA2. According to the present invention, the head region consists of the amino acids of a Group 2 influenza HA protein corresponding to, approximately, amino acids 60-329 of the full-length HA protein of influenza A virus (A/Denmark/35/2005 (H3N2)) (SEQ ID NO:4). Similarly, as used herein, the stem region is formed from the amino acids of a Group 2 influenza HA protein corresponding to amino acids 1-59 and 330-519 of the full-length HA protein of influenza A virus (A/Denmark/35/2005 (H3N2)) (SEQ ID NO:4). As used herein, the term approximately, with regard to the head and stem regions means that the sequences cited above may vary in length by several (e.g., 1, 2, 3, 4, 5, 6, 7, 8, 9, or 10) amino acids without affecting the nature of the invention. Thus, for example, the head region may consist of amino acids 64-329, amino acids 60-326 or amino acids 62-327. Generally, the head and stem region will not vary from the locations recited above by more than ten amino acids. In certain aspects of the invention, the head region consists of the amino acid sequence between, and including, the amino acid residues corresponding to Cys68 and Cys321 of influenza A virus (A/Denmark/35/2005 (H3N2)) (SEQ ID NO:4). With regard to HA proteins, it is understood by those skilled in the art that HA proteins from different influenza viruses may have different lengths due to sequence differences (insertions, deletions) in the protein. Thus, reference to a corresponding region refers to a region of another protein that is identical, or nearly so (e.g., at least 90% identical, at least 95%, identical, at least 98% identical or at least 99% identical), in sequence, structure and/or function to the region being compared. For example, with regard to the stem region of an HA protein, the corresponding region in another HA protein may not have the same residue numbers, but will have a nearly identical sequence and will perform the same function. As an example, in the embodiment stated above, the head region of the HA protein from influenza virus A virus (A/Denmark/35/2005 (H3N2)) (SEQ ID NO:4) begins at amino acid 60. The corresponding amino acid at the beginning of the head region in A/New Caledonia/20/1999 (H1) is amino acid C60. To better clarify sequence comparisons between viruses, numbering systems are used by those in the field, which relate amino acid positions to a reference sequence. Thus, corresponding amino acid residues in HA proteins from different strains of influenza may not have the same residue number with respect to their distance from the n-terminal amino acid of the protein. For example, using the H3 numbering system, reference to residue 100 in A/New Caledonia/20/1999 (1999 NC, H1) does not mean it is the 100th residue from the N-terminal amino acid. Instead, residue 100 of A/New Caledonia/20/1999 (1999 NC, H1) aligns with residue 100 of influenza H3N2 strain. The use of such numbering systems is understood by those skilled in the art. While the H3 numbering system can be used to identify the location of amino acids, unless otherwise noted, the location of amino acid residues in HA proteins will be identified by general reference to the position of a corresponding amino acid from a sequence disclosed herein.

The inventors have also discovered that by combining specific sequences of the influenza virus HA protein with unrelated proteins, and nanoparticles made therefrom that are capable of presenting the HA protein to the immune system, immune responses to targeted regions of the HA protein can be elicited. Thus, one embodiment of the present invention is a protein construct comprising a Group 2 influenza virus HA protein joined to at least a portion of a monomeric subunit protein, wherein the head region of the Group 2 influenza virus HA protein has been replaced with an amino acid sequence comprising less than 5 contiguous amino acid residues from the head region of an influenza HA protein, and wherein the protein construct is capable of forming a nanoparticle.

By joining at least a portion of a Group 2 influenza HA protein to a monomeric subunit, protein constructs of the present invention are capable of assembling into nanoparticles expressing trimers of Group 2 influenza HA protein on their surface. Such trimers are in a pre-fusion form, and connection to the monomeric subunit, and expression on the nanoparticle stabilize the pre-fusion proteins in their trimeric form. Because of this, the HA protein is presented in a more native form, meaning certain surfaces of the stem polypeptides are not exposed, thereby reducing the risk that the stem polypeptides may induce an unfavorable antibody response.

In certain aspects, the at least a portion of a Group 2 influenza virus HA protein comprises at least one immunogenic portion from the stem region of a Group 2 influenza virus HA protein, wherein the protein construct elicits protective antibodies against an influenza virus. In certain aspects, the at least a portion of a Group 2 influenza virus HA protein comprises at least one immunogenic portion from the stem region of an HA protein selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein.

In certain aspects, the at least a portion of a Group 2 influenza virus HA protein comprises at least one immunogenic portion from the HA portion of a protein comprising an amino acid sequence at least 80%, at least 85% identical, at least 90% identical, at least 95% identical, at least 97% identical, or at least 99%, identical to a sequence selected from the group consisting of SEQ ID NO:4-SEQ ID NO:26. In certain aspects, the at least a portion of a Group 2 influenza virus HA protein comprises at least one immunogenic portion from the HA portion of a protein comprising an amino acid sequence selected from the group consisting of SEQ ID NO:4-SEQ ID NO:26. In certain aspects, the at least a portion of a Group 2 influenza virus HA protein comprises at least one immunogenic portion from the HA portion of a protein comprising an amino acid sequence at least 80% identical, at least 85% identical, at least 90% identical, at least 95% identical, at least 97% identical, or at least 99% identical to a sequence selected from the group consisting of SEQ ID NO: 47-SEQ ID NO:159. In certain aspects, the at least a portion of a Group 2 influenza virus HA protein comprises at least one immunogenic portion from the HA portion of a protein comprising an amino acid sequence at least 80% identical, at least 85% identical, at least 90% identical, at least 95% identical, at least 97% identical, or at least 99%, identical to a sequence selected from the group consisting of SEQ ID NO: 47-SEQ ID NO:159. In certain aspects, the at least a portion of a Group 2 influenza virus HA protein comprises at least one immunogenic portion from the HA portion of a protein comprising an amino acid sequence selected from the group consisting of SEQ ID NO:47-SEQ ID NO:159. In certain aspects, the at least a portion of a Group 2 influenza virus HA protein comprises at least one immunogenic portion from the HA portion of a protein comprising an amino acid sequence selected from the group consisting of SEQ ID NO:47-SEQ ID NO:159. In one embodiment protein constructs comprising immunogenic portions of a Group 2 influenza HA protein elicit the production of broadly protective antibodies against influenza virus.

Immunogenic portions of proteins can comprise epitopes, which are clusters of amino acid residues that are recognized by the immune system, thereby eliciting an immune response. Such epitopes may consist of contiguous amino acids residues (i.e., amino acid residues that are adjacent to one another in the protein), or they may consist of non-contiguous amino acid residues (i.e., amino acid residues that are not adjacent one another in the protein) but which are in close special proximity in the finally folded protein. It is well understood by those skilled in the art that epitopes require a minimum of six amino acid residues in order to be recognized by the immune system. Thus, in certain aspects the immunogenic portion from a Group 2 influenza HA protein comprises at least one epitope. In one embodiment the at least a portion of a Group 2 influenza virus HA protein comprises at least 6 amino acids, at least 10 amino acids, at least 25 amino acids, at least 50 amino acids, at least 75 amino acids or at least 100 amino acids from the stem region of a Group 2 influenza HA protein. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the stem region of a Group 2 influenza HA protein selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the stem region of a Group 2 influenza HA protein having an amino acid sequence at least 80% identical, at least 85% identical, at least 90% identical, at least 95% identical, at least 97% identical, or at least 99% identical to an HA protein from an influenza virus selected from those listed in Table 2. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the stem region of a Group 2 influenza HA protein from an influenza virus selected from those listed in Table 2, and variants thereof. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the stem region of a Group 2 influenza HA protein comprising a sequence at least 80%, at least 85% identical, at least 90% identical, at least 95% identical, at least 97% identical, or at least 99%, identical to a sequence selected from the group consisting of SEQ ID NO:4-SEQ ID NO:26. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the stem region of a Group 2 influenza HA protein comprising a sequence selected from the group consisting of SEQ ID NO:4-SEQ ID NO:26. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the HA portion of a protein comprising a sequence at least 80%, at least 85% identical, at least 90% identical, at least 95% identical, at least 97% identical, or at least 99%, identical to a sequence selected from the group consisting of SEQ ID NO:47-SEQ ID NO:159. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the HA portion of a protein comprising a sequence selected from the group consisting of SEQ ID NO:47-SEQ ID NO:159.

In certain aspects of the invention, the amino acids are contiguous amino acids from the stem region of a Group 2 influenza virus HA protein. In certain aspects, protein constructs of the invention comprising at least 6 amino acids, at least 10 amino acids, at least 25 amino acids, at least 50 amino acids, at least 75 amino acids or at least 100 amino acids from the stem region of a Group 2 influenza virus HA protein elicit the production of broadly protective antibodies against influenza virus. In certain aspects of the invention, a protein construct comprises at least 6 amino acids, at least 10 amino acids, at least 25 amino acids, at least 50 amino acids, at least 75 amino acids or at least 100 amino acids from the stem region of a Group 2 influenza virus HA protein comprising an amino acid sequence at least 80% identical, at least 85% identical, at least 90% identical, at least 95% identical, at least 97% identical, or at least 99% identical to sequence selected from the group consisting of SEQ ID NO:4-SEQ ID NO:26. In certain aspects of the present invention, a protein construct comprises at least 6 amino acids, at least 10 amino acids, at least 25 amino acids, at least 50 amino acids, at least 75 amino acids or at least 100 amino acids from the stem region of a Group 2 influenza virus HA protein comprising an amino acid sequence selected from the group consisting of SEQ ID NO:4-SEQ ID NO:26. In certain aspects, the amino acids are non-contiguous, but are in close spatial proximity in the final protein.

While the present application exemplifies the use of stem region sequences from several exemplary Group 2 influenza virus HA proteins, the invention may also be practiced using stem regions from proteins comprising variations of the disclosed Group 2 influenza HA sequences. Thus, in certain aspects of the invention, the Group 2 influenza HA protein is from a virus selected from the Group 2 viruses listed in Table 2, and variants thereof. In certain aspects, the Group 2 influenza virus HA protein comprises an amino acid sequence at least 80%, at least 85%, at least 90%, at least 92%, at least 94%, at least 96%, at least 98% or at least 99% identical the stem region of a Group 2 influenza virus HA protein comprising an amino acid sequence selected from the group consisting of SEQ ID NO:4-SEQ ID NO:26. In certain aspects, the Group 2 influenza HA protein comprises an amino acid sequence selected from the group consisting of SEQ ID NO:4-SEQ ID NO:26.

In certain aspects of the invention, the head region sequence of the HA protein in the protein construct is replaced with a linker sequence. Any linker sequence may be used so long as the stem region sequences are able to adopt the desired conformation. While any amino acids may be used to make the linker sequence, in certain aspects of the invention the amino acids lack large or charged side chains. Preferred amino acids to use include, but are not limited to, cysteine, serine, glycine, alanine, valine and proline. In one embodiment, the linker is made from one or more amino acids selected from the group consisting of serine, glycine, cysteine, valine, proline and/or phenylalanine residues. In certain embodiments, it may be desirable to include an amino acid residue, the side chain of which is capable of forming a covalent bond, such as a disulfide bond, with another amino acid. One example of such an amino acid is cysteine. The length of the linker sequence may vary, but preferred embodiments use the shortest possible sequence in order to allow the stem sequences to form the desired structure. In certain aspects, the linker sequence is less than 12 amino acids in length. In one embodiment, the linker sequence is less than 10 amino acids in length. In one embodiment, the linker sequence is less than 5 amino acids in length. In preferred embodiments, the linker sequence lacks contiguous amino acid sequences from the head region of an HA protein. In certain aspects, the linker sequence comprises less than 5 contiguous amino acids from the head region of an HA protein. In certain aspects the head region sequence is replaced with an amino acid sequence comprising SEQ ID N034, SEQ ID NO:35, or variants thereof.

The inventors have also discovered that the stability of protein constructs and nanoparticles of the invention can be improved by making further alterations to the Group 2 influenza virus HA protein of the disclosed protein constructs. For example, the inventors have discovered that extending the length of helix A improves the performance of protein constructs of the invention. Thus, one embodiment is a protein construct of the invention in which helix A has been extended by the addition of amino acids. One embodiment is a protein construct of the invention, wherein the protein construct comprises a Group 2 influenza virus HA protein joined to at least a portion of a monomeric subunit, wherein the head region of the Group 2 influenza virus HA protein has been replaced with an amino acid sequence comprising less than 5 contiguous amino acid residues from the head region of an influenza HA protein, and wherein the carboxy-terminal end of helix A (i.e., the portion that links to the amino end of helix C) has been extended by the addition of amino acid residues. It should be appreciated that because the goal is to extend the helix, the sequence of amino acids added to the carboxy-terminal end of helix A should preferably form a helix. In certain aspects of the invention, the length of helix A is extended by adding an amino acid sequence comprising SEQ ID NOs:36 or 37, or helix-forming variants thereof, to the carboxyl-end of helix A. In certain aspects of the invention, the length of helix A is extended by adding a sequence comprising, or consisting of, $X_1LMX_2Q$ (SEQ ID NO: 160), or helix-forming variants thereof, to the carboxyl-end of helix A, wherein the amino acids at positions $X_1$ and $X_2$ are acidic amino acids. It should be noted that $X_1$ and $X_2$ can, but need not, be the same amino acid residue. In certain aspects, the residues at the first and fourth position of such a linker are selected from the group consisting of glutamine, glutamic acid, asparagine, aspartic acid, glycine, and proline. In one embodiment, helix A is extended by adding an amino acid sequence consisting of SEQ ID NOs:36 or 37, or helix-forming variants thereof, to the carboxyl-end of helix A. In certain aspects of the invention, the length of helix A is extended by adding a sequence comprising ALMAQ (SEQ ID NO: 36) or ELMEQ (SEQ ID NO: 37), or helix-forming variants thereof, to the carboxyl-end of helix A. In certain aspects of the invention, the length of helix A is extended by adding a sequence consisting of ALMAQ (SEQ ID NO: 36) or ELMEQ (SEQ ID NO: 37), or helix-forming variants thereof, to the carboxyl-end of helix A.

In addition to extension of helix A, the inventors have discovered that modification of the amino acid sequence joining the carboxyl-end of helix A to the amino-end of helix C (herein referred to as the inter-helix region or inter-helix loop, one example of which is represented by SEQ ID NO:38), improves the stability and performance of protein constructs and nanoparticles of the invention. More particularly, the inventors have found that shortening the length of the inter-helix region improves the stability and performance of protein constructs and nanoparticles of the invention. Thus, in certain aspects of the invention, the amino acid sequence joining the carboxyl-end of helix A to the amino-end of helix C in a protein construct of the invention is modified to improve the stability of a protein construct of the invention. It should be appreciated that improving the stability of a protein construct of the invention means stabilizing the three-dimensional structure of a protein construct of the invention, and in particular the stem-region of a protein construct of the invention, such that it approximates the three-dimensional structure of the stem region of a native Group 2 influenza HA protein, and is able to elicit an immune response to a Group 2 influenza virus. Thus, in certain aspects of the invention, the inter-helix region of a protein construct of the invention is shortened. Such shortening can be achieved by removing amino acids from the existing inter-helix region, or by replacing amino acids of the inter-helix region with a linker sequence. In certain aspects, the inter-helix region of a protein construct of the invention is shortened to less than 6 amino acids. In certain aspects, amino acids of the inter-helix region are replaced with a linker sequence. In certain aspects of the invention, amino acids of an inter-helix region corresponding to the inter-helix region of an influenza virus A (Denmark/35/2005 (H3N2)) HA protein (SEQ ID NO:4) are replaced with a linker sequence. In certain aspects of the invention, amino acids of an inter-helix region corresponding to amino acids 402-437 of an influenza virus A (Denmark/35/2005(H3N2)) HA protein (SEQ ID NO:4) are replaced with a linker sequence. In certain aspects of the invention, an inter-helix region comprising amino acids 402-437 of SEQ ID NO:4 is replaced with a linker sequence. In certain aspects of the invention, an inter-helix region corresponding to a region of influenza virus A (Denmark/35/2005(H3N2)) HA protein (SEQ ID NO:4) represented by SEQ ID NO:38 is replaced with a linker sequence. In certain aspects of the invention, an inter-helix region of the Group 2 influenza virus HA protein comprising an amino acid sequence at least 90%, at least 97%, at least 99% identical to SEQ ID NO: 38, is replaced with a linker sequence. In one embodiment, a region of the Group 2 influenza virus HA protein comprising SEQ ID NO: 38, is replaced with a linker sequence. In certain aspects of the invention, a region of the Group 2 influenza virus HA protein consisting of SEQ ID NO: 38, is replaced with a linker sequence. In certain aspects of the invention, the inter-helix region is replaced with a linker sequence comprising GGPD (SEQ ID NO:39). In certain aspects of the invention, an inter-helix region corresponding to amino acids 402-437 of SEQ ID NO:4 is replaced with a linker sequence having the physical spatial, and/or chemical properties of a peptide consisting of GGPD (SEQ ID NO:39). In certain aspects of the invention, an inter-helix region corresponding to amino acids 402-437 of SEQ ID NO:4 is replaced with a linker sequence having the propensity to form a helix. In certain aspects of the invention, an inter-helix region corresponding to amino acids 402-437 of SEQ ID NO:4 is replaced with a linker sequence comprising GGPD (SEQ ID NO:39), or conservative variants thereof. In certain aspects of the invention, the inter-helix region is replaced with a linker sequence consisting of GGPD (SEQ ID NO:39).

As has been previously described, protein constructs of the invention can contain one, several or all of the mutations and sequence alterations described herein. Thus, for example, a protein construct in which helix A has been extended, as described supra, can also have the inter-helix region shortened or replaced with a linker sequence, as described supra. Thus, one aspect of the invention is a protein construct comprising a Group 2 influenza virus HA protein joined to at least a portion of a monomeric subunit protein, wherein the head region of the Group 2 influenza virus HA protein has been replaced with an amino acid sequence comprising less than 5 contiguous amino acid residues from the head region of an influenza HA protein, wherein the inter-helix region has been shortened or replaced with a linker sequence, and wherein the protein construct is capable of forming a nanoparticle. Methods of replacing the HA protein head region, and methods of shortening or replacing the inter-helix region are disclosed herein. It should be understood that in embodiments in which the carboxyl end of helix A has been extended by the addition of amino acids, the inter-helix region would be replaced with a linker that joins the amino-terminal end of helix C with the carboxyl-terminal end of the extension sequence of helix A.

The inventors have further discovered that the stability of protein constructs of the invention can be improved by making site-specific mutations in the sequence of the Group 2 influenza virus stem region. In particular, mutations that form ionic bonds, salt bridges, of that increase hydrophobic packing, and the like, can strengthen the stability of protein constructs and nanoparticles of the invention. Thus, in certain aspects of the invention, a protein construct of the invention comprises one or more mutations that forms or strengthens an ionic interaction, or a salt bridge, or that increases hydrophobic packing. Any type of mutation that has the desired effect of increasing the stability of a protein construct of the invention can be made, although substitution mutations are preferred. In certain aspects of the invention, a mutation is made in the Group 2 influenza virus HA protein at an amino acid location corresponding to a location in SEQ ID NO:4 selected from the group consisting of K396, L397, L400, S438, N440, E448, T452 and N461. In one embodiment, the amino acid corresponding to K396 in the influenza virus A (Denmark/35/2005(H3N2) HA protein (SEQ ID NO:4) is changed to an amino acid residue selected from the group consisting of methionine, leucine, isoleucine, alanine and valine. In certain aspects of the invention, the amino acid corresponding to K396 in the influenza virus A (Denmark/35/2005(H3N2) HA protein (SEQ ID NO:4) is changed to a methionine or a leucine. In one embodiment, the amino acid corresponding to L397 in the influenza virus A (Denmark/35/2005(H3N2) HA protein (SEQ ID NO:4) is changed to an amino acid residue selected from the group consisting of methionine, leucine, isoleucine, alanine and valine. In certain aspects of the invention, the amino acid corresponding to L397 in the influenza virus A (Denmark/35/2005(H3N2) HA protein (SEQ ID NO:4) is changed to a valine. In certain aspects of the invention, the amino acid corresponding to L400 in the influenza virus A (Denmark/35/2005(H3N2) HA protein (SEQ ID NO:4) is changed to an amino acid residue selected from the group consisting of methionine, leucine, isoleucine, alanine and valine. In certain aspects of the invention, the amino acid corresponding to L400 in the influenza virus A (Denmark/35/2005(H3N2) HA protein (SEQ ID NO:4) is changed to a valine. In certain aspects of the invention, the amino acid corresponding to S438 in the influenza virus A (Denmark/35/2005(H3N2) HA protein (SEQ ID NO:4) is changed to an amino acid residue selected from the group consisting of asparagine, glutamine, serine, threonine, and cysteine. In certain aspects of the invention, the amino acid corresponding to S438 in the influenza virus A (Denmark/35/2005(H3N2) HA protein (SEQ ID NO:4) is changed to a cysteine. In certain aspects of the invention, the amino acid corresponding to N440 in the influenza virus A (Denmark/35/2005(H3N2) HA protein (SEQ ID NO:4) is changed to an amino acid residue selected from the group consisting of methionine, leucine, isoleucine, alanine and valine. In certain aspects of the invention, the amino acid corresponding to N440 in the influenza virus A (Denmark/35/2005(H3N2) HA protein (SEQ ID NO:4) is changed to a leucine. In certain aspects of the invention, the amino acid corresponding to E448 in the influenza virus A (Denmark/35/2005(H3N2) HA protein (SEQ ID NO:4) is changed to an amino acid residue selected from the group consisting of methionine, leucine, isoleucine, alanine and valine. In certain aspects of the invention, the amino acid corresponding to E448 in the influenza virus A (Denmark/35/2005(H3N2) HA protein (SEQ ID NO:4) is changed to a leucine. In certain aspects of the invention, the amino acid corresponding to T452 in the influenza virus A (Denmark/35/2005(H3N2) HA protein (SEQ ID NO:4) is changed to an amino acid residue selected from the group consisting of methionine, leucine, isoleucine, alanine and valine. In certain aspects of the invention, the amino acid corresponding to T452 in the influenza virus A (Denmark/35/2005(H3N2) HA protein (SEQ ID NO:4) is changed to a valine. In certain aspects of the invention, the amino acid corresponding to N461 in the influenza virus A (Denmark/35/2005(H3N2) HA protein (SEQ ID NO:4) is changed to an amino acid residue selected from the group consisting of histidine, lysine, glutamic acid, aspartic acid, and arginine. In certain aspects of the invention, the amino acid corresponding to N461 in the influenza virus A (Denmark/35/2005(H3N2) HA protein (SEQ ID NO:4) is changed to an amino acid residue selected from the group consisting of histidine, lysine, and arginine. In certain aspects of the invention, the amino acid corresponding to N461 in the influenza virus A (Denmark/35/2005(H3N2) HA protein (SEQ ID NO:4) is changed to an arginine.

Additional mutations that may stabilize protein constructs of the invention include a mutation at an amino acid location corresponding to a location in SEQ ID NO:4 selected from the group consisting of G39, T46, N54, T58, L331, N338, and Q392. It should be understood that mutations at such locations can include those in which the amino acid being inserted is similar in properties to those suggested herein.

In certain aspects of the invention, the amino acid corresponding to G39 in the influenza virus A (Denmark/35/2005 (H3N2) HA protein (SEQ ID NO:4) is changed to an amino acid residue selected from the group consisting of cysteine, serine, threonine, proline, asparagine, and glutamine. In certain aspects of the invention, the amino acid corresponding to G39 in the influenza virus A (Denmark/35/2005 (H3N2) HA protein (SEQ ID NO:4) is changed to a cysteine.

In certain aspects of the invention, the amino acid corresponding to T46 in the influenza virus A (Denmark/35/2005 (H3N2) HA protein (SEQ ID NO:4) is changed to an amino acid residue selected from the group consisting of cysteine, serine, threonine, proline, asparagine, and glutamine. In certain aspects of the invention, the amino acid corresponding to T46 in the influenza virus A (Denmark/35/2005 (H3N2) HA protein (SEQ ID NO:4) is changed to a cysteine.

In certain aspects of the invention, the amino acid corresponding to N54 in the influenza virus A (Denmark/35/2005 (H3N2) HA protein (SEQ ID NO:4) is changed to an amino acid residue selected from the group consisting of histidine, arginine and lysine. In certain aspects of the invention, the amino acid corresponding to N54 in the influenza virus A (Denmark/35/2005(H3N2) HA protein (SEQ ID NO:4) is changed to a histidine.

In certain aspects of the invention, the amino acid corresponding to T58 in the influenza virus A (Denmark/35/2005 (H3N2) HA protein (SEQ ID NO:4) is changed to an amino acid residue selected from the group consisting of methionine, leucine, isoleucine, alanine and valine. In certain aspects of the invention, the amino acid corresponding to T58 in the influenza virus A (Denmark/35/2005(H3N2) HA protein (SEQ ID NO:4) is changed to a leucine.

In certain aspects of the invention, the amino acid corresponding to L331 in the influenza virus A (Denmark/35/2005(H3N2) HA protein (SEQ ID NO:4) is changed to an amino acid residue selected from the group consisting of histidine, arginine and lysine. In certain aspects of the invention, the amino acid corresponding to L331 in the influenza virus A (Denmark/35/2005(H3N2) HA protein (SEQ ID NO:4) is changed to a lysine.

In certain aspects of the invention, the amino acid corresponding to N338 in the influenza virus A (Denmark/35/2005(H3N2) HA protein (SEQ ID NO:4) is changed to an amino acid residue selected from the group consisting of cysteine, serine, proline, asparagine, glutamine, and threonine. In certain aspects of the invention, the amino acid corresponding to N338 in the influenza virus A (Denmark/35/2005(H3N2) HA protein (SEQ ID NO:4) is changed to a cysteine.

In certain aspects of the invention, the amino acid corresponding to Q392 in the influenza virus A (Denmark/35/2005(H3N2) HA protein (SEQ ID NO:4) is changed to an amino acid residue selected from the group consisting of cysteine, serine, proline, asparagine, glutamine, and threonine. In certain aspects of the invention, the amino acid corresponding to Q392 in the influenza virus A (Denmark/35/2005(H3N2) HA protein (SEQ ID NO:4) is changed to a cysteine.

In addition to the above, the inventors have discovered that mutations adding glycan linkage sites can be beneficial. Thus, in certain aspects of the invention, the protein construct comprise one or more mutations, or one or more pairs of mutations, selected from the group consisting of Q49N/E51T (mutation to add a group 1 glycan), E56N/V59T (mutations in head linker and adjacent residue), V59N/P61T (mutations in head linker), G62N/G64T (mutations in head linker), V329N/L331T (mutations in head linker and adjacent residue), L331N/L333T, D437N/Y439T (mutations in interhelix linker and adjacent residue), Q432N/G434T (inserted G) (mutations in interhelix linker and adjacent residue), Q372N/S374T, and A492N/I494T.

In addition, in certain aspects of the invention, the loop corresponding to amino acids 339-357 in the influenza virus A (Denmark/35/2005(H3N2) HA protein (SEQ ID NO:4) can be replaced with a glycine linker.

As has been previously described, protein constructs of the invention can contain one, several or all of the mutations and sequence alterations described herein. Thus, for example, a protein construct in which helix A has been extended, as described herein, can also have the inter-helix region shortened or replaced with a linker sequence, as described herein, and can also contain one or more of the site-specific mutations described herein. Thus, one aspect of the invention is a protein construct comprising a Group 2 influenza virus HA protein joined to at least a portion of a monomeric subunit protein, wherein the head region of the Group 2 influenza virus HA protein has been replaced with an amino acid sequence comprising less than 5 contiguous amino acid residues from the head region of an influenza HA protein, wherein the inter-helix region has been shortened or replaced with a linker sequence, wherein the HA portion of the protein construct comprises one or more site-specific mutation at a location corresponding to a location in SEQ ID NO:4 selected from the group consisting of K396, L397, L400, S438, N440, E448, T452, N461, G39, T46, N54, T58, L331, N338, and D437, and wherein the protein construct is capable of forming a nanoparticle. Such constructs may also comprise one or more mutations, or one or more pairs of mutations, selected from the group consisting of Q49N/E51T, E56N/V59T (mutations in head linker and adjacent residue), V59N/P61T (mutations in head linker), G62N/G64T (mutations in head linker), V329N/L331T (mutations in head linker and adjacent residue), L331N/L333T, D437N/Y439T (mutations in interhelix linker and adjacent residue), Q432N/G434T (inserted G) (mutations in interhelix linker and adjacent residue), Q372N/S374T, and A492N/I494T. Methods of replacing the HA protein head region, extending helix A, shortening or replacing the inter-helix region, and suitable site-specific mutations have been disclosed herein. It should be understood that in embodiments in which the carboxyl end of helix A has been extended by the addition of amino acids, the inter-helix region would be replaced with a linker that joins the amino-terminal end of helix C with the carboxyl-terminal end of the extension sequence of helix A.

Heretofore has been described specific aspects of a protein construct of the invention, useful for producing nanoparticle vaccines. To aid in clarifying the invention, the inventors will now describe various aspects in alternative and greater detail. It should be understood that any aspects of the invention described below also apply to embodiments and aspects of protein constructs already described herein.

Protein constructs of the present invention can be made using recombinant technology to link together various portions of Group 3 influenza HA proteins, and make sequences alterations thereto. Recombinant technology can also be used to add appropriate linkers and monomeric subunits. In this way, protein constructs can be produced that comprise specific sequences necessary to produce protein constructs and consequently, nanoparticle vaccines of the invention. Thus, one embodiment of the present invention is a protein construct (also referred to herein as a fusion protein) comprising a first amino acid sequence from the stem region of a Group 2 influenza virus HA protein and a second amino acid sequence from the stem region of a Group 2 influenza virus HA protein, the first and second amino acid sequences being covalently linked by a linker sequence, wherein the first amino acid sequence comprises at least 20 contiguous amino acid residues from the amino acid sequence upstream of the amino-terminal end of the head region sequence;

wherein the second amino acid sequence comprises at least 20 contiguous amino acid residues from the amino acid sequence downstream of the carboxyl-terminal end of the head region sequence; and, wherein the first or second amino acid sequence is joined to at least a portion of a monomeric subunit domain such that the protein construct is capable of forming a nanoparticle.

In certain aspects of the invention, the first amino acid sequence is from the stem region of a Group 2 influenza virus HA protein from a virus selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein. In certain aspects of the invention, the first amino acid sequence is from the stem region of an HA protein from a Group 2 virus listed in Table 2. In certain aspects of the invention, the first amino acid sequence is from the stem region of a Group 2 influenza HA protein, wherein the HA protein comprises an amino acid sequences at least 85%, at least 90%, at least 95% or at least 97% identical to a sequence selected from the group consisting of SEQ ID NO:4-SEQ ID NO:26 and SEQ ID NO:47-SEQ ID NO:159.

In certain aspects of the invention, the first amino acid sequence is from the stem region of a Group 2 influenza HA protein, wherein the HA protein comprises a sequence selected from the group consisting of SEQ ID NO:4-SEQ ID NO:26 and SEQ ID NO:47-SEQ ID NO:159.

In certain aspects of the invention, the second amino acid sequence is from the stem region of a Group 2 influenza HA protein from a virus selected from the group consisting of an influenza H3 virus, an influenza H4 virus, an H7 influenza virus, an H10 influenza virus, an H14 influenza virus, and an H15 influenza virus. In certain aspects of the invention, the second amino acid sequence is from the stem region of an HA protein from a Group 2 virus listed in Table 2. In certain aspects of the invention, the second amino acid sequence is from the stem region of a Group 2 influenza virus HA protein, wherein the HA protein comprises an amino acid sequences at least 85%, at least 90%, at least 95% or at least 97% identical to a sequence selected from the group consisting of SEQ ID NO:4-SEQ ID NO:26 and SEQ ID NO:47-SEQ ID NO:159. In certain aspects of the invention, the second amino acid sequence is from the stem region of a Group 2 influenza virus HA protein comprising a sequence selected from the group consisting of SEQ ID NO:4-SEQ ID NO:26 and SEQ ID NO:47-SEQ ID NO:159.

As noted above, the first amino acid sequence comprises at least 20 contiguous amino acid residues from the amino acid sequence upstream of the amino-terminal end of the head region sequence. According to the present invention, the term upstream refers to the entirety of the amino acid sequence linked to the amino-terminal end of the first amino acid residue of the head region. Preferred upstream sequences are those that are immediately adjacent to the head region sequence. In certain aspects of the invention, the amino-terminal end of the head region is located at the amino acid residue corresponding to Q60 of the HA protein of influenza A (Denmark/35/2005 (H3N2)) HA protein (SEQ ID NO:4) In certain aspects of the invention, the first amino acid sequence comprises at least 20 contiguous amino acid residues from the region of a Group 2 influenza virus HA protein corresponding to amino acid residues 1-59 of the HA protein of influenza A Denmark/35/2005 (H3N2)) represented by SEQ ID NO:4. In certain aspects of the invention, the first amino acid sequence comprises at least 20 contiguous amino acid residues from a sequence at least 85%, at least 90%, at least 95% or at least 97% identical to a sequence selected from the group consisting of SEQ ID NO:27, SEQ ID NO:28 and SEQ ID NO:29. In certain aspects of the invention, the first amino acid sequence comprises at least 20 contiguous amino acid residues from a sequence selected from the group consisting of SEQ ID NO:27, SEQ ID NO:28 and SEQ ID NO:29.

In certain aspects of the invention, the first amino acid sequence comprises at least 40 contiguous amino acid residues from the amino acid region of an HA protein corresponding to amino acid residues 1-59 of influenza A Denmark/35/2005 (H3N2)) HA protein (SEQ ID NO:4). In certain aspects of the invention, the first amino acid sequence comprises at least 40 contiguous amino acid residues from a sequence at least 85%, at least 90%, at least 95% or at least 97% identical to SEQ ID NO:27 or SEQ ID NO:28. In certain aspects of the invention, the first amino acid sequence comprises at least 40 contiguous amino acid residues from SEQ ID NO:27 or SEQ ID NO:28.

In certain aspects of the invention, the first amino acid sequence comprises a sequence at least 85%, at least 90%, at least 95% or at least 97% identical to SEQ ID NO:27. In one embodiment, the first amino acid sequence comprises SEQ ID NO:27.

As noted above, the second amino acid sequence comprises at least 20 contiguous amino acid residues from the amino acid sequence downstream of the carboxyl-terminal end of the head region sequence. According to the present invention, the term downstream refers to the entirety of the amino acid sequence linked to the carboxyl-terminal amino acid residue of the head region. Preferred upstream sequences are those that are immediately adjacent to the head region sequence. In certain aspects of the invention, the carboxyl-terminal end of the head region is located at the amino acid position corresponding to T329 of the HA protein of influenza A (Denmark/35/2005(H3N2)) HA protein represented by SEQ ID NO:4. Thus, in certain aspects of the invention, the second amino acid sequence comprises at least 20 contiguous amino acids from a region of a Group 2 influenza HA protein corresponding to amino acid residues 330-519 of influenza A (Denmark/35/2005) (H3N2) HA protein. In certain aspects of the invention, the second amino acid sequence comprises at least 20 contiguous amino acids from a region of a Group 2 influenza HA protein comprising amino acid residues 330-519 of influenza A (Denmark/35/2005(H3N2)) (SEQ ID NO:4). In one embodiment, the second amino acid sequence comprises at least 20 contiguous amino acid residues from a sequence at least 85%, at least 90%, at least 95% or at least 97% identical to a sequence selected from the group consisting of SEQ ID NO:30, SEQ ID NO:31, SEQ ID NO:32 and SEQ ID NO:33. In one embodiment, the second amino acid sequence comprises at least 20 contiguous amino acid residues from a sequence selected from the group consisting of SEQ ID NO:30, SEQ ID NO:31, SEQ ID NO:32 and SEQ ID NO:33.

In certain aspects of the invention, the second amino acid sequence comprises at least 40 contiguous amino acids from a region of a Group 2 influenza HA protein corresponding to amino acid residues 330-519 of influenza A (Denmark/35/2005) (H3N2) HA protein. In certain aspects of the invention, the second amino acid sequence comprises at least 40 contiguous amino acids from a region of a Group 2 influenza HA protein comprising amino acid residues 330-519 of influenza A (Denmark/35/2005(H3N2)) (SEQ ID NO:4). In certain aspects of the invention, the second amino acid sequence comprises at least 40 contiguous amino acid residues from a sequence at least 85%, at least 90%, at least 95% or at least 97% identical to a sequence selected from the group consisting of SEQ ID NO:30, SEQ ID NO:31, and SEQ ID NO:32. In certain aspects of the invention, the second amino acid sequence comprises at least 20 contiguous amino acid residues from a sequence selected from the group consisting of SEQ ID NO:30, SEQ ID NO:31, and SEQ ID NO:32.

In certain aspects of the invention, the second amino acid sequence comprises an amino acid sequence at least 85%, at least 90%, at least 95% or at least 97% identical to SEQ ID NO:36. In one embodiment, the second amino acid sequence comprises SEQ ID NO:36.

In certain aspects of the invention, the second amino acid sequence comprises at least 60, at least 72, at least 75, at least 100, at least 150, at least 175, or at least 190 contiguous amino acids from a region of a Group 2 influenza HA protein corresponding to amino acid residues 330-519 of influenza A (Denmark/35/2005) (H3N2) HA protein. In certain aspects of the invention, the second amino acid sequence comprises at least 60, at least 72, at least 75, at least 100, at least 150, at least 175, or at least 190 contiguous amino acids from a region of a Group 2 influenza HA protein comprising amino acid residues 330-519 of influenza A (Denmark/35/2005(H3N2)) (SEQ ID NO:4). In certain aspects of the invention, the second amino acid sequence comprises at least 40, at least 60, at least 72, at least 75, at least 100, at least 150, at least 175, or at least 190 contiguous amino acid residues from a sequence at least 85%, at least 90%, at least 95% or at least 97% identical to SEQ ID NO:30. In one embodiment, the second amino acid sequence comprises at least 40, at least 60, at least 72, at least 75, at least 100, at least 150, at least 175, or at least 190 contiguous amino acid residues from SEQ ID NO:30.

As noted above, the first and second amino acid sequences of the protein construct can be joined by a linker sequence. Any linker sequence can be used as long as the linker sequence has less than five contiguous amino acid residues from the head region of an HA protein and so long as the first and second amino acids are able to form the desired conformation. In one embodiment, the linker sequence is less than 10 amino acids, less than 7 amino acids or less than 5 amino acids in length. In one embodiment, the linker sequence comprises glycine and serine. In one embodiment, the linker sequence joins the carboxyl-terminal end of the first amino acid sequence to the amino-terminal end of the second amino acid sequence. In certain aspects of the invention, the linker sequence joins the carboxyl-terminal end of the second amino acid sequence to the amino-terminal end of the first amino acid sequence. In certain aspects of the invention, the linker sequence is similar in chemical and special properties to a peptide consisting of SEQ ID NO:34 or SEQ ID NO:35. In certain aspects of the invention, the linker comprises SEQ ID NO:34 or SEQ ID NO:35, or conservative variants thereof. In one embodiment, the linker comprises SEQ ID NO:34 or SEQ ID NO:35. In certain aspects of the invention, the linker consists of SEQ ID NO:34 or SEQ ID NO:35.

In certain aspects of the invention, the second amino acid sequence comprises an amino acid sequence from a Group 2 influenza virus HA protein, corresponding to amino acids 330-519 of influenza A (Denmark/35/2005 (H3N2)) HA protein (SEQ ID NO:4), wherein the region corresponding to the inter-helix region of the HA protein (SEQ ID NO:4) is replaced with a linker peptide. In certain aspects of the invention, the inter-helix region of the influenza A (Denmark/35/2005 (H3N2)) HA protein (SEQ ID NO:4) consists essentially of amino acids 402-437 of SEQ ID NO:4. Thus, in certain aspects of the invention, the second amino acid sequence comprises an amino acid sequence from a Group 2 influenza virus HA protein, corresponding to amino acids 330-519 of influenza A (Denmark/35/2005 (H3N2)) HA protein (SEQ ID NO:4), wherein the region corresponding to amino acids 402-437 of SEQ ID NO:4 is replaced with a linker peptide. In certain aspects of the invention, the second amino acid sequence comprises an amino acid sequence at least 80% identical, at least 85% identical, at least 90% identical, at least 95% identical, at least 97% identical or at least 99% identical to SEQ ID NO:30, wherein the region corresponding to the inter-helix region (i.e., amino acids 402-437 of SEQ ID NO:4), is replaced with a linker peptide. In certain aspects of the invention, the second amino acid sequence comprises SEQ ID NO:30, wherein the region corresponding to the inter-helix region (i.e., amino acids 402-437 of SEQ ID NO:4), is replaced with a linker peptide. In certain aspects of the invention, the second amino acid sequence comprises SEQ ID NO:30, wherein amino acids 73-108 of SEQ ID NO:30 are replaced with a linker peptide. Any linker sequence can be used as the linker peptide in the second amino acid sequence, as long as the protein construct is able to form the desired conformation. In certain aspects of the invention, the linker peptide is less than 10 amino acids, less than 7 amino acids or less than 5 amino acids in length. In one embodiment, the linker peptide is four amino acids in length. In certain aspects of the invention, the linker sequence comprises one or more amino acids selected from the group consisting of glycine, serine, proline and aspartic acid. In certain aspects of the invention, the linker peptide comprises an amino acid sequence having chemical and spatial properties similar to a peptide consisting of SEQ ID NO:39. In certain aspects of the invention, the linker peptide comprises SEQ ID NO:39, or conservative variants thereof. In certain aspects of the invention, the linker peptide comprises SEQ ID NO:38. In certain aspects of the invention, the linker peptide consists of SEQ ID NO:39.

In certain aspects of the invention, the second amino acid sequence comprises a sequence at least 80% identical, at least 85% identical, at least 90% identical, at least 95% identical, at least 97% identical or at least 99% identical to a sequence selected from the group consisting of SEQ ID NO:40, SEQ ID NO:41, SEQ ID NO:42 and SEQ ID NO:43. In certain aspects of the invention, the second amino acid sequence comprises a sequence selected from the group consisting of SEQ ID NO:40, SEQ ID NO:41, SEQ ID NO:42, and SEQ ID NO:43.

One embodiment of the present invention is a protein construct (also referred to as a fusion protein) comprising a first amino acid sequence from the stem region of a Group 2 influenza virus HA protein, a second amino acid sequence from the stem region of a Group 2 influenza virus HA protein, and a third amino acid sequence from the stem region of a Group 2 influenza virus HA protein;

wherein the first amino acid sequence comprises at least 20 contiguous amino acid residues from the amino acid sequence upstream of the amino-terminal end of the head region sequence of an influenza A virus HA protein, or an amino acid sequence at least 85% identical, at least 90% identical, at least 95% identical, at least 97% identical, or at least 99% identical, to at least 40 contiguous amino acids from the amino acid sequence upstream of the amino-terminal end of the head region sequence of an influenza A virus HA protein;

wherein the second amino acid sequence comprises at least 20 contiguous amino acid residues from the amino acid sequence that connects the carboxyl-terminal end of the head region sequence to the inter-helix region of an influenza A virus HA protein, or an amino acid sequence at least 85% identical, at least 90% identical, at least 95% identical, at least 97% identical, or at least 99% identical, to at least 40 contiguous amino acid residues from the amino acid sequence that connects the carboxyl-terminal end of the head region sequence to the inter-helix region of an influenza A virus HA protein;

wherein the third amino acid sequence comprises at least 20 contiguous amino acid residues from the amino acid sequence that connects the carboxyl-terminal end of the inter-helix region to the transmembrane domain (TM) of an influenza A virus HA protein, or an amino acid sequence at least 85% identical, at least 90% identical, at least 95% identical, at least 97% identical, or at least 99% identical, to at least 40 contiguous amino acid residues from the amino acid sequence that connects the carboxyl-terminal end of the inter-helix region to the transmembrane domain of an influenza A virus HA protein;

wherein the first and second amino acid sequences are joined by a linker sequence; wherein the second and third amino acid sequences are joined by a linker peptide; and, wherein the first or third amino acid sequence is joined to at least a portion of a monomeric subunit domain such that the protein construct is capable of forming a nanoparticle.

In certain aspects of the invention, the first amino acid sequence is from a Group 2 influenza HA protein. In one embodiment, the first amino acid sequence is from a Group 2 influenza HA protein from a virus selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein. In certain aspects of the invention, the first amino acid sequence is from a Group 2 influenza HA protein from a Group 2 virus listed in Table 2. In certain aspects of the invention, the first amino acid sequence is from the stem region of a Group 2 influenza HA protein having an amino acid sequences at least 85%, at least 90%, at least 95% or at least 97% identical to a sequence selected from the group consisting of SEQ ID NO:4-SEQ ID NO:26 and SEQ ID NO:47-159. In certain aspects of the invention, the first amino acid sequence is from the stem region of a Group 2 influenza HA protein comprising a sequence selected from the group consisting of SEQ ID NO:4-SEQ ID NO:26 and SEQ ID NO:47-159.

In certain aspects of the invention, the first amino acid sequence comprises at least 20 contiguous amino acid residues from the region of a Group 2 influenza virus HA protein corresponding to amino acid residues 1-59 of the HA protein of influenza A Denmark/35/2005 (H3N2)). In certain aspects of the invention, the first amino acid sequence comprises at least 20 contiguous amino acid residues from a sequence at least 85%, at least 90%, at least 95% or at least 97% identical to a sequence selected from the group consisting of SEQ ID NO:27, SEQ ID NO:28 and SEQ ID NO:29. In certain aspects of the invention, the first amino acid sequence comprises at least 20 contiguous amino acid residues from a sequence selected from the group consisting of SEQ ID NO:27, SEQ ID NO:28 and SEQ ID NO:29.

In certain aspects of the invention, the first amino acid sequence comprises at least 40 contiguous amino acid residues from the amino acid region of an HA protein corresponding to amino acid residues 1-59 of influenza A Denmark/35/2005 (H3N2)). In certain aspects of the invention, the first amino acid sequence comprises at least 40 contiguous amino acid residues from a sequence at least 85%, at least 90%, at least 95% or at least 97% identical to SEQ ID NO:27 and SEQ ID NO:28. In certain aspects of the invention, the first amino acid sequence comprises at least 40 contiguous amino acid residues from SEQ ID NO:27 and SEQ ID NO:28.

In certain aspects of the invention, the first amino acid sequence comprises a sequence corresponding to amino acid residues 1-59 of influenza A Denmark/35/2005 (H3N2)) HA protein (SEQ ID NO:4). In certain aspects of the invention, the first amino acid sequence comprises a sequence at least 85%, at least 90%, at least 95% or at least 97% identical to SEQ ID NO:27. In certain aspects of the invention, the first amino acid sequence comprises SEQ ID NO:27. In certain aspects of the invention, the first amino acid sequence consists of SEQ ID NO:27.

In certain aspects of the invention, the second amino acid sequence is from a Group 2 influenza HA protein. In certain aspects of the invention, the second amino acid sequence is from a Group 2 influenza HA protein from a virus selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein. In certain aspects of the invention, the second amino acid sequence is from a Group 2 influenza HA protein from a Group 2 virus listed in Table 2. In certain aspects of the invention, the second amino acid sequence is from the stem region of a Group 2 influenza HA protein having an amino acid sequences at least 85%, at least 90%, at least 95% or at least 97% identical to a sequence selected from the group consisting of SEQ ID NO:4-SEQ ID NO:26 and SEQ ID NO:47-159. In certain aspects of the invention, the second amino acid sequence is from the stem region of a Group 2 influenza HA protein comprising a sequence selected from the group consisting of SEQ ID NO:4-SEQ ID NO:26 and SEQ ID NO:47-159.

In certain aspects of the invention, the second amino acid sequence comprises at least 20 contiguous amino acids from a region of a Group 2 influenza HA protein corresponding to amino acid residues 330-401 of influenza A (Denmark/35/2005(H3N2)) (SEQ ID NO:4). In certain aspects of the invention, the second amino acid sequence comprises at least 20 contiguous amino acid residues from a sequence at least 85%, at least 90%, at least 95% or at least 97% identical to a sequence selected from the group consisting of SEQ ID NO:30, SEQ ID NO:31, SEQ ID NO:32 and SEQ ID NO:33. In certain aspects of the invention, the second amino acid sequence comprises at least 20 contiguous amino acid residues from a sequence selected from the group consisting of SEQ ID NO:30, SEQ ID NO:31, SEQ ID NO:32 and SEQ ID NO:33. In certain aspects of the invention, the second amino acid sequence comprises at least 40 contiguous amino acid residues from a sequence at least 85%, at least 90%, at least 95% or at least 97% identical to a sequence selected from the group consisting of SEQ ID NO:30, SEQ ID NO:31, and SEQ ID NO:32. In certain aspects of the invention, the second amino acid sequence comprises at least 40 contiguous amino acid residues from a sequence selected from the group consisting of SEQ ID NO:30, SEQ ID NO:31, and SEQ ID NO:32.

In certain aspects of the invention, the second amino acid sequence comprises an amino acid sequence at least 85%, at least 90%, at least 95% or at least 97% identical to SEQ ID NO:31. In certain aspects of the invention, the second amino acid sequence comprises SEQ ID NO:31.

In certain aspects of the invention, the second amino acid sequence comprises at least 60, or at least 72, contiguous amino acids from the amino acid sequence of a Group 2 influenza HA protein, that is immediately downstream of the carboxyl-terminal end of the head region sequence of the HA protein. In certain aspects of the invention, the second amino acid sequence comprises at least 60, or at least 72 contiguous amino acids from the amino acid region of a Group 2 influenza virus HA protein, that corresponds to amino acid residues 330-401 of an influenza A (Denmark/35/2005 (H3N2)) HA protein (SEQ ID NO:4).

The first and second amino acid sequences are connected by a linker sequence. In certain aspects of the invention, the linker sequence is less than 10 amino acids, less than 7 amino acids or less than 5 amino acids in length. In certain aspects of the invention, the linker sequence comprises glycine and serine. In certain aspects of the invention, the linker sequence joins the carboxyl-terminal end of the first amino acid sequence to the amino-terminal end of the second amino acid sequence. In certain aspects of the invention, the linker sequence joins the carboxyl-terminal end of the second amino acid sequence to the amino-terminal end of the first amino acid sequence. In certain aspects of the invention, the linker sequence is similar in chemical and special properties to a peptide consisting of SEQ ID NO:34 or SEQ ID NO:35. In certain aspects of the invention, the linker comprises SEQ ID NO:34 or SEQ ID NO:35, or conservative variants thereof. In one embodiment, the linker comprises SEQ ID NO:34 or SEQ ID NO:35. In certain aspects of the invention, the linker consists of SEQ ID NO:34 or SEQ ID NO:35.

In certain aspects of the invention, the third amino acid sequence is from a Group 2 influenza HA protein. In certain aspects of the invention, the third amino acid sequence is from a Group 2 influenza HA protein from a virus selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein. In certain aspects of the invention, the third amino acid sequence is from a Group 2 influenza HA protein from a Group 2 virus listed in Table 2. In certain aspects of the invention, the third amino acid sequence is from the stem region of a Group 2 influenza HA protein having an amino acid sequences at least 85%, at least 90%, at least 95% or at least 97% identical to a sequence selected from the group consisting of SEQ ID NO:4-SEQ ID NO:26 and SEQ ID NO:47-159. In certain aspects of the invention, the third amino acid sequence is from the stem region of a Group 2 influenza HA protein comprising a sequence selected from the group consisting of SEQ ID NO:4-SEQ ID NO:26, and SEQ ID NO:47-159.

In certain aspects of the invention, the third amino acid sequence comprises at least 20 contiguous amino acids from a region of a Group 2 influenza HA protein corresponding to amino acid residues 438-519 of influenza A (Denmark/35/2005(H3N2)) HA protein (SEQ ID NO:4). In certain aspects of the invention, the second amino acid sequence comprises at least 20 contiguous amino acid residues from a sequence at least 85%, at least 90%, at least 95% or at least 97% identical to a sequence selected from the group consisting of SEQ ID NO:44, SEQ ID NO:45 and SEQ ID NO:46. In certain aspects of the invention, the third amino acid sequence comprises at least 20 contiguous amino acid residues from a sequence selected from the group consisting of SEQ ID NO:44, SEQ ID NO:45 and SEQ ID NO:46. In certain aspects of the invention, the third amino acid sequence comprises at least 40 contiguous amino acid residues from a sequence at least 85%, at least 90%, at least 95% or at least 97% identical to a sequence selected from the group consisting of SEQ ID NO:44, SEQ ID NO:45 and SEQ ID NO:46. In certain aspects of the invention, the third amino acid sequence comprises at least 40 contiguous amino acid residues from a sequence selected from the group consisting of SEQ ID NO:44, SEQ ID NO:45, and SEQ ID NO:46.

In certain aspects of the invention, the third amino acid sequence comprises an amino acid sequence at least 85%, at least 90% at least 95% or at least 97% identical to a sequence selected from the group consisting of SEQ ID NO:44, SEQ ID NO:45 and SEQ ID NO:46. In certain aspects of the invention, the third amino acid sequence comprises an amino acid sequence selected from the group consisting of SEQ ID NO:44, SEQ ID NO:45, and SEQ ID NO:46.

In certain aspects of the invention, the third amino acid sequence comprises at least 60, or at least 75, contiguous amino acids from the amino acid sequence of a Group 2 influenza HA protein, that is immediately downstream of the carboxyl-terminal end of the inter-helix region sequence of a Group 2 influenza A (Denmark/35/2005 (H3N2)) HA protein. In certain aspects of the invention, the second amino acid sequence comprises at least 60, or at least 75 contiguous amino acids from the amino acid region of a Group 2 influenza virus HA protein, that corresponds to amino acid residues 438-519 of an influenza A (Denmark/35/2005 (H3N2)) HA protein (SEQ ID NO:4).

The linker peptide can comprise any sequence of amino acids, as long as the protein construct is able to form the desired conformation. In certain aspects of the invention, the linker peptide is less than 10 amino acids, less than 7 amino acids or less than 5 amino acids in length. In certain aspects of the invention, the linker peptide is four amino acids in length. In certain aspects of the invention, the linker sequence comprises an amino acid selected from the group consisting of glycine, serine, proline and aspartic acid. In certain aspects of the invention, the linker peptide comprises SEQ ID NO:39. In certain aspects of the invention, the linker peptide consists of SEQ ID NO:39.

As has been discussed, mutations to various locations in protein constructs of the invention can stabilize the three-dimensional structure of the protein constructs and/or nanoparticles comprising the construct. Thus, in certain aspects of the invention, the first amino acid sequence comprises at least one mutation at an amino acid location corresponding to a location in SEQ ID NO:4 selected from the group consisting G39, T46, and T58. In certain aspects of the invention, the first amino acid sequence comprises at least one mutation selected from the group consisting of G39C, T46C, and N54H, T58L (numbering based on the sequence of the influenza A (Denmark/35/2005) (H3N2)) HA protein).

In certain aspects of the invention, the second amino acid sequence comprises at least one mutation at an amino acid location corresponding to a location in SEQ ID NO:4 selected from the group consisting of L331, N338, Q392, K396, L397 and L400. In certain aspects of the invention, the first amino acid sequence comprises at least one mutation selected from the group consisting of L331K, N338C, Q392C, and L400V (numbering based on the sequence of the influenza A (Denmark/35/2005) (H3N2)) HA protein).

In certain aspects of the invention, the third amino acid sequence comprises at least one mutation at an amino acid location corresponding to a location in SEQ ID NO:4 selected from the group consisting of S438, N440, E448, T452, and N461. In certain aspects of the invention, the first amino acid sequence comprises at least one mutation selected from the group consisting of S438C, N440L, E448L, T452V, and N461R (numbering based on the sequence of the influenza A (Denmark/35/2005) (H3N2)) HA protein).

As noted above, protein constructs of the invention can be joined to at least a portion of a monomeric subunit protein such that the protein construct is capable of forming a nanoparticle. In certain aspects of the invention, the at least a portion of the monomeric subunit protein is joined to the third amino acid sequence. In a preferred embodiment, the at least a portion of the monomeric subunit protein is joined to the carboxyl end of the third amino acid sequence. In certain aspects of the invention, the portion comprises at least 50, at least 100 or at least 150 amino acids from a monomeric subunit. In certain aspects of the invention, the monomeric subunit is ferritin. In certain aspects of the invention, the monomeric subunit is lumazine synthase. In certain aspects of the invention, the portion comprises at least 50, at least 100 or at least 150 amino acids from SEQ ID NO:1, SEQ ID NO:2 or SEQ ID NO:3. In certain aspects of the invention, the monomeric subunit comprises a sequence at least 85% identical, at least 90% identical or at least 95% identical to SEQ ID NO:1, SEQ ID NO:2 or SEQ ID NO:3. In certain aspects of the invention, the monomeric subunit comprises a sequence selected from the group consisting of SEQ ID NO:1, SEQ ID NO:2 and SEQ ID NO:3.

While the modifications made to the Group 2 influenza virus HA proteins disclosed herein have been described as separate embodiments, it should be appreciated that all such modification may be contained in a single protein construct. For example, a protein construct could be made in which a first amino acid sequence is joined by a linker to a second amino acid sequence, wherein the second amino acid sequence comprises an amino acid sequence from the region downstream of the carboxyl-terminal end of the head region of a group 2 influenza HA protein, but in which the inter-helix region corresponding to amino acids 402-437 of the Group 2 influenza A (Denmark/35/2005) (H3N2)) HA protein has been replaced with a linker peptide, and wherein one or more mutations have been introduced into the second amino acid sequence at a location corresponding to a location selected from the group consisting of L331, N338, K396, L397, L400, S438, N440, E448, T452, and N461, of the Group 2 influenza A (Denmark/35/2005) (H3N2)) HA protein, in order to increase the strength of the interaction between these amino acid residues in the folded protein.

While the protein constructs described heretofore can be used to produce nanoparticles capable of generating an immune response against one or more influenza viruses, in some embodiments, it may be useful to engineer further mutations into the amino acid sequences of proteins of the present invention. For example, it may be useful to alter sites such as enzyme recognition sites or glycosylation sites in the monomeric subunit protein, the trimerization domain, or linker sequences, in order to give the protein beneficial properties (e.g., solubility, half-life, mask portions of the protein from immune surveillance). In this regard, it is known that the monomeric subunit of ferritin is not glycosylated naturally. However, it can be glycosylated if it is expressed as a secreted protein in mammalian or yeast cells. Thus, in certain aspects of the invention, potential N-linked glycosylation sites in the amino acid sequences from the monomeric ferritin subunit are mutated so that the mutated ferritin subunit sequences are no longer glycosylated at the mutated site. One such sequence of a mutated monomeric ferritin subunit is represented by SEQ ID NO:2. Further description of useful mutations are disclosed in International Application No. PCT/US2015/032695.

In some instances, it may be desirable to block the production of an immune response against certain amino acid sequences in the protein construct. This may be done by adding a glycosylation site near the site to be blocked such that the glycans sterically hinder the ability of the immune system to reach the blocked site. Thus, in certain aspects of the invention, the sequence of the protein construct has been altered to include one or more glycosylation sites. Examples of such sites include, but are not limited to, Asn-X-Ser, Asn-X-Thr and Asn-X-Cys. In some instances, the glycosylation site can be introduced into a linker sequence. Further examples of useful sites at which to introduce glycosylation sites include, but are not limited to, locations in Group 2 influenza HA proteins corresponding to amino acids 45-47, or amino acids 370-372 of the HA protein of influenza A New Caledonia/20/1999 (H1). Methods of introducing glycosylation sites are known to those skilled in the art.

Proteins and protein constructs of the present invention are encoded by nucleic acid molecules of the present invention. In addition, they are expressed by nucleic acid constructs of the present invention. As used herein a nucleic acid construct is a recombinant expression vector, i.e., a vector linked to a nucleic acid molecule encoding a protein such that the nucleic acid molecule can affect expression of the protein when the nucleic acid construct is administered to, for example, a subject or an organ, tissue or cell. The vector also enables transport of the nucleic acid molecule to a cell within an environment, such as, but not limited to, an organism, tissue, or cell culture. A nucleic acid construct of the present disclosure is produced by human intervention. The nucleic acid construct can be DNA, RNA or variants thereof. The vector can be a DNA plasmid, a viral vector, or other vector. In certain aspects of the invention, a vector can be a cytomegalovirus (CMV), retrovirus, adenovirus, adeno-associated virus, herpes virus, vaccinia virus, poliovirus, sindbis virus, or any other DNA or RNA virus vector. In certain aspects of the invention, a vector can be a pseudo-typed lentiviral or retroviral vector. In certain aspects of the invention, a vector can be a DNA plasmid. In certain aspects of the invention, a vector can be a DNA plasmid comprising viral components and plasmid components to enable nucleic acid molecule delivery and expression. Methods for the construction of nucleic acid constructs of the present disclosure are well known. See, for example, *Molecular Cloning: A Laboratory Manual*, 3$^{rd}$ edition, Sambrook et al. 2001 Cold Spring Harbor Laboratory Press, and *Current Protocols in Molecular Biology*, Ausubel et al. eds., John Wiley & Sons, 1994. In certain aspects of the invention, the vector is a DNA plasmid, such as a CMV/R plasmid such as CMV/R or CMV/R 8 KB (also referred to herein as CMV/R 8 kb). Examples of CMV/R and CMV/R 8 kb are provided herein. CMV/R is also described in U.S. Pat. No. 7,094,598 B2, issued Aug. 22, 2006.

As used herein, a nucleic acid molecule comprises a nucleic acid sequence that encodes a protein construct of the present invention. A nucleic acid molecule can be produced recombinantly, synthetically, or by a combination of recombinant and synthetic procedures. A nucleic acid molecule of the disclosure can have a wild-type nucleic acid sequence or a codon-modified nucleic acid sequence to, for example, incorporate codons better recognized by the human translation system. In certain aspects of the invention, a nucleic acid molecule can be genetically-engineered to introduce, or eliminate, codons encoding different amino acids, such as to introduce codons that encode an N-linked glycosylation site. Methods to produce nucleic acid molecules of the disclosure are known in the art, particularly once the nucleic acid sequence is known. It is to be appreciated that a nucleic acid construct can comprise one nucleic acid molecule or more than one nucleic acid molecule. It is also to be appreciated that a nucleic acid molecule can encode one protein or more than one protein.

In certain aspects of the invention the nucleic acid molecule of the invention encodes a protein construct of the invention. In certain aspects of the invention, a nucleic acid molecule encodes a protein at least 80% identical, at least 85% identical, at least 90% identical, at least 95% identical, at least 97% identical, at least 99% identical to a protein construct listed in Table 2. In certain aspects of the invention, a nucleic acid molecule encodes a protein comprising an amino acid sequence at least 80% identical, at least 85% identical, at least 90% identical, at least 95% identical, at least 97% identical, at least 99% identical to a sequence selected from the group consisting of SEQ ID NO:47-159.

Also encompassed by the present invention are expression systems for producing protein constructs of the present invention. In certain aspects of the invention, nucleic acid molecules of the present invention are operationally linked to a promoter. As used herein, operationally linked means that proteins encoded by the linked nucleic acid molecules can be expressed when the linked promoter is activated. Promoters useful for practicing the present invention are known to those skilled in the art. One embodiment of the present invention is a recombinant cell comprising a nucleic acid molecule of the present invention. One embodiment of the present invention is a recombinant virus comprising a nucleic acid molecule of the present invention.

As indicated above, the recombinant production of the protein constructs of the present invention can be accomplished using any suitable conventional recombinant technology currently known in the field. For example, production of a nucleic acid molecule encoding a fusion protein can be carried out in *E. coli* using a nucleic acid molecule encoding a suitable monomeric subunit protein, such as the *Helicobacter pylori* ferritin monomeric subunit, and fusing it to a nucleic acid molecule encoding a suitable influenza protein disclosed herein. The construct may then be transformed into protein expression cells, grown to suitable size, and induced to produce the fusion protein.

As has been described, because protein constructs of the present invention comprise a monomeric subunit protein, they can self-assemble. According to the present invention, the supramolecule resulting from such self-assembly is referred to as an HA expressing, monomeric subunit-based nanoparticle. For ease of discussion, the HA expressing, monomeric subunit-based nanoparticle will simply be referred to as a, or the, nanoparticle (np). Nanoparticles of the present invention have similar structural characteristics as the nanoparticles of the monomeric protein from which they are made. For example, with regard to ferritin, a ferritin-based nanoparticle contains 24 subunits and has 432 symmetry. In the case of nanoparticles of the present invention, the subunits are the protein constructs comprising a monomeric subunit (e.g., ferritin, lumazine synthase, etc.) joined to a Group 2 influenza virus HA protein. Such nanoparticles display at least a portion of the Group 2 influenza virus HA protein on their surface as HA trimers. In such a construction, the HA trimer is accessible to the immune system and thus can elicit an immune response. Thus, one embodiment of the invention is a nanoparticle comprising any protein construct disclosed or described herein. One embodiment of the present invention is a nanoparticle comprising a protein construct of the present invention, wherein the protein construct comprises amino acids from the stem region of a Group 2 influenza virus HA protein joined to a monomeric subunit protein. In certain aspects of the invention, the nanoparticle displays the Group 2 influenza virus HA protein on its surface as a HA trimer. In certain aspects of the invention, the Group 2 influenza virus HA protein is capable of eliciting protective antibodies to an influenza virus.

One embodiment of the invention is a nanoparticle comprising a protein construct of the invention. In certain aspects of the invention, the protein construct comprises a Group 2 influenza HA protein wherein the head region of the Group 2 influenza HA protein has been replaced with an amino acid sequence comprising less than 5 contiguous amino acid residues from the head region of an influenza HA protein. In certain aspects of the invention, the HA protein of the protein construct has also been altered by extending the length of helix A. In certain aspects of the invention, the HA protein of the protein construct has also been altered by shortening the inter-helix region or replacing the inter-helix region with a linker sequence. In certain aspects of the invention, the HA protein of the protein construct has also been altered by mutating specific locations to stabilize the trimeric structure. Examples of suitable locations include, but are not limited to, locations corresponding to a location in SEQ ID NO:4 selected from the group consisting of L331, N338, K396, L397, L400, S438, N440, E448, T452, N461, G39, T46, N54 and T58, and wherein the protein construct is capable of forming a nanoparticle. Methods of replacing the HA protein head region, extending helix A, shortening or replacing the inter-helix region, and suitable site-specific mutations have been disclosed herein. In certain aspects of the invention, the nanoparticle comprises a protein construct comprising a first amino acid sequence from the stem region of a Group 2 influenza virus HA protein and a second amino acid sequence from the stem region of a Group 2 influenza virus HA protein, the first and second amino acid sequences being covalently linked by a linker sequence,
    wherein the first amino acid sequence comprises at least 20 contiguous amino acid residues from the amino acid sequence upstream of the amino-terminal end of the head region sequence;
    wherein the second amino acid sequence comprises at least 20 contiguous amino acid residues from the amino acid sequence downstream of the carboxyl-terminal end of the head region sequence; and,
    wherein the first or second amino acid sequence is joined to at least a portion of a monomeric subunit domain such that the protein construct is capable of forming a nanoparticle.

In certain aspects of the invention, the first amino acid sequence is from the stem region of a Group 2 influenza virus HA protein from a virus selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein. In certain aspects of the invention, the first amino acid sequence is from the stem region of an HA protein from a Group 2 virus listed in Table 2. In certain aspects of the invention, the first amino acid sequence is from the stem region of a Group 2 influenza HA protein having an amino acid sequences at least 85%, at least 90%, at least 95% or at least 97% identical to a sequence selected from the group consisting of SEQ ID NO:4-SEQ ID NO:26 and SEQ ID NO:47-SEQ ID NO:159. In certain aspects of the invention, the first amino acid sequence is from the stem region of a Group 2 influenza HA protein comprising a sequence selected from the group consisting of SEQ ID NO:4-SEQ ID NO:26 and SEQ ID NO:47-SEQ ID NO:159.

In certain aspects of the invention, the second amino acid sequence is from the stem region of a Group 2 influenza HA protein from a virus selected from the group consisting of an influenza H3 virus, an influenza H4 virus, an H7 influenza virus, an H10 influenza virus, an H14 influenza virus, and an H15 influenza virus. In certain aspects of the invention, the second amino acid sequence is from the stem region of an HA protein from a Group 2 virus listed in Table 2. In certain aspects of the invention, the second amino acid sequence is from the stem region of a Group 2 influenza virus HA protein having an amino acid sequences at least 85%, at least 90%, at least 95% or at least 97% identical to a sequence selected from the group consisting of SEQ ID NO:4-SEQ ID NO:26 and SEQ ID NO:47-SEQ ID NO:159. In certain aspects of the invention, the second amino acid sequence is from the stem region of a Group 2 influenza virus HA protein comprising a sequence selected from the group consisting of SEQ ID NO:4-SEQ ID NO:26 and SEQ ID NO:47-SEQ ID NO:159.

As noted above, the first amino acid sequence comprises at least 20 contiguous amino acid residues from the amino acid sequence upstream of the amino-terminal end of the head region sequence. According to the present invention, the term upstream refers to the entirety of the amino acid sequence linked to the amino-terminal end of the first amino acid residue of the head region. Preferred upstream sequences are those that are immediately adjacent to the head region sequence. In certain aspects of the invention, the amino-terminal end of the head region is located at the amino acid residue corresponding to Q60 of the HA protein of influenza A (Denmark/35/2005 (H3N2)) HA protein (SEQ ID NO:4) In certain aspects of the invention, the first amino acid sequence comprises at least 20 contiguous amino acid residues from the region of a Group 2 influenza virus HA protein corresponding to amino acid residues 1-59 of the HA protein of influenza A Denmark/35/2005 (H3N2)) represented by SEQ ID NO:4. In certain aspects of the invention, the first amino acid sequence comprises at least 20 contiguous amino acid residues from a sequence at least 85%, at least 90%, at least 95% or at least 97% identical to a sequence selected from the group consisting of SEQ ID NO:27, SEQ ID NO:28 and SEQ ID NO:29. In certain aspects of the invention, the first amino acid sequence comprises at least 20 contiguous amino acid residues from a sequence selected from the group consisting of SEQ ID NO:27, SEQ ID NO:28, and SEQ ID NO:29.

In certain aspects of the invention, the first amino acid sequence comprises at least 40 contiguous amino acid residues from the amino acid region of an HA protein corresponding to amino acid residues 1-59 of influenza A Denmark/35/2005 (H3N2)) HA protein (SEQ ID NO:4). In certain aspects of the invention, the first amino acid sequence comprises at least 40 contiguous amino acid residues from a sequence at least 85%, at least 90%, at least 95% or at least 97% identical to SEQ ID NO:27 or SEQ ID NO:28. In certain aspects of the invention, the first amino acid sequence comprises at least 40 contiguous amino acid residues from SEQ ID NO:27 or SEQ ID NO:28.

In certain aspects of the invention, the first amino acid sequence comprises a sequence at least 85%, at least 90%, at least 95% or at least 97% identical to SEQ ID NO:27. In certain aspects of the invention, the first amino acid sequence comprises SEQ ID NO:27.

As noted above, the second amino acid sequence comprises at least 20 contiguous amino acid residues from the amino acid sequence downstream of the carboxyl-terminal end of the head region sequence. According to the present invention, the term downstream refers to the entirety of the amino acid sequence linked to the carboxyl-terminal amino acid residue of the head region. Preferred upstream sequences are those that are immediately adjacent to the head region sequence. In certain aspects of the invention, the carboxyl-terminal end of the head region is located at the amino acid position corresponding to T329 of the HA protein of influenza A (Denmark/35/2005(H3N2)) HA protein represented by SEQ ID NO:4. Thus, in certain aspects of the invention, the second amino acid sequence comprises at least 20 contiguous amino acids from a region of a Group 2 influenza HA protein corresponding to amino acid residues 330-519 of influenza A (Denmark/35/2005) (H3N2) HA protein. In certain aspects of the invention, the second amino acid sequence comprises at least 20 contiguous amino acids from a region of a Group 2 influenza HA protein comprising amino acid residues 330-519 of influenza A (Denmark/35/2005(H3N2)) (SEQ ID NO:4). In certain aspects of the invention, the second amino acid sequence comprises at least 20 contiguous amino acid residues from a sequence at least 85%, at least 90%, at least 95% or at least 97% identical to a sequence selected from the group consisting of SEQ ID NO:30, SEQ ID NO:31, SEQ ID NO:32 and SEQ ID NO:33. In certain aspects of the invention, the second amino acid sequence comprises at least 20 contiguous amino acid residues from a sequence selected from the group consisting of SEQ ID NO:30, SEQ ID NO:31, SEQ ID NO:32, and SEQ ID NO:33.

In certain aspects of the invention, the second amino acid sequence comprises at least 40 contiguous amino acids from a region of a Group 2 influenza HA protein corresponding to amino acid residues 330-519 of influenza A (Denmark/35/2005) (H3N2) HA protein. In certain aspects of the invention, the second amino acid sequence comprises at least 40 contiguous amino acids from a region of a Group 2 influenza HA protein comprising amino acid residues 330-519 of influenza A (Denmark/35/2005(H3N2)) (SEQ ID NO:4). In certain aspects of the invention, the second amino acid sequence comprises at least 40 contiguous amino acid residues from a sequence at least 85%, at least 90%, at least 95% or at least 97% identical to a sequence selected from the group consisting of SEQ ID NO:30, SEQ ID NO:31, and SEQ ID NO:32. In certain aspects of the invention, the second amino acid sequence comprises at least 20 contiguous amino acid residues from a sequence selected from the group consisting of SEQ ID NO:30, SEQ ID NO:31, and SEQ ID NO:32.

In certain aspects of the invention, the second amino acid sequence comprises an amino acid sequence at least 85%, at least 90%, at least 95% or at least 97% identical to SEQ ID NO:37. In certain aspects of the invention, the second amino acid sequence comprises SEQ ID NO:37.

In certain aspects of the invention, the second amino acid sequence comprises at least 60, at least 72, at least 75, at least 100, at least 150, at least 175, or at least 190 contiguous amino acids from a region of a Group 2 influenza HA protein corresponding to amino acid residues 330-519 of influenza A (Denmark/35/2005) (H3N2) HA protein. In certain aspects of the invention, the second amino acid sequence comprises at least 60, at least 72, at least 75, at least 100, at least 150, at least 175, or at least 190 contiguous amino acids from a region of a Group 2 influenza HA protein comprising amino acid residues 330-519 of influenza A (Denmark/35/2005(H3N2)) (SEQ ID NO:4). In certain aspects of the invention, the second amino acid sequence comprises at least 40, at least 60, at least 72, at least 75, at least 100, at least 150, at least 175, or at least 190 contiguous amino acid residues from a sequence at least 85%, at least 90%, at least 95% or at least 97% identical to SEQ ID NO:30. In certain aspects of the invention, the second amino acid sequence comprises at least 40, at least 60, at least 72, at least 75, at least 100, at least 150, at least 175, or at least 190 contiguous amino acid residues from SEQ ID NO:30.

In certain aspects of the invention, the nanoparticle comprises a protein construct comprising an amino acid sequence at least 80%, at least about 85%, at least about 90%, at least about 95%, at least about 97% or at least about 99% identical to a protein construct sequence recited in Table 2, wherein the nanoparticle is capable of selectively binding anti-influenza antibodies. In certain aspects of the invention, the nanoparticle comprises a protein construct comprising an amino acid sequence at least 80%, at least about 85%, at least about 90%, at least about 95%, at least about 97% or at least about 99% identical to a sequence selected from the group consisting of SEQ ID NO:47-159, wherein the nanoparticle is capable of selectively binding anti-influenza antibodies. In certain aspects of the invention, the nanoparticle comprises a protein construct comprising an amino acid sequence selected from the group consisting of SEQ ID NOs: 47-159.

Nanoparticles of the present invention can be used to elicit an immune response to influenza virus. One type of immune response is a B-cell response, which results in the production of antibodies against the antigen that elicited the immune response. Thus, in certain aspects of the invention the nanoparticle elicits antibodies that bind to the stem region of an influenza A HA protein from a virus selected from the group consisting of influenza A viruses, influenza B viruses and influenza C viruses. One embodiment of the present invention is a nanoparticle that elicits antibodies that bind to the stem region of influenza HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein. One embodiment of the present invention is a nanoparticle that elicits antibodies that bind to the stem region of an influenza HA protein from a virus listed in Table 2.

While all antibodies are capable of binding to the antigen which elicited the immune response that resulted in antibody production, preferred antibodies are those that provide broad heterosubtypic protection against influenza virus. Thus, one embodiment of the present invention is a nanoparticle that elicits protective antibodies that bind to the stem region of influenza HA protein from a virus selected from the group consisting of influenza A viruses, influenza B viruses and influenza C viruses. One embodiment of the present invention is a nanoparticle that elicits protective antibodies that bind to the stem region of influenza HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein. One embodiment of the present invention is a nanoparticle that elicits antibodies that bind to the stem region of an influenza HA protein from a virus listed in Table 2. One embodiment of the present invention is a nanoparticle that elicits antibodies that bind to a protein comprising an amino acid sequence at least 80% identical to a sequence selected from the group consisting of SEQ ID NOs: 4-26. One embodiment of the present invention is a nanoparticle that elicits antibodies that bind to a protein comprising an amino acid sequence selected from the group consisting of SEQ ID NOs: 4-26.

Protective antibodies elicited by proteins of the present invention can protect against viral infections by affecting any step in the life cycle of the virus. For example, protective antibodies may prevent an influenza virus from attaching to a cell, entering a cell, releasing viral ribonucleoproteins into the cytoplasm, forming new viral particles in the infected cell and budding new viral particles from the infected host cell membrane. In certain aspects of the invention, protective antibodies elicited by proteins of the present invention prevent influenza virus from entering the host cell. In certain aspects of the invention, protective antibodies elicited by proteins of the present invention prevent fusion of viral membranes with endosomal membranes. In certain aspects of the invention, protective antibodies elicited by proteins of the present invention prevent release of ribonucleoproteins into the cytoplasm of the host cell. In certain aspects of the invention, protective antibodies elicited by proteins of the present invention prevent assembly of new virus in the infected host cell. In certain aspects of the invention, protective antibodies elicited by proteins of the present invention prevent release of newly formed virus from the infected host cell.

Because the amino acid sequence of the stem region of influenza virus is highly conserved, protective antibodies elicited by nanoparticles of the present invention may be broadly protective. That is, protective antibodies elicited by nanoparticles of the present invention may protect against influenza viruses of more than one type, subtype and/or strain. Thus, one embodiment of the present invention is a nanoparticle that elicits broadly protective antibodies that bind the stem region of influenza HA protein. One embodiment is a nanoparticle that elicits antibodies that bind the stem region of an HA protein from more than one type of influenza virus selected from the group consisting of influenza type A viruses, influenza type B viruses and influenza type C viruses. One embodiment is a nanoparticle that elicits antibodies that bind the stem region of an HA protein from more than one sub-type of influenza virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. One embodiment is a nanoparticle that elicits antibodies that bind the stem region of an HA protein from more than strain of influenza virus. One embodiment of the present invention is a nanoparticle that elicits antibodies that bind more than one protein comprising an amino acid sequence at least 80% identical to a sequence selected from the group consisting of SEQ ID NO:4-SEQ ID NO:26. One embodiment of the present invention is a nanoparticle that elicits antibodies that bind to more than one protein comprising an amino acid sequence selected from the group consisting of SEQ ID NOs: 4-26.

As noted above, the HA sequence is linked to a portion of a monomeric subunit protein. As used herein, a monomeric subunit protein refers to a protein monomer that is capable of binding to other monomeric subunit proteins such that the monomeric subunit proteins self-assemble into a nanoparticle. Any monomeric subunit protein can be used to produce the protein construct of the present invention, so long as the protein construct is capable of forming a multimeric structure displaying HA protein on its surface. In certain aspects of the invention the monomeric subunit is ferritin.

Ferritin is a globular protein found in all animals, bacteria, and plants, that acts primarily to control the rate and location of polynuclear $Fe(III)_2O_3$ formation through the transportation of hydrated iron ions and protons to and from a mineralized core. The globular form of ferritin is made up of monomeric subunit proteins (also referred to as monomeric ferritin subunits), which are polypeptides having a molecule weight of approximately 17-20 kDa. An example of the sequence of one such monomeric ferritin subunit is represented by SEQ ID NO 1. Each monomeric ferritin subunit has the topology of a helix bundle which includes a four antiparallel helix motif, with a fifth shorter helix (the c-terminal helix) lying roughly perpendicular to the long axis of the 4 helix bundle. According to convention, the helices are labeled A, B, C, and D & E from the N-terminus respectively. The N-terminal sequence lies adjacent to the nanoparticle three-fold axis and extends to the surface, while the E helices pack together at the four-fold axis with the C-terminus extending into the particle core. The consequence of this packing creates two pores on the nanoparticle surface. It is expected that one or both of these pores represent the point by which the hydrated iron diffuses into and out of the nanoparticle. Following production, these monomeric ferritin subunit proteins self-assemble into the globular ferritin protein. Thus, the globular form of ferritin comprises 24 monomeric, ferritin subunit proteins, and has a capsid-like structure having 432 symmetry.

According to the present invention, a monomeric ferritin subunit of the present invention is a full length, single polypeptide of a ferritin protein, or any portion thereof, which is capable of directing self-assembly of monomeric ferritin subunits into the globular form of the protein. Examples of such proteins include, but are not limited to SEQ ID NO:1 and SEQ ID NO:2. Amino acid sequences from monomeric ferritin subunits of any known ferritin protein can be used to produce protein constructs of the present invention, so long as the monomeric ferritin subunit is capable of self-assembling into a nanoparticle displaying HA on its surface. In certain aspects of the invention, the monomeric subunit is from a ferritin protein selected from the group consisting of a bacterial ferritin protein, a plant ferritin protein, an algal ferritin protein, an insect ferritin protein, a fungal ferritin protein and a mammalian ferritin protein. In certain aspects of the invention, the ferritin protein is from *Helicobacter pylori*.

Protein constructs of the present invention need not comprise the full-length sequence of a monomeric subunit polypeptide of a ferritin protein. Portions, or regions, of the monomeric ferritin subunit protein can be utilized so long as the portion comprises an amino acid sequence that directs self-assembly of monomeric ferritin subunits into the globular form of the protein. One example of such a region is located between amino acids 5 and 167 of the *Helicobacter pylori* ferritin protein. More specific regions are described in Zhang, Y. Self-Assembly in the Ferritin Nano-Cage Protein Super Family. 2011, Int. J. Mol. Sci., 12, 5406-5421, which is incorporated herein by reference in its entirety.

In certain aspects of the invention the Group 2 influenza virus HA protein is joined to at least 50, at least 100 or least 150 amino acids from ferritin, wherein the protein construct is capable of forming a nanoparticle. In certain aspects of the invention the Group 2 influenza virus HA protein is joined to at least 50, at least 100 or least 150 amino acids from SEQ ID NO:1 or SEQ ID NO:2, wherein the protein construct is capable of forming a nanoparticle. In certain aspects of the invention the Group 2 influenza virus HA protein is joined to a protein comprising an amino acid sequence at least 85%, at least 90% or at least 95% identical to the sequence of ferritin, wherein the protein construct is capable of forming a nanoparticle. In certain aspects of the invention the Group 2 influenza virus HA protein is joined to a protein comprising an amino acid sequence at least 85%, at least 90%, at least 95% identical to SEQ ID NO:1 or SEQ ID NO:2, wherein the protein construct is capable of forming a nanoparticle.

In certain aspects of the invention the monomeric subunit is lumazine synthase. In certain aspects of the invention the Group 2 influenza virus HA protein is joined to at least 50, at least 100 or least 150 amino acids from lumazine synthase, wherein the protein construct is capable of forming a nanoparticle. Thus, in certain aspects of the invention the Group 2 influenza virus HA protein is joined to a protein at least 85%, at least 90%, at least 95% identical to lumazine synthase, wherein the protein construct is capable of forming a nanoparticle.

As used herein, a nanoparticle of the present invention refers to a three-dimensional particle formed by self-assembly of protein constructs (fusion proteins) of the present invention. Nanoparticles of the present invention are generally spheroid in shape, although other shapes are not excluded, and are generally from about 20 nm to about 100 nm in diameter. Nanoparticles of the present invention may, but need not, comprise other molecules, such as proteins, lipids, carbohydrates, etc., than the protein constructs from which they are formed.

Because nanoparticles of the present invention can elicit an immune response to an influenza virus, they are useful as vaccines to protect individuals against infection by influenza virus. Thus, one embodiment of the present invention is a vaccine comprising a nanoparticle of the present invention. Vaccines of the present invention can also contain other components such as adjuvants, buffers and the like. Although any adjuvant can be used, preferred embodiments can contain: chemical adjuvants such as aluminum phosphate, benzyalkonium chloride, ubenimex, and QS21; genetic adjuvants such as the IL-2 gene or fragments thereof, the granulocyte macrophage colony-stimulating factor (GM-CSF) gene or fragments thereof, the IL-18 gene or fragments thereof, the chemokine (C-C motif) ligand 21 (CCL21) gene or fragments thereof, the IL-6 gene or fragments thereof, CpG, LPS, TLR agonists, and other immune stimulatory genes; protein adjuvants such IL-2 or fragments thereof, the granulocyte macrophage colony-stimulating factor (GM-CSF) or fragments thereof, IL-18 or fragments thereof, the chemokine (C-C motif) ligand 21 (CCL21) or fragments thereof, IL-6 or fragments thereof, CpG, LPS, TLR agonists and other immune stimulatory cytokines or fragments thereof; lipid adjuvants such as cationic liposomes, N3 (cationic lipid), monophosphoryl lipid A (MPL1); other adjuvants including cholera toxin, enterotoxin, Fms-like tyrosine kinase-3 ligand (Flt-3L), bupivacaine, marcaine, and alevamisole.

One embodiment of the present invention is a nanoparticle vaccine that includes more than one influenza HA protein. Such a vaccine can include a combination of different influenza HA proteins, either on a single nanoparticle or as a mixture of nanoparticles, at least two of which have unique influenza HA proteins. A multivalent vaccine can comprise as many influenza HA proteins as necessary in order to result in production of the immune response necessary to protect against a desired breadth of virus strains. In certain aspects of the invention, the vaccine comprises an HA protein from at least two different influenza strains (bi-valent). In certain aspects of the invention, the vaccine comprises a HA protein from at least three different influenza strains (tri-valent). In certain aspects of the invention, the vaccine comprises an HA protein from at least four different influenza strains (tetra-valent). In certain aspects of the invention, the vaccine comprises an HA protein from at least five different influenza strains (penta-valent). In certain aspects of the invention, the vaccine comprises an HA protein from at least six different influenza strains (hexa-valent). In various embodiments, a vaccine comprises an HA protein from each of 7, 8, 9, or 10 different strains of influenza virus. An example of such a combination is a nanoparticle vaccine that comprises influenza A group 1 HA protein, an influenza A group 2 HA protein, and an influenza B HA protein. In certain aspects of the invention, the influenza HA proteins are H1 HA, H3 HA, and B HA. Another example of a multivalent vaccine is a nanoparticle vaccine that comprises HA proteins from four different influenza viruses. In certain aspects of the invention, the multivalent vaccine comprises one or more HA proteins at least 80% identical, at least 85% identical, at least 90% identical, at least 95% identical, at least 97% identical or at least 99% identical to one or more HA proteins listed in Table 2. In certain aspects of the invention, the multivalent vaccine comprises one or more HA proteins listed in Table 2.

One embodiment of the present invention is a method to vaccinate an individual against influenza virus, the method comprising administering a nanoparticle to an individual such that an immune response against influenza virus is produced in the individual, wherein the nanoparticle comprises a monomeric subunit protein joined to a Group 2 influenza virus HA protein, and wherein the nanoparticle displays the influenza HA on its surface. In certain aspects of the invention, the nanoparticle is a monovalent nanoparticle. In certain aspects of the invention, the nanoparticle is multivalent nanoparticle. Another embodiment of the present invention is a method to vaccinate an individual against infection with influenza virus, the method comprising:

a) obtaining a nanoparticle comprising monomeric subunits, wherein the monomeric subunits are joined to an influenza hemagglutinin protein, and wherein the nanoparticle displays a Group 2 influenza virus HA protein on its surface; and, b) administering the nanoparticle to an individual such that an immune response against an influenza virus is produced.

One embodiment of the present invention is a method to vaccinate an individual against influenza virus, the method comprising administering a vaccine of the embodiments to an individual such that an immune response against influenza virus is produced in the individual, wherein the vaccine comprises at least one nanoparticle comprising a monomeric subunit joined to an influenza HA protein, and wherein the nanoparticle displays the influenza HA on its surface. In certain aspects of the invention, the vaccine is a monovalent vaccine. In certain aspects of the invention, the vaccine is multivalent vaccine. One embodiment of the present invention is a method to vaccinate an individual against infection with influenza virus, the method comprising:

a) obtaining a vaccine comprising at least one nanoparticle comprising a protein construct of the present invention, wherein the protein construct comprises a monomeric subunit protein joined to a Group 2 influenza virus HA protein, and wherein the nanoparticle displays the influenza HA on its surface; and, b) administering the vaccine to an individual such that an immune response against an influenza virus is produced.

Certain aspects of the invention, the nanoparticle is a monovalent nanoparticle. Certain aspects of the invention, the nanoparticle is multivalent nanoparticle.

Certain aspects of the invention, the nanoparticle has octahedral symmetry. Certain aspects of the invention, the influenza HA protein is capable of eliciting antibodies to an influenza virus. Certain aspects of the invention, the influenza HA protein is capable of eliciting broadly antibodies to an influenza virus. In preferred embodiments the elicited antibodies are protective antibodies. In a preferred embodiment, the elicited antibodies are broadly heterosubtypic protective.

Vaccines of the present invention can be used to vaccinate individuals using a prime/boost protocol. Such a protocol is described in U.S. Patent Publication No. 20110177122, which is incorporated herein by reference in its entirety. In such a protocol, a first vaccine composition may be administered to the individual (prime) and then after a period of time, a second vaccine composition may be administered to the individual (boost). Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks. Certain aspects of the invention, the boosting composition is formulated for administration about 1 week, or 2 weeks, or 3 weeks, or 4 weeks, or 5 weeks, or 6 weeks, or 7 weeks, or 8 weeks, or 9 weeks, or 16 weeks, or 20 weeks, or 24 weeks, or 28 weeks, or 32 weeks after administration of the priming composition The first and second vaccine compositions can be, but need not be, the same composition. Thus, certain aspects of the invention of the present invention, the step of administering the vaccine comprises administering a first vaccine composition, and then at a later time, administering a second vaccine composition. Certain aspects of the invention, the first vaccine composition comprises a nanoparticle of the present invention. Certain aspects of the invention, the first vaccine composition comprises a nanoparticle of the invention.

Certain aspects of the invention, the individual being vaccinated has been exposed to influenza virus. As used herein, the terms exposed, exposure, and the like, indicate the subject has come in contact with a person of animal that is known to be infected with an influenza virus. Vaccines of the present invention may be administered using techniques well known to those in the art. Techniques for formulation and administration may be found, for example, in "Remington's Pharmaceutical Sciences", 18th ed., 1990, Mack Publishing Co., Easton, Pa. Vaccines may be administered by means including, but not limited to, traditional syringes, needleless injection devices, or micro-projectile bombardment gene guns. Suitable routes of administration include, but are not limited to, parenteral delivery, such as intramuscular, intradermal, subcutaneous, intramedullary injections, as well as, intrathecal, direct intraventricular, intravenous, intraperitoneal, intranasal, or intraocular injections, just to name a few. For injection, the compounds of one embodiment of the invention may be formulated in aqueous solutions, preferably in physiologically compatible buffers such as Hanks' solution, Ringer's solution, or physiological saline buffer.

Certain aspects of the invention, vaccines, or nanoparticles, of the present invention can be used to protect an individual against infection by heterologous influenza virus. That is, a vaccine made using HA protein from one strain of influenza virus is capable of protecting an individual against infection by different strains of influenza. For example, a vaccine made using HA protein from influenza A/Denmark/35/2005)(H3N2), can be used to protect an individual against infection by an influenza virus recited in Table 2.

Certain aspects of the invention, vaccines, or nanoparticles, of the present invention can be used to protect an individual against infection by an antigenically divergent influenza virus. Antigenically divergent refers to the tendency of a strain of influenza virus to mutate over time, thereby changing the amino acids that are displayed to the immune system. Such mutation over time is also referred to as antigenic drift. Thus, for example, a vaccine made using HA protein from the influenza A/Denmark/35/2005)(H3N2) strain of influenza virus is capable of protecting an individual against infection by earlier, antigenically divergent Denmark strains of influenza, and by evolving (or diverging) influenza strains of the future.

Because nanoparticles of the present invention display Group 2 influenza virus HA proteins that are antigenically similar to an intact HA, they can be used in assays for detecting antibodies against influenza virus (anti-influenza antibodies).

Thus, one embodiment of the present invention is a method for detecting anti-influenza virus antibodies using nanoparticles of the present invention. A detection method of the present invention can generally be accomplished by:

a. contacting at least a portion of a sample being tested for the presence of anti-influenza antibodies with a nanoparticle of the present invention; and, b. detecting the presence of a nanoparticle/antibody complex;

wherein the presence of a nanoparticle/antibody complex indicates that the sample contains anti-influenza antibodies.

Certain aspects of the invention of the present invention, a sample is obtained, or collected, from an individual to be tested for the presence of anti-influenza virus antibodies. The individual may or may not be suspected of having anti-influenza antibodies or of having been exposed to influenza virus. A sample is any specimen obtained from the individual that can be used to test for the presence of anti-influenza virus antibodies. A preferred sample is a body fluid that can be used to detect the presence of anti-influenza virus antibodies. Examples of body fluids that may be used to practice the present method include, but are not limited to, blood, plasma, serum, lacrimal fluid and saliva. Those skilled in the art can readily identify samples appropriate for practicing the disclosed methods.

Blood, or blood-derived fluids such as plasma, serum, and the like, are particularly suitable as the sample. Such samples can be collected and prepared from individuals using methods known in the art. The sample may be refrigerated or frozen before assay.

Any nanoparticle of the present invention can be used to practice the disclosed method as long as the nanoparticle binds to anti-influenza virus antibodies. Useful nanoparticles, and methods of their production, have been described in detail herein. In a preferred embodiment, the nanoparticle comprises a protein construct, wherein the protein construct comprises at least 25, at least 50, at least 75, at least 100, or at least 150 contiguous amino acids from a monomeric subunit protein joined to (fused to) at least one epitope from a Group 2 influenza virus HA protein such that the nanoparticle comprises trimers of the Group 2 influenza virus HA protein epitope on its surface, and wherein the protein construct is capable of self-assembling into nanoparticles.

As used herein, the term contacting refers to the introduction of a sample being tested for the presence of anti-influenza antibodies to a nanoparticle of the present invention, for example, by combining or mixing the sample and the nanoparticle of the present invention, such that the nanoparticle is able to come into physical contact with antibodies in the sample, if present. When anti-influenza virus antibodies are present in the sample, an antibody/nanoparticle complex is then formed. Such complex formation refers to the ability of an anti-influenza virus antibodies to selectively bind to the HA portion of the protein construct in the nanoparticle in order to form a stable complex that can be detected. Binding of anti-influenza virus antibodies in the sample to the nanoparticle is accomplished under conditions suitable to form a complex. Such conditions (e.g., appropriate concentrations, buffers, temperatures, reaction times) as well as methods to optimize such conditions are known to those skilled in the art. Binding can be measured using a variety of methods standard in the art including, but not limited to, agglutination assays, precipitation assays, enzyme immunoassays (e.g., ELISA), immunoprecipitation assays, immunoblot assays and other immunoassays as described, for example, in Sambrook et al., Molecular Cloning: A Laboratory Manual, (Cold Spring Harbor Labs Press, 1989), and Harlow et al., Antibodies, a Laboratory Manual (Cold Spring Harbor Labs Press, 1988), both of which are incorporated by reference herein in their entirety. These references also provide examples of complex formation conditions.

As used herein, the phrases selectively binds HA, selective binding to HA, and the like, refer to the ability of an antibody to preferentially bind a HA protein as opposed to binding proteins unrelated to HA, or non-protein components in the sample or assay. An antibody that selectively binds HA is one that binds HA but does not significantly bind other molecules or components that may be present in the sample or assay. Significant binding, is considered, for example, binding of an anti-HA antibody to a non-HA molecule with an affinity or avidity great enough to interfere with the ability of the assay to detect and/or determine the level of, anti-influenza antibodies in the sample. Examples of other molecules and compounds that may be present in the sample, or the assay, include, but are not limited to, non-HA proteins, such as albumin, lipids and carbohydrates.

Certain aspects of the invention, an anti-influenza virus antibody/nanoparticle complex, also referred to herein as an antibody/nanoparticle complex, can be formed in solution. Certain aspects of the invention an antibody/nanoparticle complex can be formed in which the nanoparticle is immobilized on (e.g., coated onto) a substrate. Immobilization techniques are known to those skilled in the art. Suitable substrate materials include, but are not limited to, plastic, glass, gel, celluloid, fabric, paper, and particulate materials. Examples of substrate materials include, but are not limited to, latex, polystyrene, nylon, nitrocellulose, agarose, cotton, PVDF (poly-vinylidene-fluoride), and magnetic resin. Suitable shapes for substrate material include, but are not limited to, a well (e.g., microtiter dish well), a microtiter plate, a dipstick, a strip, a bead, a lateral flow apparatus, a membrane, a filter, a tube, a dish, a celluloid-type matrix, a magnetic particle, and other particulates. Particularly preferred substrates include, for example, an ELISA plate, a dipstick, an immunodot strip, a radioimmunoassay plate, an agarose bead, a plastic bead, a latex bead, a cotton thread, a plastic chip, an immunoblot membrane, an immunoblot paper and a flow-through membrane. Certain aspects of the invention, a substrate, such as a particulate, can include a detectable marker. For descriptions of examples of substrate materials, see, for example, Kemeny, D. M. (1991) A Practical Guide to ELISA, Pergamon Press, Elmsford, N.Y. pp 33-44, and Price, C. and Newman, D. eds. Principles and Practice of Immunoassay, 2nd edition (1997) Stockton Press, NY, N.Y., both of which are incorporated herein by reference in their entirety.

In accordance with the present invention, once formed, an anti-influenza virus antibody/nanoparticle complex is detected. Detection can be qualitative, quantitative, or semi-quantitative. As used herein, the phrases detecting complex formation, detecting the complex, and the like, refer to identifying the presence of anti-influenza virus antibody complexed with the nanoparticle. If complexes are formed, the amount of complexes formed can, but need not be, quantified. Complex formation, or selective binding, between a putative anti-influenza virus antibody and a nanoparticle can be measured (i.e., detected, determined) using a variety of methods standard in the art (see, for example, Sambrook et al. supra.), examples of which are disclosed herein. A complex can be detected in a variety of ways including, but not limited to use of one or more of the following assays: a hemagglutination inhibition assay, a radial diffusion assay, an enzyme-linked immunoassay, a competitive enzyme-linked immunoassay, a radioimmunoassay, a fluorescence immunoassay, a chemiluminescent assay, a lateral flow assay, a flow-through assay, a particulate-based assay (e.g., using particulates such as, but not limited to, magnetic particles or plastic polymers, such as latex or polystyrene beads), an immunoprecipitation assay, a BioCoreJ assay (e.g., using colloidal gold), an immunodot assay (e.g., CMG Immunodot System, Fribourg, Switzerland), and an immunoblot assay (e.g., a western blot), an phosphorescence assay, a flow-through assay, a chromatography assay, a PAGe-based assay, a surface plasmon resonance assay, a spectrophotometric assay, and an electronic sensory assay. Such assays are well known to those skilled in the art.

Assays can be used to give qualitative or quantitative results depending on how they are used. Some assays, such as agglutination, particulate separation, and precipitation assays, can be observed visually (e.g., either by eye or by a machines, such as a densitometer or spectrophotometer) without the need for a detectable marker.

In other assays, conjugation (i.e., attachment) of a detectable marker to the nanoparticle, or to a reagent that selectively binds to the nanoparticle, aids in detecting complex formation. A detectable marker can be conjugated to the nanoparticle, or nanoparticle-binding reagent, at a site that does not interfere with ability of the nanoparticle to bind to an anti-influenza virus antibody. Methods of conjugation are known to those of skill in the art. Examples of detectable markers include, but are not limited to, a radioactive label, a fluorescent label, a chemiluminescent label, a chromophoric label, an enzyme label, a phosphorescent label, an electronic label; a metal sol label, a colored bead, a physical label, or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or ImmunoPure7 NeutrAvidin).

Certain aspects of the invention, an antibody/nanoparticle complex can be detected by contacting a sample with a specific compound, such as an antibody, that binds to an anti-influenza antibody, ferritin, or to the antibody/nanoparticle complex, conjugated to a detectable marker. A detectable marker can be conjugated to the specific compound in such a manner as not to block the ability of the compound to bind to the complex being detected. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or ImmunoPure7 NeutrAvidin).

In another embodiment, a complex is detected by contacting the complex with an indicator molecule. Suitable indicator molecules include molecules that can bind to the anti-influenza virus antibody/nanoparticle complex, the anti-influenza virus antibody, or the nanoparticle. As such, an indicator molecule can comprise, for example, a reagent that binds the anti-influenza virus antibody, such as an antibody that recognizes immunoglobulins. Preferred indicator molecules that are antibodies include, for example, antibodies reactive with the antibodies from species of individual in which the anti-influenza virus antibodies are produced. An indicator molecule itself can be attached to a detectable marker of the present invention. For example, an antibody can be conjugated to biotin, horseradish peroxidase, alkaline phosphatase or fluorescein.

The present invention can further comprise one or more layers and/or types of secondary molecules or other binding molecules capable of detecting the presence of an indicator molecule. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be readily selected by those skilled in the art. Preferred tertiary molecules can also be selected by those skilled in the art based upon the characteristics of the secondary molecule. The same strategy can be applied for subsequent layers.

Preferably, the indicator molecule is conjugated to a detectable marker. A developing agent is added, if required, and the substrate is submitted to a detection device for analysis. In some protocols, washing steps are added after one or both complex formation steps in order to remove excess reagents. If such steps are used, they involve conditions known to those skilled in the art such that excess reagents are removed but the complex is retained.

Because assays of the present invention can detect anti-influenza virus antibodies in a sample, including a blood sample, such assays can be used to identify individuals having anti-influenza antibodies. Thus, one embodiment of the present invention is a method to identify an individual having anti-influenza virus antibodies, the method comprising:
 a. contacting a sample from an individual being tested for anti-influenza antibodies with a nanoparticle of the present invention; and,
 b. analyzing the contacted sample for the presence of a nanoparticle/antibody complex
  wherein the presence of a nanoparticle/antibody complex indicates the individual has anti-influenza antibodies.

Any of the disclosed assay formats can be used to conduct the disclosed method. Examples of useful assay formats include, but are not limited to, a radial diffusion assay, an enzyme-linked immunoassay, a competitive enzyme-linked immunoassay, a radioimmunoassay, a fluorescence immunoassay, a chemiluminescent assay, a lateral flow assay, a flow-through assay, a particulate-based assay (e.g., using particulates such as, but not limited to, magnetic particles or plastic polymers, such as latex or polystyrene beads), an immunoprecipitation assay, a BioCoreJ assay (e.g., using colloidal gold), an immunodot assay (e.g., CMG Immunodot System, Fribourg, Switzerland), and an immunoblot assay (e.g., a western blot), an phosphorescence assay, a flow-through assay, a chromatography assay, a PAGe-based assay, a surface plasmon resonance assay, bio-layer interferometry assay, a spectrophotometric assay, and an electronic sensory assay.

If no anti-influenza antibodies are detected in the sample, such a result indicates the individual does not have anti-influenza virus antibodies. The individual being tested may or may not be suspected of having antibodies to influenza virus. The disclosed methods may also be used to determine if an individual has been exposed to one or more specific type, group, sub-group or strain of influenza virus. To make such a determination, a sample is obtained from an individual that has tested negative for antibodies (i.e., lacked antibodies) to one or more specific type, group, sub-group or strain of influenza virus sometime in their past (e.g., greater than about 1 year, greater than about 2 years, greater than about 3 years, greater than about 4 years, greater than about 5 years, etc.). The sample is then tested for the presence of anti-influenza virus antibodies to one or more type, group, sub-group or strain, of influenza virus using a nanoparticle-based assay of the present invention. If the assay indicates the presence of such antibodies, the individual is then identified as having been exposed to one or more type, group sub-group or strain, of influenza virus sometime after the test identifying them as negative for anti-influenza antibodies. Thus, one embodiment of the present invention is method to identify an individual that has been exposed to influenza virus, the method comprising:
 a. contacting at least a portion of a sample from an individual being tested for anti-influenza antibodies with a nanoparticle of the present invention; and,
 b. analyzing the contacted sample for the presence or level of an antibody/nanoparticle complex, wherein the presence or level of antibody/nanoparticle complex indicates the presence or level of recent anti-influenza antibodies;
 c. comparing the recent anti-influenza antibody level with a past anti-influenza antibody level;
 wherein an increase in the recent anti-influenza antibody level over the past anti-influenza antibody level indicates the individual has been exposed to influenza virus subsequent to determination of the past anti-influenza antibody level.

Methods of the present invention are also useful for determining the response of an individual to a vaccine. Thus, one embodiment is a method for measuring the response of an individual to an influenza vaccine, the method comprising:
 a. administering to the individual a vaccine for influenza virus;
 b. contacting at least a portion of a sample from the individual with a nanoparticle of the present invention;
 c. analyzing the contacted sample for the presence or level of an antibody/nanoparticle complex, wherein the presence or level of antibody/nanoparticle complex indicates the presence or level of recent anti-influenza antibodies
 wherein an increase in the level of antibody in the sample over the pre-vaccination level of antibody in the individual indicates the vaccine induced an immune response in the individual.

The influenza vaccine administered to the individual may, but need not, comprise a vaccine of the present invention, as long as the nanoparticle comprises an HA protein that can bind an anti-influenza antibody induced by the administered vaccine. Methods of administering influenza vaccines are known to those of skill in the art.

Analysis of the sample obtained from the individual may be performed using any of the disclosed assay formats. Certain aspects of the invention, analysis of the sample is performed using an assay format selected from the group consisting of, a radial diffusion assay, an enzyme-linked immunoassay, a competitive enzyme-linked immunoassay, a radioimmunoassay, a fluorescence immunoassay, a chemiluminescent assay, a lateral flow assay, a flow-through assay, a particulate-based assay (e.g., using particulates such as, but not limited to, magnetic particles or plastic polymers, such as latex or polystyrene beads), an immunoprecipitation assay, a BioCoreJ assay (e.g., using colloidal gold), an immunodot assay (e.g., CMG Immunodot System, Fribourg, Switzerland), and an immunoblot assay (e.g., a western blot), an phosphorescence assay, a flow-through assay, a chromatography assay, a PAGE-based assay, a surface plasmon resonance assay, bio-layer interferometry assay, a spectrophotometric assay, and an electronic sensory assay.

Certain aspects of the invention, the method includes a step of determining the level of anti-influenza antibody present in the individual prior to administering the vaccine. However, it is also possible to determine the level of anti-influenza antibody present in the individual from prior medical records, if such information is available.

While not necessary to perform the disclosed method, it may be preferable to wait some period of time between the step of administering the vaccine and the step of determining the level of anti-influenza antibody in the individual. Certain aspects of the invention, determination of the level of anti-influenza antibodies present in the individual is performed at least 1 day, at least 2 days, at least 3 days, at least 4 days, at least 5 days, at least 6 days, at least one week, at least two weeks, at least three weeks, at least four weeks, at least two months, at least three months or at least six months, following administration of the vaccine.

The present invention also includes kits suitable for detecting anti-influenza antibodies. Suitable means of detection include the techniques disclosed herein, utilizing nanoparticles of the present invention. Kits may also comprise a detectable marker, such as an antibody that selectively binds to the nanoparticle, or other indicator molecules. The kit can also contain associated components, such as, but not limited to, buffers, labels, containers, inserts, tubings, vials, syringes and the like.

Examples

This example characterizes the properties and activities of five H10 variants of Group 2 HA nanoparticles, designed using the parameters and methodology disclosed herein. All of the variants were based on the human A/Jiangxi/IPB13/2013(H10N8) strain. Nucleic acid molecules encoding the H10 variants were introduced into Expi293 cells, and the cells cultured under conditions suitable for expression of the encoded variant proteins. Expressed nanoparticles were purified from cell culture supernatant using lectin affinity chromatography followed by size exclusion chromatography (SEC). Chromatograms for the purified nanoparticles are shown in FIGS. 32A-32E.

The purified nanoparticles were analyzed by negative stain electron microscopy, which indicated that individual nanoparticles were formed with the HA stems projecting outward in a periodic arrangement. A representative electron micrograph for each variant is show in FIG. 33.

The antigenicity of the H10ssF variants was evaluated in an ELISA format by measuring affinity to HA stem antibodies FI6, CT149 and CR8020. The results of this evaluation are shown in FIGS. 34A-34D.

Figure 35A:
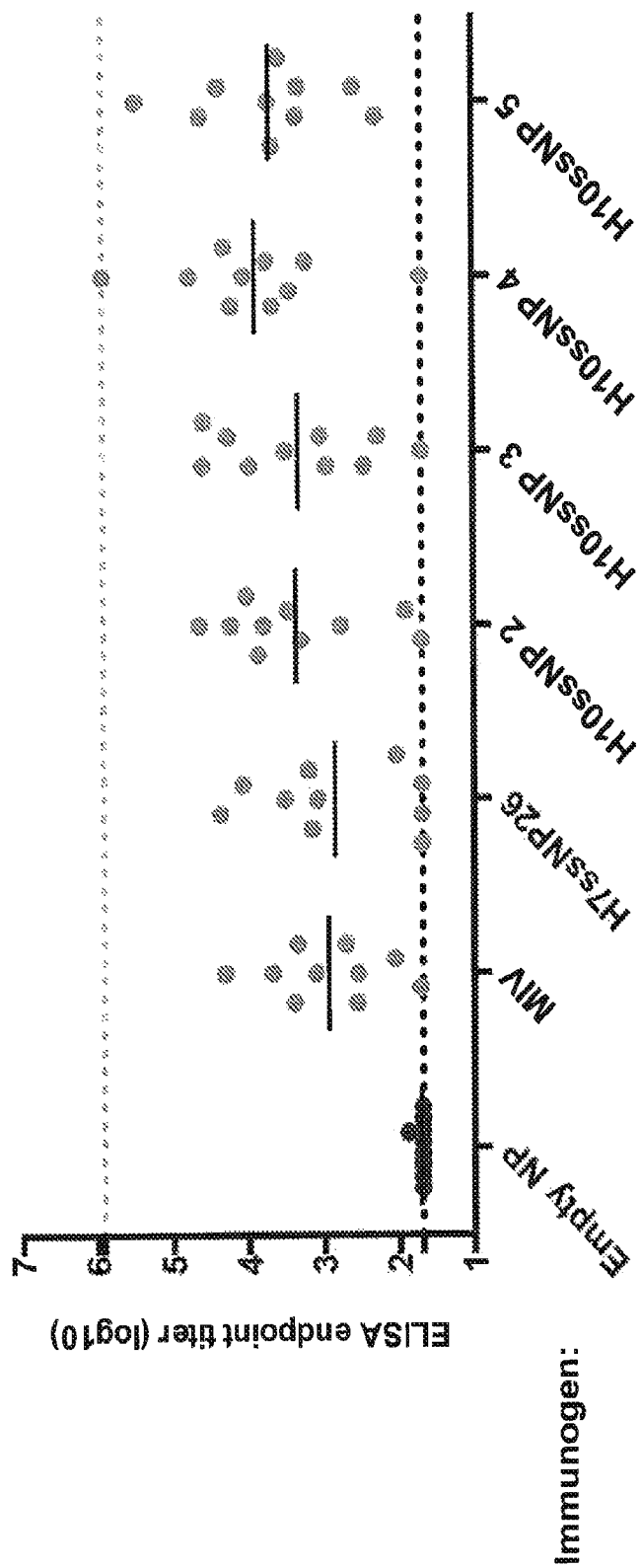
FIGS. 35A & 35B show immune responses of H10ssF-immunized mice to group 2 HAs. ELISA antibody endpoint titers of sera from BALB/c mice (n=10) immunized 3× with five different versions of SSAS-adjuvanted H10ssF (2 ug/mouse) to immobilized A/Hong Kong/1/1968 (H3N2) HA (FIG. 35A) and A/Anhui/1/2013 (H7N9) (FIG. 35B). Responses to sera from mice immunized with empty ferritin nanoparticle alone, H7N9 AH13 Monovalent inactivated vaccine (MIV) or H7ssF26 serve as controls. Geometric mean titers are shown by horizontal lines. The bottom dotted line indicates the baseline titer of 50 and the top dotted line indicates the highest value recorded.
Figure 35B:
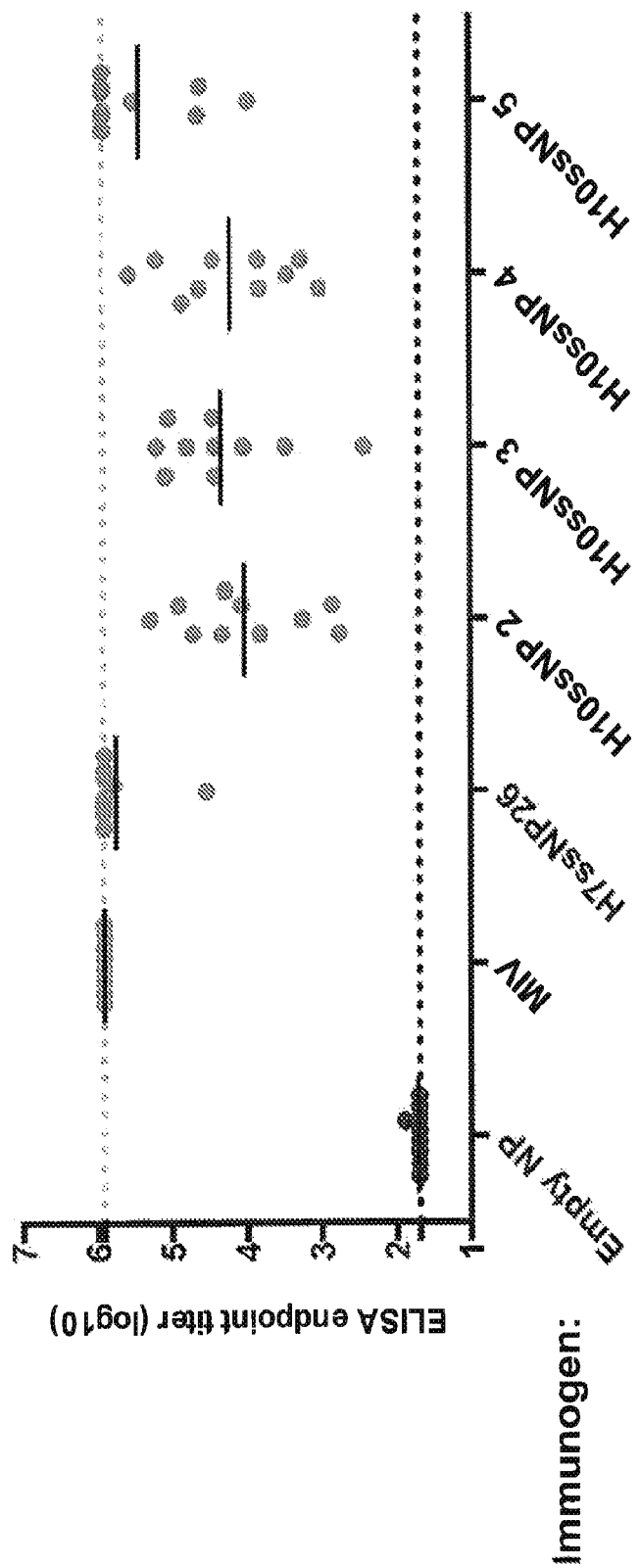
Figure 36C:
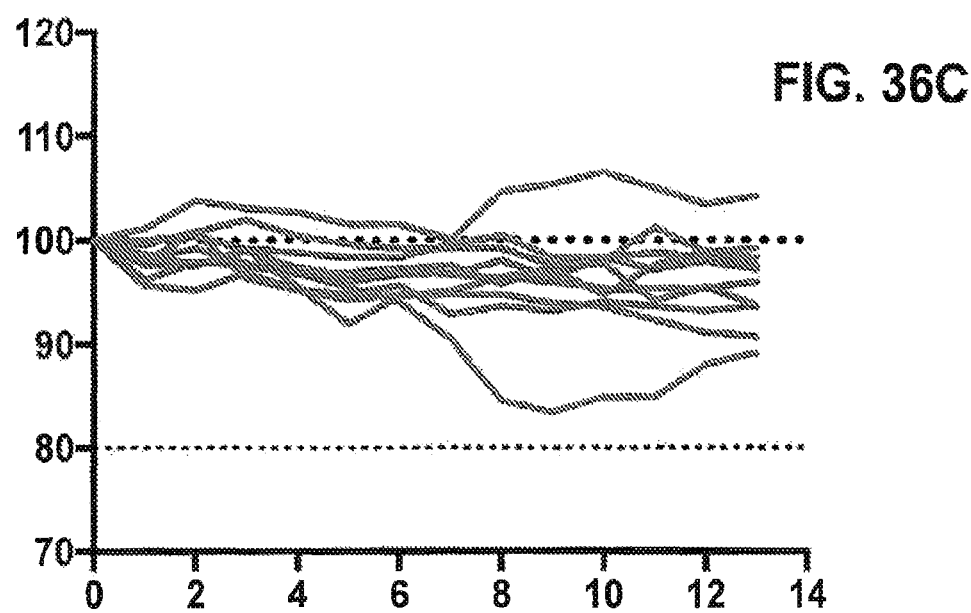
Figure 36D:
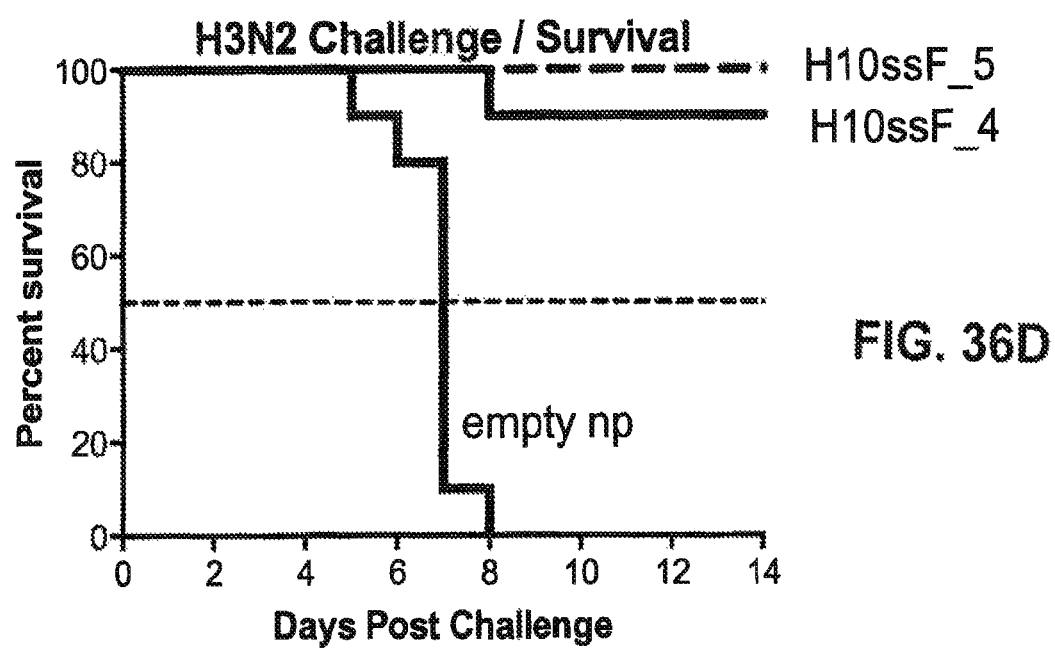
Figure 37A:
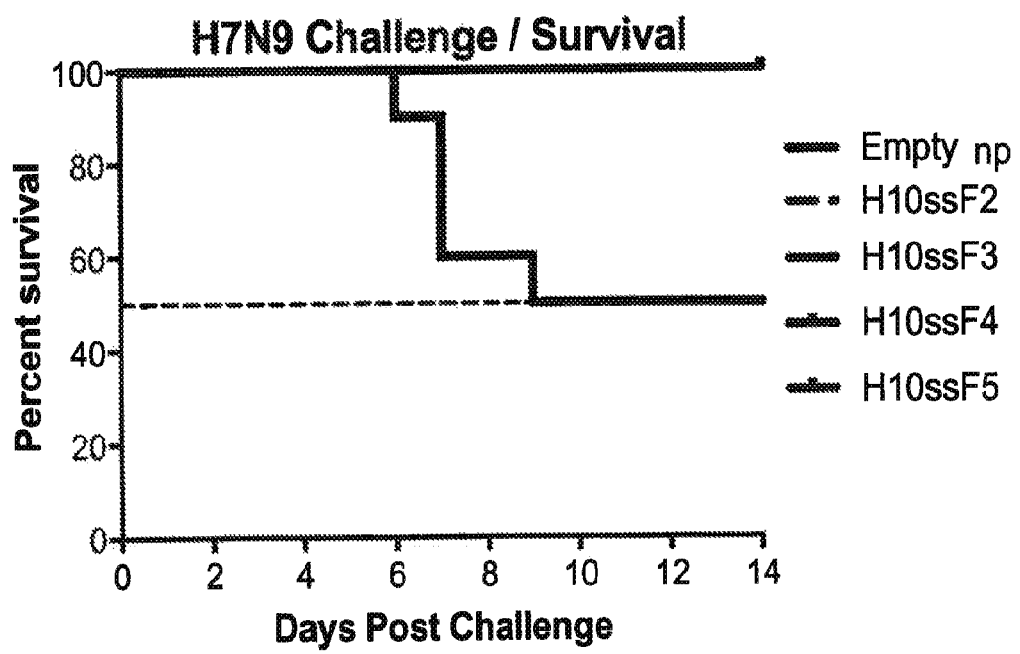
FIGS. 37A-37G show responses of H10ssF-immunized mice to a lethal H7N9 challenge.
Figure 37B:
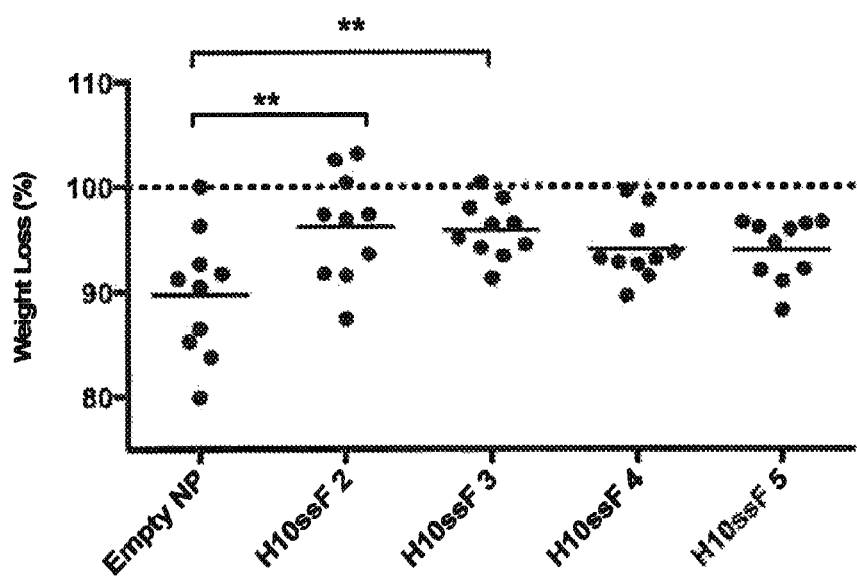
Figure 37C:
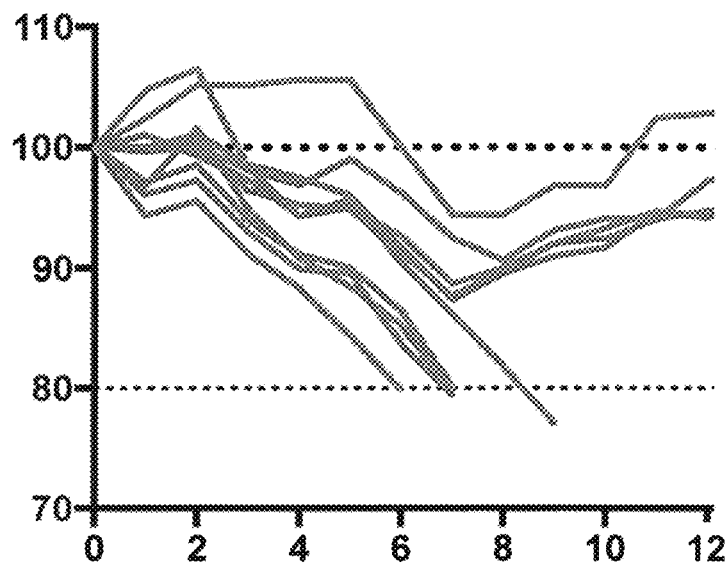
Figure 37D:
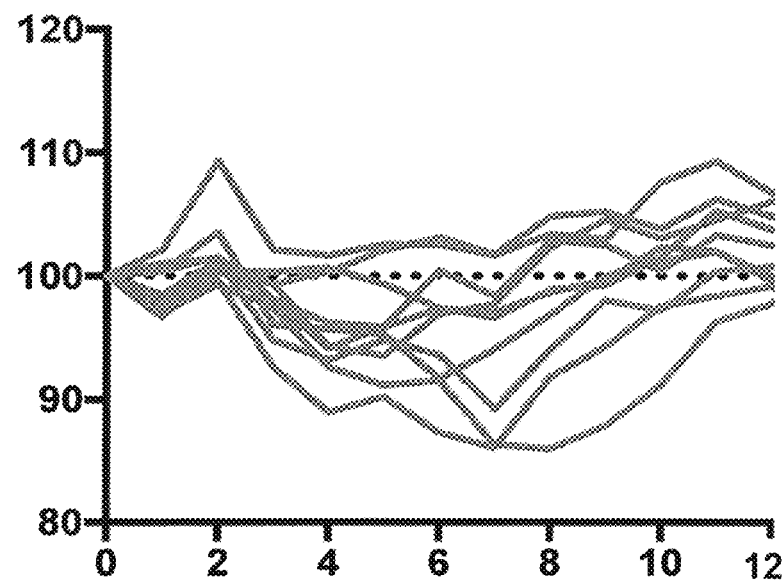
Figure 37E:
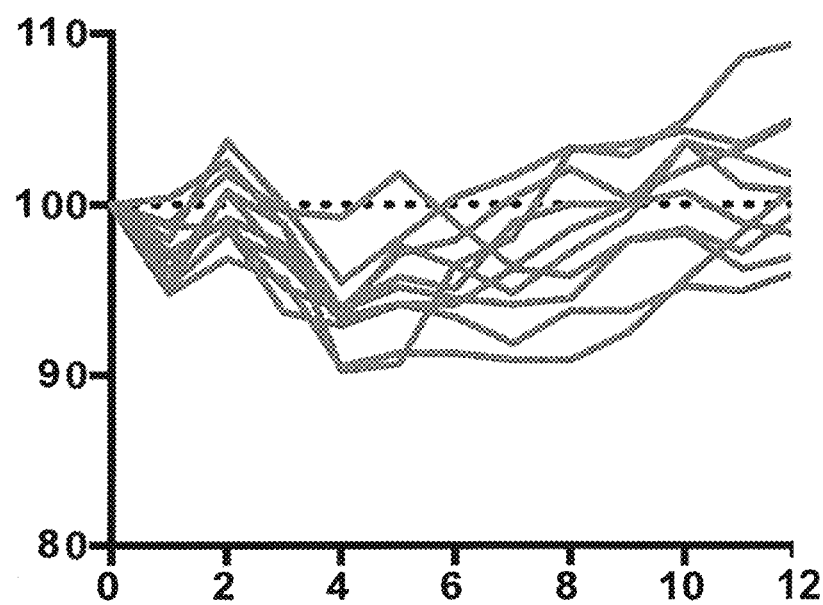
Figure 37F:
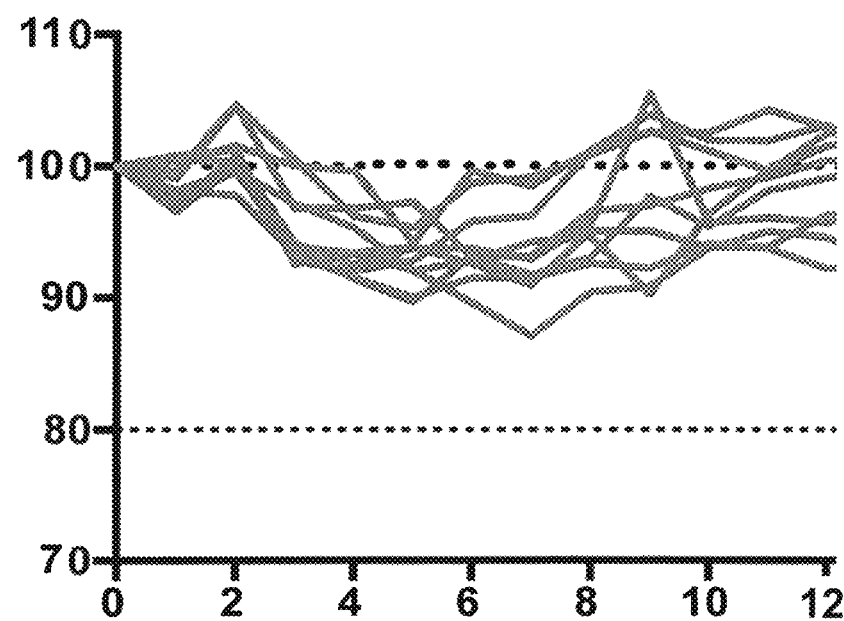
Figure 37G:
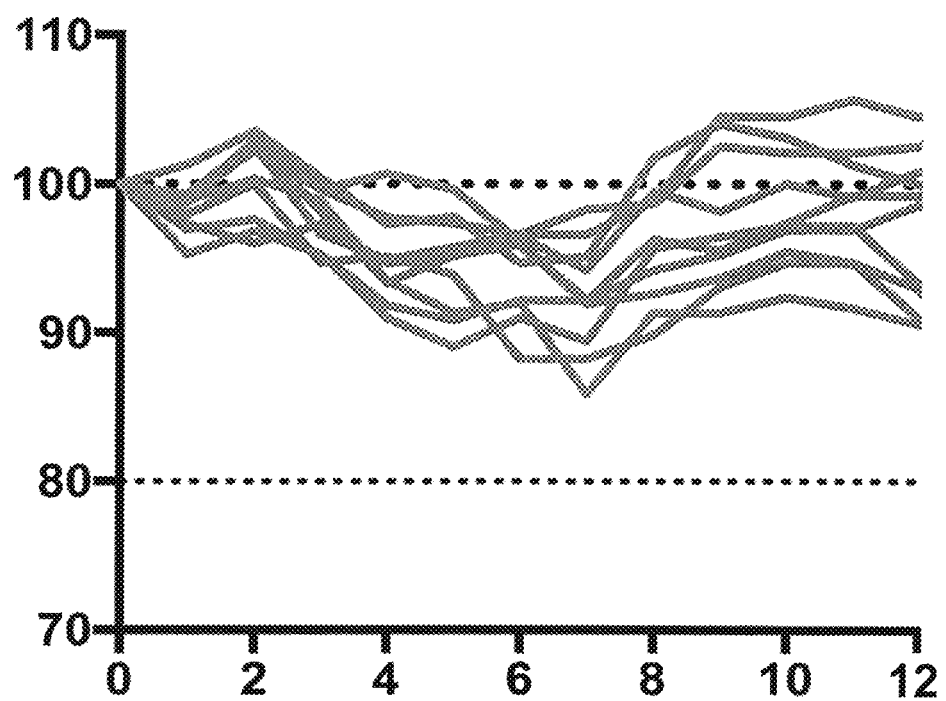

The nanoparticles were then tested for their ability to elicit an immune response against various influenza strains in mice. BALB/c mice (n=10) were immunized with 2 ug of one of the variant nanoparticles using SAS adjuvant. The immunization was repeated 2 more times at periodic intervals. 2 weeks after the last immunization, sera was collected and tested (by ELISA) for its ability to recognize HA protein from H3N2 and H7N9. The results, which are illustrated in FIGS. 35A & 35B, demonstrate that the sera was cross-reactive for both H3N2 and H7N9 HA protein.

The immunized mice were then challenged with a lethal dose of H3N2 (A/Philippines/1982) or H7N9 (A/Shanghai/2/2013-like), and weight loss and survival monitored. The results, which are shown in FIGS. 36A-36D and FIGS. 37A-37G, showed that immunization with the variants nanoparticles protected against both challenge strains without significant weight loss. These results demonstrate that H10ssF immunogens can provide heterosubtypic protection against H3N2 and H7N9 strains.

Figure 40C:
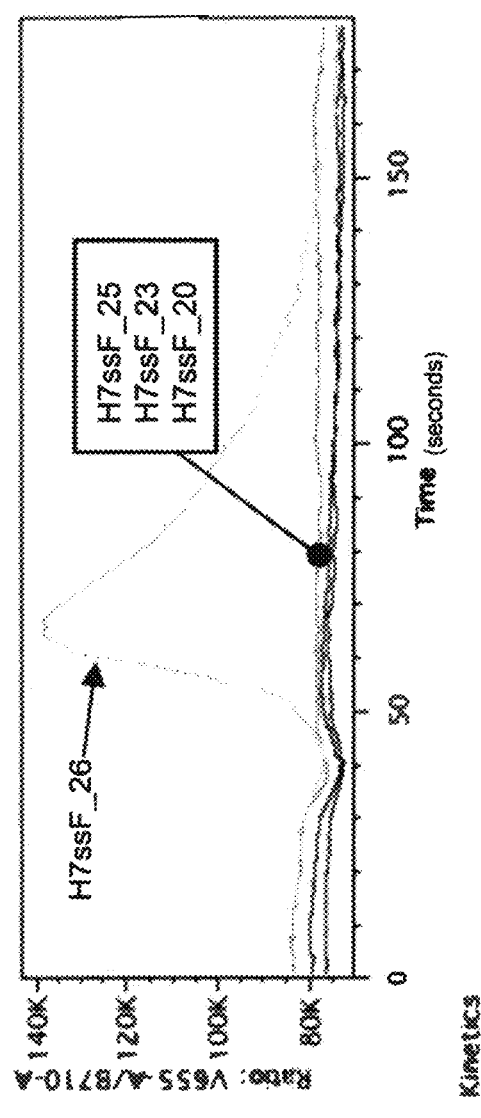
FIGS. 40A-40C shows the ability of various protein constructs of the invention to activate B cells expressing germline-reverted 16.a.26 B cell receptors (BCRs). The graphs show calcium flux (indicating B-cell activation) resulting from contact of the B-cells with an anti-IgM positive control (and no activation using H1 negative control) (FIG. 40A), H3-ss-np protein constructs (FIG. 40B), H7-ss-np protein constructs (FIG. 40C), and H10ssF protein constructs (FIG. 40D).
Figure 40D:
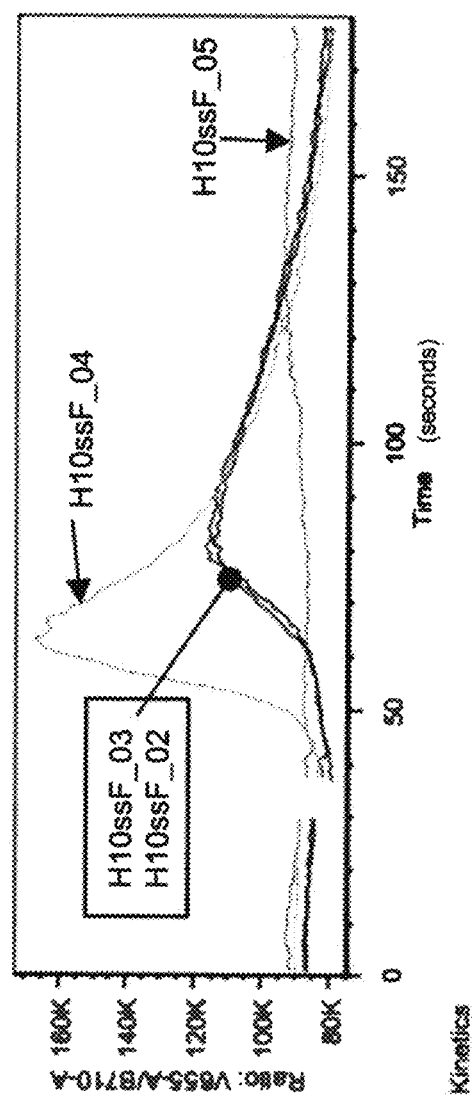

It has been shown that the human, broadly neutralizing stem monoclonal antibody (mAb) 16.a.26), which uses a VH1-18 v-gene, can potently neutralize both group 1 and group 2 influenza viruses. Thus, several HA-SS-np variants, including H3N2, H7N9 and H10N8 subtypes, were evaluated for their ability to activate B cells expressing a germline-reverted version of mAb 16.a.26. In the assay, activation of B-cells is indicated by Ca++ flux. The results of this evaluation, which are shown in FIG. 40, show that the variant nanoparticles H3ssF_256, H7ssF_26 and H10ssF_04 each resulted high levels of activation similar to that observed by the IgM positive control. As shown in FIG. 41, all three of these designs share the same helix A C-terminal extension (ELMEQ), suggesting that this particular motif is useful for eliciting a 16.a.26 bNAb response against influenza HA proteins.

What is claimed:

1. A nanoparticle comprising a fusion protein that comprises a monomeric subunit protein joined to a Group 2 influenza virus hemagglutinin (HA) protein, wherein at least 95% of the amino acid sequence of a head region of the HA protein is replaced with a linker sequence;
   wherein a helix A in a stem region of the HA protein is extended in length by the addition of helix-forming amino acid residues, thereby improving the stability of the fusion protein; and
   wherein the fusion protein comprises an amino acid sequence at least 80% identical to SEQ ID NO: 49.

2. The nanoparticle of claim 1, wherein an inter-helix loop in the stem region of the HA protein is replaced with a linker sequence.

3. The nanoparticle of claim 1, wherein the stem region of the HA protein comprises one or more mutations that forms, or strengthens, an ionic interaction or a salt bridge within the HA protein.

4. The nanoparticle of claim 1, wherein the stem region of the HA protein comprises one or more mutations that increases hydrophobic packing within the HA protein.

5. The nanoparticle of claim 1, wherein the monomeric subunit protein is a ferritin monomeric subunit protein or a lumazine synthase monomeric subunit protein.

6. The nanoparticle of claim 1, wherein the fusion protein comprises an amino acid sequence set forth as SEQ ID NO: 49.

7. The nanoparticle of claim 1, wherein the helix A in the stem region of the HA protein is extended in length by the addition of five helix-forming amino acid residues.

8. A fusion protein comprising a monomeric subunit protein joined to a Group 2 influenza virus hemagglutinin (HA) protein, wherein at least 95% of the amino acid sequence of a head region of the HA protein is replaced with a linker sequence;
   wherein a helix A in the stem region of the HA protein is extended in length by the addition of helix-forming amino acid residues, thereby improving the stability of the fusion protein; and
   wherein the fusion protein comprises an amino acid sequence at least 80% identical to SEQ ID NO:49.

9. The fusion protein of claim 8, wherein an inter-helix loop in the stem region of the HA protein is replaced with a linker sequence.

10. The fusion protein of claim 8, wherein the stem region of the HA protein comprises one or more mutations that forms, or strengthens, an ionic interaction or a salt bridge within the HA protein.

11. The fusion protein of claim 8, wherein the stem region of the HA protein comprises one or more mutations that increases hydrophobic packing within the HA protein.

12. The fusion protein of claim 8, wherein the monomeric subunit protein is a ferritin monomeric subunit protein or a lumazine synthase monomeric subunit protein.

13. A nucleic acid molecule encoding the fusion protein of claim 8.

14. The fusion protein of claim 8, wherein the fusion protein comprises an amino acid sequence set forth as SEQ ID NO: 49.

15. A method of vaccinating an individual against influenza virus, comprising administering a prophylactically or therapeutically effective amount of the nanoparticle of claim 1 to the individual.

* * * * *

SEQUENCE LISTING

<160> NUMBER OF SEQ ID NOS: 160

<210> SEQ ID NO 1
<211> LENGTH: 168
<212> TYPE: PRT
<213> ORGANISM: Helicobacter pylori

<400> SEQUENCE: 1

```
Met Leu Ser Asp Ile Ile Lys Leu Leu Asn Glu Gln Val Asn Lys Glu
1               5                   10                  15

Met Gln Ser Ser Asn Leu Tyr Met Ser Met Ser Ser Trp Cys Tyr Thr
            20                  25                  30

His Ser Leu Asp Gly Ala Gly Leu Phe Leu Phe Asp His Ala Ala Glu
        35                  40                  45

Glu Tyr Glu His Ala Lys Lys Leu Ile Ile Phe Leu Asn Glu Asn Asn
    50                  55                  60

Val Pro Val Gln Leu Thr Ser Ile Ser Ala Pro Glu His Lys Phe Glu
65                  70                  75                  80

Gly Leu Thr Gln Ile Phe Gln Lys Ala Tyr Glu His Glu Gln His Ile
                85                  90                  95

Ser Glu Ser Ile Asn Asn Ile Val Asp His Ala Ile Lys Ser Lys Asp
            100                 105                 110

His Ala Thr Phe Asn Phe Leu Gln Trp Tyr Val Ala Glu Gln His Glu
        115                 120                 125

Glu Val Leu Phe Lys Asp Ile Leu Asp Lys Ile Glu Leu Ile Gly
    130                 135                 140

Asn Glu Asn His Gly Leu Tyr Leu Ala Asp Gln Tyr Val Lys Gly Ile
145                 150                 155                 160

Ala Lys Ser Arg Lys Ser Gly Ser
                165

<210> SEQ ID NO 2
<211> LENGTH: 165
<212> TYPE: PRT
<213> ORGANISM: Artificial Sequence
<220> FEATURE:
<223> OTHER INFORMATION: Synthetic

<400> SEQUENCE: 2

Asp Ile Ile Lys Leu Leu Asn Glu Gln Val Asn Lys Glu Met Gln Ser
1               5                   10                  15

Ser Asn Leu Tyr Met Ser Met Ser Ser Trp Cys Tyr Thr His Ser Leu
            20                  25                  30

Asp Gly Ala Gly Leu Phe Leu Phe Asp His Ala Ala Glu Glu Tyr Glu
        35                  40                  45

His Ala Lys Lys Leu Ile Ile Phe Leu Asn Glu Asn Asn Val Pro Val
    50                  55                  60

Gln Leu Thr Ser Ile Ser Ala Pro Glu His Lys Phe Glu Gly Leu Thr
65                  70                  75                  80

Gln Ile Phe Gln Lys Ala Tyr Glu His Glu Gln His Ile Ser Glu Ser
                85                  90                  95

Ile Asn Asn Ile Val Asp His Ala Ile Lys Ser Lys Asp His Ala Thr
            100                 105                 110

Phe Asn Phe Leu Gln Trp Tyr Val Ala Glu Gln His Glu Glu Val
        115                 120                 125

Leu Phe Lys Asp Ile Leu Asp Lys Ile Glu Leu Ile Gly Asn Glu Asn
    130                 135                 140

His Gly Leu Tyr Leu Ala Asp Gln Tyr Val Lys Gly Ile Ala Lys Ser
145                 150                 155                 160

Arg Lys Ser Gly Ser
                165

<210> SEQ ID NO 3
<211> LENGTH: 154
```

<212> TYPE: PRT
<213> ORGANISM: Aquifex aeolicus

<400> SEQUENCE: 3

```
Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Cys Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150
```

<210> SEQ ID NO 4
<211> LENGTH: 566
<212> TYPE: PRT
<213> ORGANISM: Influenza virus A

<400> SEQUENCE: 4

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190
```

```
Leu Tyr Ile Trp Gly Val His His Pro Gly Thr Asp Asn Asp Gln Ile
            195                 200                 205

Ser Leu Tyr Ala Gln Ala Ser Gly Arg Ile Thr Val Ser Thr Lys Arg
210                 215                 220

Ser Gln Gln Thr Val Ile Pro Asn Ile Gly Ser Arg Pro Arg Val Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
                275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Ile Gly Gln Ala Ala Asp Leu Lys
                370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Val Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
                450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
                515                 520                 525

Asp Trp Ile Leu Trp Ile Ser Phe Ala Ile Ser Cys Phe Leu Leu Cys
                530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 5
<211> LENGTH: 184
<212> TYPE: PRT
<213> ORGANISM: Influenza virus A

<400> SEQUENCE: 5
```

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
50                  55                  60

Gly Glu Ile Cys Asp Asn Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Ile Arg Arg Ser Asn
145                 150                 155                 160

Ser Ser Phe Phe Ser Arg Leu Asn Trp Leu Thr His Leu Asn Phe Lys
                165                 170                 175

Tyr Pro Ala Leu Asn Val Thr Met
                180

<210> SEQ ID NO 6
<211> LENGTH: 188
<212> TYPE: PRT
<213> ORGANISM: Influenza virus A

<400> SEQUENCE: 6

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu
```

<210> SEQ ID NO 7
<211> LENGTH: 220
<212> TYPE: PRT
<213> ORGANISM: Influenza virus A

<400> SEQUENCE: 7

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Asn Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Ser Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ser Ser Gly Arg Ile Thr Val
    210                 215                 220

<210> SEQ ID NO 8
<211> LENGTH: 227
<212> TYPE: PRT
<213> ORGANISM: Influenza virus A

<400> SEQUENCE: 8

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Asn Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn

```
            100                 105                 110
Cys Tyr Pro Tyr Asp Val Pro Asp Tyr Ala Ser Leu Arg Ser Leu Val
        115                 120                 125
Ala Ser Ser Gly Thr Leu Glu Phe Asn Asn Glu Ser Phe Asn Trp Thr
    130                 135                 140
Gly Val Thr Gln Asn Gly Thr Ser Ser Ala Cys Ile Arg Arg Ser Asn
145                 150                 155                 160
Ser Ser Phe Phe Ser Arg Leu Asn Trp Leu Thr His Leu Asn Phe Lys
                165                 170                 175
Tyr Pro Ala Leu Asn Val Thr Met Pro Asn Asn Glu Gln Phe Asp Lys
            180                 185                 190
Leu Tyr Ile Trp Gly Val His His Pro Gly Thr Asp Lys Asp Gln Ile
        195                 200                 205
Phe Leu Tyr Ala Gln Ser Ser Gly Arg Ile Thr Val Ser Thr Lys Arg
    210                 215                 220
Ser Gln Gln
225

<210> SEQ ID NO 9
<211> LENGTH: 251
<212> TYPE: PRT
<213> ORGANISM: Influenza virus A

<400> SEQUENCE: 9

Met Lys Thr Ile Ile Ala Leu Ser Tyr Ile Leu Cys Leu Val Phe Ala
1               5                   10                  15
Gln Lys Leu Pro Gly Asn Asp Asn Ser Thr Ala Thr Leu Cys Leu Gly
            20                  25                  30
His His Ala Val Pro Asn Gly Thr Ile Val Lys Thr Ile Thr Asn Asp
        35                  40                  45
Gln Ile Glu Val Thr Asn Ala Thr Glu Leu Val Gln Ser Ser Ser Thr
    50                  55                  60
Gly Glu Ile Cys Asp Ser Pro His Gln Ile Leu Asp Gly Lys Asn Cys
65                  70                  75                  80
Thr Leu Ile Asp Ala Leu Leu Gly Asp Pro Gln Cys Asp Gly Phe Gln
                85                  90                  95
Asn Lys Lys Trp Asp Leu Phe Val Glu Arg Ser Lys Ala Tyr Ser Asn
            100                 105                 110
Cys Tyr Pro Phe Asp Val Pro Asp Tyr Ala Ser Leu Arg Ser Leu Val
        115                 120                 125
Ala Ser Ser Gly Thr Leu Glu Phe Asn Asn Glu Ser Phe Asn Trp Thr
    130                 135                 140
Gly Val Thr Gln Asn Gly Thr Ser Ser Ala Cys Ile Arg Arg Ser Lys
145                 150                 155                 160
Ser Ser Phe Phe Ser Arg Leu Asn Trp Leu Thr His Leu Asn Phe Lys
                165                 170                 175
Tyr Pro Ala Leu Asn Val Thr Met Pro Asn Asp Glu Gln Phe Asp Lys
            180                 185                 190
Leu Tyr Ile Trp Gly Val His His Pro Gly Thr Asp Lys Asp Gln Ile
        195                 200                 205
Phe Leu Tyr Ala Gln Ala Ser Gly Arg Ile Thr Val Ser Thr Lys Arg
    210                 215                 220
Ser Gln Gln Thr Val Ile Pro Asn Ile Gly Ser Arg Pro Arg Ile Arg
225                 230                 235                 240
```

```
Asn Ile Pro Ser Arg Ile Ser Ile Tyr Trp Gly
                245                 250
```

<210> SEQ ID NO 10
<211> LENGTH: 388
<212> TYPE: PRT
<213> ORGANISM: Influenza virus A

<400> SEQUENCE: 10

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Ser Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365
```

-continued

Phe Arg His Gln Asn Ser Glu Gly Arg Gly Gln Ala Ala Asp Leu Lys
        370                 375                 380

Ser Thr Gln Ala
385

<210> SEQ ID NO 11
<211> LENGTH: 372
<212> TYPE: PRT
<213> ORGANISM: Influenza virus A

<400> SEQUENCE: 11

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ile Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asp Trp Thr
    130                 135                 140

Gly Val Thr Gln Asn Gly Thr Ser Ser Ala Cys Lys Arg Arg Ser Asn
145                 150                 155                 160

Lys Ser Phe Phe Ser Arg Leu Asn Trp Leu Thr His Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Ser Asp Gln Ile
        195                 200                 205

Ser Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asp Val Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala

```
                    340                 345                 350
Gly Phe Ile Glu Asn Gly Trp Glu Gly Met Val Asp Gly Trp Tyr Gly
            355                 360                 365

Phe Arg His Gln
        370

<210> SEQ ID NO 12
<211> LENGTH: 400
<212> TYPE: PRT
<213> ORGANISM: Influenza virus A

<400> SEQUENCE: 12

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Asn Ser Ser Ile
        50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Ser
130                 135                 140

Gly Val Thr Gln Asn Gly Thr Ser Ser Ala Cys Met Arg Arg Ser Asn
145                 150                 155                 160

Ser Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ser Ser Gly Arg Ile Thr Val Ser Thr Lys Arg
210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335
```

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
            355                 360                 365

Phe Arg His Gln Asn Ser Glu Gly Arg Gly Gln Ala Ala Asp Leu Lys
        370                 375                 380

Ser Thr Gln Ala Ala Ile Asp Gln Ile Asn Gly Lys Leu Asn Arg Leu
385                 390                 395                 400

<210> SEQ ID NO 13
<211> LENGTH: 400
<212> TYPE: PRT
<213> ORGANISM: Influenza virus A

<400> SEQUENCE: 13

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Ser
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Ser Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

```
Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

<210> SEQ ID NO 14
<211> LENGTH: 400
<212> TYPE: PRT
<213> ORGANISM: Influenza virus A

<400> SEQUENCE: 14

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Ala
    50                  55                  60

Gly Glu Ile Cys Asp Ser Pro His His Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Arg Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ala Ser Gly Arg Ile Thr Val Ser Thr Lys Arg
    210                 215                 220

Ser Gln Gln Ala Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
```

```
                 290                 295                 300
Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Met Asp Gly Trp Tyr Gly
            355                 360                 365

Phe Arg His Gln Asn Ser Glu Gly Arg Gly Gln Ala Ala Asp Leu Lys
        370                 375                 380

Ser Thr Gln Ala Ala Ile Asp Gln Ile Asn Gly Lys Leu Asn Arg Leu
385                 390                 395                 400

<210> SEQ ID NO 15
<211> LENGTH: 372
<212> TYPE: PRT
<213> ORGANISM: Influenza virus A

<400> SEQUENCE: 15

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val

```
Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
        290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365

Phe Arg His Arg
    370

<210> SEQ ID NO 16
<211> LENGTH: 370
<212> TYPE: PRT
<213> ORGANISM: Influenza virus A

<400> SEQUENCE: 16

Met Asn Thr Gln Ile Leu Val Phe Ala Leu Val Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Val Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Thr Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Arg Asp Pro Ala Leu Ile Val Trp Gly Ile His
            180                 185                 190

His Ser Gly Ser Thr Thr Glu Gln Thr Lys Leu Tyr Gly Ser Gly Ser
        195                 200                 205

Lys Leu Ile Thr Val Gly Ser Ser Asn Tyr Gln Gln Ser Phe Val Pro
    210                 215                 220

Ser Pro Gly Ala Arg Pro Gln Val Asn Gly Gln Ser Gly Arg Ile Asp
225                 230                 235                 240

Phe His Trp Leu Ile Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270
```

```
Ser Met Gly Ile Gln Ser Gly Val Gln Val Asp Ala Asn Cys Glu Gly
            275                 280                 285

Asp Cys Tyr His Ser Gly Gly Thr Ile Ile Ser Asn Leu Pro Phe Gln
    290                 295                 300

Asn Ile Asn Ser Arg Ala Val Gly Lys Cys Pro Arg Tyr Val Lys Gln
305                 310                 315                 320

Glu Ser Leu Met Leu Ala Thr Gly Met Lys Asn Val Pro Glu Leu Pro
                325                 330                 335

Lys Gly Arg Gly Leu Phe Gly Ala Ile Ala Gly Phe Ile Glu Asn Gly
                340                 345                 350

Trp Glu Gly Leu Ile Asp Gly Trp Tyr Gly Phe Arg His Gln Asn Ala
                355                 360                 365

Gln Gly
    370

<210> SEQ ID NO 17
<211> LENGTH: 386
<212> TYPE: PRT
<213> ORGANISM: Influenza virus A

<400> SEQUENCE: 17

Met Asn Thr Gln Ile Leu Val Phe Ala Leu Val Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Thr Val Glu Arg Thr Asn Val Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
                100                 105                 110

Glu Glu Ala Leu Arg Gln Ile Leu Arg Glu Ser Gly Gly Ile Asp Lys
            115                 120                 125

Glu Thr Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asp Pro Ala Leu Ile Ile Trp Gly Ile His
                180                 185                 190

His Ser Gly Ser Thr Thr Glu Gln Thr Lys Leu Tyr Gly Ser Gly Asn
            195                 200                 205

Lys Leu Ile Thr Val Gly Ser Ser Asn Tyr Gln Gln Ser Phe Val Pro
    210                 215                 220

Ser Pro Gly Ala Arg Pro Gln Val Asn Gly Gln Ser Gly Arg Ile Asp
225                 230                 235                 240

Phe His Trp Leu Ile Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
```

```
                    260                 265                 270
Ser Met Gly Ile Gln Ser Gly Val Gln Val Asp Ala Asn Cys Glu Gly
                275                 280                 285

Asp Cys Tyr His Ser Gly Gly Thr Ile Ile Ser Asn Leu Pro Phe Gln
            290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Ile Pro
                325                 330                 335

Lys Arg Arg Arg Arg Gly Leu Phe Gly Ala Ile Ala Gly Phe Ile Glu
            340                 345                 350

Asn Gly Trp Glu Gly Leu Ile Asp Gly Trp Tyr Gly Phe Arg His Gln
        355                 360                 365

Asn Ala Gln Gly Glu Gly Thr Ala Ala Asp Tyr Lys Ser Thr Gln Ser
    370                 375                 380

Ala Ile
385

<210> SEQ ID NO 18
<211> LENGTH: 388
<212> TYPE: PRT
<213> ORGANISM: Influenza virus A

<400> SEQUENCE: 18

Met Asn Thr Gln Ile Leu Val Phe Ala Leu Val Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Val Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Thr Thr
    130                 135                 140

Ser Thr Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asp Pro Ala Leu Ile Ile Trp Gly Ile His
            180                 185                 190

His Ser Gly Ser Thr Thr Glu Gln Thr Lys Leu Tyr Gly Ser Gly Asn
        195                 200                 205

Lys Leu Ile Thr Val Gly Ser Ser Asn Tyr Gln Gln Ser Phe Val Pro
    210                 215                 220

Ser Pro Gly Glu Arg Pro Gln Val Asn Gly Gln Ser Gly Arg Ile Asp
225                 230                 235                 240
```

```
Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Ile Pro
                325                 330                 335

Lys Gly Ser Arg Val Arg Arg Gly Leu Phe Gly Ala Ile Ala Gly Phe
            340                 345                 350

Ile Glu Asn Gly Trp Glu Gly Leu Ile Asp Gly Trp Tyr Gly Phe Arg
        355                 360                 365

His Gln Asn Ala Gln Gly Glu Gly Thr Ala Ala Asp Tyr Lys Ser Thr
    370                 375                 380

Gln Ser Ala Ile
385

<210> SEQ ID NO 19
<211> LENGTH: 363
<212> TYPE: PRT
<213> ORGANISM: Influenza virus A

<400> SEQUENCE: 19

Met Asn Thr Gln Ile Leu Val Phe Ala Leu Val Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Thr Val Glu Arg Thr Asn Val Pro Arg Ile Cys Ser Lys Gly Lys
        50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Ile Asn
            100                 105                 110

Glu Glu Ala Leu Arg Gln Ile Leu Arg Glu Ser Gly Gly Ile Asp Lys
        115                 120                 125

Glu Thr Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asp Pro Ala Leu Ile Thr Trp Gly Ile His
            180                 185                 190

His Ser Gly Ser Thr Thr Glu Gln Thr Lys Leu Tyr Gly Ser Gly Asn
        195                 200                 205

Lys Leu Ile Thr Val Gly Ser Ser Asn Tyr Gln Gln Ser Phe Val Pro
    210                 215                 220
```

Ser Pro Gly Ala Arg Pro Gln Val Asn Gly Gln Ser Gly Arg Ile Asp
225                 230                 235                 240

Phe His Trp Leu Val Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
        290                 295                 300

Asn Ile Asn Ser Arg Ala Val Gly Lys Cys Pro Arg Tyr Val Lys Gln
305                 310                 315                 320

Glu Ser Leu Met Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe
355                 360

<210> SEQ ID NO 20
<211> LENGTH: 560
<212> TYPE: PRT
<213> ORGANISM: Influenza virus A

<400> SEQUENCE: 20

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Thr Val Glu Arg Thr Asn Ile Pro Arg Ile Cys Ser Lys Gly Lys
        50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
                100                 105                 110

Glu Glu Ala Leu Arg Gln Ile Leu Arg Glu Ser Gly Gly Ile Asp Lys
            115                 120                 125

Glu Ala Met Gly Phe Thr Tyr Ser Gly Ile Arg Thr Asp Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asp Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
210                 215                 220

Ser Pro Gly Ala Arg Pro Gln Val Asn Gly Leu Ser Gly Arg Ile Asp

Phe His Trp Leu Met Leu Asn Pro Asn Asp Thr Val Thr Phe Ser Phe
            225                 230                 235                 240

Asn Gly Ala Phe Ile Ala Pro Asp Arg Ala Ser Phe Leu Arg Gly Lys
            245                 250                 255

Ser Met Gly Ile Gln Ser Gly Val Gln Val Asp Ala Asn Cys Glu Gly
            260                 265                 270

Asp Cys Tyr His Ser Gly Gly Thr Ile Ile Ser Asn Leu Pro Phe Gln
            275                 280                 285

Asn Ile Asp Ser Arg Ala Val Gly Lys Cys Pro Arg Tyr Val Lys Gln
290                 295                 300

Arg Ser Leu Leu Leu Ala Thr Gly Met Lys Asn Val Pro Glu Ile Pro
305                 310                 315                 320

Lys Gly Arg Gly Leu Phe Gly Ala Ile Ala Gly Phe Ile Glu Asn Gly
            325                 330                 335

Trp Glu Gly Leu Ile Asp Gly Trp Tyr Gly Phe Arg His Gln Asn Ala
            340                 345                 350

Gln Gly Glu Gly Thr Ala Ala Asp Tyr Lys Ser Thr Gln Ser Ala Ile
            355                 360                 365

Asp Gln Ile Thr Gly Lys Leu Asn Arg Leu Ile Glu Lys Thr Asn Gln
370                 375                 380

Gln Phe Glu Leu Ile Asp Asn Glu Phe Asn Glu Val Glu Lys Gln Ile
385                 390                 395                 400

Gly Asn Val Ile Asn Trp Thr Arg Asp Ser Ile Thr Glu Val Trp Ser
            405                 410                 415

Tyr Asn Ala Glu Leu Leu Val Ala Met Glu Asn Gln His Thr Ile Asp
            420                 425                 430

Leu Ala Asp Ser Glu Met Asp Lys Leu Tyr Glu Arg Val Lys Arg Gln
            435                 440                 445

Leu Arg Glu Asn Ala Glu Glu Asp Gly Thr Gly Cys Phe Glu Ile Phe
450                 455                 460

His Lys Cys Asp Asp Asp Cys Met Ala Ser Ile Arg Asn Asn Thr Tyr
465                 470                 475                 480

Asp His Ser Lys Tyr Arg Glu Glu Ala Met Gln Asn Arg Ile Gln Ile
            485                 490                 495

Asp Pro Val Lys Leu Ser Ser Gly Tyr Lys Asp Val Ile Leu Trp Phe
            500                 505                 510

Ser Phe Gly Ala Ser Cys Phe Ile Leu Leu Ala Ile Val Met Gly Leu
            515                 520                 525

Val Phe Ile Cys Val Lys Asn Gly Asn Met Arg Cys Thr Ile Cys Ile
530                 535                 540

545                 550                 555                 560

<210> SEQ ID NO 21
<211> LENGTH: 560
<212> TYPE: PRT
<213> ORGANISM: Influenza virus A

<400> SEQUENCE: 21

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

-continued

```
Glu Thr Val Glu Arg Thr Asn Ile Pro Arg Ile Cys Ser Lys Gly Lys
 50                  55                  60

Arg Thr Val Asp Leu Gly Gln Cys Gly Leu Leu Gly Thr Ile Thr Gly
 65                  70                  75                  80

Pro Pro Gln Cys Asp Gln Phe Leu Glu Phe Ser Ala Asp Leu Ile Ile
                 85                  90                  95

Glu Arg Arg Glu Gly Ser Asp Val Cys Tyr Pro Gly Lys Phe Val Asn
                100                 105                 110

Glu Glu Ala Leu Arg Gln Ile Leu Arg Glu Ser Gly Gly Ile Asp Lys
                115                 120                 125

Glu Ala Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asn Pro Ala Leu Ile Val Trp Gly Ile His
                180                 185                 190

His Ser Gly Ser Thr Ala Glu Gln Thr Lys Leu Tyr Gly Ser Gly Asn
            195                 200                 205

Lys Leu Val Thr Val Gly Ser Ser Asn Tyr Gln Gln Ser Phe Ala Pro
210                 215                 220

Ser Pro Gly Ala Arg Thr Gln Val Asn Gly Gln Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
                260                 265                 270

Ser Met Gly Ile Gln Ser Gly Val Gln Val Asp Ala Asp Cys Glu Gly
            275                 280                 285

Asp Cys Tyr His Ser Gly Gly Thr Ile Ile Ser Asn Leu Pro Phe Gln
290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
                340                 345                 350

Trp Glu Gly Leu Ile Asp Gly Trp Tyr Gly Phe Arg His Gln Asn Ala
            355                 360                 365

Gln Gly Glu Gly Thr Ala Ala Asp Tyr Lys Ser Thr Gln Ser Ala Ile
370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Thr Glu Val Glu Lys Gln Ile
                405                 410                 415

Gly Asn Val Ile Asn Trp Thr Arg Asp Ser Ile Thr Glu Val Trp Ser
                420                 425                 430

Tyr Asn Ala Glu Leu Leu Val Ala Met Glu Asn Gln His Thr Ile Asp
            435                 440                 445

Leu Ala Asp Ser Glu Met Asp Lys Leu Tyr Glu Arg Val Lys Arg Gln
450                 455                 460

Leu Arg Glu Asn Ala Glu Glu Asp Gly Thr Gly Cys Phe Glu Ile Phe
```

| | | | | | | | | | | | | | | | |
|---|---|---|---|---|---|---|---|---|---|---|---|---|---|---|---|
| | 465 | | | | 470 | | | | 475 | | | | 480 | | |

His Lys Cys Asp Asp Cys Met Ala Ser Ile Arg Asn Asn Thr Tyr
　　　　　　　　485　　　　　　　　　　490　　　　　　　　　495

Asp His Ser Lys Tyr Arg Glu Glu Ala Met Gln Asn Arg Ile Gln Ile
　　　　　　　　500　　　　　　　　　　505　　　　　　　　　510

Asp Pro Val Lys Leu Ser Ser Gly Tyr Lys Asp Val Ile Leu Trp Phe
　　　　　　　　515　　　　　　　　　　520　　　　　　　　　525

Ser Phe Gly Ala Ser Cys Phe Ile Leu Leu Ala Ile Ala Met Gly Leu
　　　　530　　　　　　　　　　535　　　　　　　　　　540

Val Phe Ile Cys Val Lys Asn Gly Asn Met Arg Cys Thr Ile Cys Ile
545　　　　　　　　　　550　　　　　　　　　　555　　　　　　　　　560

<210> SEQ ID NO 22
<211> LENGTH: 554
<212> TYPE: PRT
<213> ORGANISM: Influenza virus A

<400> SEQUENCE: 22

Met Asn Thr Gln Ile Leu Val Phe Ala Leu Ile Ala Ile Ile Pro Thr
1　　　　　　　　5　　　　　　　　　　10　　　　　　　　　　15

Asn Ala Asp Lys Ile Cys Leu Gly His His Ala Val Ser Asn Gly Thr
　　　　　　　　20　　　　　　　　　　25　　　　　　　　　　30

Lys Val Asn Thr Leu Thr Glu Arg Gly Val Glu Val Val Asn Ala Thr
　　　　　　　　35　　　　　　　　　　40　　　　　　　　　　45

Glu Thr Val Glu Arg Thr Asn Ile Pro Arg Ile Cys Ser Lys Gly Lys
　　　　50　　　　　　　　　　55　　　　　　　　　　60

Lys Thr Val Asp Leu Gly Gln Cys Gly Leu Leu Gly Thr Ile Thr Gly
65　　　　　　　　　　70　　　　　　　　　　75　　　　　　　　　80

Pro Pro Gln Cys Asp Gln Phe Leu Glu Phe Ser Ala Asp Leu Ile Ile
　　　　　　　　85　　　　　　　　　　90　　　　　　　　　　95

Glu Arg Arg Glu Gly Ser Asp Val Cys Tyr Pro Gly Lys Phe Val Asn
　　　　　　　　100　　　　　　　　　105　　　　　　　　　110

Glu Glu Ala Leu Arg Gln Ile Leu Arg Glu Ser Gly Gly Ile Asp Lys
　　　　　　　　115　　　　　　　　　120　　　　　　　　　125

Glu Ala Met Gly Phe Thr Tyr Ser Gly Ile Arg Ala Asn Gly Ala Thr
　　　　130　　　　　　　　　　135　　　　　　　　　　140

Ser Ala Cys Arg Arg Ser Gly Ser Ser Phe Tyr Ala Glu Met Lys Trp
145　　　　　　　　　　150　　　　　　　　　　155　　　　　　　　　160

Leu Leu Ser Asn Thr Asp Asn Ala Ala Phe Pro Gln Met Thr Lys Ser
　　　　　　　　165　　　　　　　　　170　　　　　　　　　175

Tyr Lys Asn Thr Arg Lys Ser Pro Ala Leu Ile Val Trp Gly Ile His
　　　　　　　　180　　　　　　　　　185　　　　　　　　　190

His Ser Val Ser Thr Ala Glu Gln Thr Lys Leu Tyr Gly Ser Gly Asn
　　　　　　　　195　　　　　　　　　200　　　　　　　　　205

Lys Leu Val Thr Val Gly Ser Ser Asn Tyr Gln Gln Ser Phe Val Pro
　　　　210　　　　　　　　　　215　　　　　　　　　　220

Ser Pro Gly Ala Arg Pro Gln Val Asn Gly Leu Ser Gly Arg Ile Asp
225　　　　　　　　　　230　　　　　　　　　　235　　　　　　　　　240

Phe His Trp Leu Met Leu Asn Pro Asn Asp Thr Val Thr Phe Ser Phe
　　　　　　　　245　　　　　　　　　250　　　　　　　　　255

Asn Gly Ala Phe Ile Ala Pro Asp Arg Ala Ser Phe Leu Arg Gly Lys
　　　　　　　　260　　　　　　　　　265　　　　　　　　　270

Ser Met Gly Ile Gln Ser Gly Val Gln Val Asp Ala Asn Cys Glu Gly
　　　　275　　　　　　　　　　280　　　　　　　　　　285

```
Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
                340                 345                 350

Trp Glu Gly Leu Ile Asp Gly Trp Tyr Gly Phe Arg His Gln Asn Ala
            355                 360                 365

Gln Gly Glu Gly Thr Ala Ala Asp Tyr Lys Ser Thr Gln Ser Ala Ile
370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
                420                 425                 430

Tyr Asn Ala Glu Leu Leu Val Ala Met Glu Asn Gln His Thr Ile Asp
            435                 440                 445

Leu Ala Asp Ser Glu Met Asp Lys Leu Tyr Glu Arg Val Lys Arg Gln
450                 455                 460

Leu Arg Glu Asn Ala Glu Asp Gly Thr Gly Cys Phe Glu Ile Phe
465                 470                 475                 480

His Lys Cys Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
                500                 505                 510

Asp Pro Val Lys Leu Ser Ser Gly Tyr Lys Asp Val Ile Leu Trp Phe
                515                 520                 525

Ser Phe Gly Ala Ser Cys Phe Ile Leu Leu Ala Ile Val Met Gly Leu
            530                 535                 540

Val Phe Ile Cys Val Lys Asn Gly Asn Met
545                 550

<210> SEQ ID NO 23
<211> LENGTH: 560
<212> TYPE: PRT
<213> ORGANISM: Influenza virus A

<400> SEQUENCE: 23

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
                100                 105                 110
```

```
Glu Glu Ala Leu Arg Gln Ile Leu Arg Glu Ser Gly Gly Ile Asp Lys
            115                 120                 125

Glu Ala Met Gly Phe Thr Tyr Ser Gly Ile Arg Ala Asn Gly Thr Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
                180                 185                 190

His Ser Val Ser Thr Ala Glu Gln Thr Lys Leu Tyr Gly Ser Gly Asn
                195                 200                 205

Lys Leu Val Thr Val Gly Ser Ser Asn Tyr Gln Gln Ser Phe Val Pro
            210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
                260                 265                 270

Ser Met Gly Ile Gln Ser Gly Val Gln Val Asp Ala Asn Cys Glu Gly
            275                 280                 285

Asp Cys Tyr His Ser Gly Gly Thr Ile Ile Ser Ser Leu Pro Phe Gln
            290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
                340                 345                 350

Trp Glu Gly Leu Ile Asp Gly Trp Tyr Gly Phe Arg His Gln Asn Ala
            355                 360                 365

Gln Gly Glu Gly Thr Ala Ala Asp Tyr Lys Ser Thr Gln Ser Ala Ile
            370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
            435                 440                 445

Leu Ala Asp Ser Glu Met Asp Lys Leu Tyr Glu Arg Val Lys Arg Gln
450                 455                 460

Leu Arg Glu Asn Ala Glu Asp Gly Thr Gly Cys Phe Glu Ile Phe
465                 470                 475                 480

His Lys Cys Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
                500                 505                 510

Asp Pro Val Lys Leu Ser Ser Gly Tyr Lys Asp Val Ile Leu Trp Phe
                515                 520                 525
```

Ser Phe Gly Ala Ser Cys Phe Ile Leu Leu Ala Ile Val Met Gly Leu
530                535                540

Val Phe Ile Cys Val Lys Asn Gly Asn Met Arg Cys Thr Ile Cys Ile
545                550                555                560

<210> SEQ ID NO 24
<211> LENGTH: 560
<212> TYPE: PRT
<213> ORGANISM: Influenza virus A

<400> SEQUENCE: 24

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Thr Val Glu Arg Thr Asn Ile Pro Arg Ile Cys Ser Lys Gly Lys
50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Lys
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
            355                 360                 365

Gln Gly Glu Gly Thr Ala Ala Asp Tyr Lys Ser Thr Gln Ser Ala Ile
        370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
            435                 440                 445

Leu Ala Asp Ser Glu Met Asp Lys Leu Tyr Glu Arg Val Lys Arg Gln
450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Val Met Gly Leu
            530                 535                 540

Val Phe Ile Cys Val Lys Asn Gly Asn Met Arg Cys Thr Ile Cys Ile
545                 550                 555                 560

<210> SEQ ID NO 25
<211> LENGTH: 560
<212> TYPE: PRT
<213> ORGANISM: Influenza virus A

<400> SEQUENCE: 25

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Ala Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser

```
                    165                 170                 175
Tyr Lys Asn Thr Arg Lys Ser Pro Ala Leu Ile Val Trp Gly Ile His
                180                 185                 190
His Ser Val Ser Thr Ala Glu Gln Thr Lys Leu Tyr Gly Ser Gly Asn
            195                 200                 205
Lys Leu Val Thr Val Gly Ser Ser Asn Tyr Gln Gln Ser Phe Val Pro
        210                 215                 220
Ser Pro Gly Ala Arg Pro Gln Val Asn Gly Leu Ser Gly Arg Ile Asp
225                 230                 235                 240
Phe His Trp Leu Met Leu Asn Pro Asn Asp Thr Val Thr Phe Ser Phe
                245                 250                 255
Asn Gly Ala Phe Ile Ala Pro Asp Arg Ala Ser Phe Leu Arg Gly Lys
            260                 265                 270
Ser Met Gly Ile Gln Ser Gly Val Gln Val Asp Ala Asn Cys Glu Gly
        275                 280                 285
Asp Cys Tyr His Ser Gly Gly Thr Ile Ile Ser Ser Leu Pro Phe Gln
        290                 295                 300
Asn Ile Asp Ser Arg Ala Val Gly Lys Cys Pro Arg Tyr Val Lys Gln
305                 310                 315                 320
Arg Ser Leu Leu Leu Ala Thr Gly Met Lys Asn Val Pro Glu Ile Pro
                325                 330                 335
Lys Gly Arg Gly Leu Phe Gly Ala Ile Ala Gly Phe Ile Glu Asn Gly
            340                 345                 350
Trp Glu Gly Leu Ile Asp Gly Trp Tyr Gly Phe Arg His Gln Asn Ala
        355                 360                 365
Gln Gly Glu Gly Thr Ala Ala Asp Tyr Lys Ser Thr Gln Ser Ala Ile
        370                 375                 380
Asp Gln Ile Thr Gly Lys Leu Asn Arg Leu Ile Glu Lys Thr Asn Gln
385                 390                 395                 400
Gln Phe Glu Leu Ile Asp Asn Glu Phe Asn Glu Val Glu Lys Gln Ile
                405                 410                 415
Gly Asn Val Ile Asn Trp Thr Arg Asp Ser Ile Thr Glu Val Trp Ser
            420                 425                 430
Tyr Asn Ala Glu Leu Leu Val Ala Met Glu Asn Gln His Thr Ile Asp
        435                 440                 445
Leu Ala Asp Ser Glu Met Asp Lys Leu Tyr Glu Arg Val Lys Arg Gln
        450                 455                 460
Leu Arg Glu Asn Ala Glu Glu Asp Gly Thr Gly Cys Phe Glu Ile Phe
465                 470                 475                 480
His Lys Cys Asp Asp Asp Cys Met Ala Ser Ile Arg Asn Asn Thr Tyr
                485                 490                 495
Asp His Ser Lys Tyr Arg Glu Glu Ala Met Gln Asn Arg Ile Gln Ile
            500                 505                 510
Asp Pro Val Lys Leu Ser Ser Gly Tyr Lys Asp Val Ile Leu Trp Phe
        515                 520                 525
Ser Phe Gly Ala Ser Cys Phe Ile Leu Leu Ala Ile Val Met Gly Leu
        530                 535                 540
Val Phe Ile Cys Val Lys Asn Gly Asn Met Arg Cys Thr Ile Cys Ile
545                 550                 555                 560

<210> SEQ ID NO 26
<211> LENGTH: 561
<212> TYPE: PRT
<213> ORGANISM: Artificial Sequence
```

<220> FEATURE:
<223> OTHER INFORMATION: Synthetic

<400> SEQUENCE: 26

```
Met Tyr Lys Ile Val Val Ile Ile Ala Leu Leu Gly Ala Val Lys Gly
1               5                   10                  15

Leu Asp Lys Ile Cys Leu Gly His His Ala Val Ala Asn Gly Thr Ile
            20                  25                  30

Val Lys Thr Leu Thr Asn Glu Gln Glu Val Thr Asn Ala Thr Glu
        35                  40                  45

Thr Val Glu Ser Thr Gly Ile Asn Arg Leu Cys Met Lys Gly Arg Lys
    50                  55                  60

His Lys Asp Leu Gly Asn Cys His Pro Ile Gly Met Leu Ile Gly Thr
65                  70                  75                  80

Pro Ala Cys Asp Leu His Leu Thr Gly Met Trp Asp Thr Leu Ile Glu
                85                  90                  95

Arg Glu Asn Ala Ile Ala Tyr Cys Tyr Pro Gly Ala Thr Val Asn Val
            100                 105                 110

Glu Ala Leu Arg Gln Lys Ile Met Glu Ser Gly Gly Ile Asn Lys Ile
        115                 120                 125

Ser Thr Gly Phe Thr Tyr Gly Ser Ser Ile Asn Ser Ala Gly Thr Thr
130                 135                 140

Arg Ala Cys Met Arg Asn Gly Gly Asn Ser Phe Tyr Ala Glu Leu Lys
145                 150                 155                 160

Trp Leu Val Ser Lys Ser Lys Gly Gln Asn Phe Pro Gln Thr Thr Asn
                165                 170                 175

Thr Tyr Arg Asn Thr Asp Thr Ala Glu His Leu Ile Met Trp Gly Ile
            180                 185                 190

His His Pro Ser Ser Thr Gln Glu Lys Asn Asp Leu Tyr Gly Thr Gln
        195                 200                 205

Ser Leu Ser Ile Ser Val Gly Ser Ser Thr Tyr Arg Asn Asn Phe Val
210                 215                 220

Pro Val Val Gly Ala Arg Pro Gln Val Asn Gly Gln Ser Gly Arg Ile
225                 230                 235                 240

Asp Phe His Trp Thr Leu Val Gln Pro Gly Asp Asn Ile Thr Phe Ser
                245                 250                 255

His Asn Gly Gly Leu Ile Ala Pro Ser Arg Val Ser Lys Leu Ile Gly
            260                 265                 270

Arg Gly Leu Gly Ile Gln Ser Asp Ala Pro Ile Asp Asn Asn Cys Glu
        275                 280                 285

Ser Lys Cys Phe Trp Arg Gly Gly Ser Ile Asn Thr Arg Leu Pro Phe
290                 295                 300

Gln Asn Leu Ser Pro Arg Thr Val Gly Gln Cys Pro Lys Tyr Val Asn
305                 310                 315                 320

Arg Arg Ser Leu Met Leu Ala Thr Gly Met Arg Asn Val Pro Glu Leu
                325                 330                 335

Ile Gln Gly Arg Gly Leu Phe Gly Ala Ile Ala Gly Phe Leu Glu Asn
            340                 345                 350

Gly Trp Glu Gly Met Val Asp Gly Trp Tyr Gly Phe Arg His Gln Asn
        355                 360                 365

Ala Gln Gly Thr Gly Gln Ala Ala Asp Tyr Lys Ser Thr Gln Ala Ala
370                 375                 380

Ile Asp Gln Ile Thr Gly Lys Leu Asn Arg Leu Val Glu Lys Thr Asn
385                 390                 395                 400
```

```
Thr Glu Phe Glu Ser Ile Glu Ser Glu Phe Ser Glu Ile Glu His Gln
                405                 410                 415

Ile Gly Asn Val Ile Asn Trp Thr Lys Asp Ser Ile Thr Asp Ile Trp
            420                 425                 430

Thr Tyr Gln Ala Glu Leu Leu Val Ala Met Glu Asn Gln His Thr Ile
        435                 440                 445

Asp Met Ala Asp Ser Glu Met Leu Asn Leu Tyr Glu Arg Val Arg Lys
    450                 455                 460

Gln Leu Arg Gln Asn Ala Glu Glu Asp Gly Lys Gly Cys Phe Glu Ile
465                 470                 475                 480

Tyr His Ala Cys Asp Asp Ser Cys Met Glu Ser Ile Arg Asn Asn Thr
                485                 490                 495

Tyr Asp His Ser Gln Tyr Arg Glu Glu Ala Leu Leu Asn Arg Leu Asn
            500                 505                 510

Ile Asn Pro Val Thr Leu Ser Ser Gly Tyr Lys Asp Ile Ile Leu Trp
        515                 520                 525

Phe Ser Phe Gly Ala Ser Cys Phe Val Leu Leu Ala Val Val Met Gly
    530                 535                 540

Leu Phe Phe Phe Cys Leu Lys Asn Gly Asn Met Arg Cys Thr Ile Cys
545                 550                 555                 560

Ile

<210> SEQ ID NO 27
<211> LENGTH: 59
<212> TYPE: PRT
<213> ORGANISM: Influenza virus A

<400> SEQUENCE: 27

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val
    50                  55

<210> SEQ ID NO 28
<211> LENGTH: 40
<212> TYPE: PRT
<213> ORGANISM: Influenza virus A

<400> SEQUENCE: 28

Pro Gly Asn Asp Asn Ser Thr Ala Thr Leu Cys Leu Gly His His Ala
1               5                   10                  15

Val Pro Asn Gly Thr Ile Val Lys Thr Ile Thr Asn Asp Gln Ile Glu
            20                  25                  30

Val Thr Asn Ala Thr Glu Leu Val
        35                  40

<210> SEQ ID NO 29
<211> LENGTH: 25
<212> TYPE: PRT
<213> ORGANISM: Influenza virus A

<400> SEQUENCE: 29

Ala Val Pro Asn Gly Thr Ile Val Lys Thr Ile Thr Asn Asp Gln Ile

-continued

```
                1               5                  10                  15
Glu Val Thr Asn Ala Thr Glu Leu Val
                20                  25

<210> SEQ ID NO 30
<211> LENGTH: 190
<212> TYPE: PRT
<213> ORGANISM: Influenza virus A

<400> SEQUENCE: 30

Leu Lys Leu Ala Thr Gly Met Arg Asn Val Pro Glu Lys Gln Thr Arg
1               5                   10                  15

Gly Ile Phe Gly Ala Ile Ala Gly Phe Ile Glu Asn Gly Trp Glu Gly
                20                  25                  30

Met Val Asp Gly Trp Tyr Gly Phe Arg His Gln Asn Ser Glu Gly Ile
            35                  40                  45

Gly Gln Ala Ala Asp Leu Lys Ser Thr Gln Ala Ala Ile Asn Gln Ile
        50                  55                  60

Asn Gly Lys Leu Asn Arg Leu Ile Gly Lys Thr Asn Glu Lys Phe His
65                  70                  75                  80

Gln Ile Glu Lys Glu Phe Ser Glu Val Glu Gly Arg Ile Gln Asp Leu
                85                  90                  95

Glu Lys Tyr Val Glu Asp Thr Lys Val Asp Leu Trp Ser Tyr Asn Ala
            100                 105                 110

Glu Leu Leu Val Ala Leu Glu Asn Gln His Thr Ile Asp Leu Thr Asp
        115                 120                 125

Ser Glu Met Asn Lys Leu Phe Glu Arg Thr Lys Lys Gln Leu Arg Glu
    130                 135                 140

Asn Ala Glu Asp Met Gly Asn Gly Cys Phe Lys Ile Tyr His Lys Cys
145                 150                 155                 160

Asp Asn Ala Cys Ile Gly Ser Ile Arg Asn Gly Thr Tyr Asp His Asp
                165                 170                 175

Val Tyr Arg Asp Glu Ala Leu Asn Asn Arg Phe Gln Ile Lys
            180                 185                 190

<210> SEQ ID NO 31
<211> LENGTH: 66
<212> TYPE: PRT
<213> ORGANISM: Influenza virus A

<400> SEQUENCE: 31

Leu Lys Leu Ala Thr Gly Met Arg Asn Val Pro Glu Lys Gln Thr Arg
1               5                   10                  15

Gly Ile Phe Gly Ala Ile Ala Gly Phe Ile Glu Asn Gly Trp Glu Gly
                20                  25                  30

Met Val Asp Gly Trp Tyr Gly Phe Arg His Gln Asn Ser Glu Gly Ile
            35                  40                  45

Gly Gln Ala Ala Asp Leu Lys Ser Thr Gln Ala Ala Ile Asn Gln Ile
        50                  55                  60

Asn Gly
65

<210> SEQ ID NO 32
<211> LENGTH: 50
<212> TYPE: PRT
<213> ORGANISM: Influenza virus A

<400> SEQUENCE: 32
```

Leu Lys Leu Ala Thr Gly Met Arg Asn Val Pro Glu Lys Gln Thr Arg
1               5                   10                  15

Gly Ile Phe Gly Ala Ile Ala Gly Phe Ile Glu Asn Gly Trp Glu Gly
            20                  25                  30

Met Val Asp Gly Trp Tyr Gly Phe Arg His Gln Asn Ser Glu Gly Ile
        35                  40                  45

Gly Gln
    50

<210> SEQ ID NO 33
<211> LENGTH: 25
<212> TYPE: PRT
<213> ORGANISM: Influenza virus A

<400> SEQUENCE: 33

Leu Lys Leu Ala Thr Gly Met Arg Asn Val Pro Glu Lys Gln Thr Arg
1               5                   10                  15

Gly Ile Phe Gly Ala Ile Ala Gly Phe
            20                  25

<210> SEQ ID NO 34
<211> LENGTH: 7
<212> TYPE: PRT
<213> ORGANISM: Artificial sequence
<220> FEATURE:
<223> OTHER INFORMATION: Synthetic

<400> SEQUENCE: 34

Val Phe Pro Gly Cys Gly Val
1               5

<210> SEQ ID NO 35
<211> LENGTH: 6
<212> TYPE: PRT
<213> ORGANISM: Artificial sequence
<220> FEATURE:
<223> OTHER INFORMATION: Synthetic

<400> SEQUENCE: 35

Cys Phe Asn Gly Ile Cys
1               5

<210> SEQ ID NO 36
<211> LENGTH: 5
<212> TYPE: PRT
<213> ORGANISM: Artificial sequence
<220> FEATURE:
<223> OTHER INFORMATION: Synthetic

<400> SEQUENCE: 36

Ala Leu Met Ala Gln
1               5

<210> SEQ ID NO 37
<211> LENGTH: 5
<212> TYPE: PRT
<213> ORGANISM: Artificial sequence
<220> FEATURE:
<223> OTHER INFORMATION: Synthetic

<400> SEQUENCE: 37

Glu Leu Met Glu Gln
1               5

<210> SEQ ID NO 38
<211> LENGTH: 36
<212> TYPE: PRT
<213> ORGANISM: Artificial sequence
<220> FEATURE:
<223> OTHER INFORMATION: Synthetic

<400> SEQUENCE: 38

Gly Lys Thr Asn Glu Lys Phe His Gln Ile Glu Lys Glu Phe Ser Glu
1               5                   10                  15

Val Glu Gly Arg Ile Gln Asp Leu Glu Lys Tyr Val Glu Asp Thr Lys
            20                  25                  30

Val Asp Leu Trp
            35

<210> SEQ ID NO 39
<211> LENGTH: 4
<212> TYPE: PRT
<213> ORGANISM: Artificial sequence
<220> FEATURE:
<223> OTHER INFORMATION: Synthetic

<400> SEQUENCE: 39

Gly Gly Pro Asp
1

<210> SEQ ID NO 40
<211> LENGTH: 49
<212> TYPE: PRT
<213> ORGANISM: Artificial sequence
<220> FEATURE:
<223> OTHER INFORMATION: Synthetic

<400> SEQUENCE: 40

Asp Leu Lys Ser Thr Gln Ala Ala Ile Asn Gln Ile Asn Gly Lys Leu
1               5                   10                  15

Asn Arg Leu Ile Ala Leu Met Ala Gln Gly Gly Pro Asp Ser Tyr Asn
            20                  25                  30

Ala Glu Leu Leu Val Ala Leu Glu Asn Gln His Thr Ile Asp Leu Thr
        35                  40                  45

Asp

<210> SEQ ID NO 41
<211> LENGTH: 68
<212> TYPE: PRT
<213> ORGANISM: Artificial sequence
<220> FEATURE:
<223> OTHER INFORMATION: Synthetic

<400> SEQUENCE: 41

Asn Ser Glu Gly Ile Gly Gln Ala Ala Asp Leu Lys Ser Thr Gln Ala
1               5                   10                  15

Ala Ile Asn Gln Ile Asn Gly Lys Leu Asn Arg Leu Ile Ala Leu Met
            20                  25                  30

Ala Gln Gly Gly Pro Asp Ser Tyr Asn Ala Glu Leu Leu Val Ala Leu
        35                  40                  45

Glu Asn Gln His Thr Ile Asp Leu Thr Asp Ser Glu Met Asn Lys Leu
    50                  55                  60

Phe Glu Arg Thr
65

-continued

```
<210> SEQ ID NO 42
<211> LENGTH: 88
<212> TYPE: PRT
<213> ORGANISM: Artificial sequence
<220> FEATURE:
<223> OTHER INFORMATION: Synthetic

<400> SEQUENCE: 42

Asn Ser Glu Gly Ile Gly Gln Ala Ala Asp Leu Lys Ser Thr Gln Ala
1               5                   10                  15

Ala Ile Asn Gln Ile Asn Gly Lys Leu Asn Arg Leu Ile Ala Leu Met
            20                  25                  30

Ala Gln Gly Gly Pro Asp Ser Tyr Asn Ala Glu Leu Leu Val Ala Leu
        35                  40                  45

Glu Asn Gln His Thr Ile Asp Leu Thr Asp Ser Glu Met Asn Lys Leu
    50                  55                  60

Phe Glu Arg Thr Lys Lys Gln Leu Arg Glu Asn Ala Glu Asp Met Gly
65                  70                  75                  80

Asn Gly Cys Phe Lys Ile Tyr His
                85

<210> SEQ ID NO 43
<211> LENGTH: 163
<212> TYPE: PRT
<213> ORGANISM: Artificial sequence
<220> FEATURE:
<223> OTHER INFORMATION: Synthetic

<400> SEQUENCE: 43

Leu Lys Leu Ala Thr Gly Met Arg Asn Val Pro Glu Lys Gln Thr Arg
1               5                   10                  15

Gly Ile Phe Gly Ala Ile Ala Gly Phe Ile Glu Asn Gly Trp Glu Gly
            20                  25                  30

Met Val Asp Gly Trp Tyr Gly Phe Arg His Gln Asn Ser Glu Gly Ile
        35                  40                  45

Gly Gln Ala Ala Asp Leu Lys Ser Thr Gln Ala Ala Ile Asn Gln Ile
    50                  55                  60

Asn Gly Lys Leu Asn Arg Leu Ile Ala Leu Met Ala Gln Gly Gly Pro
65                  70                  75                  80

Asp Ser Tyr Asn Ala Glu Leu Leu Val Ala Leu Glu Asn Gln His Thr
                85                  90                  95

Ile Asp Leu Thr Asp Ser Glu Met Asn Lys Leu Phe Glu Arg Thr Lys
            100                 105                 110

Lys Gln Leu Arg Glu Asn Ala Glu Asp Met Gly Asn Gly Cys Phe Lys
        115                 120                 125

Ile Tyr His Lys Cys Asp Asn Ala Cys Ile Gly Ser Ile Arg Asn Gly
    130                 135                 140

Thr Tyr Asp His Asp Val Tyr Arg Asp Glu Ala Leu Asn Asn Arg Phe
145                 150                 155                 160

Gln Ile Lys

<210> SEQ ID NO 44
<211> LENGTH: 42
<212> TYPE: PRT
<213> ORGANISM: Artificial sequence
<220> FEATURE:
<223> OTHER INFORMATION: Synthetic

<400> SEQUENCE: 44
```

Ser Tyr Asn Ala Glu Leu Leu Val Ala Leu Glu Asn Gln His Thr Ile
1               5                   10                  15

Asp Leu Thr Asp Ser Glu Met Asn Lys Leu Phe Glu Arg Thr Lys Lys
            20                  25                  30

Gln Leu Arg Glu Asn Ala Glu Asp Met Gly
        35                  40

<210> SEQ ID NO 45
<211> LENGTH: 62
<212> TYPE: PRT
<213> ORGANISM: Artificial sequence
<220> FEATURE:
<223> OTHER INFORMATION: Synthetic

<400> SEQUENCE: 45

Ser Tyr Asn Ala Glu Leu Leu Val Ala Leu Glu Asn Gln His Thr Ile
1               5                   10                  15

Asp Leu Thr Asp Ser Glu Met Asn Lys Leu Phe Glu Arg Thr Lys Lys
            20                  25                  30

Gln Leu Arg Glu Asn Ala Glu Asp Met Gly Asn Gly Cys Phe Lys Ile
        35                  40                  45

Tyr His Lys Cys Asp Asn Ala Cys Ile Gly Ser Ile Arg Asn
    50                  55                  60

<210> SEQ ID NO 46
<211> LENGTH: 82
<212> TYPE: PRT
<213> ORGANISM: Artificial sequence
<220> FEATURE:
<223> OTHER INFORMATION: Synthetic

<400> SEQUENCE: 46

Ser Tyr Asn Ala Glu Leu Leu Val Ala Leu Glu Asn Gln His Thr Ile
1               5                   10                  15

Asp Leu Thr Asp Ser Glu Met Asn Lys Leu Phe Glu Arg Thr Lys Lys
            20                  25                  30

Gln Leu Arg Glu Asn Ala Glu Asp Met Gly Asn Gly Cys Phe Lys Ile
        35                  40                  45

Tyr His Lys Cys Asp Asn Ala Cys Ile Gly Ser Ile Arg Asn Gly Thr
    50                  55                  60

Tyr Asp His Asp Val Tyr Arg Asp Glu Ala Leu Asn Asn Arg Phe Gln
65                  70                  75                  80

Ile Lys

<210> SEQ ID NO 47
<211> LENGTH: 396
<212> TYPE: PRT
<213> ORGANISM: Artificial sequence
<220> FEATURE:
<223> OTHER INFORMATION: Synthetic

<400> SEQUENCE: 47

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
    370                 375                 380

Val Lys Gly Ile Ala Lys Ser Arg Lys Ser Gly Ser
385                 390                 395

<210> SEQ ID NO 48
<211> LENGTH: 395
<212> TYPE: PRT
<213> ORGANISM: Artificial sequence
<220> FEATURE:
<223> OTHER INFORMATION: Synthetic

<400> SEQUENCE: 48

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Cys Phe Asn Gly Ile Cys
 50                  55                  60

Leu Lys Leu Ala Thr Gly Met Arg Asn Val Pro Glu Lys Gln Thr Arg
 65                  70                  75                  80

Gly Ile Phe Gly Ala Ile Ala Gly Phe Ile Glu Asn Gly Trp Glu Gly
                 85                  90                  95

Met Val Asp Gly Trp Tyr Gly Phe Arg His Gln Asn Ser Glu Gly Ile
                100                 105                 110

Gly Gln Ala Ala Asp Leu Lys Ser Thr Gln Ala Ala Ile Asn Gln Ile
                115                 120                 125

Asn Gly Met Val Asn Arg Val Ile Ala Leu Met Ala Gln Gly Gly Pro
            130                 135                 140

Asp Ala Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Arg Thr Lys
                165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
        195                 200                 205

Thr Tyr Asp His Asp Val Tyr Arg Asp Glu Ala Leu Asn Asn Arg Phe
    210                 215                 220

Gln Ile Lys Ser Gly Gly Asp Ile Ile Lys Leu Leu Asn Glu Gln Val
225                 230                 235                 240

Asn Lys Glu Met Gln Ser Ser Asn Leu Tyr Met Ser Met Ser Ser Trp
                245                 250                 255

Cys Tyr Thr His Ser Leu Asp Gly Ala Gly Leu Phe Leu Phe Asp His
                260                 265                 270

Ala Ala Glu Glu Tyr Glu His Ala Lys Lys Leu Ile Ile Phe Leu Asn
            275                 280                 285

Glu Asn Asn Val Pro Val Gln Leu Thr Ser Ile Ser Ala Pro Glu His
        290                 295                 300

Lys Phe Glu Gly Leu Thr Gln Ile Phe Gln Lys Ala Tyr Glu His Glu
305                 310                 315                 320

Gln His Ile Ser Glu Ser Ile Asn Asn Ile Val Asp His Ala Ile Lys
                325                 330                 335

Ser Lys Asp His Ala Thr Phe Asn Phe Leu Gln Trp Tyr Val Ala Glu
            340                 345                 350

Gln His Glu Glu Glu Val Leu Phe Lys Asp Ile Leu Asp Lys Ile Glu
        355                 360                 365

Leu Ile Gly Asn Glu Asn His Gly Leu Tyr Leu Ala Asp Gln Tyr Val
370                 375                 380

Lys Gly Ile Ala Lys Ser Arg Lys Ser Gly Ser
385                 390                 395

<210> SEQ ID NO 49
<211> LENGTH: 396
<212> TYPE: PRT
<213> ORGANISM: Artificial sequence
<220> FEATURE:
<223> OTHER INFORMATION: Synthetic

<400> SEQUENCE: 49

```
Met Lys Thr Ile Ile Ala Leu Ser Tyr Ile Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Glu Leu Met Glu Gln Gly Gly
130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
370                 375                 380

Val Lys Gly Ile Ala Lys Ser Arg Lys Ser Gly Ser
385                 390                 395
```

<210> SEQ ID NO 50
<211> LENGTH: 396

```
<212> TYPE: PRT
<213> ORGANISM: Artificial sequence
<220> FEATURE:
<223> OTHER INFORMATION: Synthetic

<400> SEQUENCE: 50

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Cys Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Cys Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Glu Leu Met Glu Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
    370                 375                 380
```

Val Lys Gly Ile Ala Lys Ser Arg Lys Ser Gly Ser
385                 390                 395

<210> SEQ ID NO 51
<211> LENGTH: 395
<212> TYPE: PRT
<213> ORGANISM: Artificial sequence
<220> FEATURE:
<223> OTHER INFORMATION: Synthetic

<400> SEQUENCE: 51

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Val
    50                  55                  60

Leu Lys Leu Ala Thr Gly Met Arg Asn Val Pro Glu Lys Gln Thr Arg
65                  70                  75                  80

Gly Ile Phe Gly Ala Ile Ala Gly Phe Ile Glu Asn Gly Trp Glu Gly
                85                  90                  95

Met Val Asp Gly Trp Tyr Gly Phe Arg His Gln Asn Ser Glu Gly Ile
            100                 105                 110

Gly Gln Ala Ala Asp Leu Lys Ser Thr Gln Ala Ala Ile Asn Gln Ile
        115                 120                 125

Asn Gly Met Val Asn Arg Val Ile Ala Leu Met Ala Gln Gly Gly Pro
    130                 135                 140

Asp Cys Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Arg Thr Lys
                165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
        195                 200                 205

Thr Tyr Asp His Asp Val Tyr Arg Asp Glu Ala Leu Asn Asn Arg Phe
    210                 215                 220

Gln Ile Lys Ser Gly Gly Asp Ile Ile Lys Leu Leu Asn Glu Gln Val
225                 230                 235                 240

Asn Lys Glu Met Gln Ser Ser Asn Leu Tyr Met Ser Met Ser Ser Trp
                245                 250                 255

Cys Tyr Thr His Ser Leu Asp Gly Ala Gly Leu Phe Leu Phe Asp His
            260                 265                 270

Ala Ala Glu Glu Tyr Glu His Ala Lys Lys Leu Ile Ile Phe Leu Asn
        275                 280                 285

Glu Asn Asn Val Pro Val Gln Leu Thr Ser Ile Ser Ala Pro Glu His
    290                 295                 300

Lys Phe Glu Gly Leu Thr Gln Ile Phe Gln Lys Ala Tyr Glu His Glu
305                 310                 315                 320

Gln His Ile Ser Glu Ser Ile Asn Asn Ile Val Asp His Ala Ile Lys
                325                 330                 335

Ser Lys Asp His Ala Thr Phe Asn Phe Leu Gln Trp Tyr Val Ala Glu
            340                 345                 350

Gln His Glu Glu Val Leu Phe Lys Asp Ile Leu Asp Lys Ile Glu
355                 360                 365

Leu Ile Gly Asn Glu Asn His Gly Leu Tyr Leu Ala Asp Gln Tyr Val
370                 375                 380

Lys Gly Ile Ala Lys Ser Arg Lys Ser Gly Ser
385                 390                 395

<210> SEQ ID NO 52
<211> LENGTH: 395
<212> TYPE: PRT
<213> ORGANISM: Artificial sequence
<220> FEATURE:
<223> OTHER INFORMATION: Synthetic

<400> SEQUENCE: 52

Met Lys Thr Ile Ile Ala Leu Ser Tyr Ile Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Cys Gly Val
50                  55                  60

Leu Lys Leu Ala Thr Gly Met Arg Asn Val Pro Glu Lys Gln Thr Arg
65                  70                  75                  80

Gly Ile Phe Gly Ala Ile Ala Gly Phe Ile Glu Asn Gly Trp Glu Gly
                85                  90                  95

Met Val Asp Gly Trp Tyr Gly Phe Arg His Gln Asn Ser Glu Gly Ile
            100                 105                 110

Gly Gln Ala Ala Asp Leu Lys Ser Thr Gln Ala Ala Ile Asn Gln Ile
        115                 120                 125

Asn Gly Met Val Asn Arg Val Ile Ala Leu Met Ala Gln Gly Gly Pro
130                 135                 140

Asp Cys Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Arg Thr Lys
                165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
        195                 200                 205

Thr Tyr Asp His Asp Val Tyr Arg Asp Glu Ala Leu Asn Asn Arg Phe
210                 215                 220

Gln Ile Lys Ser Gly Gly Asp Ile Ile Lys Leu Leu Asn Glu Gln Val
225                 230                 235                 240

Asn Lys Glu Met Gln Ser Ser Asn Leu Tyr Met Ser Met Ser Ser Trp
                245                 250                 255

Cys Tyr Thr His Ser Leu Asp Gly Ala Gly Leu Phe Leu Phe Asp His
            260                 265                 270

Ala Ala Glu Glu Tyr Glu His Ala Lys Lys Leu Ile Ile Phe Leu Asn
        275                 280                 285

Glu Asn Asn Val Pro Val Gln Leu Thr Ser Ile Ser Ala Pro Glu His
    290                 295                 300

Lys Phe Glu Gly Leu Thr Gln Ile Phe Gln Lys Ala Tyr Glu His Glu
305                 310                 315                 320

```
Gln His Ile Ser Glu Ser Ile Asn Asn Ile Val Asp His Ala Ile Lys
                325                 330                 335

Ser Lys Asp His Ala Thr Phe Asn Phe Leu Gln Trp Tyr Val Ala Glu
            340                 345                 350

Gln His Glu Glu Glu Val Leu Phe Lys Asp Ile Leu Asp Lys Ile Glu
            355                 360                 365

Leu Ile Gly Asn Glu Asn His Gly Leu Tyr Leu Ala Asp Gln Tyr Val
        370                 375                 380

Lys Gly Ile Ala Lys Ser Arg Lys Ser Gly Ser
385                 390                 395
```

<210> SEQ ID NO 53
<211> LENGTH: 396
<212> TYPE: PRT
<213> ORGANISM: Artificial sequence
<220> FEATURE:
<223> OTHER INFORMATION: Synthetic

<400> SEQUENCE: 53

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Glu Glu Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285
```

```
Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
370                 375                 380

Val Lys Gly Ile Ala Lys Ser Arg Lys Ser Gly Ser
385                 390                 395

<210> SEQ ID NO 54
<211> LENGTH: 396
<212> TYPE: PRT
<213> ORGANISM: Artificial sequence
<220> FEATURE:
<223> OTHER INFORMATION: Synthetic

<400> SEQUENCE: 54

Met Lys Thr Ile Ile Ala Leu Ser Tyr Ile Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255
```

```
Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
            275                 280                 285

Asn Glu Asn Asn Val Pro Val Gln Leu Thr Ser Ile Ser Ala Pro Glu
            290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
            370                 375                 380

Val Lys Gly Ile Ala Lys Ser Arg Lys Ser Gly Ser
385                 390                 395
```

<210> SEQ ID NO 55
<211> LENGTH: 396
<212> TYPE: PRT
<213> ORGANISM: Artificial sequence
<220> FEATURE:
<223> OTHER INFORMATION: Synthetic

<400> SEQUENCE: 55

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
            115                 120                 125

Ile Asn Gly Met Leu Asn Arg Val Ile Ala Leu Met Ala Gln Gly Gly
        130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
            195                 200                 205

Gly Thr Tyr Asp His Asp Val Tyr Arg Asp Glu Ala Leu Asn Asn Arg
    210                 215                 220
```

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
            245                 250                 255

Trp Cys Tyr Thr His Ser Leu Asp Gly Ala Gly Leu Phe Leu Phe Asp
                260                 265                 270

His Ala Ala Glu Glu Tyr Glu His Ala Lys Lys Leu Ile Ile Phe Leu
            275                 280                 285

Asn Glu Asn Asn Val Pro Val Gln Leu Thr Ser Ile Ser Ala Pro Glu
            290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
                340                 345                 350

Glu Gln His Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
370                 375                 380

Val Lys Gly Ile Ala Lys Ser Arg Lys Ser Gly Ser
385                 390                 395

<210> SEQ ID NO 56
<211> LENGTH: 396
<212> TYPE: PRT
<213> ORGANISM: Artificial sequence
<220> FEATURE:
<223> OTHER INFORMATION: Synthetic

<400> SEQUENCE: 56

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Leu Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
            195                 200                 205

Gly Thr Tyr Asp His Asp Val Tyr Arg Asp Glu Ala Leu Asn Asn Arg
210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
            245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
            275                 280                 285

Asn Glu Asn Asn Val Pro Val Gln Leu Thr Ser Ile Ser Ala Pro Glu
290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
            370                 375                 380

Val Lys Gly Ile Ala Lys Ser Arg Lys Ser Gly Ser
385                 390                 395

<210> SEQ ID NO 57
<211> LENGTH: 396
<212> TYPE: PRT
<213> ORGANISM: Artificial sequence
<220> FEATURE:
<223> OTHER INFORMATION: Synthetic

<400> SEQUENCE: 57

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Gly Cys Gly
50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
            115                 120                 125

Ile Asn Gly Met Leu Asn Arg Leu Ile Ala Leu Met Ala Gln Gly Gly
            130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
            195                 200                 205

Gly Thr Tyr Asp His Asp Val Tyr Arg Asp Glu Ala Leu Asn Asn Arg
        210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
                260                 265                 270

His Ala Ala Glu Glu Tyr Glu His Ala Lys Lys Leu Ile Ile Phe Leu
            275                 280                 285

Asn Glu Asn Asn Val Pro Val Gln Leu Thr Ser Ile Ser Ala Pro Glu
            290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
        370                 375                 380

Val Lys Gly Ile Ala Lys Ser Arg Lys Ser Gly Ser
385                 390                 395

<210> SEQ ID NO 58
<211> LENGTH: 396
<212> TYPE: PRT
<213> ORGANISM: Artificial sequence
<220> FEATURE:
<223> OTHER INFORMATION: Synthetic

<400> SEQUENCE: 58

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65              70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

```
Ile Asn Gly Leu Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
                180                 185                 190

Lys Ile Tyr His Lys Cys Asp Asn Ala Cys Ile Gly Ser Ile Arg Asn
            195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
                260                 265                 270

His Ala Ala Glu Glu Tyr Glu His Ala Lys Lys Leu Ile Ile Phe Leu
            275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
    355                 360                 365

Glu Leu Ile Gly Asn Glu Asn His Gly Leu Tyr Leu Ala Asp Gln Tyr
    370                 375                 380

Val Lys Gly Ile Ala Lys Ser Arg Lys Ser Gly Ser
385                 390                 395
```

<210> SEQ ID NO 59
<211> LENGTH: 396
<212> TYPE: PRT
<213> ORGANISM: Artificial sequence
<220> FEATURE:
<223> OTHER INFORMATION: Synthetic

<400> SEQUENCE: 59

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95
```

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
            115                 120                 125

Ile Asn Gly Met Val Asn Arg Val Ile Ala Trp Met Ala Gln Gly Gly
        130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
    370                 375                 380

Val Lys Gly Ile Ala Lys Ser Arg Lys Ser Gly Ser
385                 390                 395

<210> SEQ ID NO 60
<211> LENGTH: 396
<212> TYPE: PRT
<213> ORGANISM: Artificial sequence
<220> FEATURE:
<223> OTHER INFORMATION: Synthetic

<400> SEQUENCE: 60

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Trp Pro Gly Cys Gly
    50                  55                  60

Val Leu Lys Leu Ala Thr Gly Met Arg Asn Val Pro Glu Lys Gln Thr
 65                  70                  75                  80

Arg Gly Ile Phe Gly Ala Ile Ala Gly Phe Ile Glu Asn Gly Trp Glu
                 85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
370                 375                 380

Val Lys Gly Ile Ala Lys Ser Arg Lys Ser Gly Ser
385                 390                 395

<210> SEQ ID NO 61
<211> LENGTH: 396
<212> TYPE: PRT
<213> ORGANISM: Artificial sequence
<220> FEATURE:
<223> OTHER INFORMATION: Synthetic

<400> SEQUENCE: 61

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Cys Asn Asp
            35                  40                  45

Gln Ile Glu Val Thr Asn Ala Thr Glu Leu Val Phe Pro Gly Cys Gly
 50                  55                  60

Val Leu Lys Leu Ala Thr Gly Met Arg Asn Val Pro Glu Lys Gln Thr
 65                  70                  75                  80

Arg Gly Ile Phe Gly Ala Ile Ala Gly Phe Ile Glu Asn Gly Trp Glu
                 85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Cys
        115                 120                 125

Ile Asn Gly Met Val Asn Arg Val Ile Ala Leu Met Ala Gln Gly Gly
130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
370                 375                 380

Val Lys Gly Ile Ala Lys Ser Arg Lys Ser Gly Ser
385                 390                 395

<210> SEQ ID NO 62
<211> LENGTH: 396
<212> TYPE: PRT
<213> ORGANISM: Artificial sequence
<220> FEATURE:
<223> OTHER INFORMATION: Synthetic

<400> SEQUENCE: 62

```
Met Lys Thr Ile Ile Ala Leu Ser Tyr Ile Leu Cys Leu Val Phe Ala
1               5                   10                  15
Gln Lys Leu Pro Gly Asn Asp Asn Ser Thr Ala Thr Leu Cys Leu Gly
            20                  25                  30
His His Ala Val Pro Asn Gly Thr Ile Val Lys Thr Ile Thr Asn Asp
        35                  40                  45
Asn Ile Thr Val Thr Asn Ala Thr Glu Leu Val Phe Pro Gly Cys Gly
    50                  55                  60
Val Leu Lys Leu Ala Thr Gly Met Arg Asn Val Pro Glu Lys Gln Thr
65                  70                  75                  80
Arg Gly Ile Phe Gly Ala Ile Ala Gly Phe Ile Glu Asn Gly Trp Glu
                85                  90                  95
Gly Met Val Asp Gly Trp Tyr Gly Phe Arg His Gln Asn Ser Glu Gly
            100                 105                 110
Ile Gly Gln Ala Ala Asp Leu Lys Ser Thr Gln Ala Ala Ile Asn Gln
        115                 120                 125
Ile Asn Gly Met Val Asn Arg Val Ile Ala Leu Met Ala Gln Gly Gly
    130                 135                 140
Pro Asp Cys Tyr Leu Ala Glu Leu Leu Val Ala Leu Leu Asn Gln His
145                 150                 155                 160
Val Ile Asp Leu Thr Asp Ser Glu Met Asn Lys Leu Phe Glu Arg Thr
                165                 170                 175
Lys Lys Gln Leu Arg Glu Asn Ala Glu Asp Met Gly Asn Gly Cys Phe
            180                 185                 190
Lys Ile Tyr His Lys Cys Asp Asn Ala Cys Ile Gly Ser Ile Arg Asn
        195                 200                 205
Gly Thr Tyr Asp His Asp Val Tyr Arg Asp Glu Ala Leu Asn Asn Arg
    210                 215                 220
Phe Gln Ile Lys Ser Gly Gly Asp Ile Ile Lys Leu Leu Asn Glu Gln
225                 230                 235                 240
Val Asn Lys Glu Met Gln Ser Ser Asn Leu Tyr Met Ser Met Ser Ser
                245                 250                 255
Trp Cys Tyr Thr His Ser Leu Asp Gly Ala Gly Leu Phe Leu Phe Asp
            260                 265                 270
His Ala Ala Glu Glu Tyr Glu His Ala Lys Lys Leu Ile Ile Phe Leu
        275                 280                 285
Asn Glu Asn Asn Val Pro Val Gln Leu Thr Ser Ile Ser Ala Pro Glu
    290                 295                 300
His Lys Phe Glu Gly Leu Thr Gln Ile Phe Gln Lys Ala Tyr Glu His
305                 310                 315                 320
Glu Gln His Ile Ser Glu Ser Ile Asn Asn Ile Val Asp His Ala Ile
                325                 330                 335
Lys Ser Lys Asp His Ala Thr Phe Asn Phe Leu Gln Trp Tyr Val Ala
            340                 345                 350
Glu Gln His Glu Glu Val Leu Phe Lys Asp Ile Leu Asp Lys Ile
        355                 360                 365
Glu Leu Ile Gly Asn Glu Asn His Gly Leu Tyr Leu Ala Asp Gln Tyr
    370                 375                 380
Val Lys Gly Ile Ala Lys Ser Arg Lys Ser Gly Ser
385                 390                 395

<210> SEQ ID NO 63
<211> LENGTH: 395
<212> TYPE: PRT
```

<213> ORGANISM: Artificial sequence
<220> FEATURE:
<223> OTHER INFORMATION: Synthetic

<400> SEQUENCE: 63

```
Met Lys Thr Ile Ile Ala Leu Ser Tyr Ile Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Cys Gly Val
50                  55                  60

Leu Lys Leu Ala Thr Gly Met Arg Asn Val Pro Glu Lys Gln Thr Arg
65                  70                  75                  80

Gly Ile Phe Gly Ala Ile Ala Gly Phe Ile Glu Asn Gly Trp Glu Gly
                85                  90                  95

Met Val Asp Gly Trp Tyr Gly Phe Arg His Gln Asn Ser Glu Gly Ile
            100                 105                 110

Gly Gln Ala Ala Asp Leu Lys Ser Thr Gln Ala Ala Ile Asn Gln Ile
        115                 120                 125

Asn Gly Met Val Asn Arg Val Ile Ala Leu Met Ala Gln Gly Gly Pro
130                 135                 140

Asp Cys Tyr Leu Ala Glu Leu Leu Val Ala Leu Leu Asn Gln His Val
145                 150                 155                 160

Ile Asp Leu Thr Asp Ser Glu Met Asn Lys Leu Phe Glu Arg Thr Lys
                165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
        195                 200                 205

Thr Tyr Asp His Asp Val Tyr Arg Asp Glu Ala Leu Asn Asn Arg Phe
210                 215                 220

Gln Ile Lys Ser Gly Gly Asp Ile Ile Lys Leu Leu Asn Glu Gln Val
225                 230                 235                 240

Asn Lys Glu Met Gln Ser Ser Asn Leu Tyr Met Ser Met Ser Ser Trp
                245                 250                 255

Cys Tyr Thr His Ser Leu Asp Gly Ala Gly Leu Phe Leu Phe Asp His
            260                 265                 270

Ala Ala Glu Glu Tyr Glu His Ala Lys Lys Leu Ile Ile Phe Leu Asn
        275                 280                 285

Glu Asn Asn Val Pro Val Gln Leu Thr Ser Ile Ser Ala Pro Glu His
290                 295                 300

Lys Phe Glu Gly Leu Thr Gln Ile Phe Gln Lys Ala Tyr Glu His Glu
305                 310                 315                 320

Gln His Ile Ser Glu Ser Ile Asn Asn Ile Val Asp His Ala Ile Lys
                325                 330                 335

Ser Lys Asp His Ala Thr Phe Asn Phe Leu Gln Trp Tyr Val Ala Glu
            340                 345                 350

Gln His Glu Glu Val Leu Phe Lys Asp Ile Leu Asp Lys Ile Glu
        355                 360                 365

Leu Ile Gly Asn Glu Asn His Gly Leu Tyr Leu Ala Asp Gln Tyr Val
370                 375                 380

Lys Gly Ile Ala Lys Ser Arg Lys Ser Gly Ser
```

385    390    395

<210> SEQ ID NO 64
<211> LENGTH: 395
<212> TYPE: PRT
<213> ORGANISM: Artificial sequence
<220> FEATURE:
<223> OTHER INFORMATION: Synthetic

<400> SEQUENCE: 64

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Cys Gly Val
    50                  55                  60

Leu Lys Leu Ala Thr Gly Met Arg Asn Val Pro Glu Lys Gln Thr Arg
65                  70                  75                  80

Gly Ile Phe Gly Ala Ile Ala Gly Phe Ile Glu Asn Gly Trp Glu Gly
                85                  90                  95

Met Val Asp Gly Trp Tyr Gly Phe Arg His Gln Asn Ser Glu Gly Ile
            100                 105                 110

Gly Gln Ala Ala Asp Leu Lys Ser Thr Gln Ala Ala Ile Asn Gln Ile
        115                 120                 125

Asn Gly Met Val Asn Arg Val Ile Ala Leu Met Glu Glu Gly Gly Pro
130                 135                 140

Asp Cys Tyr Leu Ala Glu Leu Leu Val Ala Leu Leu Asn Gln His Val
145                 150                 155                 160

Ile Asp Leu Thr Asp Ser Glu Met Asn Lys Leu Phe Glu Arg Thr Lys
                165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
        195                 200                 205

Thr Tyr Asp His Asp Val Tyr Arg Asp Glu Ala Leu Asn Asn Arg Phe
    210                 215                 220

Gln Ile Lys Ser Gly Gly Asp Ile Ile Lys Leu Leu Asn Glu Gln Val
225                 230                 235                 240

Asn Lys Glu Met Gln Ser Ser Asn Leu Tyr Met Ser Met Ser Ser Trp
                245                 250                 255

Cys Tyr Thr His Ser Leu Asp Gly Ala Gly Leu Phe Leu Phe Asp His
            260                 265                 270

Ala Ala Glu Glu Tyr Glu His Ala Lys Lys Leu Ile Ile Phe Leu Asn
        275                 280                 285

Glu Asn Asn Val Pro Val Gln Leu Thr Ser Ile Ser Ala Pro Glu His
    290                 295                 300

Lys Phe Glu Gly Leu Thr Gln Ile Phe Gln Lys Ala Tyr Glu His Glu
305                 310                 315                 320

Gln His Ile Ser Glu Ser Ile Asn Asn Ile Val Asp His Ala Ile Lys
                325                 330                 335

Ser Lys Asp His Ala Thr Phe Asn Phe Leu Gln Trp Tyr Val Ala Glu
            340                 345                 350

Gln His Glu Glu Glu Val Leu Phe Lys Asp Ile Leu Asp Lys Ile Glu

```
                 355                 360                 365

Leu Ile Gly Asn Glu Asn His Gly Leu Tyr Leu Ala Asp Gln Tyr Val
    370                 375                 380

Lys Gly Ile Ala Lys Ser Arg Lys Ser Gly Ser
385                 390                 395

<210> SEQ ID NO 65
<211> LENGTH: 395
<212> TYPE: PRT
<213> ORGANISM: Artificial sequence
<220> FEATURE:
<223> OTHER INFORMATION: Synthetic

<400> SEQUENCE: 65

Met Lys Thr Ile Ile Ala Leu Ser Tyr Ile Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Asn Ile Thr Val Thr Asn Ala Thr Glu Leu Val Phe Pro Cys Gly Val
50                  55                  60

Leu Lys Leu Ala Thr Gly Met Arg Asn Val Pro Glu Lys Gln Thr Arg
65                  70                  75                  80

Gly Ile Phe Gly Ala Ile Ala Gly Phe Ile Glu Asn Gly Trp Glu Gly
                85                  90                  95

Met Val Asp Gly Trp Tyr Gly Phe Arg His Gln Asn Ser Glu Gly Ile
            100                 105                 110

Gly Gln Ala Ala Asp Leu Lys Ser Thr Gln Ala Ala Ile Asn Gln Ile
        115                 120                 125

Asn Gly Met Val Asn Arg Val Ile Ala Leu Met Glu Glu Gly Gly Pro
130                 135                 140

Asp Cys Tyr Leu Ala Glu Leu Leu Val Ala Leu Leu Asn Gln His Val
145                 150                 155                 160

Ile Asp Leu Thr Asp Ser Glu Met Asn Lys Leu Phe Glu Arg Thr Lys
                165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
        195                 200                 205

Thr Tyr Asp His Asp Val Tyr Arg Asp Glu Ala Leu Asn Asn Arg Phe
210                 215                 220

Gln Ile Lys Ser Gly Gly Asp Ile Ile Lys Leu Leu Asn Glu Gln Val
225                 230                 235                 240

Asn Lys Glu Met Gln Ser Ser Asn Leu Tyr Met Ser Met Ser Ser Trp
                245                 250                 255

Cys Tyr Thr His Ser Leu Asp Gly Ala Gly Leu Phe Leu Phe Asp His
            260                 265                 270

Ala Ala Glu Glu Tyr Glu His Ala Lys Lys Leu Ile Ile Phe Leu Asn
        275                 280                 285

Glu Asn Asn Val Pro Val Gln Leu Thr Ser Ile Ser Ala Pro Glu His
290                 295                 300

Lys Phe Glu Gly Leu Thr Gln Ile Phe Gln Lys Ala Tyr Glu His Glu
305                 310                 315                 320

Gln His Ile Ser Glu Ser Ile Asn Asn Ile Val Asp His Ala Ile Lys
```

```
                  325                 330                 335
Ser Lys Asp His Ala Thr Phe Asn Phe Leu Gln Trp Tyr Val Ala Glu
            340                 345                 350

Gln His Glu Glu Val Leu Phe Lys Asp Ile Leu Asp Lys Ile Glu
            355                 360                 365

Leu Ile Gly Asn Glu Asn His Gly Leu Tyr Leu Ala Asp Gln Tyr Val
            370                 375                 380

Lys Gly Ile Ala Lys Ser Arg Lys Ser Gly Ser
385                 390                 395

<210> SEQ ID NO 66
<211> LENGTH: 396
<212> TYPE: PRT
<213> ORGANISM: Artificial sequence
<220> FEATURE:
<223> OTHER INFORMATION: Synthetic

<400> SEQUENCE: 66

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Glu Glu Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
```

```
                290                 295                 300
His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
                340                 345                 350

Glu Gln His Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
        370                 375                 380

Val Lys Gly Ile Ala Lys Ser Arg Lys Ser Gly Ser
385                 390                 395

<210> SEQ ID NO 67
<211> LENGTH: 396
<212> TYPE: PRT
<213> ORGANISM: Artificial sequence
<220> FEATURE:
<223> OTHER INFORMATION: Synthetic

<400> SEQUENCE: 67

Met Lys Thr Ile Ile Ala Leu Ser Tyr Ile Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Asn Ile Thr Val Thr Asn Ala Thr Glu Leu Val Phe Pro Gly Cys Gly
        50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Glu Glu Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
```

```
                260                 265                 270
His Ala Ala Glu Glu Tyr Glu His Ala Lys Lys Leu Ile Ile Phe Leu
            275                 280                 285

Asn Glu Asn Asn Val Pro Val Gln Leu Thr Ser Ile Ser Ala Pro Glu
        290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
            370                 375                 380

Val Lys Gly Ile Ala Lys Ser Arg Lys Ser Gly Ser
385                 390                 395

<210> SEQ ID NO 68
<211> LENGTH: 396
<212> TYPE: PRT
<213> ORGANISM: Artificial sequence
<220> FEATURE:
<223> OTHER INFORMATION: Synthetic

<400> SEQUENCE: 68

Met Lys Thr Ile Ile Ala Leu Ser Tyr Ile Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
                35                  40                  45

Gln Ile Glu Val Thr Asn Ala Thr Glu Leu Val Phe Pro Gly Cys Gly
        50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Asn Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
```

```
               225                 230                 235                 240
Val Asn Lys Glu Met Gln Ser Ser Asn Leu Tyr Met Ser Met Ser Ser
                        245                 250                 255

Trp Cys Tyr Thr His Ser Leu Asp Gly Ala Gly Leu Phe Leu Phe Asp
            260                 265                 270

His Ala Glu Glu Tyr Glu His Ala Lys Lys Leu Ile Ile Phe Leu
            275                 280                 285

Asn Glu Asn Asn Val Pro Val Gln Leu Thr Ser Ile Ser Ala Pro Glu
        290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
    370                 375                 380

Val Lys Gly Ile Ala Lys Ser Arg Lys Ser Gly Ser
385                 390                 395
```

<210> SEQ ID NO 69
<211> LENGTH: 396
<212> TYPE: PRT
<213> ORGANISM: Artificial sequence
<220> FEATURE:
<223> OTHER INFORMATION: Synthetic

<400> SEQUENCE: 69

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Gly Cys Gly
        50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Thr Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
```

```
                    195                 200                 205
Gly Thr Tyr Asp His Asp Val Tyr Arg Asp Glu Ala Leu Asn Asn Arg
        210                 215                 220
Phe Gln Ile Lys Ser Gly Asp Ile Ile Lys Leu Leu Asn Glu Gln
225                 230                 235                 240
Val Asn Lys Glu Met Gln Ser Ser Asn Leu Tyr Met Ser Met Ser Ser
                245                 250                 255
Trp Cys Tyr Thr His Ser Leu Asp Gly Ala Gly Leu Phe Leu Phe Asp
                260                 265                 270
His Ala Ala Glu Glu Tyr Glu His Ala Lys Lys Leu Ile Ile Phe Leu
                275                 280                 285
Asn Glu Asn Asn Val Pro Val Gln Leu Thr Ser Ile Ser Ala Pro Glu
290                 295                 300
His Lys Phe Glu Gly Leu Thr Gln Ile Phe Gln Lys Ala Tyr Glu His
305                 310                 315                 320
Glu Gln His Ile Ser Glu Ser Ile Asn Asn Ile Val Asp His Ala Ile
                325                 330                 335
Lys Ser Lys Asp His Ala Thr Phe Asn Phe Leu Gln Trp Tyr Val Ala
                340                 345                 350
Glu Gln His Glu Glu Val Leu Phe Lys Asp Ile Leu Asp Lys Ile
            355                 360                 365
Glu Leu Ile Gly Asn Glu Asn His Gly Leu Tyr Leu Ala Asp Gln Tyr
        370                 375                 380
Val Lys Gly Ile Ala Lys Ser Arg Lys Ser Gly Ser
385                 390                 395

<210> SEQ ID NO 70
<211> LENGTH: 396
<212> TYPE: PRT
<213> ORGANISM: Artificial sequence
<220> FEATURE:
<223> OTHER INFORMATION: Synthetic

<400> SEQUENCE: 70

Met Lys Thr Ile Ile Ala Leu Ser Tyr Ile Leu Cys Leu Val Phe Ala
1               5                   10                  15
Gln Lys Leu Pro Gly Asn Asp Asn Ser Thr Ala Thr Leu Cys Leu Gly
                20                  25                  30
His His Ala Val Pro Asn Gly Thr Ile Val Lys Thr Ile Thr Asn Asp
            35                  40                  45
Gln Ile Glu Val Thr Asn Ala Thr Glu Leu Val Phe Pro Gly Cys Gly
    50                  55                  60
Val Leu Lys Leu Ala Thr Gly Met Arg Asn Val Pro Glu Lys Gln Thr
65                  70                  75                  80
Arg Gly Ile Phe Gly Ala Ile Ala Gly Phe Ile Glu Asn Gly Trp Glu
                85                  90                  95
Gly Met Val Asp Gly Trp Tyr Gly Phe Arg His Gln Asn Ser Glu Gly
                100                 105                 110
Ile Gly Gln Ala Ala Asp Leu Lys Ser Thr Gln Ala Ala Ile Asn Gln
            115                 120                 125
Ile Asn Gly Met Val Asn Arg Val Ile Ala Leu Met Ala Gln Gly Gly
        130                 135                 140
Pro Ala Cys Tyr Leu Ala Glu Leu Leu Val Ala Leu Leu Asn Gln His
145                 150                 155                 160
Val Ile Asp Leu Thr Asp Ser Glu Met Asn Lys Leu Phe Glu Arg Thr
```

165                 170                 175
Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
            195                 200                 205

Gly Thr Tyr Asp His Asp Val Tyr Arg Asp Glu Ala Leu Asn Asn Arg
            210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
            245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
            275                 280                 285

Asn Glu Asn Asn Val Pro Val Gln Leu Thr Ser Ile Ser Ala Pro Glu
            290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
            325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
            370                 375                 380

Val Lys Gly Ile Ala Lys Ser Arg Lys Ser Gly Ser
385                 390                 395

<210> SEQ ID NO 71
<211> LENGTH: 396
<212> TYPE: PRT
<213> ORGANISM: Artificial sequence
<220> FEATURE:
<223> OTHER INFORMATION: Synthetic

<400> SEQUENCE: 71

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Asn Cys Gly
50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
            85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
            115                 120                 125

Ile Asn Gly Met Val Asn Arg Val Ile Ala Leu Met Ala Gln Gly Gly

```
                130                 135                 140
Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
                195                 200                 205

Gly Thr Tyr Asp His Asp Val Tyr Arg Asp Glu Ala Leu Asn Asn Arg
        210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
    370                 375                 380

Val Lys Gly Ile Ala Lys Ser Arg Lys Ser Gly Ser
385                 390                 395

<210> SEQ ID NO 72
<211> LENGTH: 396
<212> TYPE: PRT
<213> ORGANISM: Artificial sequence
<220> FEATURE:
<223> OTHER INFORMATION: Synthetic

<400> SEQUENCE: 72

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Gly Cys Gly
        50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
```

```
               100                 105                 110
Ile Gly Gln Ala Ala Asp Leu Lys Ser Thr Gln Ala Ala Ile Asn Gln
            115                 120                 125

Ile Asn Gly Met Val Asn Arg Val Ile Ala Leu Met Ala Gln Gly Pro
        130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
    370                 375                 380

Val Lys Gly Ile Ala Lys Ser Arg Lys Ser Gly Ser
385                 390                 395

<210> SEQ ID NO 73
<211> LENGTH: 395
<212> TYPE: PRT
<213> ORGANISM: Artificial sequence
<220> FEATURE:
<223> OTHER INFORMATION: Synthetic

<400> SEQUENCE: 73

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Cys Phe Asn Gly Ile Cys
    50                  55                  60

Leu Lys Leu Ala Thr Gly Met Arg Asn Val Pro Glu Lys Gln Thr Arg
```

```
            65                  70                  75                  80
    Gly Ile Phe Gly Ala Ile Ala Gly Phe Ile Glu Asn Gly Trp Glu Gly
                        85                  90                  95

Met Val Asp Gly Trp Tyr Gly Phe Arg His Gln Asn Ser Glu Gly Ile
                        100                 105                 110

Gly Gln Ala Ala Asp Leu Lys Ser Thr Gln Ala Ala Ile Asn Gln Ile
                        115                 120                 125

Asn Gly Met Val Asn Arg Val Ile Ala Leu Met Ala Gln Gly Pro Pro
                130                 135                 140

Asp Cys Tyr Leu Ala Glu Leu Leu Val Ala Leu Leu Asn Gln His Val
    145                 150                 155                 160

Ile Asp Leu Thr Asp Ser Glu Met Arg Lys Leu Phe Glu Arg Thr Lys
                        165                 170                 175

Lys Gln Leu Arg Glu Asn Ala Glu Asp Met Gly Asn Gly Cys Phe Lys
                        180                 185                 190

Ile Tyr His Lys Cys Asp Asn Ala Cys Ile Gly Ser Ile Arg Asn Gly
                        195                 200                 205

Thr Tyr Asp His Asp Val Tyr Arg Asp Glu Ala Leu Asn Asn Arg Phe
                210                 215                 220

Gln Ile Lys Ser Gly Gly Asp Ile Ile Lys Leu Leu Asn Glu Gln Val
    225                 230                 235                 240

Asn Lys Glu Met Gln Ser Ser Asn Leu Tyr Met Ser Met Ser Ser Trp
                        245                 250                 255

Cys Tyr Thr His Ser Leu Asp Gly Ala Gly Leu Phe Leu Phe Asp His
                        260                 265                 270

Ala Ala Glu Glu Tyr Glu His Ala Lys Lys Leu Ile Ile Phe Leu Asn
                        275                 280                 285

Glu Asn Asn Val Pro Val Gln Leu Thr Ser Ile Ser Ala Pro Glu His
                290                 295                 300

Lys Phe Glu Gly Leu Thr Gln Ile Phe Gln Lys Ala Tyr Glu His Glu
    305                 310                 315                 320

Gln His Ile Ser Glu Ser Ile Asn Asn Ile Val Asp His Ala Ile Lys
                        325                 330                 335

Ser Lys Asp His Ala Thr Phe Asn Phe Leu Gln Trp Tyr Val Ala Glu
                        340                 345                 350

Gln His Glu Glu Val Leu Phe Lys Asp Ile Leu Asp Lys Ile Glu
                        355                 360                 365

Leu Ile Gly Asn Glu Asn His Gly Leu Tyr Leu Ala Asp Gln Tyr Val
                370                 375                 380

Lys Gly Ile Ala Lys Ser Arg Lys Ser Gly Ser
    385                 390                 395

<210> SEQ ID NO 74
<211> LENGTH: 395
<212> TYPE: PRT
<213> ORGANISM: Artificial sequence
<220> FEATURE:
<223> OTHER INFORMATION: Synthetic

<400> SEQUENCE: 74

Met Lys Thr Ile Ile Ala Leu Ser Tyr Ile Leu Cys Leu Val Phe Ala
    1               5                   10                  15

Gln Lys Leu Pro Gly Asn Asp Asn Ser Thr Ala Thr Leu Cys Leu Gly
                        20                  25                  30

His His Ala Val Pro Asn Cys Thr Ile Val Lys Thr Ile Thr Asn Asp
```

```
                  35                  40                  45
Gln Ile Glu Val Thr Asn Ala Thr Glu Leu Cys Phe Asn Gly Ile Cys
             50                  55                  60
Leu Lys Leu Ala Thr Gly Met Arg Cys Val Pro Glu Lys Gln Thr Arg
 65                  70                  75                  80
Gly Ile Phe Gly Ala Ile Ala Gly Phe Ile Glu Asn Gly Trp Glu Gly
                 85                  90                  95
Met Val Asp Gly Trp Tyr Gly Phe Arg His Gln Asn Ser Glu Gly Ile
            100                 105                 110
Gly Gln Ala Ala Asp Leu Lys Ser Thr Gln Ala Ala Ile Asn Gln Ile
        115                 120                 125
Asn Gly Met Val Asn Arg Val Ile Glu Leu Met Glu Gln Gly Gly Pro
    130                 135                 140
Asp Cys Tyr Leu Ala Glu Leu Leu Val Ala Leu Leu Asn Gln His Val
145                 150                 155                 160
Ile Asp Leu Thr Asp Ser Glu Met Arg Lys Leu Phe Glu Arg Thr Lys
                165                 170                 175
Lys Gln Leu Arg Glu Asn Ala Glu Asp Met Gly Asn Gly Cys Phe Lys
            180                 185                 190
Ile Tyr His Lys Cys Asp Asn Ala Cys Ile Gly Ser Ile Arg Asn Gly
        195                 200                 205
Thr Tyr Asp His Asp Val Tyr Arg Asp Glu Ala Leu Asn Asn Arg Phe
    210                 215                 220
Gln Ile Lys Ser Gly Gly Asp Ile Ile Lys Leu Leu Asn Glu Gln Val
225                 230                 235                 240
Asn Lys Glu Met Gln Ser Ser Asn Leu Tyr Met Ser Met Ser Ser Trp
                245                 250                 255
Cys Tyr Thr His Ser Leu Asp Gly Ala Gly Leu Phe Leu Phe Asp His
            260                 265                 270
Ala Ala Glu Glu Tyr Glu His Ala Lys Lys Leu Ile Ile Phe Leu Asn
        275                 280                 285
Glu Asn Asn Val Pro Val Gln Leu Thr Ser Ile Ser Ala Pro Glu His
    290                 295                 300
Lys Phe Glu Gly Leu Thr Gln Ile Phe Gln Lys Ala Tyr Glu His Glu
305                 310                 315                 320
Gln His Ile Ser Glu Ser Ile Asn Asn Ile Val Asp His Ala Ile Lys
                325                 330                 335
Ser Lys Asp His Ala Thr Phe Asn Phe Leu Gln Trp Tyr Val Ala Glu
            340                 345                 350
Gln His Glu Glu Glu Val Leu Phe Lys Asp Ile Leu Asp Lys Ile Glu
        355                 360                 365
Leu Ile Gly Asn Glu Asn His Gly Leu Tyr Leu Ala Asp Gln Tyr Val
    370                 375                 380
Lys Gly Ile Ala Lys Ser Arg Lys Ser Gly Ser
385                 390                 395

<210> SEQ ID NO 75
<211> LENGTH: 396
<212> TYPE: PRT
<213> ORGANISM: Artificial sequence
<220> FEATURE:
<223> OTHER INFORMATION: Synthetic

<400> SEQUENCE: 75

Met Lys Thr Ile Ile Ala Leu Ser Tyr Ile Phe Cys Leu Ala Leu Ala
```

```
              1               5              10              15
              Gln Asp Leu Pro Gly Asn Asp Asn Ser Thr Ala Thr Leu Cys Leu Gly
                             20              25              30

His His Ala Val Pro Asn Gly Thr Leu Val Lys Thr Ile Thr Asp Asp
                             35              40              45

Gln Ile Glu Val Thr Asn Ala Thr Glu Leu Val Phe Pro Gly Cys Gly
                             50              55              60

Val Leu Lys Leu Ala Thr Gly Met Arg Asn Val Pro Glu Lys Gln Thr
               65              70              75              80

Arg Gly Leu Phe Gly Ala Ile Ala Gly Phe Ile Glu Asn Gly Trp Glu
                                 85              90              95

Gly Met Ile Asp Gly Trp Tyr Gly Phe Arg His Gln Asn Ser Glu Gly
                            100             105             110

Thr Gly Gln Ala Ala Asp Leu Lys Ser Thr Gln Ala Ala Ile Asp Gln
                            115             120             125

Ile Asn Gly Met Val Asn Arg Val Ile Ala Leu Met Ala Gln Gly Gly
                            130             135             140

Pro Asp Cys Tyr Leu Ala Glu Leu Leu Val Ala Leu Leu Asn Gln His
              145             150             155             160

Val Ile Asp Leu Thr Asp Ser Glu Met Arg Lys Leu Phe Glu Lys Thr
                                165             170             175

Arg Arg Gln Leu Arg Glu Asn Ala Glu Asp Met Gly Asn Gly Cys Phe
                            180             185             190

Lys Ile Tyr His Lys Cys Asp Asn Ala Cys Ile Glu Ser Ile Arg Asn
                            195             200             205

Gly Thr Tyr Asp His Asp Val Tyr Arg Asp Glu Ala Leu Asn Asn Arg
                            210             215             220

Phe Gln Ile Lys Ser Gly Gly Asp Ile Ile Lys Leu Leu Asn Glu Gln
              225             230             235             240

Val Asn Lys Glu Met Gln Ser Ser Asn Leu Tyr Met Ser Met Ser Ser
                                245             250             255

Trp Cys Tyr Thr His Ser Leu Asp Gly Ala Gly Leu Phe Leu Phe Asp
                            260             265             270

His Ala Ala Glu Glu Tyr Glu His Ala Lys Lys Leu Ile Ile Phe Leu
                            275             280             285

Asn Glu Asn Asn Val Pro Val Gln Leu Thr Ser Ile Ser Ala Pro Glu
                            290             295             300

His Lys Phe Glu Gly Leu Thr Gln Ile Phe Gln Lys Ala Tyr Glu His
              305             310             315             320

Glu Gln His Ile Ser Glu Ser Ile Asn Asn Ile Val Asp His Ala Ile
                                325             330             335

Lys Ser Lys Asp His Ala Thr Phe Phe Leu Gln Trp Tyr Val Ala
                            340             345             350

Glu Gln His Glu Glu Val Leu Phe Lys Asp Ile Leu Asp Lys Ile
                            355             360             365

Glu Leu Ile Gly Asn Glu Asn His Gly Leu Tyr Leu Ala Asp Gln Tyr
                            370             375             380

Val Lys Gly Ile Ala Lys Ser Arg Lys Ser Gly Ser
              385             390             395

<210> SEQ ID NO 76
<211> LENGTH: 396
<212> TYPE: PRT
<213> ORGANISM: Artificial sequence
```

<220> FEATURE:
<223> OTHER INFORMATION: Synthetic

<400> SEQUENCE: 76

Met Lys Thr Ile Ile Ala Leu Ser Tyr Ile Phe Cys Leu Val Phe Ala
1               5                   10                  15

Gln Asn Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Thr Gly Gln Ala Ala Asp Leu Lys Ser Thr Gln Ala Ala Ile Asp Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Lys Thr
                165                 170                 175

Arg Arg Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
    370                 375                 380

Val Lys Gly Ile Ala Lys Ser Arg Lys Ser Gly Ser
385                 390                 395

<210> SEQ ID NO 77
<211> LENGTH: 396
<212> TYPE: PRT
<213> ORGANISM: Artificial sequence
<220> FEATURE:
<223> OTHER INFORMATION: Synthetic

<400> SEQUENCE: 77

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Thr Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Glu Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
        355                 360                 365
```

Glu Leu Ile Gly Asn Glu Asn His Gly Leu Tyr Leu Ala Asp Gln Tyr
    370                 375                 380

Val Lys Gly Ile Ala Lys Ser Arg Lys Ser Gly Ser
385                 390                 395

<210> SEQ ID NO 78
<211> LENGTH: 396
<212> TYPE: PRT
<213> ORGANISM: Artificial sequence
<220> FEATURE:
<223> OTHER INFORMATION: Synthetic

<400> SEQUENCE: 78

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Arg Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Arg Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Arg Gly Gln Ala Ala Asp Leu Lys Ser Thr Gln Ala Ala Ile Asp Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Lys Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

```
Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
370                 375                 380

Val Lys Gly Ile Ala Lys Ser Arg Lys Ser Gly Ser
385                 390                 395

<210> SEQ ID NO 79
<211> LENGTH: 395
<212> TYPE: PRT
<213> ORGANISM: Artificial sequence
<220> FEATURE:
<223> OTHER INFORMATION: Synthetic

<400> SEQUENCE: 79

Met Lys Thr Ile Ile Ala Leu Ser Tyr Ile Phe Cys Leu Ala Leu Ala
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Phe Pro Gly Cys Val
    50                  55                  60

Leu Lys Leu Ala Thr Gly Met Arg Asn Val Pro Glu Lys Gln Thr Arg
65                  70                  75                  80

Gly Leu Phe Gly Ala Ile Ala Gly Phe Ile Glu Asn Gly Trp Glu Gly
                85                  90                  95

Met Ile Asp Gly Trp Tyr Gly Phe Arg His Gln Asn Ser Glu Gly Thr
            100                 105                 110

Gly Gln Ala Ala Asp Leu Lys Ser Thr Gln Ala Ala Ile Asp Gln Ile
        115                 120                 125

Asn Gly Met Val Asn Arg Val Ile Ala Leu Met Ala Gln Gly Gly Pro
    130                 135                 140

Asp Cys Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Lys Thr Arg
                165                 170                 175

Arg Gln Leu Arg Glu Asn Ala Glu Asp Met Gly Asn Gly Cys Phe Lys
            180                 185                 190

Ile Tyr His Lys Cys Asp Asn Ala Cys Ile Glu Ser Ile Arg Asn Gly
        195                 200                 205

Thr Tyr Asp His Asp Val Tyr Arg Asp Glu Ala Leu Asn Asn Arg Phe
    210                 215                 220

Gln Ile Lys Ser Gly Gly Asp Ile Ile Lys Leu Leu Asn Glu Gln Val
225                 230                 235                 240

Asn Lys Glu Met Gln Ser Ser Asn Leu Tyr Met Ser Met Ser Ser Trp
                245                 250                 255

Cys Tyr Thr His Ser Leu Asp Gly Ala Gly Leu Phe Leu Phe Asp His
            260                 265                 270

Ala Ala Glu Glu Tyr Glu His Ala Lys Lys Leu Ile Ile Phe Leu Asn
        275                 280                 285

Glu Asn Asn Val Pro Val Gln Leu Thr Ser Ile Ser Ala Pro Glu His
    290                 295                 300
```

Lys Phe Glu Gly Leu Thr Gln Ile Phe Gln Lys Ala Tyr Glu His Glu
305                 310                 315                 320

Gln His Ile Ser Glu Ser Ile Asn Asn Ile Val Asp His Ala Ile Lys
            325                 330                 335

Ser Lys Asp His Ala Thr Phe Asn Phe Leu Gln Trp Tyr Val Ala Glu
        340                 345                 350

Gln His Glu Glu Glu Val Leu Phe Lys Asp Ile Leu Asp Lys Ile Glu
            355                 360                 365

Leu Ile Gly Asn Glu Asn His Gly Leu Tyr Leu Ala Asp Gln Tyr Val
    370                 375                 380

Lys Gly Ile Ala Lys Ser Arg Lys Ser Gly Ser
385                 390                 395

<210> SEQ ID NO 80
<211> LENGTH: 395
<212> TYPE: PRT
<213> ORGANISM: Artificial sequence
<220> FEATURE:
<223> OTHER INFORMATION: Synthetic

<400> SEQUENCE: 80

Met Lys Thr Ile Ile Ala Leu Ser Tyr Ile Phe Cys Leu Val Phe Ala
1               5                   10                  15

Gln Asn Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Phe Pro Gly Cys Val
    50                  55                  60

Leu Lys Leu Ala Thr Gly Met Arg Asn Val Pro Glu Lys Gln Thr Arg
65                  70                  75                  80

Gly Ile Phe Gly Ala Ile Ala Gly Phe Ile Glu Asn Gly Trp Glu Gly
                85                  90                  95

Met Val Asp Gly Trp Tyr Gly Phe Arg His Gln Asn Ser Glu Gly Thr
            100                 105                 110

Gly Gln Ala Ala Asp Leu Lys Ser Thr Gln Ala Ala Ile Asp Gln Ile
        115                 120                 125

Asn Gly Met Val Asn Arg Val Ile Ala Leu Met Ala Gln Gly Gly Pro
    130                 135                 140

Asp Cys Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Lys Thr Arg
                165                 170                 175

Arg Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
        195                 200                 205

Thr Tyr Asp His Asp Val Tyr Arg Asp Glu Ala Leu Asn Asn Arg Phe
    210                 215                 220

Gln Ile Lys Ser Gly Gly Asp Ile Ile Lys Leu Leu Asn Glu Gln Val
225                 230                 235                 240

Asn Lys Glu Met Gln Ser Ser Asn Leu Tyr Met Ser Met Ser Ser Trp
                245                 250                 255

Cys Tyr Thr His Ser Leu Asp Gly Ala Gly Leu Phe Leu Phe Asp His
            260                 265                 270

```
Ala Ala Glu Glu Tyr Glu His Ala Lys Lys Leu Ile Ile Phe Leu Asn
        275                 280                 285

Glu Asn Asn Val Pro Val Gln Leu Thr Ser Ile Ser Ala Pro Glu His
    290                 295                 300

Lys Phe Glu Gly Leu Thr Gln Ile Phe Gln Lys Ala Tyr Glu His Glu
305                 310                 315                 320

Gln His Ile Ser Glu Ser Ile Asn Asn Ile Val Asp His Ala Ile Lys
                325                 330                 335

Ser Lys Asp His Ala Thr Phe Asn Phe Leu Gln Trp Tyr Val Ala Glu
                340                 345                 350

Gln His Glu Glu Val Leu Phe Lys Asp Ile Leu Asp Lys Ile Glu
                355                 360                 365

Leu Ile Gly Asn Glu Asn His Gly Leu Tyr Leu Ala Asp Gln Tyr Val
        370                 375                 380

Lys Gly Ile Ala Lys Ser Arg Lys Ser Gly Ser
385                 390                 395

<210> SEQ ID NO 81
<211> LENGTH: 395
<212> TYPE: PRT
<213> ORGANISM: Artificial sequence
<220> FEATURE:
<223> OTHER INFORMATION: Synthetic

<400> SEQUENCE: 81

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Gly Cys Val
        50                  55                  60

Leu Lys Leu Ala Thr Gly Met Arg Asn Val Pro Glu Lys Gln Thr Arg
65                  70                  75                  80

Gly Ile Phe Gly Ala Ile Ala Gly Phe Ile Glu Asn Gly Trp Glu Gly
                85                  90                  95

Met Val Asp Gly Trp Tyr Gly Phe Arg His Gln Asn Ser Glu Gly Thr
            100                 105                 110

Gly Gln Ala Ala Asp Leu Lys Ser Thr Gln Ala Ala Ile Asn Gln Ile
        115                 120                 125

Asn Gly Met Val Asn Arg Val Ile Ala Leu Met Ala Gln Gly Gly Pro
130                 135                 140

Asp Cys Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Arg Thr Lys
                165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Glu Ser Ile Arg Asn Gly
        195                 200                 205

Thr Tyr Asp His Asp Val Tyr Arg Asp Glu Ala Leu Asn Asn Arg Phe
    210                 215                 220

Gln Ile Lys Ser Gly Gly Asp Ile Ile Lys Leu Leu Asn Glu Gln Val
225                 230                 235                 240
```

```
Asn Lys Glu Met Gln Ser Ser Asn Leu Tyr Met Ser Met Ser Ser Trp
            245                 250                 255

Cys Tyr Thr His Ser Leu Asp Gly Ala Gly Leu Phe Leu Phe Asp His
            260                 265                 270

Ala Ala Glu Glu Tyr Glu His Ala Lys Lys Leu Ile Ile Phe Leu Asn
            275                 280                 285

Glu Asn Asn Val Pro Val Gln Leu Thr Ser Ile Ser Ala Pro Glu His
            290                 295                 300

Lys Phe Glu Gly Leu Thr Gln Ile Phe Gln Lys Ala Tyr Glu His Glu
305                 310                 315                 320

Gln His Ile Ser Glu Ser Ile Asn Asn Ile Val Asp His Ala Ile Lys
            325                 330                 335

Ser Lys Asp His Ala Thr Phe Asn Phe Leu Gln Trp Tyr Val Ala Glu
            340                 345                 350

Gln His Glu Glu Glu Val Leu Phe Lys Asp Ile Leu Asp Lys Ile Glu
            355                 360                 365

Leu Ile Gly Asn Glu Asn His Gly Leu Tyr Leu Ala Asp Gln Tyr Val
            370                 375                 380

Lys Gly Ile Ala Lys Ser Arg Lys Ser Gly Ser
385                 390                 395

<210> SEQ ID NO 82
<211> LENGTH: 395
<212> TYPE: PRT
<213> ORGANISM: Artificial sequence
<220> FEATURE:
<223> OTHER INFORMATION: Synthetic

<400> SEQUENCE: 82

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
            35                  40                  45

Arg Ile Glu Val Thr Asn Ala Thr Glu Leu Val Phe Pro Gly Cys Val
        50                  55                  60

Leu Lys Leu Ala Thr Gly Met Arg Asn Val Pro Glu Arg Gln Thr Arg
65                  70                  75                  80

Gly Ile Phe Gly Ala Ile Ala Gly Phe Ile Glu Asn Gly Trp Glu Gly
            85                  90                  95

Met Val Asp Gly Trp Tyr Gly Phe Arg His Gln Asn Ser Glu Gly Arg
            100                 105                 110

Gly Gln Ala Ala Asp Leu Lys Ser Thr Gln Ala Ala Ile Asp Gln Ile
            115                 120                 125

Asn Gly Met Val Asn Arg Val Ile Ala Leu Met Ala Gln Gly Gly Pro
            130                 135                 140

Asp Cys Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Lys Thr Lys
            165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
            195                 200                 205
```

```
Thr Tyr Asp His Asp Val Tyr Arg Asp Glu Ala Leu Asn Asn Arg Phe
    210                 215                 220

Gln Ile Lys Ser Gly Gly Asp Ile Ile Lys Leu Leu Asn Glu Gln Val
225                 230                 235                 240

Asn Lys Glu Met Gln Ser Ser Asn Leu Tyr Met Ser Met Ser Ser Trp
                245                 250                 255

Cys Tyr Thr His Ser Leu Asp Gly Ala Gly Leu Phe Leu Phe Asp His
                260                 265                 270

Ala Ala Glu Glu Tyr Glu His Ala Lys Lys Leu Ile Ile Phe Leu Asn
            275                 280                 285

Glu Asn Asn Val Pro Val Gln Leu Thr Ser Ile Ser Ala Pro Glu His
        290                 295                 300

Lys Phe Glu Gly Leu Thr Gln Ile Phe Gln Lys Ala Tyr Glu His Glu
305                 310                 315                 320

Gln His Ile Ser Glu Ser Ile Asn Asn Ile Val Asp His Ala Ile Lys
                325                 330                 335

Ser Lys Asp His Ala Thr Phe Asn Phe Leu Gln Trp Tyr Val Ala Glu
                340                 345                 350

Gln His Glu Glu Val Leu Phe Lys Asp Ile Leu Asp Lys Ile Glu
            355                 360                 365

Leu Ile Gly Asn Glu Asn His Gly Leu Tyr Leu Ala Asp Gln Tyr Val
    370                 375                 380

Lys Gly Ile Ala Lys Ser Arg Lys Ser Gly Ser
385                 390                 395

<210> SEQ ID NO 83
<211> LENGTH: 388
<212> TYPE: PRT
<213> ORGANISM: Artificial sequence
<220> FEATURE:
<223> OTHER INFORMATION: Synthetic

<400> SEQUENCE: 83

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
                100                 105                 110

Ile Gly Gln Ala Ala Asp Leu Lys Ser Thr Gln Ala Ala Ile Asn Gln
            115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175
```

```
Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
210                 215                 220

Phe Gln Ile Lys Ala Gly Pro Pro Gly Met Gln Ile Tyr Glu Gly
225                 230                 235                 240

Lys Leu Thr Ala Glu Gly Leu Arg Phe Gly Ile Val Ala Ser Arg Phe
                245                 250                 255

Asn His Ala Leu Val Asp Arg Leu Val Glu Gly Ala Ile Asp Cys Ile
            260                 265                 270

Val Arg His Gly Gly Arg Glu Glu Asp Ile Thr Leu Val Arg Val Pro
        275                 280                 285

Gly Ser Trp Glu Ile Pro Val Ala Ala Gly Glu Leu Ala Arg Lys Glu
    290                 295                 300

Asp Ile Asp Ala Val Ile Ala Ile Gly Val Leu Ile Arg Gly Ala Thr
305                 310                 315                 320

Pro His Phe Asp Tyr Ile Ala Ser Glu Val Ser Lys Gly Leu Ala Asp
                325                 330                 335

Leu Ser Leu Glu Leu Arg Lys Pro Ile Thr Phe Gly Val Ile Thr Ala
            340                 345                 350

Asp Thr Leu Glu Gln Ala Ile Glu Arg Ala Gly Thr Lys His Gly Asn
        355                 360                 365

Lys Gly Trp Glu Ala Ala Leu Ser Ala Ile Glu Met Ala Asn Leu Phe
    370                 375                 380

Lys Ser Leu Arg
385

<210> SEQ ID NO 84
<211> LENGTH: 388
<212> TYPE: PRT
<213> ORGANISM: Artificial sequence
<220> FEATURE:
<223> OTHER INFORMATION: Synthetic

<400> SEQUENCE: 84

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Glu Glu Gly Gly
    130                 135                 140
```

```
Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ala Gly Pro Gly Gly Cys Gln Ile Tyr Glu Gly
225                 230                 235                 240

Lys Leu Thr Ala Glu Gly Leu Arg Phe Gly Ile Val Ala Ser Arg Phe
                245                 250                 255

Asn His Ala Leu Val Asp Arg Leu Val Glu Gly Ala Ile Asp Cys Ile
            260                 265                 270

Val Arg His Gly Gly Arg Glu Glu Asp Cys Thr Leu Val Arg Val Pro
        275                 280                 285

Gly Ser Trp Glu Ile Pro Val Ala Ala Gly Glu Leu Ala Arg Lys Glu
    290                 295                 300

Asp Ile Asp Ala Val Ile Ala Ile Gly Val Leu Ile Arg Gly Ala Thr
305                 310                 315                 320

Pro His Phe Asp Tyr Ile Ala Ser Glu Val Ser Lys Gly Leu Ala Asp
                325                 330                 335

Leu Ser Leu Glu Leu Arg Lys Pro Ile Thr Phe Gly Val Ile Thr Ala
            340                 345                 350

Asp Thr Leu Glu Gln Ala Ile Glu Arg Ala Gly Thr Lys His Gly Asn
        355                 360                 365

Lys Gly Trp Glu Ala Ala Leu Ser Ala Ile Glu Met Ala Asn Leu Phe
    370                 375                 380

Lys Ser Leu Arg
385

<210> SEQ ID NO 85
<211> LENGTH: 388
<212> TYPE: PRT
<213> ORGANISM: Artificial sequence
<220> FEATURE:
<223> OTHER INFORMATION: Synthetic

<400> SEQUENCE: 85

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Gly Cys Gly
        50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
                100                 105                 110
```

Ile Gly Gln Ala Ala Asp Leu Lys Ser Thr Gln Ala Ala Ile Asn Gln
    115                 120                 125

Ile Asn Gly Met Val Asn Arg Val Ile Ala Leu Met Glu Glu Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ala Gly Pro Pro Gly Met Gln Ile Tyr Glu Gly
225                 230                 235                 240

Lys Leu Thr Ala Glu Gly Leu Arg Phe Gly Ile Val Ala Ser Arg Phe
                245                 250                 255

Asn His Ala Leu Val Asp Arg Leu Val Glu Gly Ala Ile Asp Cys Ile
            260                 265                 270

Val Arg His Gly Gly Arg Glu Glu Asp Ile Thr Leu Val Arg Val Pro
        275                 280                 285

Gly Ser Trp Glu Ile Pro Val Ala Ala Gly Glu Leu Ala Arg Lys Glu
    290                 295                 300

Asp Ile Asp Ala Val Ile Ala Ile Gly Val Leu Ile Arg Gly Ala Thr
305                 310                 315                 320

Pro His Phe Asp Tyr Ile Ala Ser Glu Val Ser Lys Gly Leu Ala Asp
                325                 330                 335

Leu Ser Leu Glu Leu Arg Lys Pro Ile Thr Phe Gly Val Ile Thr Ala
            340                 345                 350

Asp Thr Leu Glu Gln Ala Ile Glu Arg Ala Gly Thr Lys His Gly Asn
        355                 360                 365

Lys Gly Trp Glu Ala Ala Leu Ser Ala Ile Glu Met Ala Asn Leu Phe
    370                 375                 380

Lys Ser Leu Arg
385

<210> SEQ ID NO 86
<211> LENGTH: 388
<212> TYPE: PRT
<213> ORGANISM: Artificial sequence
<220> FEATURE:
<223> OTHER INFORMATION: Synthetic

<400> SEQUENCE: 86

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

```
Arg Gly Ile Phe Gly Ala Ile Ala Gly Phe Ile Glu Asn Gly Trp Glu
                85                  90                  95
Gly Met Val Asp Gly Trp Tyr Gly Phe Arg His Gln Asn Ser Glu Gly
            100                 105                 110
Ile Gly Gln Ala Ala Asp Leu Lys Ser Thr Gln Ala Ala Ile Asn Gln
            115                 120                 125
Ile Asn Gly Met Val Asn Arg Val Ile Ala Leu Met Glu Glu Gly Gly
            130                 135                 140
Pro Asp Cys Tyr Leu Ala Glu Leu Leu Val Ala Leu Leu Asn Gln His
145                 150                 155                 160
Val Ile Asp Leu Thr Asp Ser Glu Met Arg Lys Leu Phe Glu Arg Thr
                165                 170                 175
Lys Lys Gln Leu Arg Glu Asn Ala Glu Asp Met Gly Asn Gly Cys Phe
            180                 185                 190
Lys Ile Tyr His Lys Cys Asp Asn Ala Cys Ile Gly Ser Ile Arg Asn
            195                 200                 205
Gly Thr Tyr Asp His Asp Val Tyr Arg Asp Glu Ala Leu Asn Asn Arg
            210                 215                 220
Phe Gln Ile Lys Ala Gly Ser Gly Gly Cys Gln Ile Tyr Glu Gly
225                 230                 235                 240
Lys Leu Thr Ala Glu Gly Leu Arg Phe Gly Ile Val Ala Ser Arg Phe
                245                 250                 255
Asn His Ala Leu Val Asp Arg Leu Val Glu Gly Ala Ile Asp Cys Ile
            260                 265                 270
Val Arg His Gly Gly Arg Glu Glu Asp Cys Thr Leu Val Arg Val Pro
            275                 280                 285
Gly Ser Trp Glu Ile Pro Val Ala Ala Gly Leu Ala Arg Lys Glu
            290                 295                 300
Asp Ile Asp Ala Val Ile Ala Ile Gly Val Leu Ile Arg Gly Ala Thr
305                 310                 315                 320
Pro His Phe Asp Tyr Ile Ala Ser Glu Val Ser Lys Gly Leu Ala Asp
                325                 330                 335
Leu Ser Leu Glu Leu Arg Lys Pro Ile Thr Phe Gly Val Ile Thr Ala
            340                 345                 350
Asp Thr Leu Glu Gln Ala Ile Glu Arg Ala Gly Thr Lys His Gly Asn
            355                 360                 365
Lys Gly Trp Glu Ala Ala Leu Ser Ala Ile Glu Met Ala Asn Leu Phe
            370                 375                 380
Lys Ser Leu Arg
385

<210> SEQ ID NO 87
<211> LENGTH: 388
<212> TYPE: PRT
<213> ORGANISM: Artificial sequence
<220> FEATURE:
<223> OTHER INFORMATION: Synthetic

<400> SEQUENCE: 87

Met Lys Thr Ile Ile Ala Leu Ser Tyr Ile Leu Cys Leu Val Phe Ala
1               5                   10                  15
Gln Lys Leu Pro Gly Asn Asp Asn Ser Thr Ala Thr Leu Cys Leu Gly
            20                  25                  30
His His Ala Val Pro Asn Gly Thr Ile Val Lys Thr Ile Thr Asn Asp
            35                  40                  45
```

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
 65                  70                  75                  80

Arg Gly Ile Phe Gly Ala Ile Ala Gly Phe Ile Glu Asn Gly Trp Glu
                 85                  90                  95

Gly Met Val Asp Gly Trp Tyr Gly Phe Arg His Gln Asn Ser Glu Gly
                100                 105                 110

Ile Gly Gln Ala Ala Asp Leu Lys Ser Thr Gln Ala Ala Ile Asn Gln
            115                 120                 125

Ile Asn Gly Met Val Asn Arg Val Ile Ala Leu Met Ala Gln Gly Gly
        130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
                180                 185                 190

Lys Ile Tyr His Lys Cys Asp Asn Ala Cys Ile Gly Ser Ile Arg Asn
            195                 200                 205

Gly Thr Tyr Asp His Asp Val Tyr Arg Asp Glu Ala Leu Asn Asn Arg
        210                 215                 220

Phe Gln Ile Lys Ala Gly Pro Pro Gly Gly Met Gln Ile Tyr Glu Gly
225                 230                 235                 240

Lys Leu Thr Ala Glu Gly Leu Arg Phe Gly Ile Val Ala Ser Arg Phe
                245                 250                 255

Asn His Ala Leu Val Asp Arg Leu Val Glu Gly Ala Ile Asp Cys Ile
            260                 265                 270

Val Arg His Gly Gly Arg Glu Glu Asp Ile Thr Leu Val Arg Val Pro
        275                 280                 285

Gly Ser Trp Glu Ile Pro Val Ala Ala Gly Glu Leu Ala Arg Lys Glu
290                 295                 300

Asp Ile Asp Ala Val Ile Ala Ile Gly Val Leu Ile Arg Gly Ala Thr
305                 310                 315                 320

Pro His Phe Asp Tyr Ile Ala Ser Glu Val Ser Lys Gly Leu Ala Asn
                325                 330                 335

Leu Ala Leu Glu Leu Arg Lys Pro Ile Thr Phe Gly Val Ile Thr Ala
            340                 345                 350

Asp Thr Leu Glu Gln Ala Ile Glu Arg Ala Gly Thr Lys His Gly Asn
        355                 360                 365

Lys Gly Trp Glu Ala Ala Leu Ser Ala Ile Glu Met Ala Asn Leu Phe
370                 375                 380

Lys Ser Leu Arg
385

<210> SEQ ID NO 88
<211> LENGTH: 389
<212> TYPE: PRT
<213> ORGANISM: Artificial sequence
<220> FEATURE:
<223> OTHER INFORMATION: Synthetic

<400> SEQUENCE: 88

Met Lys Thr Ile Ile Ala Leu Ser Tyr Ile Leu Cys Leu Val Phe Ala
 1               5                  10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
210                 215                 220

Phe Gln Ile Lys Ala Gly Pro Pro Gly Gly Met Gln Ile Tyr Glu
225                 230                 235                 240

Gly Lys Leu Thr Ala Glu Gly Leu Arg Phe Gly Ile Val Ala Ser Arg
                245                 250                 255

Phe Asn His Ala Leu Val Asp Arg Leu Val Glu Gly Ala Ile Asp Cys
            260                 265                 270

Ile Val Arg His Gly Gly Arg Glu Glu Asp Ile Thr Leu Val Arg Val
        275                 280                 285

Pro Gly Ser Trp Glu Ile Pro Val Ala Ala Gly Glu Leu Ala Arg Lys
290                 295                 300

Glu Asp Ile Asp Ala Val Ile Ala Ile Gly Val Leu Ile Arg Gly Ala
305                 310                 315                 320

Thr Pro His Phe Asp Tyr Ile Ala Ser Glu Val Ser Lys Gly Leu Ala
                325                 330                 335

Asp Leu Ser Leu Glu Leu Arg Lys Pro Ile Thr Phe Gly Val Ile Thr
            340                 345                 350

Ala Asp Thr Leu Glu Gln Ala Ile Glu Arg Ala Gly Thr Lys His Gly
        355                 360                 365

Asn Lys Gly Trp Glu Ala Ala Leu Ser Ala Ile Glu Met Ala Asn Leu
370                 375                 380

Phe Lys Ser Leu Arg
385

<210> SEQ ID NO 89
<211> LENGTH: 388
<212> TYPE: PRT
<213> ORGANISM: Artificial sequence
<220> FEATURE:

<223> OTHER INFORMATION: Synthetic

<400> SEQUENCE: 89

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Cys Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Cys Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Leu Val Asn Arg Val Ile Ala Trp Met Glu Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Asn Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ala Gly Pro Pro Gly Met Gln Ile Tyr Glu Gly
225                 230                 235                 240

Lys Leu Thr Ala Glu Gly Leu Arg Phe Gly Ile Val Ala Ser Arg Phe
                245                 250                 255

Asn His Ala Leu Val Asp Arg Leu Val Glu Gly Ala Ile Asp Cys Ile
            260                 265                 270

Val Arg His Gly Gly Arg Glu Glu Asp Ile Thr Leu Val Arg Val Pro
        275                 280                 285

Gly Ser Trp Glu Ile Pro Val Ala Ala Gly Glu Leu Ala Arg Lys Glu
    290                 295                 300

Asp Ile Asp Ala Val Ile Ala Ile Gly Val Leu Ile Arg Gly Ala Thr
305                 310                 315                 320

Pro His Phe Asp Tyr Ile Ala Ser Glu Val Ser Lys Gly Leu Ala Asp
                325                 330                 335

Leu Ser Leu Glu Leu Arg Lys Pro Ile Thr Phe Gly Val Ile Thr Ala
            340                 345                 350

Asp Thr Leu Glu Gln Ala Ile Glu Arg Ala Gly Thr Lys His Gly Asn
        355                 360                 365

Lys Gly Trp Glu Ala Ala Leu Ser Ala Ile Glu Met Ala Asn Leu Phe
    370                 375                 380

Lys Ser Leu Arg
385
```

<210> SEQ ID NO 90
<211> LENGTH: 281
<212> TYPE: PRT
<213> ORGANISM: Artificial sequence
<220> FEATURE:
<223> OTHER INFORMATION: Synthetic

<400> SEQUENCE: 90

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Pro Gly Ser Gly Tyr Ile Pro Glu Ala Pro Arg Asp
225                 230                 235                 240

Gly Gln Ala Tyr Val Arg Lys Asp Gly Glu Trp Val Leu Leu Ser Thr
                245                 250                 255

Phe Leu Gly Ser Gly Leu Asn Asp Ile Phe Glu Ala Gln Lys Ile Glu
            260                 265                 270

Trp His Glu Gly His His His His
        275                 280
```

<210> SEQ ID NO 91
<211> LENGTH: 283
<212> TYPE: PRT
<213> ORGANISM: Artificial sequence
<220> FEATURE:
<223> OTHER INFORMATION: Synthetic

<400> SEQUENCE: 91

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30
```

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Gly Cys Gly
 50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
210                 215                 220

Phe Gln Ile Lys Gly Gly Pro Gly Ser Gly Tyr Ile Pro Glu Ala Pro
225                 230                 235                 240

Arg Asp Gly Gln Ala Tyr Val Arg Lys Asp Gly Glu Trp Val Leu Leu
                245                 250                 255

Ser Thr Phe Leu Gly Ser Gly Leu Asn Asp Ile Phe Glu Ala Gln Lys
            260                 265                 270

Ile Glu Trp His Glu Gly His His His His
        275                 280

<210> SEQ ID NO 92
<211> LENGTH: 389
<212> TYPE: PRT
<213> ORGANISM: Artificial sequence
<220> FEATURE:
<223> OTHER INFORMATION: Synthetic

<400> SEQUENCE: 92

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Leu Val Phe Pro Gly Cys Gly Val Leu Lys Leu Ala Thr Gly Met
 50                  55                  60

Lys Asn Val Pro Glu Ile Pro Lys Gly Arg Gly Leu Phe Gly Ala Ile
65                  70                  75                  80

Ala Gly Phe Ile Glu Asn Gly Trp Glu Gly Leu Ile Asp Gly Trp Tyr
                85                  90                  95

Gly Phe Arg His Gln Asn Ala Gln Gly Glu Gly Thr Ala Ala Asp Tyr
            100                 105                 110

```
Lys Ser Thr Gln Ser Ala Ile Asp Gln Ile Thr Gly Met Val Asn Arg
        115                 120                 125

Val Ile Ala Leu Met Ala Gln Gly Gly Pro Asp Cys Tyr Leu Ala Glu
    130                 135                 140

Leu Leu Val Ala Met Leu Asn Gln His Val Ile Asp Leu Ala Asp Ser
145                 150                 155                 160

Glu Met Asp Lys Leu Tyr Glu Arg Val Lys Arg Gln Leu Arg Glu Asn
                165                 170                 175

Ala Glu Glu Asp Gly Thr Gly Cys Phe Glu Ile Phe His Lys Cys Asp
            180                 185                 190

Asp Asp Cys Met Ala Ser Ile Arg Asn Asn Thr Tyr Asp His Ser Lys
        195                 200                 205

Tyr Arg Glu Glu Ala Met Gln Asn Arg Ile Gln Ile Asp Ser Gly Gly
    210                 215                 220

Asp Ile Ile Lys Leu Leu Asn Glu Gln Val Asn Lys Glu Met Gln Ser
225                 230                 235                 240

Ser Asn Leu Tyr Met Ser Met Ser Ser Trp Cys Tyr Thr His Ser Leu
                245                 250                 255

Asp Gly Ala Gly Leu Phe Leu Phe Asp His Ala Ala Glu Glu Tyr Glu
            260                 265                 270

His Ala Lys Lys Leu Ile Ile Phe Leu Asn Glu Asn Asn Val Pro Val
        275                 280                 285

Gln Leu Thr Ser Ile Ser Ala Pro Glu His Lys Phe Glu Gly Leu Thr
    290                 295                 300

Gln Ile Phe Gln Lys Ala Tyr Glu His Glu Gln His Ile Ser Glu Ser
305                 310                 315                 320

Ile Asn Asn Ile Val Asp His Ala Ile Lys Ser Lys Asp His Ala Thr
                325                 330                 335

Phe Asn Phe Leu Gln Trp Tyr Val Ala Glu Gln His Glu Glu Glu Val
            340                 345                 350

Leu Phe Lys Asp Ile Leu Asp Lys Ile Glu Leu Ile Gly Asn Glu Asn
        355                 360                 365

His Gly Leu Tyr Leu Ala Asp Gln Tyr Val Lys Gly Ile Ala Lys Ser
    370                 375                 380

Arg Lys Ser Gly Ser
385

<210> SEQ ID NO 93
<211> LENGTH: 388
<212> TYPE: PRT
<213> ORGANISM: Artificial sequence
<220> FEATURE:
<223> OTHER INFORMATION: Synthetic

<400> SEQUENCE: 93

Met Asn Thr Gln Ile Leu Val Phe Ala Leu Ile Ala Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Leu Val Phe Pro Gly Cys Val Leu Lys Leu Ala Thr Gly Met Lys
        50                  55                  60

Asn Val Pro Glu Ile Pro Lys Gly Arg Gly Leu Phe Gly Ala Ile Ala
65                  70                  75                  80
```

Gly Phe Ile Glu Asn Gly Trp Glu Gly Leu Ile Asp Gly Trp Tyr Gly
                85                  90                  95

Phe Arg His Gln Asn Ala Gln Gly Glu Gly Thr Ala Ala Asp Tyr Lys
                100                 105                 110

Ser Thr Gln Ser Ala Ile Asp Gln Ile Thr Gly Met Val Asn Arg Val
                115                 120                 125

Ile Ala Leu Met Ala Gln Gly Gly Pro Asp Cys Tyr Leu Ala Glu Leu
            130                 135                 140

Leu Val Ala Met Leu Asn Gln His Val Ile Asp Leu Ala Asp Ser Glu
145                 150                 155                 160

Met Asp Lys Leu Tyr Glu Arg Val Lys Arg Gln Leu Arg Glu Asn Ala
                165                 170                 175

Glu Glu Asp Gly Thr Gly Cys Phe Glu Ile Phe His Lys Cys Asp Asp
                180                 185                 190

Asp Cys Met Ala Ser Ile Arg Asn Asn Thr Tyr Asp His Ser Lys Tyr
                195                 200                 205

Arg Glu Glu Ala Met Gln Asn Arg Ile Gln Ile Asp Ser Gly Gly Asp
                210                 215                 220

Ile Ile Lys Leu Leu Asn Glu Gln Val Asn Lys Glu Met Gln Ser Ser
225                 230                 235                 240

Asn Leu Tyr Met Ser Met Ser Ser Trp Cys Tyr Thr His Ser Leu Asp
                245                 250                 255

Gly Ala Gly Leu Phe Leu Phe Asp His Ala Ala Glu Glu Tyr Glu His
                260                 265                 270

Ala Lys Lys Leu Ile Ile Phe Leu Asn Glu Asn Asn Val Pro Val Gln
                275                 280                 285

Leu Thr Ser Ile Ser Ala Pro Glu His Lys Phe Glu Gly Leu Thr Gln
                290                 295                 300

Ile Phe Gln Lys Ala Tyr Glu His Glu Gln His Ile Ser Glu Ser Ile
305                 310                 315                 320

Asn Asn Ile Val Asp His Ala Ile Lys Ser Lys Asp His Ala Thr Phe
                325                 330                 335

Asn Phe Leu Gln Trp Tyr Val Ala Glu Gln His Glu Glu Glu Val Leu
                340                 345                 350

Phe Lys Asp Ile Leu Asp Lys Ile Glu Leu Ile Gly Asn Glu Asn His
                355                 360                 365

Gly Leu Tyr Leu Ala Asp Gln Tyr Val Lys Gly Ile Ala Lys Ser Arg
                370                 375                 380

Lys Ser Gly Ser
385

<210> SEQ ID NO 94
<211> LENGTH: 388
<212> TYPE: PRT
<213> ORGANISM: Artificial sequence
<220> FEATURE:
<223> OTHER INFORMATION: Synthetic

<400> SEQUENCE: 94

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
                35                  40                  45

Glu Leu Val Phe Pro Cys Gly Val Leu Lys Leu Ala Thr Gly Met Lys
 50                  55                  60

Asn Val Pro Glu Ile Pro Lys Gly Arg Gly Leu Phe Gly Ala Ile Ala
 65                  70                  75                  80

Gly Phe Ile Glu Asn Gly Trp Glu Gly Leu Ile Asp Gly Trp Tyr Gly
                 85                  90                  95

Phe Arg His Gln Asn Ala Gln Gly Glu Gly Thr Ala Ala Asp Tyr Lys
                100                 105                 110

Ser Thr Gln Ser Ala Ile Asp Gln Ile Thr Gly Met Val Asn Arg Val
            115                 120                 125

Ile Ala Leu Met Ala Gln Gly Gly Pro Asp Cys Tyr Leu Ala Glu Leu
        130                 135                 140

Leu Val Ala Met Leu Asn Gln His Val Ile Asp Leu Ala Asp Ser Glu
145                 150                 155                 160

Met Asp Lys Leu Tyr Glu Arg Val Lys Arg Gln Leu Arg Glu Asn Ala
                165                 170                 175

Glu Glu Asp Gly Thr Gly Cys Phe Glu Ile Phe His Lys Cys Asp Asp
                180                 185                 190

Asp Cys Met Ala Ser Ile Arg Asn Asn Thr Tyr Asp His Ser Lys Tyr
            195                 200                 205

Arg Glu Glu Ala Met Gln Asn Arg Ile Gln Ile Asp Ser Gly Gly Asp
        210                 215                 220

Ile Ile Lys Leu Leu Asn Glu Gln Val Asn Lys Glu Met Gln Ser Ser
225                 230                 235                 240

Asn Leu Tyr Met Ser Met Ser Ser Trp Cys Tyr Thr His Ser Leu Asp
                245                 250                 255

Gly Ala Gly Leu Phe Leu Phe Asp His Ala Ala Glu Glu Tyr Glu His
                260                 265                 270

Ala Lys Lys Leu Ile Ile Phe Leu Asn Glu Asn Asn Val Pro Val Gln
            275                 280                 285

Leu Thr Ser Ile Ser Ala Pro Glu His Lys Phe Glu Gly Leu Thr Gln
        290                 295                 300

Ile Phe Gln Lys Ala Tyr Glu His Glu Gln His Ile Ser Glu Ser Ile
305                 310                 315                 320

Asn Asn Ile Val Asp His Ala Ile Lys Ser Lys Asp His Ala Thr Phe
                325                 330                 335

Asn Phe Leu Gln Trp Tyr Val Ala Glu Gln His Glu Glu Val Leu
                340                 345                 350

Phe Lys Asp Ile Leu Asp Lys Ile Glu Leu Ile Gly Asn Glu Asn His
            355                 360                 365

Gly Leu Tyr Leu Ala Asp Gln Tyr Val Lys Gly Ile Ala Lys Ser Arg
        370                 375                 380

Lys Ser Gly Ser
385

<210> SEQ ID NO 95
<211> LENGTH: 389
<212> TYPE: PRT
<213> ORGANISM: Artificial sequence
<220> FEATURE:
<223> OTHER INFORMATION: Synthetic

<400> SEQUENCE: 95

Met Asn Thr Gln Ile Leu Val Phe Ala Leu Ile Ala Ile Ile Pro Thr
 1               5                  10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Asn Ala Thr
        35                  40                  45

Glu Leu Val Phe Pro Asn Cys Gly Val Leu Lys Leu Ala Thr Gly Met
50                  55                  60

Lys Asn Val Pro Glu Ile Pro Lys Gly Arg Gly Leu Phe Gly Ala Ile
65                  70                  75                  80

Ala Gly Phe Ile Glu Asn Gly Trp Glu Gly Leu Ile Asp Gly Trp Tyr
                85                  90                  95

Gly Phe Arg His Gln Asn Ala Gln Gly Glu Gly Thr Ala Ala Asp Tyr
            100                 105                 110

Lys Ser Thr Gln Ser Ala Ile Asp Gln Ile Thr Gly Met Val Asn Arg
        115                 120                 125

Val Ile Ala Leu Met Ala Gln Gly Gly Pro Asp Cys Tyr Leu Ala Glu
130                 135                 140

Leu Leu Val Ala Met Leu Asn Gln His Val Ile Asp Leu Ala Asp Ser
145                 150                 155                 160

Glu Met Asp Lys Leu Tyr Glu Arg Val Lys Arg Gln Leu Arg Glu Asn
                165                 170                 175

Ala Glu Glu Asp Gly Thr Gly Cys Phe Glu Ile Phe His Lys Cys Asp
            180                 185                 190

Asp Asp Cys Met Ala Ser Ile Arg Asn Asn Thr Tyr Asp His Ser Lys
        195                 200                 205

Tyr Arg Glu Glu Ala Met Gln Asn Arg Ile Gln Ile Asp Ser Gly Gly
210                 215                 220

Asp Ile Ile Lys Leu Leu Asn Glu Gln Val Asn Lys Glu Met Gln Ser
225                 230                 235                 240

Ser Asn Leu Tyr Met Ser Met Ser Ser Trp Cys Tyr Thr His Ser Leu
                245                 250                 255

Asp Gly Ala Gly Leu Phe Leu Phe Asp His Ala Ala Glu Glu Tyr Glu
            260                 265                 270

His Ala Lys Lys Leu Ile Ile Phe Leu Asn Glu Asn Asn Val Pro Val
        275                 280                 285

Gln Leu Thr Ser Ile Ser Ala Pro Glu His Lys Phe Glu Gly Leu Thr
290                 295                 300

Gln Ile Phe Gln Lys Ala Tyr Glu His Glu Gln His Ile Ser Glu Ser
305                 310                 315                 320

Ile Asn Asn Ile Val Asp His Ala Ile Lys Ser Lys Asp His Ala Thr
                325                 330                 335

Phe Asn Phe Leu Gln Trp Tyr Val Ala Glu Gln His Glu Glu Glu Val
            340                 345                 350

Leu Phe Lys Asp Ile Leu Asp Lys Ile Glu Leu Ile Gly Asn Glu Asn
        355                 360                 365

His Gly Leu Tyr Leu Ala Asp Gln Tyr Val Lys Gly Ile Ala Lys Ser
370                 375                 380

Arg Lys Ser Gly Ser
385

<210> SEQ ID NO 96
<211> LENGTH: 389
<212> TYPE: PRT
<213> ORGANISM: Artificial sequence
<220> FEATURE:

<223> OTHER INFORMATION: Synthetic

<400> SEQUENCE: 96

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Asn Ala Thr
                35                  40                  45

Glu Leu Val Phe Pro Gly Cys Gly Val Leu Lys Leu Ala Thr Gly Met
    50                  55                  60

Lys Asn Val Pro Glu Ile Pro Lys Gly Arg Gly Leu Phe Gly Ala Ile
65                  70                  75                  80

Ala Gly Phe Ile Glu Asn Gly Trp Glu Gly Leu Ile Asp Gly Trp Tyr
                85                  90                  95

Gly Phe Arg His Gln Asn Ala Gln Gly Glu Gly Thr Ala Ala Asp Tyr
            100                 105                 110

Lys Ser Thr Gln Ser Ala Ile Asp Gln Ile Thr Gly Met Val Asn Arg
        115                 120                 125

Val Ile Ala Leu Met Ala Gln Gly Pro Pro Asp Cys Tyr Leu Ala Glu
130                 135                 140

Leu Leu Val Ala Met Leu Asn Gln His Val Ile Asp Leu Ala Asp Ser
145                 150                 155                 160

Glu Met Asp Lys Leu Tyr Glu Arg Val Lys Arg Gln Leu Arg Glu Asn
                165                 170                 175

Ala Glu Glu Asp Gly Thr Gly Cys Phe Glu Ile Phe His Lys Cys Asp
            180                 185                 190

Asp Asp Cys Met Ala Ser Ile Arg Asn Asn Thr Tyr Asp His Ser Lys
        195                 200                 205

Tyr Arg Glu Glu Ala Met Gln Asn Arg Ile Gln Ile Asp Ser Gly Gly
    210                 215                 220

Asp Ile Ile Lys Leu Leu Asn Glu Gln Val Asn Lys Glu Met Gln Ser
225                 230                 235                 240

Ser Asn Leu Tyr Met Ser Met Ser Ser Trp Cys Tyr Thr His Ser Leu
                245                 250                 255

Asp Gly Ala Gly Leu Phe Leu Phe Asp His Ala Ala Glu Glu Tyr Glu
            260                 265                 270

His Ala Lys Lys Leu Ile Ile Phe Leu Asn Glu Asn Asn Val Pro Val
        275                 280                 285

Gln Leu Thr Ser Ile Ser Ala Pro Glu His Lys Phe Glu Gly Leu Thr
    290                 295                 300

Gln Ile Phe Gln Lys Ala Tyr Glu His Glu Gln His Ile Ser Glu Ser
305                 310                 315                 320

Ile Asn Asn Ile Val Asp His Ala Ile Lys Ser Lys Asp His Ala Thr
                325                 330                 335

Phe Asn Phe Leu Gln Trp Tyr Val Ala Glu Gln His Glu Glu Val
            340                 345                 350

Leu Phe Lys Asp Ile Leu Asp Lys Ile Glu Leu Ile Gly Asn Glu Asn
        355                 360                 365

His Gly Leu Tyr Leu Ala Asp Gln Tyr Val Lys Gly Ile Ala Lys Ser
    370                 375                 380

Arg Lys Ser Gly Ser
385
```

```
<210> SEQ ID NO 97
<211> LENGTH: 389
<212> TYPE: PRT
<213> ORGANISM: Artificial sequence
<220> FEATURE:
<223> OTHER INFORMATION: Synthetic

<400> SEQUENCE: 97

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Leu Val Phe Pro Gly Cys Gly Val Leu Lys Leu Ala Thr Gly Met
    50                  55                  60

Lys Asn Val Pro Glu Ile Pro Lys Gly Arg Gly Leu Phe Gly Ala Ile
65                  70                  75                  80

Ala Gly Phe Ile Glu Asn Gly Trp Glu Gly Leu Ile Asp Gly Trp Tyr
                85                  90                  95

Gly Phe Arg His Gln Asn Ala Gln Gly Glu Gly Thr Ala Ala Asp Tyr
            100                 105                 110

Lys Ser Thr Gln Ser Ala Ile Asp Gln Ile Thr Gly Met Val Asn Arg
        115                 120                 125

Val Ile Ala Leu Met Glu Glu Gly Gly Pro Asp Cys Tyr Leu Ala Glu
    130                 135                 140

Leu Leu Val Ala Met Leu Asn Gln His Val Ile Asp Leu Ala Asp Ser
145                 150                 155                 160

Glu Met Asp Lys Leu Tyr Glu Arg Val Lys Arg Gln Leu Arg Glu Asn
                165                 170                 175

Ala Glu Glu Asp Gly Thr Gly Cys Phe Glu Ile Phe His Lys Cys Asp
            180                 185                 190

Asp Asp Cys Met Ala Ser Ile Arg Asn Asn Thr Tyr Asp His Ser Lys
        195                 200                 205

Tyr Arg Glu Glu Ala Met Gln Asn Arg Ile Gln Ile Asp Ser Gly Gly
    210                 215                 220

Asp Ile Ile Lys Leu Leu Asn Glu Gln Val Asn Lys Glu Met Gln Ser
225                 230                 235                 240

Ser Asn Leu Tyr Met Ser Met Ser Ser Trp Cys Tyr Thr His Ser Leu
                245                 250                 255

Asp Gly Ala Gly Leu Phe Leu Phe Asp His Ala Ala Glu Glu Tyr Glu
            260                 265                 270

His Ala Lys Lys Leu Ile Ile Phe Leu Asn Glu Asn Asn Val Pro Val
        275                 280                 285

Gln Leu Thr Ser Ile Ser Ala Pro Glu His Lys Phe Glu Gly Leu Thr
    290                 295                 300

Gln Ile Phe Gln Lys Ala Tyr Glu His Glu Gln His Ile Ser Glu Ser
305                 310                 315                 320

Ile Asn Asn Ile Val Asp His Ala Ile Lys Ser Lys Asp His Ala Thr
                325                 330                 335

Phe Asn Phe Leu Gln Trp Tyr Val Ala Glu Gln His Glu Glu Glu Val
            340                 345                 350

Leu Phe Lys Asp Ile Leu Asp Lys Ile Glu Leu Ile Gly Asn Glu Asn
        355                 360                 365
```

His Gly Leu Tyr Leu Ala Asp Gln Tyr Val Lys Gly Ile Ala Lys Ser
            370                 375                 380

Arg Lys Ser Gly Ser
385

<210> SEQ ID NO 98
<211> LENGTH: 389
<212> TYPE: PRT
<213> ORGANISM: Artificial sequence
<220> FEATURE:
<223> OTHER INFORMATION: Synthetic

<400> SEQUENCE: 98

Met Asn Thr Gln Ile Leu Val Phe Ala Leu Ile Ala Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Asn Ala Thr
            35                  40                  45

Glu Leu Val Phe Pro Gly Cys Gly Val Leu Lys Leu Ala Thr Gly Met
        50                  55                  60

Lys Asn Val Pro Glu Ile Pro Lys Gly Arg Gly Leu Phe Gly Ala Ile
65                  70                  75                  80

Ala Gly Phe Ile Glu Asn Gly Trp Glu Gly Leu Ile Asp Gly Trp Tyr
                85                  90                  95

Gly Phe Arg His Gln Asn Ala Gln Gly Glu Gly Thr Ala Ala Asp Tyr
                100                 105                 110

Lys Ser Thr Gln Ser Ala Ile Asp Gln Ile Thr Gly Met Val Asn Arg
            115                 120                 125

Val Ile Glu Leu Met Glu Gln Gly Gly Pro Asp Cys Tyr Leu Ala Glu
        130                 135                 140

Leu Leu Val Ala Met Leu Asn Gln His Val Ile Asp Leu Ala Asp Ser
145                 150                 155                 160

Glu Met Asp Lys Leu Tyr Glu Arg Val Lys Arg Gln Leu Arg Glu Asn
                165                 170                 175

Ala Glu Glu Asp Gly Thr Gly Cys Phe Glu Ile Phe His Lys Cys Asp
                180                 185                 190

Asp Asp Cys Met Ala Ser Ile Arg Asn Asn Thr Tyr Asp His Ser Lys
            195                 200                 205

Tyr Arg Glu Glu Ala Met Gln Asn Arg Ile Gln Ile Asp Ser Gly Gly
        210                 215                 220

Asp Ile Ile Lys Leu Leu Asn Glu Gln Val Asn Lys Glu Met Gln Ser
225                 230                 235                 240

Ser Asn Leu Tyr Met Ser Met Ser Ser Trp Cys Tyr Thr His Ser Leu
                245                 250                 255

Asp Gly Ala Gly Leu Phe Leu Phe Asp His Ala Ala Glu Glu Tyr Glu
                260                 265                 270

His Ala Lys Lys Leu Ile Ile Phe Leu Asn Glu Asn Asn Val Pro Val
            275                 280                 285

Gln Leu Thr Ser Ile Ser Ala Pro Glu His Lys Phe Glu Gly Leu Thr
        290                 295                 300

Gln Ile Phe Gln Lys Ala Tyr Glu His Glu Gln His Ile Ser Glu Ser
305                 310                 315                 320

Ile Asn Asn Ile Val Asp His Ala Ile Lys Ser Lys Asp His Ala Thr
                325                 330                 335

```
Phe Asn Phe Leu Gln Trp Tyr Val Ala Glu Gln His Glu Glu Val
                340                 345                 350

Leu Phe Lys Asp Ile Leu Asp Lys Ile Glu Leu Ile Gly Asn Glu Asn
        355                 360                 365

His Gly Leu Tyr Leu Ala Asp Gln Tyr Val Lys Gly Ile Ala Lys Ser
    370                 375                 380

Arg Lys Ser Gly Ser
385
```

<210> SEQ ID NO 99
<211> LENGTH: 388
<212> TYPE: PRT
<213> ORGANISM: Artificial sequence
<220> FEATURE:
<223> OTHER INFORMATION: Synthetic

<400> SEQUENCE: 99

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Leu Cys Phe Asn Gly Ile Cys Leu Lys Leu Ala Thr Gly Met Lys
        50                  55                  60

Asn Val Pro Glu Ile Pro Lys Gly Arg Gly Leu Phe Gly Ala Ile Ala
65                  70                  75                  80

Gly Phe Ile Glu Asn Gly Trp Glu Gly Leu Ile Asp Gly Trp Tyr Gly
                85                  90                  95

Phe Arg His Gln Asn Ala Gln Gly Glu Gly Thr Ala Ala Asp Tyr Lys
            100                 105                 110

Ser Thr Gln Ser Ala Ile Asp Gln Ile Thr Gly Met Val Asn Arg Val
        115                 120                 125

Ile Ala Leu Met Ala Gln Gly Gly Pro Asp Cys Tyr Leu Ala Glu Leu
    130                 135                 140

Leu Val Ala Met Leu Asn Gln His Val Ile Asp Leu Ala Asp Ser Glu
145                 150                 155                 160

Met Asp Lys Leu Tyr Glu Arg Val Lys Arg Gln Leu Arg Glu Asn Ala
                165                 170                 175

Glu Glu Asp Gly Thr Gly Cys Phe Glu Ile Phe His Lys Cys Asp Asp
            180                 185                 190

Asp Cys Met Ala Ser Ile Arg Asn Asn Thr Tyr Asp His Ser Lys Tyr
        195                 200                 205

Arg Glu Glu Ala Met Gln Asn Arg Ile Gln Ile Asp Ser Gly Gly Asp
    210                 215                 220

Ile Ile Lys Leu Leu Asn Glu Gln Val Asn Lys Glu Met Gln Ser Ser
225                 230                 235                 240

Asn Leu Tyr Met Ser Met Ser Ser Trp Cys Tyr Thr His Ser Leu Asp
                245                 250                 255

Gly Ala Gly Leu Phe Leu Phe Asp His Ala Ala Glu Glu Tyr Glu His
            260                 265                 270

Ala Lys Lys Leu Ile Ile Phe Leu Asn Glu Asn Asn Val Pro Val Gln
        275                 280                 285

Leu Thr Ser Ile Ser Ala Pro Glu His Lys Phe Glu Gly Leu Thr Gln
    290                 295                 300
```

Ile Phe Gln Lys Ala Tyr Glu His Glu Gln His Ile Ser Glu Ser Ile
305                 310                 315                 320

Asn Asn Ile Val Asp His Ala Ile Lys Ser Lys Asp His Ala Thr Phe
            325                 330                 335

Asn Phe Leu Gln Trp Tyr Val Ala Glu Gln His Glu Glu Val Leu
        340                 345                 350

Phe Lys Asp Ile Leu Asp Lys Ile Glu Leu Ile Gly Asn Glu Asn His
            355                 360                 365

Gly Leu Tyr Leu Ala Asp Gln Tyr Val Lys Gly Ile Ala Lys Ser Arg
    370                 375                 380

Lys Ser Gly Ser
385

<210> SEQ ID NO 100
<211> LENGTH: 388
<212> TYPE: PRT
<213> ORGANISM: Artificial sequence
<220> FEATURE:
<223> OTHER INFORMATION: Synthetic

<400> SEQUENCE: 100

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Asn Ala Thr
        35                  40                  45

Glu Leu Val Phe Pro Cys Gly Val Leu Lys Leu Ala Thr Gly Met Lys
    50                  55                  60

Asn Val Pro Glu Ile Pro Lys Gly Arg Gly Leu Phe Gly Ala Ile Ala
65                  70                  75                  80

Gly Phe Ile Glu Asn Gly Trp Glu Gly Leu Ile Asp Gly Trp Tyr Gly
                85                  90                  95

Phe Arg His Gln Asn Ala Gln Gly Glu Gly Thr Ala Ala Asp Tyr Lys
            100                 105                 110

Ser Thr Gln Ser Ala Ile Asp Gln Ile Thr Gly Met Val Asn Arg Val
        115                 120                 125

Ile Ala Leu Met Ala Gln Gly Pro Pro Asp Cys Tyr Leu Ala Glu Leu
130                 135                 140

Leu Val Ala Met Leu Asn Gln His Val Ile Asp Leu Ala Asp Ser Glu
145                 150                 155                 160

Met Asp Lys Leu Tyr Glu Arg Val Lys Arg Gln Leu Arg Glu Asn Ala
                165                 170                 175

Glu Glu Asp Gly Thr Gly Cys Phe Glu Ile Phe His Lys Cys Asp Asp
            180                 185                 190

Asp Cys Met Ala Ser Ile Arg Asn Asn Thr Tyr Asp His Ser Lys Tyr
        195                 200                 205

Arg Glu Glu Ala Met Gln Asn Arg Ile Gln Ile Asp Ser Gly Gly Asp
    210                 215                 220

Ile Ile Lys Leu Leu Asn Glu Gln Val Asn Lys Glu Met Gln Ser Ser
225                 230                 235                 240

Asn Leu Tyr Met Ser Met Ser Ser Trp Cys Tyr Thr His Ser Leu Asp
                245                 250                 255

Gly Ala Gly Leu Phe Leu Phe Asp His Ala Ala Glu Glu Tyr Glu His
            260                 265                 270

```
Ala Lys Lys Leu Ile Ile Phe Leu Asn Glu Asn Asn Val Pro Val Gln
        275                 280                 285

Leu Thr Ser Ile Ser Ala Pro Glu His Lys Phe Glu Gly Leu Thr Gln
    290                 295                 300

Ile Phe Gln Lys Ala Tyr Glu His Glu Gln His Ile Ser Glu Ser Ile
305                 310                 315                 320

Asn Asn Ile Val Asp His Ala Ile Lys Ser Lys Asp His Ala Thr Phe
                325                 330                 335

Asn Phe Leu Gln Trp Tyr Val Ala Glu Gln His Glu Glu Val Leu
            340                 345                 350

Phe Lys Asp Ile Leu Asp Lys Ile Glu Leu Ile Gly Asn Glu Asn His
        355                 360                 365

Gly Leu Tyr Leu Ala Asp Gln Tyr Val Lys Gly Ile Ala Lys Ser Arg
    370                 375                 380

Lys Ser Gly Ser
385
```

<210> SEQ ID NO 101
<211> LENGTH: 276
<212> TYPE: PRT
<213> ORGANISM: Artificial sequence
<220> FEATURE:
<223> OTHER INFORMATION: Synthetic

<400> SEQUENCE: 101

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Leu Val Phe Pro Gly Cys Gly Val Leu Lys Leu Ala Thr Gly Met
        50                  55                  60

Lys Asn Val Pro Glu Ile Pro Lys Gly Arg Gly Leu Phe Gly Ala Ile
65                  70                  75                  80

Ala Gly Phe Ile Glu Asn Gly Trp Glu Gly Leu Ile Asp Gly Trp Tyr
                85                  90                  95

Gly Phe Arg His Gln Asn Ala Gln Gly Glu Gly Thr Ala Ala Asp Tyr
            100                 105                 110

Lys Ser Thr Gln Ser Ala Ile Asp Gln Ile Thr Gly Met Val Asn Arg
        115                 120                 125

Val Ile Ala Leu Met Ala Gln Gly Gly Pro Asp Cys Tyr Leu Ala Glu
    130                 135                 140

Leu Leu Val Ala Met Leu Asn Gln His Val Ile Asp Leu Ala Asp Ser
145                 150                 155                 160

Glu Met Asp Lys Leu Tyr Glu Arg Val Lys Arg Gln Leu Arg Glu Asn
                165                 170                 175

Ala Glu Glu Asp Gly Thr Gly Cys Phe Glu Ile Phe His Lys Cys Asp
            180                 185                 190

Asp Asp Cys Met Ala Ser Ile Arg Asn Asn Thr Tyr Asp His Ser Lys
        195                 200                 205

Tyr Arg Glu Glu Ala Met Gln Asn Arg Ile Gln Ile Asp Gly Gly Pro
    210                 215                 220

Gly Ser Gly Tyr Ile Pro Glu Ala Pro Arg Asp Gly Gln Ala Tyr Val
225                 230                 235                 240
```

Arg Lys Asp Gly Glu Trp Val Leu Leu Ser Thr Phe Leu Gly Ser Gly
                245                 250                 255

Leu Asn Asp Ile Phe Glu Ala Gln Lys Ile Glu Trp His Glu Gly His
            260                 265                 270

His His His His
        275

<210> SEQ ID NO 102
<211> LENGTH: 275
<212> TYPE: PRT
<213> ORGANISM: Artificial sequence
<220> FEATURE:
<223> OTHER INFORMATION: Synthetic

<400> SEQUENCE: 102

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Asn Ala Thr
        35                  40                  45

Glu Leu Val Phe Pro Gly Cys Val Leu Lys Leu Ala Thr Gly Met Lys
    50                  55                  60

Asn Val Pro Glu Ile Pro Lys Gly Arg Gly Leu Phe Gly Ala Ile Ala
65                  70                  75                  80

Gly Phe Ile Glu Asn Gly Trp Glu Gly Leu Ile Asp Gly Trp Tyr Gly
                85                  90                  95

Phe Arg His Gln Asn Ala Gln Gly Glu Gly Thr Ala Ala Asp Tyr Lys
            100                 105                 110

Ser Thr Gln Ser Ala Ile Asp Gln Ile Thr Gly Met Val Asn Arg Val
        115                 120                 125

Ile Ala Leu Met Ala Gln Gly Gly Pro Asp Cys Tyr Leu Ala Glu Leu
    130                 135                 140

Leu Val Ala Met Leu Asn Gln His Val Ile Asp Leu Ala Asp Ser Glu
145                 150                 155                 160

Met Asp Lys Leu Tyr Glu Arg Val Lys Arg Gln Leu Arg Glu Asn Ala
                165                 170                 175

Glu Glu Asp Gly Thr Gly Cys Phe Glu Ile Phe His Lys Cys Asp Asp
            180                 185                 190

Asp Cys Met Ala Ser Ile Arg Asn Asn Thr Tyr Asp His Ser Lys Tyr
        195                 200                 205

Arg Glu Glu Ala Met Gln Asn Arg Ile Gln Ile Asp Gly Gly Pro Gly
    210                 215                 220

Ser Gly Tyr Ile Pro Glu Ala Pro Arg Asp Gly Gln Ala Tyr Val Arg
225                 230                 235                 240

Lys Asp Gly Glu Trp Val Leu Leu Ser Thr Phe Leu Gly Ser Gly Leu
                245                 250                 255

Asn Asp Ile Phe Glu Ala Gln Lys Ile Glu Trp His Glu Gly His His
            260                 265                 270

His His His
        275

<210> SEQ ID NO 103
<211> LENGTH: 388
<212> TYPE: PRT
<213> ORGANISM: Artificial sequence
<220> FEATURE:

<223> OTHER INFORMATION: Synthetic

<400> SEQUENCE: 103

```
Met Tyr Lys Ile Val Ile Ile Ala Leu Leu Gly Ala Val Lys Gly
1               5                   10                  15

Leu Asp Lys Ile Cys Leu Gly His His Ala Val Ala Asn Gly Thr Ile
            20                  25                  30

Val Lys Thr Leu Thr Asn Glu Gln Glu Val Thr Asn Ala Thr Glu
        35                  40                  45

Leu Val Phe Pro Gly Cys Gly Val Leu Met Leu Ala Thr Gly Met Arg
50                  55                  60

Asn Val Pro Glu Leu Ile Gln Gly Arg Gly Leu Phe Gly Ala Ile Ala
65                  70                  75                  80

Gly Phe Leu Glu Asn Gly Trp Glu Gly Met Val Asp Gly Trp Tyr Gly
                85                  90                  95

Phe Arg His Gln Asn Ala Gln Gly Thr Gly Gln Ala Ala Asp Tyr Lys
                100                 105                 110

Ser Thr Gln Ala Ala Ile Asp Gln Ile Thr Gly Met Val Asn Arg Val
                115                 120                 125

Val Ala Leu Met Ala Gln Gly Gly Pro Asp Cys Tyr Leu Ala Glu Leu
        130                 135                 140

Leu Val Ala Met Leu Asn Gln His Val Ile Asp Met Ala Asp Ser Glu
145                 150                 155                 160

Met Arg Asn Leu Tyr Glu Arg Val Arg Lys Gln Leu Arg Gln Asn Ala
                165                 170                 175

Glu Glu Asp Gly Lys Gly Cys Phe Glu Ile Tyr His Ala Cys Asp Asp
                180                 185                 190

Ser Cys Met Glu Ser Ile Arg Asn Asn Thr Tyr Asp His Ser Gln Tyr
        195                 200                 205

Arg Glu Glu Ala Leu Leu Asn Arg Leu Asn Ile Asn Ser Gly Gly Asp
    210                 215                 220

Ile Ile Lys Leu Leu Asn Glu Gln Val Asn Lys Glu Met Gln Ser Ser
225                 230                 235                 240

Asn Leu Tyr Met Ser Met Ser Ser Trp Cys Tyr Thr His Ser Leu Asp
                245                 250                 255

Gly Ala Gly Leu Phe Leu Phe Asp His Ala Ala Glu Glu Tyr Glu His
                260                 265                 270

Ala Lys Lys Leu Ile Ile Phe Leu Asn Glu Asn Asn Val Pro Val Gln
        275                 280                 285

Leu Thr Ser Ile Ser Ala Pro Glu His Lys Phe Glu Gly Leu Thr Gln
        290                 295                 300

Ile Phe Gln Lys Ala Tyr Glu His Glu Gln His Ile Ser Glu Ser Ile
305                 310                 315                 320

Asn Asn Ile Val Asp His Ala Ile Lys Ser Lys Asp His Ala Thr Phe
                325                 330                 335

Asn Phe Leu Gln Trp Tyr Val Ala Glu Gln His Glu Glu Val Leu
                340                 345                 350

Phe Lys Asp Ile Leu Asp Lys Ile Glu Leu Ile Gly Asn Glu Asn His
            355                 360                 365

Gly Leu Tyr Leu Ala Asp Gln Tyr Val Lys Gly Ile Ala Lys Ser Arg
        370                 375                 380

Lys Ser Gly Ser
385
```

<210> SEQ ID NO 104
<211> LENGTH: 387
<212> TYPE: PRT
<213> ORGANISM: Artificial sequence
<220> FEATURE:
<223> OTHER INFORMATION: Synthetic

<400> SEQUENCE: 104

Met Tyr Lys Ile Val Val Ile Ala Leu Leu Gly Ala Val Lys Gly
1               5                   10                  15

Leu Asp Lys Ile Cys Leu Gly His His Ala Val Ala Asn Gly Thr Ile
            20                  25                  30

Val Lys Thr Leu Thr Asn Glu Gln Glu Glu Val Thr Asn Ala Thr Glu
        35                  40                  45

Leu Val Phe Pro Gly Cys Val Leu Met Leu Ala Thr Gly Met Arg Asn
    50                  55                  60

Val Pro Glu Leu Ile Gln Gly Arg Gly Leu Phe Gly Ala Ile Ala Gly
65                  70                  75                  80

Phe Leu Glu Asn Gly Trp Glu Gly Met Val Asp Gly Trp Tyr Gly Phe
                85                  90                  95

Arg His Gln Asn Ala Gln Gly Thr Gly Gln Ala Ala Asp Tyr Lys Ser
            100                 105                 110

Thr Gln Ala Ala Ile Asp Gln Ile Thr Gly Met Val Asn Arg Val Val
        115                 120                 125

Ala Leu Met Ala Gln Gly Gly Pro Asp Cys Tyr Leu Ala Glu Leu Leu
    130                 135                 140

Val Ala Met Leu Asn Gln His Val Ile Asp Met Ala Asp Ser Glu Met
145                 150                 155                 160

Arg Asn Leu Tyr Glu Arg Val Arg Lys Gln Leu Arg Gln Asn Ala Glu
                165                 170                 175

Glu Asp Gly Lys Gly Cys Phe Glu Ile Tyr His Ala Cys Asp Asp Ser
            180                 185                 190

Cys Met Glu Ser Ile Arg Asn Asn Thr Tyr Asp His Ser Gln Tyr Arg
        195                 200                 205

Glu Glu Ala Leu Leu Asn Arg Leu Asn Ile Asn Ser Gly Gly Asp Ile
    210                 215                 220

Ile Lys Leu Leu Asn Glu Gln Val Asn Lys Glu Met Gln Ser Ser Asn
225                 230                 235                 240

Leu Tyr Met Ser Met Ser Ser Trp Cys Tyr Thr His Ser Leu Asp Gly
                245                 250                 255

Ala Gly Leu Phe Leu Phe Asp His Ala Ala Glu Glu Tyr Glu His Ala
            260                 265                 270

Lys Lys Leu Ile Ile Phe Leu Asn Glu Asn Asn Val Pro Val Gln Leu
        275                 280                 285

Thr Ser Ile Ser Ala Pro Glu His Lys Phe Glu Gly Leu Thr Gln Ile
    290                 295                 300

Phe Gln Lys Ala Tyr Glu His Glu Gln His Ile Ser Glu Ser Ile Asn
305                 310                 315                 320

Asn Ile Val Asp His Ala Ile Lys Ser Lys Asp His Ala Thr Phe Asn
                325                 330                 335

Phe Leu Gln Trp Tyr Val Ala Glu Gln His Glu Glu Val Leu Phe
            340                 345                 350

Lys Asp Ile Leu Asp Lys Ile Glu Leu Ile Gly Asn Glu Asn His Gly
        355                 360                 365

-continued

Leu Tyr Leu Ala Asp Gln Tyr Val Lys Gly Ile Ala Lys Ser Arg Lys
370                 375                 380

Ser Gly Ser
385

<210> SEQ ID NO 105
<211> LENGTH: 387
<212> TYPE: PRT
<213> ORGANISM: Artificial sequence
<220> FEATURE:
<223> OTHER INFORMATION: Synthetic

<400> SEQUENCE: 105

Met Tyr Lys Ile Val Val Ile Ile Ala Leu Leu Gly Ala Val Lys Gly
1               5                   10                  15

Leu Asp Lys Ile Cys Leu Gly His His Ala Val Ala Asn Gly Thr Ile
                20                  25                  30

Val Lys Thr Leu Thr Asn Glu Gln Glu Glu Val Thr Asn Ala Thr Glu
            35                  40                  45

Leu Val Phe Pro Cys Gly Val Leu Met Leu Ala Thr Gly Met Arg Asn
        50                  55                  60

Val Pro Glu Leu Ile Gln Gly Arg Gly Leu Phe Gly Ala Ile Ala Gly
65                  70                  75                  80

Phe Leu Glu Asn Gly Trp Glu Gly Met Val Asp Gly Trp Tyr Gly Phe
                85                  90                  95

Arg His Gln Asn Ala Gln Gly Thr Gly Gln Ala Ala Asp Tyr Lys Ser
                100                 105                 110

Thr Gln Ala Ala Ile Asp Gln Ile Thr Gly Met Val Asn Arg Val Val
            115                 120                 125

Ala Leu Met Ala Gln Gly Gly Pro Asp Cys Tyr Leu Ala Glu Leu Leu
        130                 135                 140

Val Ala Met Leu Asn Gln His Val Ile Asp Met Ala Asp Ser Glu Met
145                 150                 155                 160

Arg Asn Leu Tyr Glu Arg Val Arg Lys Gln Leu Arg Gln Asn Ala Glu
                165                 170                 175

Glu Asp Gly Lys Gly Cys Phe Glu Ile Tyr His Ala Cys Asp Asp Ser
                180                 185                 190

Cys Met Glu Ser Ile Arg Asn Asn Thr Tyr Asp His Ser Gln Tyr Arg
            195                 200                 205

Glu Glu Ala Leu Leu Asn Arg Leu Asn Ile Asn Ser Gly Gly Asp Ile
        210                 215                 220

Ile Lys Leu Leu Asn Glu Gln Val Asn Lys Glu Met Gln Ser Ser Asn
225                 230                 235                 240

Leu Tyr Met Ser Met Ser Ser Trp Cys Tyr Thr His Ser Leu Asp Gly
                245                 250                 255

Ala Gly Leu Phe Leu Phe Asp His Ala Ala Glu Glu Tyr Glu His Ala
                260                 265                 270

Lys Lys Leu Ile Ile Phe Leu Asn Glu Asn Val Pro Val Gln Leu
            275                 280                 285

Thr Ser Ile Ser Ala Pro Glu His Lys Phe Glu Gly Leu Thr Gln Ile
        290                 295                 300

Phe Gln Lys Ala Tyr Glu His Glu Gln His Ile Ser Glu Ser Ile Asn
305                 310                 315                 320

Asn Ile Val Asp His Ala Ile Lys Ser Lys Asp His Ala Thr Phe Asn
                325                 330                 335

-continued

```
Phe Leu Gln Trp Tyr Val Ala Glu Gln His Glu Glu Val Leu Phe
            340                 345                 350

Lys Asp Ile Leu Asp Lys Ile Glu Leu Ile Gly Asn Glu Asn His Gly
        355                 360                 365

Leu Tyr Leu Ala Asp Gln Tyr Val Lys Gly Ile Ala Lys Ser Arg Lys
370                 375                 380

Ser Gly Ser
385

<210> SEQ ID NO 106
<211> LENGTH: 388
<212> TYPE: PRT
<213> ORGANISM: Artificial sequence
<220> FEATURE:
<223> OTHER INFORMATION: Synthetic

<400> SEQUENCE: 106

Met Tyr Lys Ile Val Val Ile Ala Leu Leu Gly Ala Val Lys Gly
1               5                   10                  15

Leu Asp Lys Ile Cys Leu Gly His His Ala Val Ala Asn Gly Thr Ile
            20                  25                  30

Val Lys Thr Leu Thr Asn Glu Gln Glu Glu Val Thr Asn Ala Thr Glu
        35                  40                  45

Leu Val Phe Pro Gly Cys Gly Val Leu Met Leu Ala Thr Gly Met Arg
    50                  55                  60

Asn Val Pro Glu Leu Ile Gln Gly Arg Gly Leu Phe Gly Ala Ile Ala
65                  70                  75                  80

Gly Phe Leu Glu Asn Gly Trp Glu Gly Met Val Asp Gly Trp Tyr Gly
                85                  90                  95

Phe Arg His Gln Asn Ala Gln Gly Thr Gly Gln Ala Ala Asp Tyr Lys
            100                 105                 110

Ser Thr Gln Ala Ala Ile Asp Gln Ile Thr Gly Met Val Asn Arg Val
        115                 120                 125

Val Glu Leu Met Glu Gln Gly Gly Pro Asp Cys Tyr Leu Ala Glu Leu
    130                 135                 140

Leu Val Ala Met Leu Asn Gln His Val Ile Asp Met Ala Asp Ser Glu
145                 150                 155                 160

Met Arg Asn Leu Tyr Glu Arg Val Arg Lys Gln Leu Arg Gln Asn Ala
                165                 170                 175

Glu Glu Asp Gly Lys Gly Cys Phe Glu Ile Tyr His Ala Cys Asp Asp
            180                 185                 190

Ser Cys Met Glu Ser Ile Arg Asn Asn Thr Tyr Asp His Ser Gln Tyr
        195                 200                 205

Arg Glu Glu Ala Leu Leu Asn Arg Leu Asn Ile Asn Ser Gly Gly Asp
    210                 215                 220

Ile Ile Lys Leu Leu Asn Glu Gln Val Asn Lys Glu Met Gln Ser Ser
225                 230                 235                 240

Asn Leu Tyr Met Ser Met Ser Ser Trp Cys Tyr Thr His Ser Leu Asp
                245                 250                 255

Gly Ala Gly Leu Phe Leu Phe Asp His Ala Ala Glu Glu Tyr Glu His
            260                 265                 270

Ala Lys Lys Leu Ile Ile Phe Leu Asn Glu Asn Asn Val Pro Val Gln
        275                 280                 285

Leu Thr Ser Ile Ser Ala Pro Glu His Lys Phe Glu Gly Leu Thr Gln
    290                 295                 300
```

Ile Phe Gln Lys Ala Tyr Glu His Glu Gln His Ile Ser Glu Ser Ile
305                 310                 315                 320

Asn Asn Ile Val Asp His Ala Ile Lys Ser Lys Asp His Ala Thr Phe
                325                 330                 335

Asn Phe Leu Gln Trp Tyr Val Ala Glu Gln His Glu Glu Val Leu
                340                 345                 350

Phe Lys Asp Ile Leu Asp Lys Ile Glu Leu Ile Gly Asn Glu Asn His
                355                 360                 365

Gly Leu Tyr Leu Ala Asp Gln Tyr Val Lys Gly Ile Ala Lys Ser Arg
370                 375                 380

Lys Ser Gly Ser
385

<210> SEQ ID NO 107
<211> LENGTH: 388
<212> TYPE: PRT
<213> ORGANISM: Artificial sequence
<220> FEATURE:
<223> OTHER INFORMATION: Synthetic

<400> SEQUENCE: 107

Met Tyr Lys Ile Val Val Ile Ile Ala Leu Leu Gly Ala Val Lys Gly
1               5                   10                  15

Leu Asp Lys Ile Cys Leu Gly His His Ala Val Ala Asn Gly Thr Ile
                20                  25                  30

Val Lys Thr Leu Thr Asn Glu Gln Glu Glu Val Thr Asn Ala Thr Glu
                35                  40                  45

Leu Val Phe Pro Gly Cys Gly Val Leu Met Leu Ala Thr Gly Met Arg
50                  55                  60

Asn Val Pro Glu Leu Ile Gln Gly Arg Gly Leu Phe Gly Ala Ile Ala
65                  70                  75                  80

Gly Phe Leu Glu Asn Gly Trp Glu Gly Met Val Asp Gly Trp Tyr Gly
                85                  90                  95

Phe Arg His Gln Asn Ala Gln Gly Thr Gly Gln Ala Ala Asp Tyr Lys
                100                 105                 110

Ser Thr Gln Ala Ala Ile Asp Gln Ile Thr Gly Met Val Asn Arg Val
                115                 120                 125

Val Ala Leu Met Ala Gln Gly Pro Pro Asp Cys Tyr Leu Ala Glu Leu
130                 135                 140

Leu Val Ala Met Leu Asn Gln His Val Ile Asp Met Ala Asp Ser Glu
145                 150                 155                 160

Met Arg Asn Leu Tyr Glu Arg Val Arg Lys Gln Leu Arg Gln Asn Ala
                165                 170                 175

Glu Glu Asp Gly Lys Gly Cys Phe Glu Ile Tyr His Ala Cys Asp Asp
                180                 185                 190

Ser Cys Met Glu Ser Ile Arg Asn Asn Thr Tyr Asp His Ser Gln Tyr
                195                 200                 205

Arg Glu Glu Ala Leu Leu Asn Arg Leu Asn Ile Asn Ser Gly Gly Asp
                210                 215                 220

Ile Ile Lys Leu Leu Asn Glu Gln Val Asn Lys Glu Met Gln Ser Ser
225                 230                 235                 240

Asn Leu Tyr Met Ser Met Ser Ser Trp Cys Tyr Thr His Ser Leu Asp
                245                 250                 255

Gly Ala Gly Leu Phe Leu Phe Asp His Ala Ala Glu Glu Tyr Glu His
                260                 265                 270

-continued

```
Ala Lys Lys Leu Ile Ile Phe Leu Asn Glu Asn Asn Val Pro Val Gln
            275                 280                 285

Leu Thr Ser Ile Ser Ala Pro Glu His Lys Phe Glu Gly Leu Thr Gln
        290                 295                 300

Ile Phe Gln Lys Ala Tyr Glu His Glu Gln His Ile Ser Glu Ser Ile
305                 310                 315                 320

Asn Asn Ile Val Asp His Ala Ile Lys Ser Lys Asp His Ala Thr Phe
                325                 330                 335

Asn Phe Leu Gln Trp Tyr Val Ala Glu Gln His Glu Glu Val Leu
            340                 345                 350

Phe Lys Asp Ile Leu Asp Lys Ile Glu Leu Ile Gly Asn Glu Asn His
            355                 360                 365

Gly Leu Tyr Leu Ala Asp Gln Tyr Val Lys Gly Ile Ala Lys Ser Arg
370                 375                 380

Lys Ser Gly Ser
385

<210> SEQ ID NO 108
<211> LENGTH: 387
<212> TYPE: PRT
<213> ORGANISM: Artificial sequence
<220> FEATURE:
<223> OTHER INFORMATION: Synthetic

<400> SEQUENCE: 108

Met Tyr Lys Ile Val Ile Ile Ala Leu Leu Gly Ala Val Lys Gly
1               5                   10                  15

Leu Asp Lys Ile Cys Leu Gly His His Ala Val Ala Asn Gly Thr Ile
            20                  25                  30

Val Lys Thr Leu Thr Asn Glu Gln Glu Glu Val Thr Asn Ala Thr Glu
        35                  40                  45

Leu Cys Phe Asn Gly Ile Cys Leu Met Leu Ala Thr Gly Met Arg Asn
    50                  55                  60

Val Pro Glu Leu Ile Gln Gly Arg Gly Leu Phe Gly Ala Ile Ala Gly
65                  70                  75                  80

Phe Leu Glu Asn Gly Trp Glu Gly Met Val Asp Gly Trp Tyr Gly Phe
                85                  90                  95

Arg His Gln Asn Ala Gln Gly Thr Gly Gln Ala Ala Asp Tyr Lys Ser
            100                 105                 110

Thr Gln Ala Ala Ile Asp Gln Ile Thr Gly Met Val Asn Arg Val Val
        115                 120                 125

Ala Leu Met Ala Gln Gly Gly Pro Asp Cys Tyr Leu Ala Glu Leu Leu
    130                 135                 140

Val Ala Met Leu Asn Gln His Val Ile Asp Met Ala Asp Ser Glu Met
145                 150                 155                 160

Arg Asn Leu Tyr Glu Arg Val Arg Lys Gln Leu Arg Gln Asn Ala Glu
                165                 170                 175

Glu Asp Gly Lys Gly Cys Phe Glu Ile Tyr His Ala Cys Asp Asp Ser
            180                 185                 190

Cys Met Glu Ser Ile Arg Asn Asn Thr Tyr Asp His Ser Gln Tyr Arg
        195                 200                 205

Glu Glu Ala Leu Leu Asn Arg Leu Asn Ile Asn Ser Gly Gly Asp Ile
    210                 215                 220

Ile Lys Leu Leu Asn Glu Gln Val Asn Lys Glu Met Gln Ser Ser Asn
225                 230                 235                 240
```

```
Leu Tyr Met Ser Met Ser Ser Trp Cys Tyr Thr His Ser Leu Asp Gly
                245                 250                 255

Ala Gly Leu Phe Leu Phe Asp His Ala Ala Glu Glu Tyr Glu His Ala
            260                 265                 270

Lys Lys Leu Ile Ile Phe Leu Asn Glu Asn Asn Val Pro Val Gln Leu
            275                 280                 285

Thr Ser Ile Ser Ala Pro Glu His Lys Phe Glu Gly Leu Thr Gln Ile
    290                 295                 300

Phe Gln Lys Ala Tyr Glu His Glu Gln His Ile Ser Glu Ser Ile Asn
305                 310                 315                 320

Asn Ile Val Asp His Ala Ile Lys Ser Lys Asp His Ala Thr Phe Asn
                325                 330                 335

Phe Leu Gln Trp Tyr Val Ala Glu Gln His Glu Glu Glu Val Leu Phe
            340                 345                 350

Lys Asp Ile Leu Asp Lys Ile Glu Leu Ile Gly Asn Glu Asn His Gly
            355                 360                 365

Leu Tyr Leu Ala Asp Gln Tyr Val Lys Gly Ile Ala Lys Ser Arg Lys
    370                 375                 380

Ser Gly Ser
385

<210> SEQ ID NO 109
<211> LENGTH: 275
<212> TYPE: PRT
<213> ORGANISM: Artificial sequence
<220> FEATURE:
<223> OTHER INFORMATION: Synthetic

<400> SEQUENCE: 109

Met Lys Thr Ile Ile Ala Leu Ser Tyr Ile Phe Cys Leu Ala Leu Ala
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
            35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Leu Phe Gly Ala Ile Ala Gly Phe Ile Glu Asn Gly Trp Glu
                85                  90                  95

Gly Met Ile Asp Gly Trp Tyr Gly Phe Arg His Gln Asn Ser Glu Gly
            100                 105                 110

Thr Gly Gln Ala Ala Asp Leu Lys Ser Thr Gln Ala Ala Ile Asp Gln
            115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Lys Thr
                165                 170                 175

Arg Arg Gln Leu Arg Glu Asn Ala Glu Asp Met Gly Asn Gly Cys Phe
            180                 185                 190

Lys Ile Tyr His Lys Cys Asp Asn Ala Cys Ile Glu Ser Ile Arg Asn
            195                 200                 205
```

Gly Thr Tyr Asp His Asp Val Tyr Arg Asp Glu Ala Leu Asn Asn Arg
    210                 215                 220

Phe Gln Ile Lys Gly Val Glu Leu Lys Ser Gly Tyr Lys Asp Trp Ile
225                 230                 235                 240

Leu Trp Ile Ser Phe Ala Ile Ser Cys Phe Leu Leu Cys Val Val Leu
                245                 250                 255

Leu Gly Phe Ile Met Trp Ala Cys Gln Arg Gly Asn Ile Arg Cys Asn
            260                 265                 270

Ile Cys Ile
        275

<210> SEQ ID NO 110
<211> LENGTH: 275
<212> TYPE: PRT
<213> ORGANISM: Artificial sequence
<220> FEATURE:
<223> OTHER INFORMATION: Synthetic

<400> SEQUENCE: 110

Met Lys Thr Ile Ile Ala Leu Ser Tyr Ile Phe Cys Leu Val Phe Ala
1               5                   10                  15

Gln Asn Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Thr Gly Gln Ala Ala Asp Leu Lys Ser Thr Gln Ala Ala Ile Asp Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Lys Thr
                165                 170                 175

Arg Arg Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Gly Val Glu Leu Lys Ser Gly Tyr Lys Asp Trp Ile
225                 230                 235                 240

Leu Trp Ile Ser Phe Ala Ile Ser Cys Phe Leu Leu Cys Val Val Leu
                245                 250                 255

Leu Gly Phe Ile Met Trp Ala Cys Gln Lys Gly Asn Ile Arg Cys Asn
            260                 265                 270

Ile Cys Ile
        275

-continued

```
<210> SEQ ID NO 111
<211> LENGTH: 275
<212> TYPE: PRT
<213> ORGANISM: Artificial sequence
<220> FEATURE:
<223> OTHER INFORMATION: Synthetic

<400> SEQUENCE: 111

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Thr Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Glu Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Gly Val Glu Leu Lys Ser Gly Tyr Lys Asp Trp Ile
225                 230                 235                 240

Leu Trp Ile Ser Phe Ala Ile Ser Cys Phe Leu Cys Val Ala Leu
                245                 250                 255

Leu Gly Phe Ile Met Trp Ala Cys Gln Lys Gly Asn Ile Arg Cys Asn
            260                 265                 270

Ile Cys Ile
        275

<210> SEQ ID NO 112
<211> LENGTH: 275
<212> TYPE: PRT
<213> ORGANISM: Artificial sequence
<220> FEATURE:
<223> OTHER INFORMATION: Synthetic

<400> SEQUENCE: 112

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30
```

His His Ala Val Pro Asn Gly Thr Ile Val Lys Thr Ile Thr Asn Asp
        35                  40                  45

Arg Ile Glu Val Thr Asn Ala Thr Glu Leu Val Phe Pro Gly Cys Gly
 50                  55                  60

Val Leu Lys Leu Ala Thr Gly Met Arg Asn Val Pro Glu Arg Gln Thr
 65                  70                  75                  80

Arg Gly Ile Phe Gly Ala Ile Ala Gly Phe Ile Glu Asn Gly Trp Glu
                 85                  90                  95

Gly Met Val Asp Gly Trp Tyr Gly Phe Arg His Gln Asn Ser Glu Gly
                100                 105                 110

Arg Gly Gln Ala Ala Asp Leu Lys Ser Thr Gln Ala Ala Ile Asp Gln
            115                 120                 125

Ile Asn Gly Met Val Asn Arg Val Ile Ala Leu Met Ala Gln Gly Gly
130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Lys Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
210                 215                 220

Phe Gln Ile Lys Gly Val Glu Leu Lys Ser Gly Tyr Lys Asp Trp Ile
225                 230                 235                 240

Leu Trp Ile Ser Phe Ala Ile Ser Cys Phe Leu Leu Cys Val Ala Leu
                245                 250                 255

Leu Gly Phe Ile Met Trp Ala Cys Gln Lys Gly Asn Ile Arg Cys Asn
            260                 265                 270

Ile Cys Ile
        275

<210> SEQ ID NO 113
<211> LENGTH: 275
<212> TYPE: PRT
<213> ORGANISM: Artificial sequence
<220> FEATURE:
<223> OTHER INFORMATION: Synthetic

<400> SEQUENCE: 113

Met Lys Thr Ile Ile Ala Leu Ser Tyr Ile Leu Cys Leu Val Phe Ala
 1               5                  10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
 50                  55                  60

Val Leu Lys Leu Ala Thr Gly Met Arg Asn Val Pro Glu Lys Gln Thr
 65                  70                  75                  80

Arg Gly Ile Phe Gly Ala Ile Ala Gly Phe Ile Glu Asn Gly Trp Glu
                 85                  90                  95

Gly Met Val Asp Gly Trp Tyr Gly Phe Arg His Gln Asn Ser Glu Gly
                100                 105                 110

```
Ile Gly Gln Ala Ala Asp Leu Lys Ser Thr Gln Ala Ala Ile Asn Gln
            115                 120                 125

Ile Asn Gly Met Val Asn Arg Val Ile Glu Leu Met Glu Gln Gly Gly
        130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
                180                 185                 190

Lys Ile Tyr His Lys Cys Asp Asn Ala Cys Ile Gly Ser Ile Arg Asn
                195                 200                 205

Gly Thr Tyr Asp His Asp Val Tyr Arg Asp Glu Ala Leu Asn Asn Arg
        210                 215                 220

Phe Gln Ile Lys Gly Val Glu Leu Lys Ser Gly Tyr Lys Asp Trp Ile
225                 230                 235                 240

Leu Trp Ile Ser Phe Ala Ile Ser Cys Phe Leu Leu Cys Val Ala Leu
                245                 250                 255

Leu Gly Phe Ile Met Trp Ala Cys Gln Lys Gly Asn Ile Arg Cys Asn
                260                 265                 270

Ile Cys Ile
        275

<210> SEQ ID NO 114
<211> LENGTH: 274
<212> TYPE: PRT
<213> ORGANISM: Artificial sequence
<220> FEATURE:
<223> OTHER INFORMATION: Synthetic

<400> SEQUENCE: 114

Met Lys Thr Ile Ile Ala Leu Ser Tyr Ile Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Gly Cys Val
        50                  55                  60

Leu Lys Leu Ala Thr Gly Met Arg Asn Val Pro Glu Lys Gln Thr Arg
65                  70                  75                  80

Gly Ile Phe Gly Ala Ile Ala Gly Phe Ile Glu Asn Gly Trp Glu Gly
                85                  90                  95

Met Val Asp Gly Trp Tyr Gly Phe Arg His Gln Asn Ser Glu Gly Ile
                100                 105                 110

Gly Gln Ala Ala Asp Leu Lys Ser Thr Gln Ala Ala Ile Asn Gln Ile
            115                 120                 125

Asn Gly Met Val Asn Arg Val Ile Ala Leu Met Ala Gln Gly Gly Pro
        130                 135                 140

Asp Cys Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Arg Thr Lys
                165                 170                 175

Lys Gln Leu Arg Glu Asn Ala Glu Asp Met Gly Asn Gly Cys Phe Lys
                180                 185                 190
```

Ile Tyr His Lys Cys Asp Asn Ala Cys Ile Gly Ser Ile Arg Asn Gly
            195                 200                 205

Thr Tyr Asp His Asp Val Tyr Arg Asp Glu Ala Leu Asn Asn Arg Phe
210                 215                 220

Gln Ile Lys Gly Val Glu Leu Lys Ser Gly Tyr Lys Asp Trp Ile Leu
225                 230                 235                 240

Trp Ile Ser Phe Ala Ile Ser Cys Phe Leu Leu Cys Val Ala Leu Leu
            245                 250                 255

Gly Phe Ile Met Trp Ala Cys Gln Lys Gly Asn Ile Arg Cys Asn Ile
            260                 265                 270

Cys Ile

<210> SEQ ID NO 115
<211> LENGTH: 274
<212> TYPE: PRT
<213> ORGANISM: Artificial sequence
<220> FEATURE:
<223> OTHER INFORMATION: Synthetic

<400> SEQUENCE: 115

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Cys Gly Val
50                  55                  60

Leu Lys Leu Ala Thr Gly Met Arg Asn Val Pro Glu Lys Gln Thr Arg
65                  70                  75                  80

Gly Ile Phe Gly Ala Ile Ala Gly Phe Ile Glu Asn Gly Trp Glu Gly
            85                  90                  95

Met Val Asp Gly Trp Tyr Gly Phe Arg His Gln Asn Ser Glu Gly Ile
            100                 105                 110

Gly Gln Ala Ala Asp Leu Lys Ser Thr Gln Ala Ala Ile Asn Gln Ile
            115                 120                 125

Asn Gly Met Val Asn Arg Val Ile Ala Leu Met Ala Gln Gly Gly Pro
130                 135                 140

Asp Cys Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Arg Thr Lys
            165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
            195                 200                 205

Thr Tyr Asp His Asp Val Tyr Arg Asp Glu Ala Leu Asn Asn Arg Phe
210                 215                 220

Gln Ile Lys Gly Val Glu Leu Lys Ser Gly Tyr Lys Asp Trp Ile Leu
225                 230                 235                 240

Trp Ile Ser Phe Ala Ile Ser Cys Phe Leu Leu Cys Val Ala Leu Leu
            245                 250                 255

Gly Phe Ile Met Trp Ala Cys Gln Lys Gly Asn Ile Arg Cys Asn Ile
            260                 265                 270

Cys Ile

<210> SEQ ID NO 116
<211> LENGTH: 274
<212> TYPE: PRT
<213> ORGANISM: Artificial sequence
<220> FEATURE:
<223> OTHER INFORMATION: Synthetic

<400> SEQUENCE: 116

Met Lys Thr Ile Ile Ala Leu Ser Tyr Ile Phe Cys Leu Ala Leu Ala
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Phe Pro Gly Cys Val
    50                  55                  60

Leu Lys Leu Ala Thr Gly Met Arg Asn Val Pro Glu Lys Gln Thr Arg
65                  70                  75                  80

Gly Leu Phe Gly Ala Ile Ala Gly Phe Ile Glu Asn Gly Trp Glu Gly
                85                  90                  95

Met Ile Asp Gly Trp Tyr Gly Phe Arg His Gln Asn Ser Glu Gly Thr
            100                 105                 110

Gly Gln Ala Ala Asp Leu Lys Ser Thr Gln Ala Ala Ile Asp Gln Ile
        115                 120                 125

Asn Gly Met Val Asn Arg Val Ile Ala Leu Met Ala Gln Gly Gly Pro
    130                 135                 140

Asp Cys Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Lys Thr Arg
                165                 170                 175

Arg Gln Leu Arg Glu Asn Ala Glu Asp Met Gly Asn Gly Cys Phe Lys
            180                 185                 190

Ile Tyr His Lys Cys Asp Asn Ala Cys Ile Glu Ser Ile Arg Asn Gly
        195                 200                 205

Thr Tyr Asp His Asp Val Tyr Arg Asp Glu Ala Leu Asn Asn Arg Phe
    210                 215                 220

Gln Ile Lys Gly Val Glu Leu Lys Ser Gly Tyr Lys Asp Trp Ile Leu
225                 230                 235                 240

Trp Ile Ser Phe Ala Ile Ser Cys Phe Leu Leu Cys Val Val Leu Leu
                245                 250                 255

Gly Phe Ile Met Trp Ala Cys Gln Arg Gly Asn Ile Arg Cys Asn Ile
            260                 265                 270

Cys Ile

<210> SEQ ID NO 117
<211> LENGTH: 274
<212> TYPE: PRT
<213> ORGANISM: Artificial sequence
<220> FEATURE:
<223> OTHER INFORMATION: Synthetic

<400> SEQUENCE: 117

Met Lys Thr Ile Ile Ala Leu Ser Tyr Ile Phe Cys Leu Val Phe Ala
1               5                   10                  15

Gln Asn Leu Pro Gly Asn Asp Asn Ser Thr Ala Thr Leu Cys Leu Gly

```
                20                  25                  30
His His Ala Val Pro Asn Gly Thr Leu Val Lys Thr Ile Thr Asn Asp
            35                  40                  45

Gln Ile Glu Val Thr Asn Ala Thr Glu Leu Val Phe Pro Gly Cys Val
        50                  55                  60

Leu Lys Leu Ala Thr Gly Met Arg Asn Val Pro Glu Lys Gln Thr Arg
65                  70                  75                  80

Gly Ile Phe Gly Ala Ile Ala Gly Phe Ile Glu Asn Gly Trp Glu Gly
                85                  90                  95

Met Val Asp Gly Trp Tyr Gly Phe Arg His Gln Asn Ser Glu Gly Thr
            100                 105                 110

Gly Gln Ala Ala Asp Leu Lys Ser Thr Gln Ala Ala Ile Asp Gln Ile
        115                 120                 125

Asn Gly Met Val Asn Arg Val Ile Ala Leu Met Ala Gln Gly Gly Pro
    130                 135                 140

Asp Cys Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Lys Thr Arg
                165                 170                 175

Arg Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
        195                 200                 205

Thr Tyr Asp His Asp Val Tyr Arg Asp Glu Ala Leu Asn Asn Arg Phe
    210                 215                 220

Gln Ile Lys Gly Val Glu Leu Lys Ser Gly Tyr Lys Asp Trp Ile Leu
225                 230                 235                 240

Trp Ile Ser Phe Ala Ile Ser Cys Phe Leu Leu Cys Val Val Leu Leu
                245                 250                 255

Gly Phe Ile Met Trp Ala Cys Gln Lys Gly Asn Ile Arg Cys Asn Ile
            260                 265                 270

Cys Ile

<210> SEQ ID NO 118
<211> LENGTH: 274
<212> TYPE: PRT
<213> ORGANISM: Artificial sequence
<220> FEATURE:
<223> OTHER INFORMATION: Synthetic

<400> SEQUENCE: 118

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Val
    50                  55                  60

Leu Lys Leu Ala Thr Gly Met Arg Asn Val Pro Glu Lys Gln Thr Arg
65                  70                  75                  80

Gly Ile Phe Gly Ala Ile Ala Gly Phe Ile Glu Asn Gly Trp Glu Gly
                85                  90                  95

Met Val Asp Gly Trp Tyr Gly Phe Arg His Gln Asn Ser Glu Gly Thr
            100                 105                 110
```

Gly Gln Ala Ala Asp Leu Lys Ser Thr Gln Ala Ala Ile Asn Gln Ile
            115                 120                 125

Asn Gly Met Val Asn Arg Val Ile Ala Leu Met Ala Gln Gly Gly Pro
    130                 135                 140

Asp Cys Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Arg Thr Lys
                165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Glu Ser Ile Arg Asn Gly
        195                 200                 205

Thr Tyr Asp His Asp Val Tyr Arg Asp Glu Ala Leu Asn Asn Arg Phe
    210                 215                 220

Gln Ile Lys Gly Val Glu Leu Lys Ser Gly Tyr Lys Asp Trp Ile Leu
225                 230                 235                 240

Trp Ile Ser Phe Ala Ile Ser Cys Phe Leu Leu Cys Val Ala Leu Leu
                245                 250                 255

Gly Phe Ile Met Trp Ala Cys Gln Lys Gly Asn Ile Arg Cys Asn Ile
            260                 265                 270

Cys Ile

<210> SEQ ID NO 119
<211> LENGTH: 274
<212> TYPE: PRT
<213> ORGANISM: Artificial sequence
<220> FEATURE:
<223> OTHER INFORMATION: Synthetic

<400> SEQUENCE: 119

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Phe Pro Gly Cys Val
    50                  55                  60

Leu Lys Leu Ala Thr Gly Met Arg Asn Val Pro Glu Arg Gln Thr Arg
65                  70                  75                  80

Gly Ile Phe Gly Ala Ile Ala Gly Phe Ile Glu Asn Gly Trp Glu Gly
                85                  90                  95

Met Val Asp Gly Trp Tyr Gly Phe Arg His Gln Asn Ser Glu Gly Arg
            100                 105                 110

Gly Gln Ala Ala Asp Leu Lys Ser Thr Gln Ala Ala Ile Asp Gln Ile
            115                 120                 125

Asn Gly Met Val Asn Arg Val Ile Ala Leu Met Ala Gln Gly Gly Pro
    130                 135                 140

Asp Cys Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Lys Thr Lys
                165                 170                 175

Lys Gln Leu Arg Glu Asn Ala Glu Asp Met Gly Asn Gly Cys Phe Lys
            180                 185                 190

```
Ile Tyr His Lys Cys Asp Asn Ala Cys Ile Gly Ser Ile Arg Asn Gly
            195                 200                 205

Thr Tyr Asp His Asp Val Tyr Arg Asp Glu Ala Leu Asn Asn Arg Phe
    210                 215                 220

Gln Ile Lys Gly Val Glu Leu Lys Ser Gly Tyr Lys Asp Trp Ile Leu
225                 230                 235                 240

Trp Ile Ser Phe Ala Ile Ser Cys Phe Leu Leu Cys Val Ala Leu Leu
                245                 250                 255

Gly Phe Ile Met Trp Ala Cys Gln Lys Gly Asn Ile Arg Cys Asn Ile
                260                 265                 270

Cys Ile

<210> SEQ ID NO 120
<211> LENGTH: 268
<212> TYPE: PRT
<213> ORGANISM: Artificial sequence
<220> FEATURE:
<223> OTHER INFORMATION: Synthetic

<400> SEQUENCE: 120

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
                35                  40                  45

Glu Leu Val Phe Pro Gly Cys Gly Val Leu Lys Leu Ala Thr Gly Met
    50                  55                  60

Lys Asn Val Pro Glu Ile Pro Lys Gly Arg Gly Leu Phe Gly Ala Ile
65                  70                  75                  80

Ala Gly Phe Ile Glu Asn Gly Trp Glu Gly Leu Ile Asp Gly Trp Tyr
                85                  90                  95

Gly Phe Arg His Gln Asn Ala Gln Gly Glu Gly Thr Ala Ala Asp Tyr
                100                 105                 110

Lys Ser Thr Gln Ser Ala Ile Asp Gln Ile Thr Gly Met Val Asn Arg
                115                 120                 125

Val Ile Ala Leu Met Ala Gln Gly Gly Pro Asp Cys Tyr Leu Ala Glu
    130                 135                 140

Leu Leu Val Ala Met Leu Asn Gln His Val Ile Asp Leu Ala Asp Ser
145                 150                 155                 160

Glu Met Asp Lys Leu Tyr Glu Arg Val Lys Arg Gln Leu Arg Glu Asn
                165                 170                 175

Ala Glu Glu Asp Gly Thr Gly Cys Phe Glu Ile Phe His Lys Cys Asp
                180                 185                 190

Asp Asp Cys Met Ala Ser Ile Arg Asn Asn Thr Tyr Asp His Ser Lys
    195                 200                 205

Tyr Arg Glu Glu Ala Met Gln Asn Arg Ile Gln Ile Asp Pro Val Lys
    210                 215                 220

Leu Ser Ser Gly Tyr Lys Asp Val Ile Leu Trp Phe Ser Phe Gly Ala
225                 230                 235                 240

Ser Cys Phe Ile Leu Leu Ala Ile Val Met Gly Leu Val Phe Ile Cys
                245                 250                 255

Val Lys Asn Gly Asn Met Arg Cys Thr Ile Cys Ile
                260                 265
```

```
<210> SEQ ID NO 121
<211> LENGTH: 267
<212> TYPE: PRT
<213> ORGANISM: Artificial sequence
<220> FEATURE:
<223> OTHER INFORMATION: Synthetic

<400> SEQUENCE: 121
```

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Leu Val Phe Pro Gly Cys Val Leu Lys Leu Ala Thr Gly Met Lys
    50                  55                  60

Asn Val Pro Glu Ile Pro Lys Gly Arg Gly Leu Phe Gly Ala Ile Ala
65                  70                  75                  80

Gly Phe Ile Glu Asn Gly Trp Glu Gly Leu Ile Asp Gly Trp Tyr Gly
                85                  90                  95

Phe Arg His Gln Asn Ala Gln Gly Glu Gly Thr Ala Ala Asp Tyr Lys
            100                 105                 110

Ser Thr Gln Ser Ala Ile Asp Gln Ile Thr Gly Met Val Asn Arg Val
        115                 120                 125

Ile Ala Leu Met Ala Gln Gly Gly Pro Asp Cys Tyr Leu Ala Glu Leu
    130                 135                 140

Leu Val Ala Met Leu Asn Gln His Val Ile Asp Leu Ala Asp Ser Glu
145                 150                 155                 160

Met Asp Lys Leu Tyr Glu Arg Val Lys Arg Gln Leu Arg Glu Asn Ala
                165                 170                 175

Glu Glu Asp Gly Thr Gly Cys Phe Glu Ile Phe His Lys Cys Asp Asp
            180                 185                 190

Asp Cys Met Ala Ser Ile Arg Asn Asn Thr Tyr Asp His Ser Lys Tyr
        195                 200                 205

Arg Glu Glu Ala Met Gln Asn Arg Ile Gln Ile Asp Pro Val Lys Leu
    210                 215                 220

Ser Ser Gly Tyr Lys Asp Val Ile Leu Trp Phe Ser Phe Gly Ala Ser
225                 230                 235                 240

Cys Phe Ile Leu Leu Ala Ile Val Met Gly Leu Val Phe Ile Cys Val
                245                 250                 255

Lys Asn Gly Asn Met Arg Cys Thr Ile Cys Ile
            260                 265

```
<210> SEQ ID NO 122
<211> LENGTH: 267
<212> TYPE: PRT
<213> ORGANISM: Artificial sequence
<220> FEATURE:
<223> OTHER INFORMATION: Synthetic

<400> SEQUENCE: 122
```

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

```
Glu Leu Val Phe Pro Cys Gly Val Leu Lys Leu Ala Thr Gly Met Lys
 50                  55                  60

Asn Val Pro Glu Ile Pro Lys Gly Arg Gly Leu Phe Gly Ala Ile Ala
 65                  70                  75                  80

Gly Phe Ile Glu Asn Gly Trp Glu Gly Leu Ile Asp Gly Trp Tyr Gly
                 85                  90                  95

Phe Arg His Gln Asn Ala Gln Gly Glu Gly Thr Ala Ala Asp Tyr Lys
                100                 105                 110

Ser Thr Gln Ser Ala Ile Asp Gln Ile Thr Gly Met Val Asn Arg Val
            115                 120                 125

Ile Ala Leu Met Ala Gln Gly Gly Pro Asp Cys Tyr Leu Ala Glu Leu
130                 135                 140

Leu Val Ala Met Leu Asn Gln His Val Ile Asp Leu Ala Asp Ser Glu
145                 150                 155                 160

Met Asp Lys Leu Tyr Glu Arg Val Lys Arg Gln Leu Arg Glu Asn Ala
                165                 170                 175

Glu Glu Asp Gly Thr Gly Cys Phe Glu Ile Phe His Lys Cys Asp Asp
                180                 185                 190

Asp Cys Met Ala Ser Ile Arg Asn Asn Thr Tyr Asp His Ser Lys Tyr
            195                 200                 205

Arg Glu Glu Ala Met Gln Asn Arg Ile Gln Ile Asp Pro Val Lys Leu
210                 215                 220

Ser Ser Gly Tyr Lys Asp Val Ile Leu Trp Phe Ser Phe Gly Ala Ser
225                 230                 235                 240

Cys Phe Ile Leu Leu Ala Ile Val Met Gly Leu Val Phe Ile Cys Val
                245                 250                 255

Lys Asn Gly Asn Met Arg Cys Thr Ile Cys Ile
                260                 265

<210> SEQ ID NO 123
<211> LENGTH: 268
<212> TYPE: PRT
<213> ORGANISM: Artificial sequence
<220> FEATURE:
<223> OTHER INFORMATION: Synthetic

<400> SEQUENCE: 123

Met Asn Thr Gln Ile Leu Val Phe Ala Leu Ile Ala Ile Ile Pro Thr
 1               5                  10                  15

Asn Ala Asp Lys Ile Cys Leu Gly His His Ala Val Ser Asn Gly Thr
                 20                  25                  30

Lys Val Asn Thr Leu Thr Glu Arg Gly Val Glu Val Val Asn Ala Thr
             35                  40                  45

Glu Leu Val Phe Pro Asn Cys Gly Val Leu Lys Leu Ala Thr Gly Met
 50                  55                  60

Lys Asn Val Pro Glu Ile Pro Lys Gly Arg Gly Leu Phe Gly Ala Ile
 65                  70                  75                  80

Ala Gly Phe Ile Glu Asn Gly Trp Glu Gly Leu Ile Asp Gly Trp Tyr
                 85                  90                  95

Gly Phe Arg His Gln Asn Ala Gln Gly Glu Gly Thr Ala Ala Asp Tyr
                100                 105                 110

Lys Ser Thr Gln Ser Ala Ile Asp Gln Ile Thr Gly Met Val Asn Arg
            115                 120                 125

Val Ile Ala Leu Met Ala Gln Gly Gly Pro Asp Cys Tyr Leu Ala Glu
130                 135                 140
```

```
Leu Leu Val Ala Met Leu Asn Gln His Val Ile Asp Leu Ala Asp Ser
145                 150                 155                 160

Glu Met Asp Lys Leu Tyr Glu Arg Val Lys Arg Gln Leu Arg Glu Asn
                165                 170                 175

Ala Glu Glu Asp Gly Thr Gly Cys Phe Glu Ile Phe His Lys Cys Asp
            180                 185                 190

Asp Asp Cys Met Ala Ser Ile Arg Asn Asn Thr Tyr Asp His Ser Lys
        195                 200                 205

Tyr Arg Glu Glu Ala Met Gln Asn Arg Ile Gln Ile Asp Pro Val Lys
    210                 215                 220

Leu Ser Ser Gly Tyr Lys Asp Val Ile Leu Trp Phe Ser Phe Gly Ala
225                 230                 235                 240

Ser Cys Phe Ile Leu Leu Ala Ile Val Met Gly Leu Val Phe Ile Cys
                245                 250                 255

Val Lys Asn Gly Asn Met Arg Cys Thr Ile Cys Ile
                260                 265
```

<210> SEQ ID NO 124
<211> LENGTH: 268
<212> TYPE: PRT
<213> ORGANISM: Artificial sequence
<220> FEATURE:
<223> OTHER INFORMATION: Synthetic

<400> SEQUENCE: 124

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Leu Val Phe Pro Gly Cys Gly Val Leu Lys Leu Ala Thr Gly Met
        50                  55                  60

Lys Asn Val Pro Glu Ile Pro Lys Gly Arg Gly Leu Phe Gly Ala Ile
65                  70                  75                  80

Ala Gly Phe Ile Glu Asn Gly Trp Glu Gly Leu Ile Asp Gly Trp Tyr
                85                  90                  95

Gly Phe Arg His Gln Asn Ala Gln Gly Glu Gly Thr Ala Ala Asp Tyr
                100                 105                 110

Lys Ser Thr Gln Ser Ala Ile Asp Gln Ile Thr Gly Met Val Asn Arg
            115                 120                 125

Val Ile Ala Leu Met Ala Gln Gly Pro Pro Asp Cys Tyr Leu Ala Glu
        130                 135                 140

Leu Leu Val Ala Met Leu Asn Gln His Val Ile Asp Leu Ala Asp Ser
145                 150                 155                 160

Glu Met Asp Lys Leu Tyr Glu Arg Val Lys Arg Gln Leu Arg Glu Asn
                165                 170                 175

Ala Glu Glu Asp Gly Thr Gly Cys Phe Glu Ile Phe His Lys Cys Asp
            180                 185                 190

Asp Asp Cys Met Ala Ser Ile Arg Asn Asn Thr Tyr Asp His Ser Lys
        195                 200                 205

Tyr Arg Glu Glu Ala Met Gln Asn Arg Ile Gln Ile Asp Pro Val Lys
    210                 215                 220

Leu Ser Ser Gly Tyr Lys Asp Val Ile Leu Trp Phe Ser Phe Gly Ala
225                 230                 235                 240
```

```
Ser Cys Phe Ile Leu Leu Ala Ile Val Met Gly Leu Val Phe Ile Cys
                245                 250                 255

Val Lys Asn Gly Asn Met Arg Cys Thr Ile Cys Ile
        260                 265
```

<210> SEQ ID NO 125
<211> LENGTH: 268
<212> TYPE: PRT
<213> ORGANISM: Artificial sequence
<220> FEATURE:
<223> OTHER INFORMATION: Synthetic

<400> SEQUENCE: 125

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Cys Thr
                20                  25                  30

Lys Val Asn Thr Leu Thr Glu Arg Gly Val Glu Val Val Asn Ala Thr
            35                  40                  45

Glu Leu Val Phe Pro Gly Cys Gly Val Leu Lys Leu Ala Thr Gly Met
        50                  55                  60

Lys Cys Val Pro Glu Ile Pro Lys Gly Arg Gly Leu Phe Gly Ala Ile
65                  70                  75                  80

Ala Gly Phe Ile Glu Asn Gly Trp Glu Gly Leu Ile Asp Gly Trp Tyr
                85                  90                  95

Gly Phe Arg His Gln Asn Ala Gln Gly Glu Gly Thr Ala Ala Asp Tyr
                100                 105                 110

Lys Ser Thr Gln Ser Ala Ile Asp Gln Ile Thr Gly Met Val Asn Arg
            115                 120                 125

Val Ile Ala Leu Met Ala Gln Gly Gly Pro Asp Cys Tyr Leu Ala Glu
        130                 135                 140

Leu Leu Val Ala Met Leu Asn Gln His Val Ile Asp Leu Ala Asp Ser
145                 150                 155                 160

Glu Met Asp Lys Leu Tyr Glu Arg Val Lys Arg Gln Leu Arg Glu Asn
                165                 170                 175

Ala Glu Glu Asp Gly Thr Gly Cys Phe Glu Ile Phe His Lys Cys Asp
                180                 185                 190

Asp Asp Cys Met Ala Ser Ile Arg Asn Asn Thr Tyr Asp His Ser Lys
            195                 200                 205

Tyr Arg Glu Glu Ala Met Gln Asn Arg Ile Gln Ile Asp Pro Val Lys
        210                 215                 220

Leu Ser Ser Gly Tyr Lys Asp Val Ile Leu Trp Phe Ser Phe Gly Ala
225                 230                 235                 240

Ser Cys Phe Ile Leu Leu Ala Ile Val Met Gly Leu Val Phe Ile Cys
                245                 250                 255

Val Lys Asn Gly Asn Met Arg Cys Thr Ile Cys Ile
        260                 265
```

<210> SEQ ID NO 126
<211> LENGTH: 268
<212> TYPE: PRT
<213> ORGANISM: Artificial sequence
<220> FEATURE:
<223> OTHER INFORMATION: Synthetic

<400> SEQUENCE: 126

```
Met Asn Thr Gln Ile Leu Val Phe Ala Leu Ile Ala Ile Ile Pro Thr
1               5                   10                  15
```

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Leu Val Phe Pro Gly Cys Gly Val Leu Lys Leu Ala Thr Gly Met
50                  55                  60

Lys Asn Val Pro Glu Ile Pro Lys Gly Arg Gly Leu Phe Gly Ala Ile
65                  70                  75                  80

Ala Gly Phe Ile Glu Asn Gly Trp Glu Gly Leu Ile Asp Gly Trp Tyr
                85                  90                  95

Gly Phe Arg His Gln Asn Ala Gln Gly Glu Gly Thr Ala Ala Asp Tyr
            100                 105                 110

Lys Ser Thr Gln Ser Ala Ile Asp Gln Ile Thr Gly Met Val Asn Arg
        115                 120                 125

Val Ile Ala Leu Met Glu Glu Gly Gly Pro Asp Cys Tyr Leu Ala Glu
130                 135                 140

Leu Leu Val Ala Met Leu Asn Gln His Val Ile Asp Leu Ala Asp Ser
145                 150                 155                 160

Glu Met Asp Lys Leu Tyr Glu Arg Val Lys Arg Gln Leu Arg Glu Asn
                165                 170                 175

Ala Glu Glu Asp Gly Thr Gly Cys Phe Glu Ile Phe His Lys Cys Asp
            180                 185                 190

Asp Asp Cys Met Ala Ser Ile Arg Asn Asn Thr Tyr Asp His Ser Lys
        195                 200                 205

Tyr Arg Glu Glu Ala Met Gln Asn Arg Ile Gln Ile Asp Pro Val Lys
210                 215                 220

Leu Ser Ser Gly Tyr Lys Asp Val Ile Leu Trp Phe Ser Phe Gly Ala
225                 230                 235                 240

Ser Cys Phe Ile Leu Leu Ala Ile Val Met Gly Leu Val Phe Ile Cys
                245                 250                 255

Val Lys Asn Gly Asn Met Arg Cys Thr Ile Cys Ile
            260                 265

<210> SEQ ID NO 127
<211> LENGTH: 268
<212> TYPE: PRT
<213> ORGANISM: Artificial sequence
<220> FEATURE:
<223> OTHER INFORMATION: Synthetic

<400> SEQUENCE: 127

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Leu Val Phe Pro Gly Cys Gly Val Leu Lys Leu Ala Thr Gly Met
50                  55                  60

Lys Asn Val Pro Glu Ile Pro Lys Gly Arg Gly Leu Phe Gly Ala Ile
65                  70                  75                  80

Ala Gly Phe Ile Glu Asn Gly Trp Glu Gly Leu Ile Asp Gly Trp Tyr
                85                  90                  95

Gly Phe Arg His Gln Asn Ala Gln Gly Glu Gly Thr Ala Ala Asp Tyr
            100                 105                 110

Lys Ser Thr Gln Ser Ala Ile Asp Gln Ile Thr Gly Met Val Asn Arg
            115                 120                 125

Val Ile Glu Leu Met Glu Gln Gly Gly Pro Asp Cys Tyr Leu Ala Glu
        130                 135                 140

Leu Leu Val Ala Met Leu Asn Gln His Val Ile Asp Leu Ala Asp Ser
145                 150                 155                 160

Glu Met Asp Lys Leu Tyr Glu Arg Val Lys Arg Gln Leu Arg Glu Asn
                165                 170                 175

Ala Glu Glu Asp Gly Thr Gly Cys Phe Glu Ile Phe His Lys Cys Asp
            180                 185                 190

Asp Asp Cys Met Ala Ser Ile Arg Asn Asn Thr Tyr Asp His Ser Lys
        195                 200                 205

Tyr Arg Glu Glu Ala Met Gln Asn Arg Ile Gln Ile Asp Pro Val Lys
    210                 215                 220

Leu Ser Ser Gly Tyr Lys Asp Val Ile Leu Trp Phe Ser Phe Gly Ala
225                 230                 235                 240

Ser Cys Phe Ile Leu Leu Ala Ile Val Met Gly Leu Val Phe Ile Cys
                245                 250                 255

Val Lys Asn Gly Asn Met Arg Cys Thr Ile Cys Ile
            260                 265

<210> SEQ ID NO 128
<211> LENGTH: 268
<212> TYPE: PRT
<213> ORGANISM: Artificial sequence
<220> FEATURE:
<223> OTHER INFORMATION: Synthetic

<400> SEQUENCE: 128

Met Asn Thr Gln Ile Leu Ile Leu Ala Leu Val Ala Ile Ile Pro Thr
1               5                   10                  15

Asn Ala Asp Lys Ile Cys Leu Gly His His Ala Val Ser Asn Gly Ala
                20                  25                  30

Lys Val Asn Thr Leu Thr Glu Arg Gly Val Glu Val Val Asn Ala Thr
            35                  40                  45

Glu Leu Val Phe Pro Gly Cys Gly Val Leu Lys Leu Ala Thr Gly Met
        50                  55                  60

Lys Asn Val Pro Glu Ile Pro Lys Gly Arg Gly Leu Phe Gly Ala Ile
65                  70                  75                  80

Ala Gly Phe Ile Glu Asn Gly Trp Glu Gly Leu Ile Asp Gly Trp Tyr
                85                  90                  95

Gly Phe Arg His Gln Asn Ala Gln Gly Glu Gly Thr Ala Ala Asp Tyr
            100                 105                 110

Lys Ser Thr Gln Ser Ala Ile Asp Gln Ile Thr Gly Met Val Asn Arg
        115                 120                 125

Val Ile Ala Leu Met Ala Gln Gly Gly Pro Asp Cys Tyr Leu Ala Glu
    130                 135                 140

Leu Leu Val Ala Met Leu Asn Gln His Val Ile Asp Leu Ala Asp Ser
145                 150                 155                 160

Glu Met Asn Lys Leu Tyr Glu Arg Val Arg Arg Gln Leu Arg Glu Asn
                165                 170                 175

Ala Glu Glu Asp Gly Thr Gly Cys Phe Glu Ile Phe His Lys Cys Asp
            180                 185                 190

Asp Asp Cys Met Ala Ser Ile Arg Asn Asn Thr Tyr Asp His Ser Lys
        195                 200                 205

Tyr Arg Glu Glu Ala Ile Gln Asn Arg Ile Gln Ile Asp Pro Val Lys
            210                 215                 220

Leu Ser Ser Gly Tyr Lys Asp Val Ile Leu Trp Phe Ser Phe Gly Ala
225                 230                 235                 240

Ser Cys Phe Ile Leu Leu Ala Ile Ala Met Gly Leu Val Phe Ile Cys
                245                 250                 255

Val Lys Asn Gly Asn Met Arg Cys Thr Ile Cys Ile
            260                 265

<210> SEQ ID NO 129
<211> LENGTH: 270
<212> TYPE: PRT
<213> ORGANISM: Artificial sequence
<220> FEATURE:
<223> OTHER INFORMATION: Synthetic

<400> SEQUENCE: 129

Met Asn Thr Gln Ile Leu Val Phe Ala Leu Val Ala Ser Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Asn Ala Thr
        35                  40                  45

Glu Leu Val Phe Pro Gly Cys Gly Val Leu Lys Leu Ala Thr Gly Met
    50                  55                  60

Lys Asn Val Pro Glu Ile Pro Lys Arg Arg Arg Gly Leu Phe Gly
65                  70                  75                  80

Ala Ile Ala Gly Phe Ile Glu Asn Gly Trp Glu Gly Leu Ile Asp Gly
                85                  90                  95

Trp Tyr Gly Phe Arg His Gln Asn Ala Gln Gly Glu Gly Thr Ala Ala
            100                 105                 110

Asp Tyr Lys Ser Thr Gln Ser Ala Ile Asp Gln Ile Thr Gly Met Val
        115                 120                 125

Asn Arg Val Ile Ala Leu Met Ala Gln Gly Gly Pro Asp Cys Tyr Leu
    130                 135                 140

Ala Glu Leu Leu Val Ala Met Leu Asn Gln His Val Ile Asp Leu Ala
145                 150                 155                 160

Asp Ser Glu Met Asn Lys Leu Tyr Glu Arg Val Lys Arg Gln Leu Arg
                165                 170                 175

Glu Asn Ala Glu Glu Asp Gly Thr Gly Cys Phe Glu Ile Phe His Lys
            180                 185                 190

Cys Asp Asp Asp Cys Met Ala Ser Ile Arg Asn Asn Thr Tyr Asp His
        195                 200                 205

Ser Lys Tyr Arg Glu Glu Ala Ile Gln Asn Arg Ile Gln Ile Asp Pro
    210                 215                 220

Val Lys Leu Ser Ser Gly Tyr Lys Asp Val Ile Leu Trp Phe Ser Phe
225                 230                 235                 240

Gly Ala Ser Cys Phe Ile Leu Leu Ala Ile Ala Met Gly Leu Val Phe
                245                 250                 255

Ile Cys Val Lys Asn Gly Asn Met Arg Cys Thr Ile Cys Ile
            260                 265                 270

<210> SEQ ID NO 130
<211> LENGTH: 275
<212> TYPE: PRT
<213> ORGANISM: Artificial sequence
<220> FEATURE:
<223> OTHER INFORMATION: Synthetic

<400> SEQUENCE: 130

Met Lys Thr Ile Ile Ala Leu Ser Tyr Ile Phe Cys Leu Ala Leu Ala
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Leu Phe Gly Ala Ile Ala Gly Phe Ile Glu Asn Gly Trp Glu
                85                  90                  95

Gly Met Ile Asp Gly Trp Tyr Gly Phe Arg His Gln Asn Ser Glu Gly
            100                 105                 110

Thr Gly Gln Ala Ala Asp Leu Lys Ser Thr Gln Ala Ala Ile Asp Gln
        115                 120                 125

Ile Asn Gly Met Val Asn Arg Val Ile Glu Leu Met Glu Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Lys Thr
                165                 170                 175

Arg Arg Gln Leu Arg Glu Asn Ala Glu Asp Met Gly Asn Gly Cys Phe
            180                 185                 190

Lys Ile Tyr His Lys Cys Asp Asn Ala Cys Ile Glu Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Gly Val Glu Leu Lys Ser Gly Tyr Lys Asp Trp Ile
225                 230                 235                 240

Leu Trp Ile Ser Phe Ala Ile Ser Cys Phe Leu Leu Cys Val Val Leu
                245                 250                 255

Leu Gly Phe Ile Met Trp Ala Cys Gln Arg Gly Asn Ile Arg Cys Asn
            260                 265                 270

Ile Cys Ile
        275

<210> SEQ ID NO 131
<211> LENGTH: 275
<212> TYPE: PRT
<213> ORGANISM: Artificial sequence
<220> FEATURE:
<223> OTHER INFORMATION: Synthetic

<400> SEQUENCE: 131

Met Lys Thr Ile Ile Ala Leu Ser Tyr Ile Phe Cys Leu Ala Leu Ala
1               5                   10                  15

Gln Asp Leu Pro Gly Asn Asp Asn Ser Thr Ala Thr Leu Cys Leu Gly
            20                  25                  30

His His Ala Val Pro Asn Cys Thr Leu Val Lys Thr Ile Thr Asp Asp
        35                  40                  45

Gln Ile Glu Val Thr Asn Ala Thr Glu Leu Val Phe Pro Gly Cys Gly

```
                50              55              60
Val Leu Lys Leu Ala Thr Gly Met Arg Cys Val Pro Glu Lys Gln Thr
65                  70                  75                  80

Arg Gly Leu Phe Gly Ala Ile Ala Gly Phe Ile Glu Asn Gly Trp Glu
                    85                  90                  95

Gly Met Ile Asp Gly Trp Tyr Gly Phe Arg His Gln Asn Ser Glu Gly
                100                 105                 110

Thr Gly Gln Ala Ala Asp Leu Lys Ser Thr Gln Ala Ala Ile Asp Gln
            115                 120                 125

Ile Asn Gly Met Val Asn Arg Val Ile Glu Leu Met Glu Gln Gly Gly
        130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Lys Thr
                165                 170                 175

Arg Arg Gln Leu Arg Glu Asn Ala Glu Asp Met Gly Asn Gly Cys Phe
                180                 185                 190

Lys Ile Tyr His Lys Cys Asp Asn Ala Cys Ile Glu Ser Ile Arg Asn
                195                 200                 205

Gly Thr Tyr Asp His Asp Val Tyr Arg Asp Glu Ala Leu Asn Asn Arg
            210                 215                 220

Phe Gln Ile Lys Gly Val Glu Leu Lys Ser Gly Tyr Lys Asp Trp Ile
225                 230                 235                 240

Leu Trp Ile Ser Phe Ala Ile Ser Cys Phe Leu Leu Cys Val Val Leu
                245                 250                 255

Leu Gly Phe Ile Met Trp Ala Cys Gln Arg Gly Asn Ile Arg Cys Asn
                260                 265                 270

Ile Cys Ile
        275

<210> SEQ ID NO 132
<211> LENGTH: 396
<212> TYPE: PRT
<213> ORGANISM: Artificial sequence
<220> FEATURE:
<223> OTHER INFORMATION: Synthetic

<400> SEQUENCE: 132

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr His Ala Thr Glu Leu Val Phe Pro Gly Cys Gly
50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                    85                  90                  95

Gly Met Val Asp Gly Trp Tyr Gly Phe Arg His Gln Asn Ser Glu Gly
                100                 105                 110

Ile Gly Gln Ala Ala Asp Leu Lys Ser Thr Gln Ala Ala Ile Asn Gln
            115                 120                 125

Ile Asn Gly Met Val Asn Arg Val Ile Ala Leu Met Ala Gln Gly Gly
```

```
            130                 135                 140
Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
                180                 185                 190

Lys Ile Tyr His Lys Cys Asp Asn Ala Cys Ile Gly Ser Ile Arg Asn
                195                 200                 205

Gly Thr Tyr Asp His Asp Val Tyr Arg Asp Glu Ala Leu Asn Asn Arg
        210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
                260                 265                 270

His Ala Ala Glu Glu Tyr Glu His Ala Lys Lys Leu Ile Ile Phe Leu
                275                 280                 285

Asn Glu Asn Asn Val Pro Val Gln Leu Thr Ser Ile Ser Ala Pro Glu
        290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
                340                 345                 350

Glu Gln His Glu Glu Val Leu Phe Lys Asp Ile Leu Asp Lys Ile
                355                 360                 365

Glu Leu Ile Gly Asn Glu Asn His Gly Leu Tyr Leu Ala Asp Gln Tyr
        370                 375                 380

Val Lys Gly Ile Ala Lys Ser Arg Lys Ser Gly Ser
385                 390                 395

<210> SEQ ID NO 133
<211> LENGTH: 379
<212> TYPE: PRT
<213> ORGANISM: Artificial sequence
<220> FEATURE:
<223> OTHER INFORMATION: Synthetic

<400> SEQUENCE: 133

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Gly Cys Gly
        50                  55                  60

Val Leu Lys Leu Ala Thr Gly Met Arg Asn Ser Gly Trp Glu Gly
65                  70                  75                  80

Met Val Asp Gly Trp Tyr Gly Phe Arg His Gln Asn Ser Glu Gly Ile
                85                  90                  95

Gly Gln Ala Ala Asp Leu Lys Ser Thr Gln Ala Ala Ile Asn Gln Ile
```

```
              100             105             110
Asn Gly Met Val Asn Arg Val Ile Ala Leu Met Ala Gln Gly Gly Pro
        115                 120             125
Asp Cys Tyr Leu Ala Glu Leu Leu Val Ala Leu Leu Asn Gln His Val
        130                 135             140
Ile Asp Leu Thr Asp Ser Glu Met Arg Lys Leu Phe Glu Arg Thr Lys
145             150                 155                 160
Lys Gln Leu Arg Glu Asn Ala Glu Asp Met Gly Asn Gly Cys Phe Lys
                165                 170             175
Ile Tyr His Lys Cys Asp Asn Ala Cys Ile Gly Ser Ile Arg Asn Gly
            180                 185                 190
Thr Tyr Asp His Asp Val Tyr Arg Asp Glu Ala Leu Asn Asn Arg Phe
        195                 200             205
Gln Ile Lys Ser Gly Gly Asp Ile Ile Lys Leu Leu Asn Glu Gln Val
        210                 215             220
Asn Lys Glu Met Gln Ser Ser Asn Leu Tyr Met Ser Met Ser Ser Trp
225             230                 235                 240
Cys Tyr Thr His Ser Leu Asp Gly Ala Gly Leu Phe Leu Phe Asp His
                245                 250             255
Ala Ala Glu Glu Tyr Glu His Ala Lys Lys Leu Ile Ile Phe Leu Asn
                260                 265             270
Glu Asn Asn Val Pro Val Gln Leu Thr Ser Ile Ser Ala Pro Glu His
        275                 280             285
Lys Phe Glu Gly Leu Thr Gln Ile Phe Gln Lys Ala Tyr Glu His Glu
        290                 295             300
Gln His Ile Ser Glu Ser Ile Asn Asn Ile Val Asp His Ala Ile Lys
305             310                 315                 320
Ser Lys Asp His Ala Thr Phe Asn Phe Leu Gln Trp Tyr Val Ala Glu
                325                 330             335
Gln His Glu Glu Glu Val Leu Phe Lys Asp Ile Leu Asp Lys Ile Glu
                340                 345             350
Leu Ile Gly Asn Glu Asn His Gly Leu Tyr Leu Ala Asp Gln Tyr Val
        355                 360             365
Lys Gly Ile Ala Lys Ser Arg Lys Ser Gly Ser
        370                 375

<210> SEQ ID NO 134
<211> LENGTH: 379
<212> TYPE: PRT
<213> ORGANISM: Artificial sequence
<220> FEATURE:
<223> OTHER INFORMATION: Synthetic

<400> SEQUENCE: 134

Met Lys Thr Ile Ile Ala Leu Ser Tyr Ile Leu Cys Leu Val Phe Ala
1               5                   10                  15
Gln Lys Leu Pro Gly Asn Asp Asn Ser Thr Ala Thr Leu Cys Leu Gly
                20                  25                  30
His His Ala Val Pro Asn Cys Thr Ile Val Lys Thr Ile Thr Asn Asp
            35                  40                  45
Gln Ile Glu Val Thr Asn Ala Thr Glu Leu Val Phe Pro Gly Cys Gly
        50                  55                  60
Val Leu Lys Leu Ala Thr Gly Met Arg Cys Gly Ser Gly Trp Glu Gly
65              70                  75                  80
Met Val Asp Gly Trp Tyr Gly Phe Arg His Gln Asn Ser Glu Gly Ile
```

```
                    85                  90                  95
Gly Gln Ala Ala Asp Leu Lys Ser Thr Gln Ala Ala Ile Asn Gln Ile
                100                 105                 110

Asn Gly Met Val Asn Arg Val Ile Glu Leu Met Glu Gln Gly Gly Pro
            115                 120                 125

Asp Cys Tyr Leu Ala Glu Leu Leu Val Ala Leu Leu Asn Gln His Val
        130                 135                 140

Ile Asp Leu Thr Asp Ser Glu Met Arg Lys Leu Phe Glu Arg Thr Lys
145                 150                 155                 160

Lys Gln Leu Arg Glu Asn Ala Glu Asp Met Gly Asn Gly Cys Phe Lys
                165                 170                 175

Ile Tyr His Lys Cys Asp Asn Ala Cys Ile Gly Ser Ile Arg Asn Gly
            180                 185                 190

Thr Tyr Asp His Asp Val Tyr Arg Asp Glu Ala Leu Asn Asn Arg Phe
        195                 200                 205

Gln Ile Lys Ser Gly Gly Asp Ile Ile Lys Leu Leu Asn Glu Gln Val
    210                 215                 220

Asn Lys Glu Met Gln Ser Ser Asn Leu Tyr Met Ser Met Ser Ser Trp
225                 230                 235                 240

Cys Tyr Thr His Ser Leu Asp Gly Ala Gly Leu Phe Leu Phe Asp His
                245                 250                 255

Ala Ala Glu Glu Tyr Glu His Ala Lys Lys Leu Ile Ile Phe Leu Asn
            260                 265                 270

Glu Asn Asn Val Pro Val Gln Leu Thr Ser Ile Ser Ala Pro Glu His
        275                 280                 285

Lys Phe Glu Gly Leu Thr Gln Ile Phe Gln Lys Ala Tyr Glu His Glu
    290                 295                 300

Gln His Ile Ser Glu Ser Ile Asn Asn Ile Val Asp His Ala Ile Lys
305                 310                 315                 320

Ser Lys Asp His Ala Thr Phe Asn Phe Leu Gln Trp Tyr Val Ala Glu
                325                 330                 335

Gln His Glu Glu Glu Val Leu Phe Lys Asp Ile Leu Asp Lys Ile Glu
            340                 345                 350

Leu Ile Gly Asn Glu Asn His Gly Leu Tyr Leu Ala Asp Gln Tyr Val
        355                 360                 365

Lys Gly Ile Ala Lys Ser Arg Lys Ser Gly Ser
    370                 375

<210> SEQ ID NO 135
<211> LENGTH: 380
<212> TYPE: PRT
<213> ORGANISM: Artificial sequence
<220> FEATURE:
<223> OTHER INFORMATION: Synthetic

<400> SEQUENCE: 135

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Gly Ser Gly Gly Trp Glu
```

```
                65                  70                  75                  80
Gly Met Val Asp Gly Trp Tyr Gly Phe Arg His Gln Asn Ser Glu Gly
                    85                  90                  95
Ile Gly Gln Ala Ala Asp Leu Lys Ser Thr Gln Ala Ala Ile Asn Gln
                100                 105                 110
Ile Asn Gly Met Val Asn Arg Val Ile Ala Leu Met Ala Gln Gly Gly
                115                 120                 125
Pro Asp Cys Tyr Leu Ala Glu Leu Leu Val Ala Leu Leu Asn Gln His
130                 135                 140
Val Ile Asp Leu Thr Asp Ser Glu Met Arg Lys Leu Phe Glu Arg Thr
145                 150                 155                 160
Lys Lys Gln Leu Arg Glu Asn Ala Glu Asp Met Gly Asn Gly Cys Phe
                165                 170                 175
Lys Ile Tyr His Lys Cys Asp Asn Ala Cys Ile Gly Ser Ile Arg Asn
                180                 185                 190
Gly Thr Tyr Asp His Asp Val Tyr Arg Asp Glu Ala Leu Asn Asn Arg
                195                 200                 205
Phe Gln Ile Lys Ser Gly Gly Asp Ile Ile Lys Leu Leu Asn Glu Gln
210                 215                 220
Val Asn Lys Glu Met Gln Ser Ser Asn Leu Tyr Met Ser Met Ser Ser
225                 230                 235                 240
Trp Cys Tyr Thr His Ser Leu Asp Gly Ala Gly Leu Phe Leu Phe Asp
                245                 250                 255
His Ala Ala Glu Glu Tyr Glu His Ala Lys Lys Leu Ile Ile Phe Leu
                260                 265                 270
Asn Glu Asn Asn Val Pro Val Gln Leu Thr Ser Ile Ser Ala Pro Glu
            275                 280                 285
His Lys Phe Glu Gly Leu Thr Gln Ile Phe Gln Lys Ala Tyr Glu His
            290                 295                 300
Glu Gln His Ile Ser Glu Ser Ile Asn Asn Ile Val Asp His Ala Ile
305                 310                 315                 320
Lys Ser Lys Asp His Ala Thr Phe Asn Phe Leu Gln Trp Tyr Val Ala
                325                 330                 335
Glu Gln His Glu Glu Val Leu Phe Lys Asp Ile Leu Asp Lys Ile
            340                 345                 350
Glu Leu Ile Gly Asn Glu Asn His Gly Leu Tyr Leu Ala Asp Gln Tyr
            355                 360                 365
Val Lys Gly Ile Ala Lys Ser Arg Lys Ser Gly Ser
370                 375                 380
```

<210> SEQ ID NO 136
<211> LENGTH: 390
<212> TYPE: PRT
<213> ORGANISM: Artificial sequence
<220> FEATURE:
<223> OTHER INFORMATION: Synthetic

<400> SEQUENCE: 136

```
Met Lys Thr Ile Ile Ala Leu Ser Tyr Ile Leu Cys Leu Val Phe Ala
1               5                   10                  15
Gln Lys Leu Pro Gly Asn Asp Asn Ser Thr Ala Thr Leu Cys Leu Gly
                20                  25                  30
His His Ala Val Pro Asn Gly Thr Ile Val Lys Thr Ile Thr Asn Asp
            35                  40                  45
Gln Ile Glu Val Thr Asn Ala Thr Glu Leu Val Phe Pro Gly Cys Gly
```

Val Leu Lys Leu Ala Thr Gly Met Arg Asn Gly Gly Ile Phe Gly Ala
65                  70                  75                  80

Ile Ala Gly Phe Ile Glu Asn Gly Trp Glu Gly Met Val Asp Gly Trp
                85                  90                  95

Tyr Gly Phe Arg His Gln Asn Ser Glu Gly Ile Gly Gln Ala Ala Asp
            100                 105                 110

Leu Lys Ser Thr Gln Ala Ala Ile Asn Gln Ile Asn Gly Met Val Asn
        115                 120                 125

Arg Val Ile Ala Leu Met Ala Gln Gly Gly Pro Asp Cys Tyr Leu Ala
    130                 135                 140

Glu Leu Leu Val Ala Leu Leu Asn Gln His Val Ile Asp Leu Thr Asp
145                 150                 155                 160

Ser Glu Met Arg Lys Leu Phe Glu Arg Thr Lys Lys Gln Leu Arg Glu
                165                 170                 175

Asn Ala Glu Asp Met Gly Asn Gly Cys Phe Lys Ile Tyr His Lys Cys
            180                 185                 190

Asp Asn Ala Cys Ile Gly Ser Ile Arg Asn Gly Thr Tyr Asp His Asp
        195                 200                 205

Val Tyr Arg Asp Glu Ala Leu Asn Asn Arg Phe Gln Ile Lys Ser Gly
    210                 215                 220

Gly Asp Ile Ile Lys Leu Leu Asn Glu Gln Val Asn Lys Glu Met Gln
225                 230                 235                 240

Ser Ser Asn Leu Tyr Met Ser Met Ser Ser Trp Cys Tyr Thr His Ser
                245                 250                 255

Leu Asp Gly Ala Gly Leu Phe Leu Phe Asp His Ala Ala Glu Glu Tyr
            260                 265                 270

Glu His Ala Lys Lys Leu Ile Ile Phe Leu Asn Glu Asn Asn Val Pro
        275                 280                 285

Val Gln Leu Thr Ser Ile Ser Ala Pro Glu His Lys Phe Glu Gly Leu
    290                 295                 300

Thr Gln Ile Phe Gln Lys Ala Tyr Glu His Glu Gln His Ile Ser Glu
305                 310                 315                 320

Ser Ile Asn Asn Ile Val Asp His Ala Ile Lys Ser Lys Asp His Ala
                325                 330                 335

Thr Phe Asn Phe Leu Gln Trp Tyr Val Ala Glu Gln His Glu Glu Glu
            340                 345                 350

Val Leu Phe Lys Asp Ile Leu Asp Lys Ile Glu Leu Ile Gly Asn Glu
        355                 360                 365

Asn His Gly Leu Tyr Leu Ala Asp Gln Tyr Val Lys Gly Ile Ala Lys
    370                 375                 380

Ser Arg Lys Ser Gly Ser
385                 390

```
<210> SEQ ID NO 137
<211> LENGTH: 390
<212> TYPE: PRT
<213> ORGANISM: Artificial sequence
<220> FEATURE:
<223> OTHER INFORMATION: Synthetic

<400> SEQUENCE: 137
```

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly

```
                    20                  25                  30
His His Ala Val Pro Asn Gly Thr Ile Val Lys Thr Ile Thr Asn Asp
                35                  40                  45

Gln Ile Glu Val Thr Asn Ala Thr Glu Leu Val Phe Pro Gly Cys Gly
            50                  55                  60

Val Leu Lys Leu Ala Thr Gly Met Arg Gly Gly Ile Phe Gly Ala
65                  70                  75                  80

Ile Ala Gly Phe Ile Glu Asn Gly Trp Glu Gly Met Val Asp Gly Trp
                85                  90                  95

Tyr Gly Phe Arg His Gln Asn Ser Glu Gly Ile Gly Gln Ala Ala Asp
                100                 105                 110

Leu Lys Ser Thr Gln Ala Ala Ile Asn Gln Ile Asn Gly Met Val Asn
            115                 120                 125

Arg Val Ile Ala Leu Met Ala Gln Gly Gly Pro Asp Cys Tyr Leu Ala
            130                 135                 140

Glu Leu Leu Val Ala Leu Leu Asn Gln His Val Ile Asp Leu Thr Asp
145                 150                 155                 160

Ser Glu Met Arg Lys Leu Phe Glu Arg Thr Lys Lys Gln Leu Arg Glu
                165                 170                 175

Asn Ala Glu Asp Met Gly Asn Gly Cys Phe Lys Ile Tyr His Lys Cys
                180                 185                 190

Asp Asn Ala Cys Ile Gly Ser Ile Arg Asn Gly Thr Tyr Asp His Asp
            195                 200                 205

Val Tyr Arg Asp Glu Ala Leu Asn Asn Arg Phe Gln Ile Lys Ser Gly
            210                 215                 220

Gly Asp Ile Ile Lys Leu Leu Asn Glu Gln Val Asn Lys Glu Met Gln
225                 230                 235                 240

Ser Ser Asn Leu Tyr Met Ser Met Ser Ser Trp Cys Tyr Thr His Ser
                245                 250                 255

Leu Asp Gly Ala Gly Leu Phe Leu Phe Asp His Ala Ala Glu Glu Tyr
                260                 265                 270

Glu His Ala Lys Lys Leu Ile Ile Phe Leu Asn Glu Asn Asn Val Pro
            275                 280                 285

Val Gln Leu Thr Ser Ile Ser Ala Pro Glu His Lys Phe Glu Gly Leu
            290                 295                 300

Thr Gln Ile Phe Gln Lys Ala Tyr Glu His Glu Gln His Ile Ser Glu
305                 310                 315                 320

Ser Ile Asn Asn Ile Val Asp His Ala Ile Lys Ser Lys Asp His Ala
                325                 330                 335

Thr Phe Asn Phe Leu Gln Trp Tyr Val Ala Glu Gln His Glu Glu Glu
                340                 345                 350

Val Leu Phe Lys Asp Ile Leu Asp Lys Ile Glu Leu Ile Gly Asn Glu
            355                 360                 365

Asn His Gly Leu Tyr Leu Ala Asp Gln Tyr Val Lys Gly Ile Ala Lys
            370                 375                 380

Ser Arg Lys Ser Gly Ser
385                 390

<210> SEQ ID NO 138
<211> LENGTH: 396
<212> TYPE: PRT
<213> ORGANISM: Artificial sequence
<220> FEATURE:
<223> OTHER INFORMATION: Synthetic
```

<400> SEQUENCE: 138

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Asn Leu Thr Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
    370                 375                 380

Val Lys Gly Ile Ala Lys Ser Arg Lys Ser Gly Ser
385                 390                 395
```

<210> SEQ ID NO 139

<211> LENGTH: 396
<212> TYPE: PRT
<213> ORGANISM: Artificial sequence
<220> FEATURE:
<223> OTHER INFORMATION: Synthetic

<400> SEQUENCE: 139

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Asn Phe Thr Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
    370                 375                 380

Val Lys Gly Ile Ala Lys Ser Arg Lys Ser Gly Ser
385                 390                 395

<210> SEQ ID NO 140
<211> LENGTH: 396
<212> TYPE: PRT
<213> ORGANISM: Artificial sequence
<220> FEATURE:
<223> OTHER INFORMATION: Synthetic

<400> SEQUENCE: 140

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Asn Cys Thr
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

```
Glu Gln His Glu Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
370                 375                 380

Val Lys Gly Ile Ala Lys Ser Arg Lys Ser Gly Ser
385                 390                 395

<210> SEQ ID NO 141
<211> LENGTH: 396
<212> TYPE: PRT
<213> ORGANISM: Artificial sequence
<220> FEATURE:
<223> OTHER INFORMATION: Synthetic

<400> SEQUENCE: 141

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Asn Leu Thr Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320
```

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
370                 375                 380

Val Lys Gly Ile Ala Lys Ser Arg Lys Ser Gly Ser
385                 390                 395

<210> SEQ ID NO 142
<211> LENGTH: 396
<212> TYPE: PRT
<213> ORGANISM: Artificial sequence
<220> FEATURE:
<223> OTHER INFORMATION: Synthetic

<400> SEQUENCE: 142

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Asn Leu Thr Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

```
Asn Glu Asn Asn Val Pro Val Gln Leu Thr Ser Ile Ser Ala Pro Glu
        290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
        370                 375                 380

Val Lys Gly Ile Ala Lys Ser Arg Lys Ser Gly Ser
385                 390                 395

<210> SEQ ID NO 143
<211> LENGTH: 396
<212> TYPE: PRT
<213> ORGANISM: Artificial sequence
<220> FEATURE:
<223> OTHER INFORMATION: Synthetic

<400> SEQUENCE: 143

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Asn Cys Thr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255
```

```
Trp Cys Tyr Thr His Ser Leu Asp Gly Ala Gly Leu Phe Leu Phe Asp
            260                 265                 270

His Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
        355                 360                 365

Glu Leu Ile Gly Asn Glu Asn His Gly Leu Tyr Leu Ala Asp Gln Tyr
370                 375                 380

Val Lys Gly Ile Ala Lys Ser Arg Lys Ser Gly Ser
385                 390                 395
```

<210> SEQ ID NO 144
<211> LENGTH: 397
<212> TYPE: PRT
<213> ORGANISM: Artificial sequence
<220> FEATURE:
<223> OTHER INFORMATION: Synthetic

<400> SEQUENCE: 144

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Asn Gly Thr
130                 135                 140

Gly Pro Asp Cys Tyr Leu Ala Glu Leu Leu Val Ala Leu Leu Asn Gln
145                 150                 155                 160

His Val Ile Asp Leu Thr Asp Ser Glu Met Arg Lys Leu Phe Glu Arg
                165                 170                 175

Thr Lys Lys Gln Leu Arg Glu Asn Ala Glu Asp Met Gly Asn Gly Cys
            180                 185                 190

Phe Lys Ile Tyr His Lys Cys Asp Asn Ala Cys Ile Gly Ser Ile Arg
        195                 200                 205

Asn Gly Thr Tyr Asp His Asp Val Tyr Arg Asp Glu Ala Leu Asn Asn
210                 215                 220
```

```
Arg Phe Gln Ile Lys Ser Gly Gly Asp Ile Ile Lys Leu Leu Asn Glu
225                 230                 235                 240

Gln Val Asn Lys Glu Met Gln Ser Ser Asn Leu Tyr Met Ser Met Ser
            245                 250                 255

Ser Trp Cys Tyr Thr His Ser Leu Asp Gly Ala Gly Leu Phe Leu Phe
        260                 265                 270

Asp His Ala Ala Glu Glu Tyr Glu His Ala Lys Lys Leu Ile Ile Phe
            275                 280                 285

Leu Asn Glu Asn Asn Val Pro Val Gln Leu Thr Ser Ile Ser Ala Pro
        290                 295                 300

Glu His Lys Phe Glu Gly Leu Thr Gln Ile Phe Gln Lys Ala Tyr Glu
305                 310                 315                 320

His Glu Gln His Ile Ser Glu Ser Ile Asn Asn Ile Val Asp His Ala
                325                 330                 335

Ile Lys Ser Lys Asp His Ala Thr Phe Asn Phe Leu Gln Trp Tyr Val
            340                 345                 350

Ala Glu Gln His Glu Glu Val Leu Phe Lys Asp Ile Leu Asp Lys
            355                 360                 365

Ile Glu Leu Ile Gly Asn Glu Asn His Gly Leu Tyr Leu Ala Asp Gln
370                 375                 380

Tyr Val Lys Gly Ile Ala Lys Ser Arg Lys Ser Gly Ser
385                 390                 395

<210> SEQ ID NO 145
<211> LENGTH: 396
<212> TYPE: PRT
<213> ORGANISM: Artificial sequence
<220> FEATURE:
<223> OTHER INFORMATION: Synthetic

<400> SEQUENCE: 145

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Asn Asn Thr Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190
```

```
Lys Ile Tyr His Lys Cys Asp Asn Ala Cys Ile Gly Ser Ile Arg Asn
            195                 200                 205

Gly Thr Tyr Asp His Asp Val Tyr Arg Asp Glu Ala Leu Asn Asn Arg
        210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
                260                 265                 270

His Ala Ala Glu Glu Tyr Glu His Ala Lys Lys Leu Ile Ile Phe Leu
                275                 280                 285

Asn Glu Asn Asn Val Pro Val Gln Leu Thr Ser Ile Ser Ala Pro Glu
                290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
                340                 345                 350

Glu Gln His Glu Glu Val Leu Phe Lys Asp Ile Leu Asp Lys Ile
                355                 360                 365

Glu Leu Ile Gly Asn Glu Asn His Gly Leu Tyr Leu Ala Asp Gln Tyr
        370                 375                 380

Val Lys Gly Ile Ala Lys Ser Arg Lys Ser Gly Ser
385                 390                 395

<210> SEQ ID NO 146
<211> LENGTH: 396
<212> TYPE: PRT
<213> ORGANISM: Artificial sequence
<220> FEATURE:
<223> OTHER INFORMATION: Synthetic

<400> SEQUENCE: 146

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Ala Leu Met Ala Gln Gly Gly
    130                 135                 140

Pro Asp Cys Tyr Leu Ala Glu Leu Leu Val Ala Leu Leu Asn Gln His
145                 150                 155                 160
```

Val Ile Asp Leu Thr Asp Ser Glu Met Arg Lys Leu Phe Glu Arg Thr
            165                 170                 175

Lys Lys Gln Leu Arg Glu Asn Ala Glu Asp Met Gly Asn Gly Cys Phe
            180                 185                 190

Lys Ile Tyr His Lys Cys Asp Asn Asn Cys Thr Gly Ser Ile Arg Asn
            195                 200                 205

Gly Thr Tyr Asp His Asp Val Tyr Arg Asp Glu Ala Leu Asn Asn Arg
        210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
            245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
            275                 280                 285

Asn Glu Asn Asn Val Pro Val Gln Leu Thr Ser Ile Ser Ala Pro Glu
            290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
            325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
            370                 375                 380

Val Lys Gly Ile Ala Lys Ser Arg Lys Ser Gly Ser
385                 390                 395

<210> SEQ ID NO 147
<211> LENGTH: 388
<212> TYPE: PRT
<213> ORGANISM: Artificial sequence
<220> FEATURE:
<223> OTHER INFORMATION: Synthetic

<400> SEQUENCE: 147

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Cys Phe Asn Gly Ile Cys
        50                  55                  60

Leu Lys Leu Ala Thr Gly Met Arg Asn Val Pro Glu Lys Gln Thr Arg
65                  70                  75                  80

Gly Ile Phe Gly Ala Ile Ala Gly Phe Ile Glu Asn Gly Trp Glu Gly
            85                  90                  95

Met Val Asp Gly Trp Tyr Gly Phe Arg His Gln Asn Ser Glu Gly Ile
            100                 105                 110

Gly Gln Ala Ala Asp Leu Lys Ser Thr Gln Ala Ala Ile Asn Gln Ile
            115                 120                 125

Asn Gly Met Val Asn Arg Val Ile Ala Leu Met Ala Gln Gly Gly Pro
130                 135                 140

Asp Ala Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Arg Thr Lys
                165                 170                 175

Lys Gln Leu Arg Glu Asn Ala Glu Asp Met Gly Asn Gly Cys Phe Lys
                180                 185                 190

Ile Tyr His Lys Cys Asp Asn Ala Cys Ile Gly Ser Ile Arg Asn Gly
                195                 200                 205

Thr Tyr Asp His Asp Val Tyr Arg Asp Glu Ala Leu Asn Asn Arg Phe
210                 215                 220

Gln Ile Lys Ala Gly Pro Pro Gly Gly Met Gln Ile Tyr Glu Gly
225                 230                 235                 240

Lys Leu Thr Ala Glu Gly Leu Arg Phe Gly Ile Val Ala Ser Arg Phe
                245                 250                 255

Asn His Ala Leu Val Asp Arg Leu Val Glu Gly Ala Ile Asp Cys Ile
                260                 265                 270

Val Arg His Gly Gly Arg Glu Glu Asp Ile Thr Leu Val Arg Val Pro
275                 280                 285

Gly Ser Trp Glu Ile Pro Val Ala Ala Gly Leu Ala Arg Lys Glu
290                 295                 300

Asp Ile Asp Ala Val Ile Ala Ile Gly Val Leu Ile Arg Gly Ala Thr
305                 310                 315                 320

Pro His Phe Asp Tyr Ile Ala Ser Glu Val Ser Lys Gly Leu Ala Asp
                325                 330                 335

Leu Ser Leu Glu Leu Arg Lys Pro Ile Thr Phe Gly Val Ile Thr Ala
                340                 345                 350

Asp Thr Leu Glu Gln Ala Ile Glu Arg Ala Gly Thr Lys His Gly Asn
                355                 360                 365

Lys Gly Trp Glu Ala Ala Leu Ser Ala Ile Glu Met Ala Asn Leu Phe
370                 375                 380

Lys Ser Leu Arg
385

<210> SEQ ID NO 148
<211> LENGTH: 388
<212> TYPE: PRT
<213> ORGANISM: Artificial sequence
<220> FEATURE:
<223> OTHER INFORMATION: Synthetic

<400> SEQUENCE: 148

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
                35                  40                  45

Gln Ile Glu Val Thr Asn Ala Thr Glu Leu Cys Phe Asn Gly Ile Cys
                50                  55                  60

Leu Lys Leu Ala Thr Gly Met Arg Asn Val Pro Glu Lys Gln Thr Arg
65                  70                  75                  80

Gly Ile Phe Gly Ala Ile Ala Gly Phe Ile Glu Asn Gly Trp Glu Gly
                85                  90                  95

-continued

Met Val Asp Gly Trp Tyr Gly Phe Arg His Gln Asn Ser Glu Gly Ile
            100                 105                 110

Gly Gln Ala Ala Asp Leu Lys Ser Thr Gln Ala Ala Ile Asn Gln Ile
        115                 120                 125

Asn Gly Met Val Asn Arg Val Ile Glu Leu Met Glu Gln Gly Gly Pro
    130                 135                 140

Asp Ala Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Arg Thr Lys
                165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
        195                 200                 205

Thr Tyr Asp His Asp Val Tyr Arg Asp Glu Ala Leu Asn Asn Arg Phe
    210                 215                 220

Gln Ile Lys Ala Gly Pro Pro Gly Gly Met Gln Ile Tyr Glu Gly
225                 230                 235                 240

Lys Leu Thr Ala Glu Gly Leu Arg Phe Gly Ile Val Ala Ser Arg Phe
                245                 250                 255

Asn His Ala Leu Val Asp Arg Leu Val Glu Gly Ala Ile Asp Cys Ile
            260                 265                 270

Val Arg His Gly Gly Arg Glu Glu Asp Ile Thr Leu Val Arg Val Pro
        275                 280                 285

Gly Ser Trp Glu Ile Pro Val Ala Ala Gly Glu Leu Ala Arg Lys Glu
    290                 295                 300

Asp Ile Asp Ala Val Ile Ala Ile Gly Val Leu Ile Arg Gly Ala Thr
305                 310                 315                 320

Pro His Phe Asp Tyr Ile Ala Ser Glu Val Ser Lys Gly Leu Ala Asp
                325                 330                 335

Leu Ser Leu Glu Leu Arg Lys Pro Ile Thr Phe Gly Val Ile Thr Ala
            340                 345                 350

Asp Thr Leu Glu Gln Ala Ile Glu Arg Ala Gly Thr Lys His Gly Asn
        355                 360                 365

Lys Gly Trp Glu Ala Ala Leu Ser Ala Ile Glu Met Ala Asn Leu Phe
    370                 375                 380

Lys Ser Leu Arg
385

<210> SEQ ID NO 149
<211> LENGTH: 388
<212> TYPE: PRT
<213> ORGANISM: Artificial sequence
<220> FEATURE:
<223> OTHER INFORMATION: Synthetic

<400> SEQUENCE: 149

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Cys Thr Ile Val Lys Thr Ile Thr Asn Asp
        35                  40                  45

Gln Ile Glu Val Thr Asn Ala Thr Glu Leu Cys Phe Asn Gly Ile Cys
    50                  55                  60

Leu Lys Leu Ala Thr Gly Met Arg Cys Val Pro Glu Lys Gln Thr Arg
 65                  70                  75                  80

Gly Ile Phe Gly Ala Ile Ala Gly Phe Ile Glu Asn Gly Trp Glu Gly
                 85                  90                  95

Met Val Asp Gly Trp Tyr Gly Phe Arg His Gln Asn Ser Glu Gly Ile
            100                 105                 110

Gly Gln Ala Ala Asp Leu Lys Ser Thr Gln Ala Ala Ile Asn Gln Ile
        115                 120                 125

Asn Gly Met Val Asn Arg Val Ile Glu Leu Met Glu Gln Gly Gly Pro
130                 135                 140

Asp Ala Tyr Leu Ala Glu Leu Leu Val Ala Leu Leu Asn Gln His Val
145                 150                 155                 160

Ile Asp Leu Thr Asp Ser Glu Met Arg Lys Leu Phe Glu Arg Thr Lys
                165                 170                 175

Lys Gln Leu Arg Glu Asn Ala Glu Asp Met Gly Asn Gly Cys Phe Lys
            180                 185                 190

Ile Tyr His Lys Cys Asp Asn Ala Cys Ile Gly Ser Ile Arg Asn Gly
        195                 200                 205

Thr Tyr Asp His Asp Val Tyr Arg Asp Glu Ala Leu Asn Asn Arg Phe
210                 215                 220

Gln Ile Lys Ala Gly Pro Pro Gly Gly Met Gln Ile Tyr Glu Gly
225                 230                 235                 240

Lys Leu Thr Ala Glu Gly Leu Arg Phe Gly Ile Val Ala Ser Arg Phe
                245                 250                 255

Asn His Ala Leu Val Asp Arg Leu Val Glu Gly Ala Ile Asp Cys Ile
            260                 265                 270

Val Arg His Gly Gly Arg Glu Glu Asp Ile Thr Leu Val Arg Val Pro
        275                 280                 285

Gly Ser Trp Glu Ile Pro Val Ala Ala Gly Glu Leu Ala Arg Lys Glu
290                 295                 300

Asp Ile Asp Ala Val Ile Ala Ile Gly Val Leu Ile Arg Gly Ala Thr
305                 310                 315                 320

Pro His Phe Asp Tyr Ile Ala Ser Glu Val Ser Lys Gly Leu Ala Asp
                325                 330                 335

Leu Ser Leu Glu Leu Arg Lys Pro Ile Thr Phe Gly Val Ile Thr Ala
            340                 345                 350

Asp Thr Leu Glu Gln Ala Ile Glu Arg Ala Gly Thr Lys His Gly Asn
        355                 360                 365

Lys Gly Trp Glu Ala Ala Leu Ser Ala Ile Glu Met Ala Asn Leu Phe
370                 375                 380

Lys Ser Leu Arg
385

<210> SEQ ID NO 150
<211> LENGTH: 389
<212> TYPE: PRT
<213> ORGANISM: Artificial sequence
<220> FEATURE:
<223> OTHER INFORMATION: Synthetic

<400> SEQUENCE: 150

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
         35                  40                  45

Gln Ile Glu Val Thr Asn Ala Thr Glu Leu Val Phe Pro Gly Cys Gly
 50                  55                  60

Val Leu Lys Leu Ala Thr Gly Met Arg Asn Val Pro Glu Lys Gln Thr
 65                  70                  75                  80

Arg Gly Ile Phe Gly Ala Ile Ala Gly Phe Ile Glu Asn Gly Trp Glu
             85                  90                  95

Gly Met Val Asp Gly Trp Tyr Gly Phe Arg His Gln Asn Ser Glu Gly
        100                 105                 110

Ile Gly Gln Ala Ala Asp Leu Lys Ser Thr Gln Ala Ala Ile Asn Gln
    115                 120                 125

Ile Asn Gly Met Val Asn Arg Val Ile Glu Leu Met Glu Gln Gly Gly
130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ala Gly Pro Pro Gly Met Gln Ile Tyr Glu
225                 230                 235                 240

Gly Lys Leu Thr Ala Glu Gly Leu Arg Phe Gly Ile Val Ala Ser Arg
                245                 250                 255

Phe Asn His Ala Leu Val Asp Arg Leu Val Glu Gly Ala Ile Asp Cys
            260                 265                 270

Ile Val Arg His Gly Gly Arg Glu Glu Asp Ile Thr Leu Val Arg Val
        275                 280                 285

Pro Gly Ser Trp Glu Ile Pro Val Ala Ala Gly Glu Leu Ala Arg Lys
    290                 295                 300

Glu Asp Ile Asp Ala Val Ile Ala Ile Gly Val Leu Ile Arg Gly Ala
305                 310                 315                 320

Thr Pro His Phe Asp Tyr Ile Ala Ser Glu Val Ser Lys Gly Leu Ala
                325                 330                 335

Asp Leu Ser Leu Glu Leu Arg Lys Pro Ile Thr Phe Gly Val Ile Thr
            340                 345                 350

Ala Asp Thr Leu Glu Gln Ala Ile Glu Arg Ala Gly Thr Lys His Gly
        355                 360                 365

Asn Lys Gly Trp Glu Ala Ala Leu Ser Ala Ile Glu Met Ala Asn Leu
    370                 375                 380

Phe Lys Ser Leu Arg
385

<210> SEQ ID NO 151
<211> LENGTH: 389
<212> TYPE: PRT
<213> ORGANISM: Artificial sequence
<220> FEATURE:
<223> OTHER INFORMATION: Synthetic

<400> SEQUENCE: 151

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Cys Thr Ile Val Lys Thr Ile Thr Asn Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Cys Val Pro Glu Lys Gln Thr
65                  70                  75                  80

Arg Gly Ile Phe Gly Ala Ile Ala Gly Phe Ile Glu Asn Gly Trp Glu
                85                  90                  95

Gly Met Val Asp Gly Trp Tyr Gly Phe Arg His Gln Asn Ser Glu Gly
            100                 105                 110

Ile Gly Gln Ala Ala Asp Leu Lys Ser Thr Gln Ala Ala Ile Asn Gln
        115                 120                 125

Ile Asn Gly Met Val Asn Arg Val Ile Glu Leu Met Glu Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Arg Thr
                165                 170                 175

Lys Lys Gln Leu Arg Glu Asn Ala Glu Asp Met Gly Asn Gly Cys Phe
            180                 185                 190

Lys Ile Tyr His Lys Cys Asp Asn Ala Cys Ile Gly Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ala Gly Pro Pro Gly Gly Met Gln Ile Tyr Glu
225                 230                 235                 240

Gly Lys Leu Thr Ala Glu Gly Leu Arg Phe Gly Ile Val Ala Ser Arg
                245                 250                 255

Phe Asn His Ala Leu Val Asp Arg Leu Val Glu Gly Ala Ile Asp Cys
            260                 265                 270

Ile Val Arg His Gly Gly Arg Glu Glu Asp Ile Thr Leu Val Arg Val
        275                 280                 285

Pro Gly Ser Trp Glu Ile Pro Val Ala Ala Gly Glu Leu Ala Arg Lys
    290                 295                 300

Glu Asp Ile Asp Ala Val Ile Ala Ile Gly Val Leu Ile Arg Gly Ala
305                 310                 315                 320

Thr Pro His Phe Asp Tyr Ile Ala Ser Glu Val Ser Lys Gly Leu Ala
                325                 330                 335

Asp Leu Ser Leu Glu Leu Arg Lys Pro Ile Thr Phe Gly Val Ile Thr
            340                 345                 350

Ala Asp Thr Leu Glu Gln Ala Ile Glu Arg Ala Gly Thr Lys His Gly
        355                 360                 365

Asn Lys Gly Trp Glu Ala Ala Leu Ser Ala Ile Glu Met Ala Asn Leu
    370                 375                 380

Phe Lys Ser Leu Arg
385

<210> SEQ ID NO 152
<211> LENGTH: 382

```
<212> TYPE: PRT
<213> ORGANISM: Artificial sequence
<220> FEATURE:
<223> OTHER INFORMATION: Synthetic

<400> SEQUENCE: 152
```

| | | | | | | | | | | | | | | | |
|---|---|---|---|---|---|---|---|---|---|---|---|---|---|---|---|
| Met | Asn | Thr | Gln | Ile | Leu | Val | Phe | Ala | Leu | Ile | Ala | Ile | Ile | Pro | Thr |
| 1 | | | | 5 | | | | | 10 | | | | | 15 | |
| Asn | Ala | Asp | Lys | Ile | Cys | Leu | Gly | His | His | Ala | Val | Ser | Asn | Cys | Thr |
| | | | 20 | | | | | 25 | | | | | 30 | | |
| Lys | Val | Asn | Thr | Leu | Thr | Glu | Arg | Gly | Val | Glu | Val | Val | Asn | Ala | Thr |
| | | | 35 | | | | | 40 | | | | | 45 | | |
| Glu | Leu | Val | Phe | Pro | Gly | Cys | Gly | Val | Leu | Lys | Leu | Ala | Thr | Gly | Met |
| | 50 | | | | | 55 | | | | | 60 | | | | |
| Lys | Cys | Val | Pro | Glu | Ile | Pro | Lys | Gly | Arg | Gly | Leu | Phe | Gly | Ala | Ile |
| 65 | | | | | 70 | | | | | 75 | | | | | 80 |
| Ala | Gly | Phe | Ile | Glu | Asn | Gly | Trp | Glu | Gly | Leu | Ile | Asp | Gly | Trp | Tyr |
| | | | | 85 | | | | | 90 | | | | | 95 | |
| Gly | Phe | Arg | His | Gln | Asn | Ala | Gln | Gly | Glu | Gly | Thr | Ala | Ala | Asp | Tyr |
| | | | 100 | | | | | 105 | | | | | 110 | | |
| Lys | Ser | Thr | Gln | Ser | Ala | Ile | Asp | Gln | Ile | Thr | Gly | Met | Val | Asn | Arg |
| | | | 115 | | | | | 120 | | | | | 125 | | |
| Val | Ile | Glu | Leu | Met | Glu | Gln | Gly | Gly | Pro | Asp | Cys | Tyr | Leu | Ala | Glu |
| 130 | | | | | 135 | | | | | 140 | | | | | |
| Leu | Leu | Val | Ala | Met | Leu | Asn | Gln | His | Val | Ile | Asp | Leu | Ala | Asp | Ser |
| 145 | | | | | 150 | | | | | 155 | | | | | 160 |
| Glu | Met | Asp | Lys | Leu | Tyr | Glu | Arg | Val | Lys | Arg | Gln | Leu | Arg | Glu | Asn |
| | | | | 165 | | | | | 170 | | | | | 175 | |
| Ala | Glu | Glu | Asp | Gly | Thr | Gly | Cys | Phe | Glu | Ile | Phe | His | Lys | Cys | Asp |
| | | | 180 | | | | | 185 | | | | | 190 | | |
| Asp | Asp | Cys | Met | Ala | Ser | Ile | Arg | Asn | Asn | Thr | Tyr | Asp | His | Ser | Lys |
| | | | 195 | | | | | 200 | | | | | 205 | | |
| Tyr | Arg | Glu | Glu | Ala | Met | Gln | Asn | Arg | Ile | Gln | Ile | Asp | Ala | Gly | Pro |
| | 210 | | | | | 215 | | | | | 220 | | | | |
| Pro | Pro | Gly | Gly | Met | Gln | Ile | Tyr | Glu | Gly | Lys | Leu | Thr | Ala | Glu | Gly |
| 225 | | | | | 230 | | | | | 235 | | | | | 240 |
| Leu | Arg | Phe | Gly | Ile | Val | Ala | Ser | Arg | Phe | Asn | His | Ala | Leu | Val | Asp |
| | | | | 245 | | | | | 250 | | | | | 255 | |
| Arg | Leu | Val | Glu | Gly | Ala | Ile | Asp | Cys | Ile | Val | Arg | His | Gly | Gly | Arg |
| | | | 260 | | | | | 265 | | | | | 270 | | |
| Glu | Glu | Asp | Ile | Thr | Leu | Val | Arg | Val | Pro | Gly | Ser | Trp | Glu | Ile | Pro |
| | | | 275 | | | | | 280 | | | | | 285 | | |
| Val | Ala | Ala | Gly | Glu | Leu | Ala | Arg | Lys | Glu | Asp | Ile | Asp | Ala | Val | Ile |
| | 290 | | | | | 295 | | | | | 300 | | | | |
| Ala | Ile | Gly | Val | Leu | Ile | Arg | Gly | Ala | Thr | Pro | His | Phe | Asp | Tyr | Ile |
| 305 | | | | | 310 | | | | | 315 | | | | | 320 |
| Ala | Ser | Glu | Val | Ser | Lys | Gly | Leu | Ala | Asp | Leu | Ser | Leu | Glu | Leu | Arg |
| | | | | 325 | | | | | 330 | | | | | 335 | |
| Lys | Pro | Ile | Thr | Phe | Gly | Val | Ile | Thr | Ala | Asp | Thr | Leu | Glu | Gln | Ala |
| | | | 340 | | | | | 345 | | | | | 350 | | |
| Ile | Glu | Arg | Ala | Gly | Thr | Lys | His | Gly | Asn | Lys | Gly | Trp | Glu | Ala | Ala |
| | | | 355 | | | | | 360 | | | | | 365 | | |
| Leu | Ser | Ala | Ile | Glu | Met | Ala | Asn | Leu | Phe | Lys | Ser | Leu | Arg | | |
| | 370 | | | | | 375 | | | | | 380 | | | | |

<210> SEQ ID NO 153
<211> LENGTH: 381
<212> TYPE: PRT
<213> ORGANISM: Artificial sequence
<220> FEATURE:
<223> OTHER INFORMATION: Synthetic

<400> SEQUENCE: 153

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Leu Cys Phe Asn Gly Ile Cys Leu Lys Leu Ala Thr Gly Met Lys
    50                  55                  60

Asn Val Pro Glu Ile Pro Lys Gly Arg Gly Leu Phe Gly Ala Ile Ala
65                  70                  75                  80

Gly Phe Ile Glu Asn Gly Trp Glu Gly Leu Ile Asp Gly Trp Tyr Gly
                85                  90                  95

Phe Arg His Gln Asn Ala Gln Gly Glu Gly Thr Ala Ala Asp Tyr Lys
            100                 105                 110

Ser Thr Gln Ser Ala Ile Asp Gln Ile Thr Gly Met Val Asn Arg Val
        115                 120                 125

Ile Ala Leu Met Ala Gln Gly Gly Pro Asp Cys Tyr Leu Ala Glu Leu
    130                 135                 140

Leu Val Ala Met Leu Asn Gln His Val Ile Asp Leu Ala Asp Ser Glu
145                 150                 155                 160

Met Asp Lys Leu Tyr Glu Arg Val Lys Arg Gln Leu Arg Glu Asn Ala
                165                 170                 175

Glu Glu Asp Gly Thr Gly Cys Phe Glu Ile Phe His Lys Cys Asp Asp
            180                 185                 190

Asp Cys Met Ala Ser Ile Arg Asn Asn Thr Tyr Asp His Ser Lys Tyr
        195                 200                 205

Arg Glu Glu Ala Met Gln Asn Arg Ile Gln Ile Asp Ala Gly Pro Pro
    210                 215                 220

Pro Gly Met Gln Ile Tyr Glu Gly Lys Leu Thr Ala Glu Gly Leu
225                 230                 235                 240

Arg Phe Gly Ile Val Ala Ser Arg Phe Asn His Ala Leu Val Asp Arg
                245                 250                 255

Leu Val Glu Gly Ala Ile Asp Cys Ile Val Arg His Gly Gly Arg Glu
            260                 265                 270

Glu Asp Ile Thr Leu Val Arg Val Pro Gly Ser Trp Glu Ile Pro Val
        275                 280                 285

Ala Ala Gly Glu Leu Ala Arg Lys Glu Asp Ile Asp Ala Val Ile Ala
    290                 295                 300

Ile Gly Val Leu Ile Arg Gly Ala Thr Pro His Phe Asp Tyr Ile Ala
305                 310                 315                 320

Ser Glu Val Ser Lys Gly Leu Ala Asp Leu Ser Leu Glu Leu Arg Lys
                325                 330                 335

Pro Ile Thr Phe Gly Val Ile Thr Ala Asp Thr Leu Glu Gln Ala Ile
            340                 345                 350

Glu Arg Ala Gly Thr Lys His Gly Asn Lys Gly Trp Glu Ala Ala Leu
        355                 360                 365
```

```
Ser Ala Ile Glu Met Ala Asn Leu Phe Lys Ser Leu Arg
    370                 375                 380
```

<210> SEQ ID NO 154
<211> LENGTH: 381
<212> TYPE: PRT
<213> ORGANISM: Artificial sequence
<220> FEATURE:
<223> OTHER INFORMATION: Synthetic

<400> SEQUENCE: 154

```
Met Asn Thr Gln Ile Leu Val Phe Ala Leu Ile Ala Ile Pro Thr
1               5                   10                  15

Asn Ala Asp Lys Ile Cys Leu Gly His His Ala Val Ser Asn Cys Thr
            20                  25                  30

Lys Val Asn Thr Leu Thr Glu Arg Gly Val Glu Val Val Asn Ala Thr
            35                  40                  45

Glu Leu Cys Phe Asn Gly Ile Cys Leu Lys Leu Ala Thr Gly Met Lys
    50                  55                  60

Cys Val Pro Glu Ile Pro Lys Gly Arg Gly Leu Phe Gly Ala Ile Ala
65                  70                  75                  80

Gly Phe Ile Glu Asn Gly Trp Glu Gly Leu Ile Asp Gly Trp Tyr Gly
                85                  90                  95

Phe Arg His Gln Asn Ala Gln Gly Glu Gly Thr Ala Ala Asp Tyr Lys
            100                 105                 110

Ser Thr Gln Ser Ala Ile Asp Gln Ile Thr Gly Met Val Asn Arg Val
            115                 120                 125

Ile Glu Leu Met Glu Gln Gly Gly Pro Asp Cys Tyr Leu Ala Glu Leu
    130                 135                 140

Leu Val Ala Met Leu Asn Gln His Val Ile Asp Leu Ala Asp Ser Glu
145                 150                 155                 160

Met Asp Lys Leu Tyr Glu Arg Val Lys Arg Gln Leu Arg Glu Asn Ala
                165                 170                 175

Glu Glu Asp Gly Thr Gly Cys Phe Glu Ile Phe His Lys Cys Asp Asp
            180                 185                 190

Asp Cys Met Ala Ser Ile Arg Asn Asn Thr Tyr Asp His Ser Lys Tyr
            195                 200                 205

Arg Glu Glu Ala Met Gln Asn Arg Ile Gln Ile Asp Ala Gly Pro Pro
    210                 215                 220

Pro Gly Met Gln Ile Tyr Glu Gly Lys Leu Thr Ala Glu Gly Leu
225                 230                 235                 240

Arg Phe Gly Ile Val Ala Ser Arg Phe Asn His Ala Leu Val Asp Arg
                245                 250                 255

Leu Val Glu Gly Ala Ile Asp Cys Ile Val Arg His Gly Gly Arg Glu
            260                 265                 270

Glu Asp Ile Thr Leu Val Arg Val Pro Gly Ser Trp Glu Ile Pro Val
    275                 280                 285

Ala Ala Gly Glu Leu Ala Arg Lys Glu Asp Ile Asp Ala Val Ile Ala
290                 295                 300

Ile Gly Val Leu Ile Arg Gly Ala Thr Pro His Phe Asp Tyr Ile Ala
305                 310                 315                 320

Ser Glu Val Ser Lys Gly Leu Ala Asp Leu Ser Leu Glu Leu Arg Lys
                325                 330                 335

Pro Ile Thr Phe Gly Val Ile Thr Ala Asp Thr Leu Glu Gln Ala Ile
            340                 345                 350
```

Glu Arg Ala Gly Thr Lys His Gly Asn Lys Gly Trp Glu Ala Ala Leu
            355                 360                 365

Ser Ala Ile Glu Met Ala Asn Leu Phe Lys Ser Leu Arg
    370                 375                 380

<210> SEQ ID NO 155
<211> LENGTH: 381
<212> TYPE: PRT
<213> ORGANISM: Artificial sequence
<220> FEATURE:
<223> OTHER INFORMATION: Synthetic

<400> SEQUENCE: 155

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Leu Val Phe Pro Cys Gly Val Leu Lys Leu Ala Thr Gly Met Lys
    50                  55                  60

Asn Val Pro Glu Ile Pro Lys Gly Arg Gly Leu Phe Gly Ala Ile Ala
65                  70                  75                  80

Gly Phe Ile Glu Asn Gly Trp Glu Gly Leu Ile Asp Gly Trp Tyr Gly
                85                  90                  95

Phe Arg His Gln Asn Ala Gln Gly Glu Gly Thr Ala Ala Asp Tyr Lys
            100                 105                 110

Ser Thr Gln Ser Ala Ile Asp Gln Ile Thr Gly Met Val Asn Arg Val
        115                 120                 125

Ile Glu Leu Met Glu Gln Gly Gly Pro Asp Cys Tyr Leu Ala Glu Leu
    130                 135                 140

Leu Val Ala Met Leu Asn Gln His Val Ile Asp Leu Ala Asp Ser Glu
145                 150                 155                 160

Met Asp Lys Leu Tyr Glu Arg Val Lys Arg Gln Leu Arg Glu Asn Ala
                165                 170                 175

Glu Glu Asp Gly Thr Gly Cys Phe Glu Ile Phe His Lys Cys Asp Asp
            180                 185                 190

Asp Cys Met Ala Ser Ile Arg Asn Asn Thr Tyr Asp His Ser Lys Tyr
        195                 200                 205

Arg Glu Glu Ala Met Gln Asn Arg Ile Gln Ile Asp Ala Gly Pro Pro
    210                 215                 220

Pro Gly Gly Met Gln Ile Tyr Glu Gly Lys Leu Thr Ala Glu Gly Leu
225                 230                 235                 240

Arg Phe Gly Ile Val Ala Ser Arg Phe Asn His Ala Leu Val Asp Arg
                245                 250                 255

Leu Val Glu Gly Ala Ile Asp Cys Ile Val Arg His Gly Gly Arg Glu
            260                 265                 270

Glu Asp Ile Thr Leu Val Arg Val Pro Gly Ser Trp Glu Ile Pro Val
        275                 280                 285

Ala Ala Gly Glu Leu Ala Arg Lys Glu Asp Ile Asp Ala Val Ile Ala
    290                 295                 300

Ile Gly Val Leu Ile Arg Gly Ala Thr Pro His Phe Asp Tyr Ile Ala
305                 310                 315                 320

Ser Glu Val Ser Lys Gly Leu Ala Asp Leu Ser Leu Glu Leu Arg Lys
                325                 330                 335

```
Pro Ile Thr Phe Gly Val Ile Thr Ala Asp Thr Leu Glu Gln Ala Ile
            340                 345                 350

Glu Arg Ala Gly Thr Lys His Gly Asn Lys Gly Trp Glu Ala Ala Leu
        355                 360                 365

Ser Ala Ile Glu Met Ala Asn Leu Phe Lys Ser Leu Arg
    370                 375                 380

<210> SEQ ID NO 156
<211> LENGTH: 382
<212> TYPE: PRT
<213> ORGANISM: Artificial sequence
<220> FEATURE:
<223> OTHER INFORMATION: Synthetic

<400> SEQUENCE: 156

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Asn Ala Thr
        35                  40                  45

Glu Leu Val Phe Pro Gly Cys Gly Val Leu Lys Leu Ala Thr Gly Met
    50                  55                  60

Lys Asn Val Pro Glu Ile Pro Lys Gly Arg Gly Leu Phe Gly Ala Ile
65                  70                  75                  80

Ala Gly Phe Ile Glu Asn Gly Trp Glu Gly Leu Ile Asp Gly Trp Tyr
                85                  90                  95

Gly Phe Arg His Gln Asn Ala Gln Gly Glu Gly Thr Ala Ala Asp Tyr
            100                 105                 110

Lys Ser Thr Gln Ser Ala Ile Asp Gln Ile Thr Gly Met Val Asn Arg
        115                 120                 125

Val Ile Glu Leu Met Glu Gln Gly Pro Pro Asp Cys Tyr Leu Ala Glu
    130                 135                 140

Leu Leu Val Ala Met Leu Asn Gln His Val Ile Asp Leu Ala Asp Ser
145                 150                 155                 160

Glu Met Asp Lys Leu Tyr Glu Arg Val Lys Arg Gln Leu Arg Glu Asn
                165                 170                 175

Ala Glu Glu Asp Gly Thr Gly Cys Phe Glu Ile Phe His Lys Cys Asp
            180                 185                 190

Asp Asp Cys Met Ala Ser Ile Arg Asn Asn Thr Tyr Asp His Ser Lys
        195                 200                 205

Tyr Arg Glu Glu Ala Met Gln Asn Arg Ile Gln Ile Asp Ala Gly Pro
    210                 215                 220

Pro Pro Gly Gly Met Gln Ile Tyr Glu Gly Lys Leu Thr Ala Glu Gly
225                 230                 235                 240

Leu Arg Phe Gly Ile Val Ala Ser Arg Phe Asn His Ala Leu Val Asp
                245                 250                 255

Arg Leu Val Glu Gly Ala Ile Asp Cys Ile Val Arg His Gly Gly Arg
            260                 265                 270

Glu Glu Asp Ile Thr Leu Val Arg Val Pro Gly Ser Trp Glu Ile Pro
        275                 280                 285

Val Ala Ala Gly Glu Leu Ala Arg Lys Glu Asp Ile Asp Ala Val Ile
    290                 295                 300

Ala Ile Gly Val Leu Ile Arg Gly Ala Thr Pro His Phe Asp Tyr Ile
305                 310                 315                 320
```

```
Ala Ser Glu Val Ser Lys Gly Leu Ala Asp Leu Ser Leu Glu Leu Arg
            325                 330                 335

Lys Pro Ile Thr Phe Gly Val Ile Thr Ala Asp Thr Leu Glu Gln Ala
        340                 345                 350

Ile Glu Arg Ala Gly Thr Lys His Gly Asn Lys Gly Trp Glu Ala Ala
    355                 360                 365

Leu Ser Ala Ile Glu Met Ala Asn Leu Phe Lys Ser Leu Arg
370                 375                 380

<210> SEQ ID NO 157
<211> LENGTH: 381
<212> TYPE: PRT
<213> ORGANISM: Artificial sequence
<220> FEATURE:
<223> OTHER INFORMATION: Synthetic

<400> SEQUENCE: 157

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Leu Val Phe Pro Cys Gly Val Leu Lys Leu Ala Thr Gly Met Lys
50                  55                  60

Asn Val Pro Glu Ile Pro Lys Gly Arg Gly Leu Phe Gly Ala Ile Ala
65                  70                  75                  80

Gly Phe Ile Glu Asn Gly Trp Glu Gly Leu Ile Asp Gly Trp Tyr Gly
                85                  90                  95

Phe Arg His Gln Asn Ala Gln Gly Glu Gly Thr Ala Ala Asp Tyr Lys
            100                 105                 110

Ser Thr Gln Ser Ala Ile Asp Gln Ile Thr Gly Met Val Asn Arg Val
        115                 120                 125

Ile Glu Leu Met Glu Gln Gly Pro Pro Asp Cys Tyr Leu Ala Glu Leu
    130                 135                 140

Leu Val Ala Met Leu Asn Gln His Val Ile Asp Leu Ala Asp Ser Glu
145                 150                 155                 160

Met Asp Lys Leu Tyr Glu Arg Val Lys Arg Gln Leu Arg Glu Asn Ala
                165                 170                 175

Glu Glu Asp Gly Thr Gly Cys Phe Glu Ile Phe His Lys Cys Asp Asp
            180                 185                 190

Asp Cys Met Ala Ser Ile Arg Asn Asn Thr Tyr Asp His Ser Lys Tyr
        195                 200                 205

Arg Glu Glu Ala Met Gln Asn Arg Ile Gln Ile Asp Ala Gly Pro Pro
    210                 215                 220

Pro Gly Gly Met Gln Ile Tyr Glu Gly Lys Leu Thr Ala Glu Gly Leu
225                 230                 235                 240

Arg Phe Gly Ile Val Ala Ser Arg Phe Asn His Ala Leu Val Asp Arg
                245                 250                 255

Leu Val Glu Gly Ala Ile Asp Cys Ile Val Arg His Gly Gly Arg Glu
            260                 265                 270

Glu Asp Ile Thr Leu Val Arg Val Pro Gly Ser Trp Glu Ile Pro Val
        275                 280                 285

Ala Ala Gly Glu Leu Ala Arg Lys Glu Asp Ile Asp Ala Val Ile Ala
    290                 295                 300
```

```
Ile Gly Val Leu Ile Arg Gly Ala Thr Pro His Phe Asp Tyr Ile Ala
305                 310                 315                 320

Ser Glu Val Ser Lys Gly Leu Ala Asp Leu Ser Leu Glu Leu Arg Lys
            325                 330                 335

Pro Ile Thr Phe Gly Val Ile Thr Ala Asp Thr Leu Glu Gln Ala Ile
            340                 345                 350

Glu Arg Ala Gly Thr Lys His Gly Asn Lys Gly Trp Glu Ala Ala Leu
            355                 360                 365

Ser Ala Ile Glu Met Ala Asn Leu Phe Lys Ser Leu Arg
    370                 375                 380
```

<210> SEQ ID NO 158
<211> LENGTH: 396
<212> TYPE: PRT
<213> ORGANISM: Artificial sequence
<220> FEATURE:
<223> OTHER INFORMATION: Synthetic

<400> SEQUENCE: 158

```
Met Lys Thr Ile Ile Ala Leu Ser Tyr Ile Phe Cys Leu Ala Leu Ala
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Asn Val Pro Glu Lys Gln Thr
65                  70                  75                  80

Arg Gly Leu Phe Gly Ala Ile Ala Gly Phe Ile Glu Asn Gly Trp Glu
                85                  90                  95

Gly Met Ile Asp Gly Trp Tyr Gly Phe Arg His Gln Asn Ser Glu Gly
            100                 105                 110

Thr Gly Gln Ala Ala Asp Leu Lys Ser Thr Gln Ala Ala Ile Asp Gln
        115                 120                 125

Ile Asn Gly Met Val Asn Arg Val Ile Glu Leu Met Glu Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Lys Thr
                165                 170                 175

Arg Arg Gln Leu Arg Glu Asn Ala Glu Asp Met Gly Asn Gly Cys Phe
            180                 185                 190

Lys Ile Tyr His Lys Cys Asp Asn Ala Cys Ile Glu Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285
```

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
    370                 375                 380

Val Lys Gly Ile Ala Lys Ser Arg Lys Ser Gly Ser
385                 390                 395

<210> SEQ ID NO 159
<211> LENGTH: 396
<212> TYPE: PRT
<213> ORGANISM: Artificial sequence
<220> FEATURE:
<223> OTHER INFORMATION: Synthetic

<400> SEQUENCE: 159

Met Lys Thr Ile Ile Ala Leu Ser Tyr Ile Phe Cys Leu Ala Leu Ala
1               5                   10                  15

Gln Asp Leu Pro Gly Asn Asp Asn Ser Thr Ala Thr Leu Cys Leu Gly
            20                  25                  30

His His Ala Val Pro Asn Cys Thr Leu Val Lys Thr Ile Thr Asp Asp
        35                  40                  45

Gln Ile Glu Val Thr Asn Ala Thr Glu Leu Val Phe Pro Gly Cys Gly
    50                  55                  60

Val Leu Lys Leu Ala Thr Gly Met Arg Cys Val Pro Glu Lys Gln Thr
65                  70                  75                  80

Arg Gly Leu Phe Gly Ala Ile Ala Gly Phe Ile Glu Asn Gly Trp Glu
                85                  90                  95

Gly Met Ile Asp Gly Trp Tyr Gly Phe Arg His Gln Asn Ser Glu Gly
            100                 105                 110

Thr Gly Gln Ala Ala Asp Leu Lys Ser Thr Gln Ala Ala Ile Asp Gln
        115                 120                 125

Ile Asn Gly Met Val Asn Arg Val Ile Glu Leu Met Glu Gln Gly Gly
    130                 135                 140

Pro Asp Cys Tyr Leu Ala Glu Leu Leu Val Ala Leu Leu Asn Gln His
145                 150                 155                 160

Val Ile Asp Leu Thr Asp Ser Glu Met Arg Lys Leu Phe Glu Lys Thr
                165                 170                 175

Arg Arg Gln Leu Arg Glu Asn Ala Glu Asp Met Gly Asn Gly Cys Phe
            180                 185                 190

Lys Ile Tyr His Lys Cys Asp Asn Ala Cys Ile Glu Ser Ile Arg Asn
        195                 200                 205

Gly Thr Tyr Asp His Asp Val Tyr Arg Asp Glu Ala Leu Asn Asn Arg
    210                 215                 220

Phe Gln Ile Lys Ser Gly Gly Asp Ile Ile Lys Leu Leu Asn Glu Gln
225                 230                 235                 240

Val Asn Lys Glu Met Gln Ser Ser Asn Leu Tyr Met Ser Met Ser Ser
                245                 250                 255

```
Trp Cys Tyr Thr His Ser Leu Asp Gly Ala Gly Leu Phe Leu Phe Asp
            260                 265                 270

His Ala Ala Glu Glu Tyr Glu His Ala Lys Lys Leu Ile Ile Phe Leu
        275                 280                 285

Asn Glu Asn Asn Val Pro Val Gln Leu Thr Ser Ile Ser Ala Pro Glu
    290                 295                 300

His Lys Phe Glu Gly Leu Thr Gln Ile Phe Gln Lys Ala Tyr Glu His
305                 310                 315                 320

Glu Gln His Ile Ser Glu Ser Ile Asn Asn Ile Val Asp His Ala Ile
                325                 330                 335

Lys Ser Lys Asp His Ala Thr Phe Asn Phe Leu Gln Trp Tyr Val Ala
            340                 345                 350

Glu Gln His Glu Glu Glu Val Leu Phe Lys Asp Ile Leu Asp Lys Ile
            355                 360                 365

Glu Leu Ile Gly Asn Glu Asn His Gly Leu Tyr Leu Ala Asp Gln Tyr
    370                 375                 380

Val Lys Gly Ile Ala Lys Ser Arg Lys Ser Gly Ser
385                 390                 395

<210> SEQ ID NO 160
<211> LENGTH: 5
<212> TYPE: PRT
<213> ORGANISM: artificial sequence
<220> FEATURE:
<223> OTHER INFORMATION: helix extension
<220> FEATURE:
<221> NAME/KEY: MISC_FEATURE
<222> LOCATION: (1)..(1)
<223> OTHER INFORMATION: X is glutamine, glutamic acid, asparagine,
      aspartic acid, glycine, alanine, or proline
<220> FEATURE:
<221> NAME/KEY: MISC_FEATURE
<222> LOCATION: (4)..(4)
<223> OTHER INFORMATION: X is glutamine, glutamic acid, asparagine,
      aspartic acid, glycine, alanine, or proline

<400> SEQUENCE: 160

Xaa Leu Met Xaa Gln
1               5
```